US012728129B2

(12) United States Patent
Koehler et al.

(10) Patent No.: US 12,728,129 B2
(45) Date of Patent: Sep. 8, 2026

(54) MACROCYCLIC BROAD SPECTRUM ANTIBIOTICS

(71) Applicant: Genentech, Inc., South San Francisco, CA (US)

(72) Inventors: Michael F.T. Koehler, South San Francisco, CA (US); Peter Andrew Smith, South San Francisco, CA (US); Dana Winter, Montreal (CA); Boubacar Sow, Montreal (CA); Claudio Sturino, Montreal (CA); Guillaume Pelletier, Saint-Lazare (CA); Jonathan Boudreault, L'Ile-Perrot (CA); Stéphanie Roy, Lachine (CA)

(73) Assignee: GENENTECH, INC., South San Francisco, CA (US)

( * ) Notice: Subject to any disclaimer, the term of this patent is extended or adjusted under 35 U.S.C. 154(b) by 841 days.

(21) Appl. No.: 17/644,861

(22) Filed: Dec. 17, 2021

(65) Prior Publication Data

US 2022/0135528 A1 May 5, 2022

Related U.S. Application Data

(62) Division of application No. 16/884,679, filed on May 27, 2020, now Pat. No. 11,208,387.

(60) Provisional application No. 62/853,457, filed on May 28, 2019.

(51) Int. Cl.

| | |
|---|---|
| ***A61K 31/505*** | (2006.01) |
| ***A61K 31/506*** | (2006.01) |
| ***A61K 38/08*** | (2019.01) |
| ***A61K 38/12*** | (2006.01) |
| ***A61K 45/06*** | (2006.01) |
| ***A61P 31/04*** | (2006.01) |
| ***C07D 239/28*** | (2006.01) |

(52) U.S. Cl.

CPC .......... *A61K 31/505* (2013.01); *A61K 31/506* (2013.01); *A61K 38/08* (2013.01); *A61K 38/12* (2013.01); *A61K 45/06* (2013.01); *A61P 31/04* (2018.01); *C07D 239/28* (2013.01)

(58) Field of Classification Search

CPC .... A61K 31/505; A61K 31/506; A61K 38/08; A61P 31/04

See application file for complete search history.

(56) References Cited

U.S. PATENT DOCUMENTS

| | | | |
|---|---|---|---|
| 3,128,280 A | 4/1964 | Rorig | |
| 5,204,328 A | 4/1993 | Nutt et al. | |
| 6,025,350 A | 2/2000 | Masamune et al. | |
| 6,048,694 A | 4/2000 | Bramucci et al. | |
| 6,951,840 B2 | 10/2005 | Belvo et al. | |
| 9,187,524 B2 | 11/2015 | Romesberg et al. | |
| 9,309,285 B2 | 4/2016 | Roberts et al. | |
| 10,392,422 B2 | 8/2019 | Roberts et al. | |
| 10,501,493 B2 | 12/2019 | Roberts et al. | |
| 11,149,009 B2 | 10/2021 | Yong et al. | |
| 2003/0130172 A1 | 7/2003 | Belvo et al. | |
| 2004/0024178 A1 | 2/2004 | Ashman et al. | |
| 2005/0153876 A1 | 7/2005 | Cameron et al. | |
| 2007/0099885 A1 | 5/2007 | Endermann et al. | |
| 2008/0275018 A1 | 11/2008 | Endermann et al. | |
| 2008/0300231 A1 | 12/2008 | Endermann et al. | |
| 2013/0130985 A1 | 5/2013 | Alewood et al. | |
| 2013/0244929 A1 | 9/2013 | Gallant et al. | |
| 2013/0281360 A1 | 10/2013 | Romesberg et al. | |
| 2014/0249073 A1 | 9/2014 | Roberts et al. | |
| 2015/0045286 A1* | 2/2015 | Romesberg .............. | C07K 7/56 514/2.7 |
| 2017/0073370 A1 | 3/2017 | Roberts et al. | |
| 2017/0088582 A1 | 3/2017 | Roberts et al. | |
| 2018/0327367 A1 | 11/2018 | Chen et al. | |
| 2020/0024309 A1 | 1/2020 | Smith et al. | |
| 2020/0239519 A1 | 7/2020 | Chen et al. | |
| 2020/0255476 A1 | 8/2020 | Petronijevic et al. | |
| 2020/0377463 A1 | 12/2020 | Koehler et al. | |
| 2022/0227860 A1 | 7/2022 | Yiqing et al. | |
| 2022/0340548 A1 | 10/2022 | Alvey et al. | |

FOREIGN PATENT DOCUMENTS

| | | |
|---|---|---|
| CL | 2021-002357 A1 | 4/2022 |
| CL | 2021-003133 | 7/2022 |
| CL | 2021-003155 | 7/2022 |
| CL | 2021-003039 | 8/2022 |
| CN | 1675236 A | 9/2005 |
| CN | 103159830 A | 6/2013 |
| CN | 103209700 | 7/2013 |
| CN | 103788176 A | 5/2014 |

(Continued)

OTHER PUBLICATIONS

US 10,351,595 B2, 07/2019, Roberts et al. (withdrawn)

Roberts et al., J Nat. Prod. 2011, vol. 74 (No. 5), pp. 956-961. (Year: 2011).*

Girgis et al., "Single-molecule nanopore sequencing reveals extreme target copy number heterogeneity in arylomycin-resistant mutants," PNAS, 118(1):e2021958118, (2021).

Paetzel et al., "Structure and mechanism of *Escherichia coli* type I signal peptidase," Biochim Biophys Acta Mol Cell Res, 1843:1497-1508, (2014).

Paetzel et al., "The structure and mechanism of bacterial type I signal peptidases. A novel antibiotic target," Pharmacol Thera, 87:27-49, (2000).

(Continued)

*Primary Examiner* — Amy L Clark
*Assistant Examiner* — Janet L Coppins
(74) *Attorney, Agent, or Firm* — Alston & Bird LLP

(57) ABSTRACT

Provided herein are antibacterial compounds, wherein the compounds in some embodiments have broad spectrum bioactivity. In various embodiments, the compounds act by inhibition of bacterial type 1 signal peptidases SpsB and/or LepB, an essential protein in bacteria. Pharmaceutical compositions and methods for treatment using the compounds described herein are also provided.

34 Claims, No Drawings

(56) References Cited

FOREIGN PATENT DOCUMENTS

| | | | |
|---|---|---|---|
| JP | 2018135357 | A | 8/2018 |
| JP | 2018184435 | A | 11/2018 |
| WO | WO 1998/017679 | A1 | 4/1998 |
| WO | WO 2001/014346 | A1 | 3/2001 |
| WO | WO 2003/106480 | A1 | 12/2003 |
| WO | WO 2011/109441 | A1 | 9/2011 |
| WO | WO 2011/112441 | A1 | 9/2011 |
| WO | WO 2012/036907 | A2 | 3/2012 |
| WO | WO 2012/166665 | A2 | 12/2012 |
| WO | WO 2013/138187 | A1 | 9/2013 |
| WO | WO 2014/081886 | A1 | 5/2014 |
| WO | WO 2015/179441 | A2 | 11/2015 |
| WO | WO 2017/064629 | A1 | 4/2017 |
| WO | WO 2017/084630 | A1 | 5/2017 |
| WO | WO 2018/149419 | A1 | 8/2018 |
| WO | WO 2018/183198 | A1 | 10/2018 |
| WO | WO 2019/067498 | A2 | 4/2019 |
| WO | WO 2020/243135 | A1 | 12/2020 |

OTHER PUBLICATIONS

Smith et al., "Mechanism of action of the arylomycin antibiotics and effects of signal peptidase I inhibition," Antimicrob Agents and Chemother, 56:5054-5060, (2012).

Tsirigotaki et al., "Protein export through the bacterial Sec pathway," Nat. Rev. Microbiol., 15:21-36, (2017).

Walsh et al., "Inhibition of protein secretion in *Escherichia coli* and sub-MIC effects of arylomycin antibiotics," Antimicrob Agents and Chemother, 63:e01253, (2019).

Exner et al., Antibiotic resistance: What is so special about multidrug-resistance Gram-negative bacteria? GMS Hygiene and Infection Control, 12:1-24, (2017).

Hu et al., "Current Status and Trends of Antibacterial Resistance in China," Clin. Infect. Dis., 67:S128-134, (2018).

Ikuta et al., "Global mortality associated with 33 bacterial pathogens in 2019: a systematic analysis for the Global Burden of Disease Study 2019," Lancet, 400:2221-2248, (2022).

Kadri et al., "Difficult-to-Treat Resistance in Gram-negative Bacteremia at 173 US Hospitals: Retrospective Cohort Analysis of Prevalence, Predictors, and Outcome of Resistance to All First-Line Agents," Clin. Infect. Dis., 67(12):1803-1814 (2018).

Koehler et al., "Lipid Tales: Optimizing Arylomycin Membrane Anchors," ACS Med. Chem. Lett., 14:1524-1530, (2023).

Mazzariol et al., "Multi-drug-resistant Gram-negative bacteria causing urinary tract infections: a review," Journal of Chemotherapy, 29(S1):2-9, (2017).

Tacconelli et al., "Discovery, research, and development of new antibiotics: the WHO priority list of antibiotic-resistant bacteria and tuberculosis," Lancet Infect. Dis., 18:318-327, (2018).

Tamma et al., "Infectious Diseases Society of America 2022 Guidance on the Treatment of Extended-Spectrum β-lactamase Producing Enterobacterales (ESBL-E), Carbapenem-Resistant Enterobacterales (CRE), and Pseudomonas aeruginosa with Difficult-to-Treat Resistance (DTR-P. aeruginosa)," Clin. Infect. Dis., 74:187-212, (2022).

Theuretzbacher et al., "Critical analysis of antibacterial agents in clinical development," Nat. Rev. Microbiol., 18:286-298, (2020).

Wagenlehner et al., "Epidemiology, definition and treatment of complicated urinary tract infections," Nat Rev Urol, 17:586-600, (2020).

Yusuf et al., "An Update on Eight "New" Antibiotics against Multidrug-Resistant Gram-Negative Bacteria," Journal of Clinical Medicine, 10:1068, (2021).

U.S. Appl. No. 16/884,679, filed May 27, 2020, U.S. Pat. No. 11,208,387, Issued.

Banker et al., Modern Pharmaceutices, 3rd ed., pp. 451 & 596, (1996).

Berge et al., "Pharmaceutical Salts," Journal of Pharmaceutical Science, 66(1):1-19, (1977).

Bockstael et al., "Evaluation of the type I signal peptidase as antibacterial target for biofilm-associated infections of *Staphylococcus epidermidis*," Microbiology, 155(11):3719-3729, (2009).

Braun et al., "Imp/OstA is required for cell envelope biogenesis in *Escherichia coli*," Molecular Microbiology, 45(5):1289-1302, (2002).

Brown et al., "New natural products as new leads for antibacterial drug discovery," Bioorganic and Medicinal Chemistry Letters, 24(2):413-418, (2014).

Bruton et al., "Lipopeptide substrates for SpsB, the *Staphylococcus aureus* type I signal peptidase: design, conformation and conversion to α-ketoamide inhibitors," European Journal of Medicinal Chemistry, 38:351-356, (2003).

Bundgaard et al., Design of Prodrugs, pp. 7-9, 21-24, (1985).

Butler et al., "Natural Products—The Future Scaffold for Novel Antibiotics ?" Biochemical Pharmacology, 71:919-929, (2006).

Buzder-Lantos et al., "Substrate based peptide aldehyde inhibits bacterial type I signal peptidase," Bioorg Med Chem Lett, 19:2880-2883, (2009).

Chen et al., "Highly Regioselective Halogenation of Pyridine N-Oxide: Practical Access to 2-Halo-Substituted Pyridines," Org. Lett., 17(12):2948-2951, (2015).

Clardy et al., "New antibiotics from bacterial natural products," Nature Biotechnology, 24:1541-1550, (2006).

Deangelis et al., "Generating active "L-Pd(0)" via Neutral or Cationic π-Allylpalladium Complexes Featuring Biaryl/Bipyrazolylphosphines: Synthetic, Mechanistic, and Structure-Activity Studies in Challenging Cross-Coupling Reactions," Journal of Organic Chemistry, 80(13):6794-6813, (2015).

Dufour et al., "Total Synthesis of Arlomycin A2, a Signal Peptidase I (SPasel) Inhibitor," J. P. Synlett, 15:2355-2359, (2008).

Dufour et al., "Intramolecular Suzuki-Miyaura Reaction for the Total Synthesis of Signal Peptidase Inhibitors, Arylomycins A(2) and B(2)," Chemistry: A European Journal, 16(34):10523-10534, (2010).

Freireich et al., "Quantitative comparison of toxicity of anticancer agents in mouse, rat, hamster, dog, monkey, and man," Cancer Chemotherapy Rep., 50(4):219-244, (1966).

Gould, Philip L., "Salt Selection for Basic Drugs," Int J. Pharm., 33:201-217, (1986).

Hallander et al., "Synergism Between Aminoglycosides and Cephalosporins with Antipseudomonal Activity: Interaction Index and Killing Curve Method," Antimicrob. Agents Chemother., 22:743-752, (1982).

Holtzel et al., "Arylomycins A and B, new biaryl-bridged lipopeptide antibiotics produced by *Streptomyces* sp. Tu 6075," Antibot (Tokyo), 55(6):571-577, (2002).

Johansson Seechurn et al., "Air-Stable Pd(R-allyl)LC1 (L=Q-Phos), P(t-Bu)3, etc.) Systems for C-C/N Couplings: Insight into the Structure-Activity Relationship and Catalyst Activation Pathway," Journal of Organic Chemistry, 76(19):7918-7932, (2011).

Kohlmann et al., "Fragment Growing and Linking Lead to Novel Nanomolar Lactate Dehydrogenase Inhibitors," J. Med. Chem., 56(3):1023-1040, (2013).

Liu et al., "Efforts toward broadening the spectrum of arylomycin antibiotic activity," Bioorg Med Chem Lett, 23:5654-5659, (2013).

Liu et al., "Synthesis and Characterization of the Arylomycin Lipoglycopeptide Antibiotics and the Crystallographic Analysis of Their Complex with Signal Peptidase," J Am Chem Soc, 133:17869-17877, (2011).

Luo et al., "Crystallographic analysis of bacterial signal peptidase in ternary complex with arylomycin A2 and a beta-sultam inhibitor," Biochemistry, 48(38):8976-8984, (2009).

Mandal et al., "Lipopeptides in microbial infection control: scope and reality for industry," Biotechnol Adv., 31(2):338-345, (2013).

Michaux et al., "Stereocontrolled routes to β,β'-disubstituted α-amino acids," Chem. Soc. Rev., 38:2093-2116, (2009).

Morisaki et al., "A Putative Bacterial ABC Transporter Circumvents the Essentiality of Signal Peptidase," Mbio, 7(5):e00412-16, (2016).

Musial-Siwek et al., "A Small Subset of Signal Peptidase Residues are Perturbed by Signal Peptide Binding," Chem Biol Drug Des., 72(2):140-146, (2008).

(56) References Cited

OTHER PUBLICATIONS

Nilsson et al., "A signal peptide with a proline next to the cleavage site inhibits leader peptidase when present in a sec-independent protein," FEBS Letters, 299(3):243-246, (1992).
Paetzel et al., "Crystallographic and biophysical analysis of a bacterial signal peptidase in complex with a lipopeptide-based inhibitor," J Biol Chem, 279(29):30781-30790, (2004).
PCT/CN2016/106597 International Preliminary Report on Patentability dated May 22, 2018.
PCT/CN2016/106597 International Search Report and Written Opinion dated Mar. 8, 2017.
PCT/CN2016/106597 Supplementary International Search Report dated Jul. 5, 2017.
PCT/CN2016/106598 International Preliminary Report on Patentability dated May 22, 2018.
PCT/CN2016/106598 International Search Report and Written Opinion dated Mar. 2, 2017.
PCT/CN2016/106598 Supplementary International Search Report dated Jun. 12, 2017.
PCT/CN2018/076957 International Search Report and Written Opinion dated Jun. 8, 2018.
PCT/US2012/039727 International Preliminary Report on Patentability mailed Dec. 2, 2013.
PCT/US2012/39727 International Search Report and Written Opinion mailed Jan. 3, 2013.
PCT/US2013/071093 International Preliminary Report on Patentability dated May 26, 2015.
PCT/US2013/071093 International Search Report and Written Opinion mailed Apr. 1, 2014.
PCT/US2014/051151 International Preliminary Report on Patentability dated Feb. 16, 2016.
PCT/US2015/031631 International Preliminary Report on Patentability dated Nov. 22, 2016.
PCT/US2015/031631 International Search Report and Written Opinion dated Nov. 3, 2015.
PubChem-CID-53377499, "Compound Summary (8S, 11S, 14S)-3,17, 18-Trihydroxy-14-[[2-[[(2R)-2-[[(2R)-3-hydroxy-2-(methyla mino)propanoyl]amino]propanoyl]amino]acetyl]-methylamino]-11-methyl-10,13-dioxo-9,12-diazatricyclo[13.3.1.12,6]icosa-1(18),2,4,6(20), 15(19), 16-hexaene-8-carboxylic acid," (Oct. 5, 2011).
Reetz et al., "Direct geminal dimethylation of ketones and exhaustive methylation of carboxylic acid chlorides using dichlorodimethyltitanium," Chem. Ber., 118(3):1050-1057, (1985).
Roberts et al., "Initial efforts toward the optimization of arylomycins for antibiotic activity," J Med Chem, 54(14):4954-4963, (2011).
Roberts et al., "Structural and Initial Biological Analysis of Synthetic Arylomycin A2," J Am Chem Soc., 129(51):15830-8, (2007).
Roberts et al., "Synthesis and Biological Characterization of Arylomycin B Antibiotics," J. Nat. Prod. 74:956-961, (2011).
Schallenberger et al., "Type I Signal Peptidase and Protein Secretion and *Stphylococcus aureus*," J Bacterol, 94(10):2677-86, (2012).
Schimana et al., "Arylomycins A and B, new biaryl-bridged lipopeptide antibiotics produced by *Streptomyces* sp. Tu 6075. I. Taxonomy, fermentation, isolation and biological activities," J Antibiot (Tokyo), 55(6):565-570, (2002).
Schmitt et al., "Synthesis of Mono- and Bis(fluoroalkyl)pyrimidines from FARs, Fluorinated Acetoacetates, and Malononitrile Provides Easy Access to Novel High-Value Pyrimidine Scaffolds," Chemistry, 24(6):1311-1316, (2018).
Silverman. The Organic Chemistry of Drug Design and Drug Action, published 1992 by Academic Press, pp. 19-21.
Smith et al., "Broad Spectrum Antibiotic Activity of the Arylomycin Natural Products Is Masked by Natural Target Mutations," Chem Biol, 17:1223-1231, (2010).
Smith et al., "Optimized arylomycins are a new class of Gram-negative antibiotics," Nature, 561(7722):189-194, (2018).
Steinmetz et al., "Thuggacins, macrolide antibiotics active against *Mycobacterium tuberculosis*: isolation from myxobacteria, structure elucidation, conformation analysis and biosynthesis," Chemistry, 13(20):5822-5832, (2007).
Tan and Romesberg, "Latent antibiotics and the potential of the arylomycins for broad-spectrum antibacterial activity," Medicinal Chemistry Communications, 3(8):916-925, (2012).
Therien et al., "Broadening the Spectrum of β-Lactam Antibiotics through Inhibition of Signal Peptidase Type 1," Antimicrobial Agents and Chemotherapy, 56:4662-4670, (2012).
Van Bambeke et al., "The bacterial envelope as a target for novel anti-MRSA antibiotics," Trends in Pharmacological Sciences, 29:124-134, (2008).
Wang et al., "Application of Nitrile in Drug Design," Chinese Journal of Organic Chemistry, 32:1643-1652, (Dec. 2012) (epub. Apr. 2012) (English Abstract only).
Wang, Y. et al., "A survey of the role of nitrile groups in protein-ligand interactions," Future Medicinal Chemistry, 10(23):2723-2728, (2018).
West, Solid State Chemistry and its Applications . . . Wiley, New York. pp. 358 & 365. (1988).
Will et al., "Analysis of mitochondrial function using phosphorescent oxygen-sensitive probes," Nature Protocols, 1(6):2563-2572, (2006).
Wolff, Burger's Medicinal Chemistry and Drug Discovery, 5th Ed., Part 1, pp. 975-977, (1995).
Australian Application No. 2016357926, Examination Report No. 1 mailed May 26, 2020.
Australian Application No. 2016357927, Examination Report No. 1 mailed Jun. 5, 2020.
European Application No. 16840309.5, Article 94(3) Communication mailed Jun. 18, 2020.
Iranian Application No. 139850140003004248, Office Action mailed May 13, 2020, including English translation.
Japanese Application No. 2017-513597, Office Action dated May 15, 2019, including English translation.
Japanese Application No. 2017-513597, Office Action dated May 20, 2020, including English translation.
PCT/US2011/049967 International Preliminary Report on Patentability mailed Mar. 19, 2013.
PCT/US2011/049967 International Search Report and Written Opinion mailed Apr. 6, 2012.
PCT/US2013/029913 International Preliminary Report on Patentability mailed Sep. 16, 2014.
PCT/US2013/029913 International Search Report and Written Opinion mailed Aug. 1, 2013.
PCT/US2014/051151 International Search Report and Written Opinion mailed Nov. 7, 2014.
PCT/US2018/024351 International Search Report and Written Opinion mailed Jun. 11, 2018.
PCT/US2018/024351 International Preliminary Report on Patentability mailed Oct. 1, 2019.
PCT/US2018/052791 International Preliminary Report on Patentability mailed Mar. 31, 2020.
PCT/US2018/052791 International Search Report and Written Opinion dated Apr. 17, 2019.
PCT/US2020/034670 International Search Report and Written Opinion mailed Sep. 30, 2020.
Russian Application No. 2018122505, Official Action mailed Apr. 12, 2021.
U.S. Appl. No. 15/777,499, Non-Final Office Action mailed Mar. 19, 2020.
U.S. Appl. No. 15/777,509, Non-Final Office Action mailed Jun. 9, 2020.
U.S. Appl. No. 16/539,947, Non-Final Office Action mailed Jun. 30, 2020.
U.S. Appl. No. 14/086,908 Office Action dated Jan. 5, 2015.
U.S. Appl. No. 14/086,908 Office Action dated May 29, 2015.
U.S. Appl. No. 14/123,024 Office Action dated May 1, 2015.
U.S. Appl. No. 14/123,024 Office Action dated May 19, 2016.
U.S. Appl. No. 14/123,024 Office Action dated Oct. 15, 2015.
U.S. Appl. No. 15/312,614 Office Action dated Jul. 17, 2018.
U.S. Appl. No. 15/358,100 Office Action dated Aug. 3, 2018.

(56) References Cited

OTHER PUBLICATIONS

U.S. Appl. No. 15/358,100 Office Action dated Nov. 26, 2018.
U.S. Appl. No. 15/777,499 Office Action dated Mar. 20, 2019.
U.S. Appl. No. 15/777,499 Office Action dated Oct. 3, 2019.
Dieppois et al., "In vitro activity of two novel antibiotics, GDC-5780 and GDC-0829 against a global panel of gram-negative prirority pathogens," Poster #BES1603, 34th European Congress of Clinical Microbiology and Infectious Diseases (ECCMID), 1, p. , Barcelona, Spain, (Apr. 27-30, 2024).
Dieppois et al., "In vitro killing kinetics of GDC-5780, a novel antibiotic for gram-negative bacteria, against a panel of Enterobacteriaceae isolates," Poster #2340, 34th European Congress of Clinical Microbiology and Infectious Diseases (ECCMID), 1, p. , Barcelona, Spain, (Apr. 27-30, 2024).
Girgis et al., "Low frequency of spontaneous resistance to LepB inhibitors, GDC-5780 and GDC-0829, in target gram-negative bacterial species," Poster #P2336, 34th European Congress of Clinical Microbiology and Infectious Diseases (ECCMID), 1, p. , Barcelona, Spain, (Apr. 27-30, 2024).
Koehler et al., "Developing arylomycins into novel antibiotics against gram-negative bacteria," Poster #P2357, 34th European Congress of Clinical Microbiology and Infectious Diseases (ECCMID), 1, p. , Barcelona, Spain, (Apr. 27-30, 2024).
Koehler et al., "Optimised arylomycins GDC-5780 and GDC-0829 represent a promising novel class of antibiotics against gram-negative pathogens," 34th European Congress of Clinical Microbiology and Infectious Diseases (ECCMID), 12 pgs., Barcelona, Spain, (Apr. 27-30, 2024).
Xu et al., "Determination of the PK/PD driver for the LepB inhibitor, GDC-0829, a novel broad-spectrum antibiotic against gram-negative bacterial infections," Poster #P2315, 34th European Congress of Clinical Microbiology and Infectious Diseases (ECCMID), 1, p. , Barcelona, Spain, (Apr. 27-30, 2024).
Xu et al., "Determination of the PK/PD driver for the LepB inhibitor, GDC-5780, a novel gram-negative antibiotic against Enterobacteriaceae infections," Poster #P2268, 34th European Congress of Clinical Microbiology and Infectious Diseases (ECCMID), 1, p. , Barcelona, Spain, (Apr. 27-30, 2024).

* cited by examiner

MACROCYCLIC BROAD SPECTRUM ANTIBIOTICS

CROSS-REFERENCE OF RELATED APPLICATIONS

This application is a division of U.S. patent application Ser. No. 16/884,679, filed on May 27, 2020, which claims the benefit of priority to U.S. Provisional Patent Application No. 62/853,457, filed on May 28, 2019, the contents of which are incorporated by reference herein in their entirety for all purposes.

BACKGROUND

Antibiotic resistance is a serious and growing phenomenon in contemporary medicine and has emerged as a major public health concern of the 21st century. For example, certain antibacterial compounds have been described in International Patent Publication No. WO 2018/149419, the content of which is incorporated by reference herein in its entirety. Some of these antibacterial compounds are shown in Table 1.

TABLE 1

| Cp. # | Structure | Name |
|---|---|---|
| 254 | 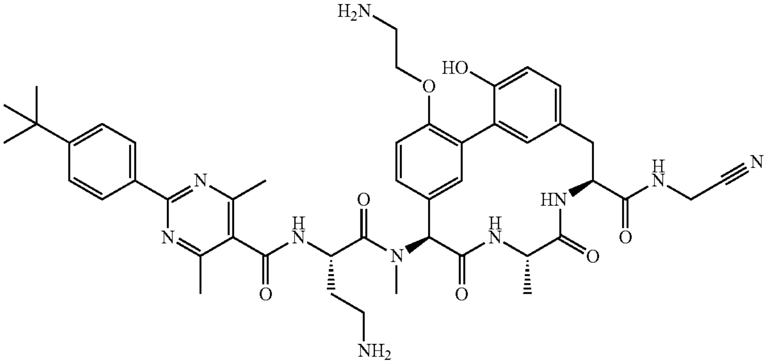 [SMILES: Cc1nc(-c2ccc(C(C)(C)C)cc2)nc(C)c1C(=O)N[C@@H](CCN)C(=O)N(C)[C@@H]1C(=O)N[C@@H](C)C(=O)N[C@H](C(=O)NCC#N)Cc2ccc(O)c(c2)-c2cc1ccc2OCCN] | rac-(8S,11S,14S)-18-(2-aminoethoxy)-N-(cyanomethyl)-3-hydroxy-11-methyl-14-[methyl-[rac-(2S)-4-amino-2-[[2-(4-tert-butylphenyl)-4,6-dimethyl-pyrimidine-5-carbonyl]amino]butanoyl]amino]-10,13-dioxo-9,12-diazatricyclo[13.3.1.12,6]icosa-1(18),2(20),3,5,15(19),16-hexaene-8-carboxamide |
| 561-15 | 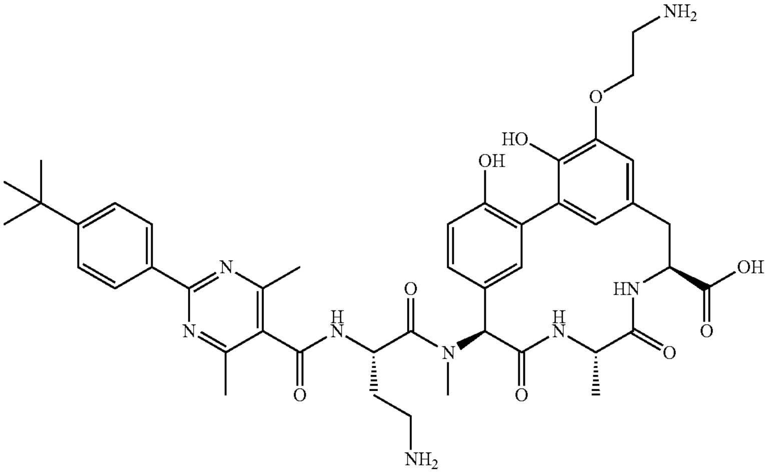 [SMILES: Cc1nc(-c2ccc(C(C)(C)C)cc2)nc(C)c1C(=O)N[C@@H](CCN)C(=O)N(C)[C@@H]1C(=O)N[C@@H](C)C(=O)N[C@H](C(=O)O)Cc2cc(OCCN)c(O)c(c2)-c2cc1ccc2O] | rac-(8S,11S,14S)-4-(2-aminoethoxy)-3,18-dihydroxy-11-methyl-14-[methyl-[rac-(2S)-4-amino-2-[[2-(4-tert-butylphenyl)-4,6-dimethyl-pyrimidine-5-carbonyl]amino]butanoyl]amino]-10,13-dioxo-9,12-diazatricyclo[13.3.1.12,6]icosa-1(18),2,4,6(20),15(19),16-hexaene-8-carboxylic acid |

TABLE 1-continued

| Cp. # | Structure | Name |
| --- | --- | --- |
| 563 | 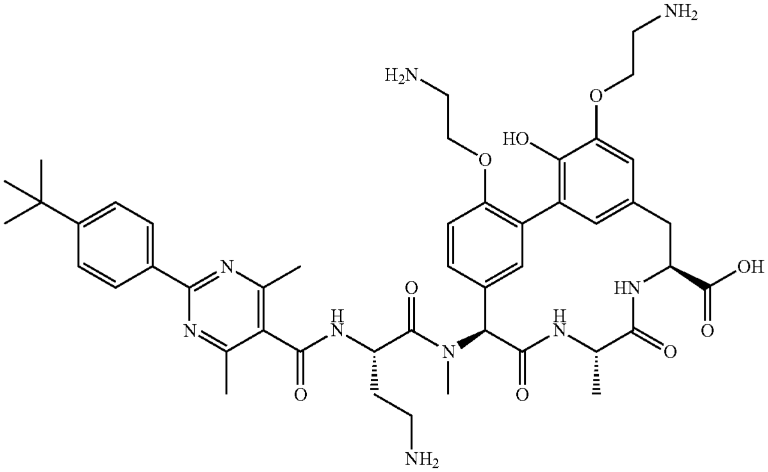 [SMILES: Cc1nc(-c2ccc(C(C)(C)C)cc2)nc(C)c1C(=O)N[C@@H](CCN)C(=O)N(C)[C@@H]1C(=O)N[C@@H](C)C(=O)N[C@H](C(=O)O)Cc2cc(OCCN)c(O)c(c2)-c2cc1ccc2OCCN] | rac-(8S,11S,14S)-4,18-bis(2-aminoethoxy)-3-hydroxy-11-methyl-14-[methyl-[rac-(2S)-4-amino-2-[[2-(4-tert-butylphenyl)-4,6-dimethyl-pyrimidine-5-carbonyl]amino]butanoyl]amino]-10,13-dioxo-9,12-diazatricyclo[13.3.1.12,6]icosa-1(18),2,4,6(20),15(19),16-hexaene-8-carboxylic acid |
| 582 | 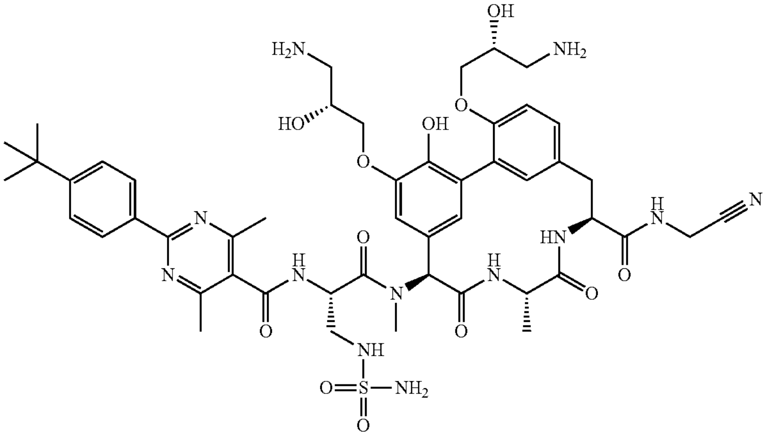 [SMILES: Cc1nc(-c2ccc(C(C)(C)C)cc2)nc(C)c1C(=O)N[C@@H](CNS(N)(=O)=O)C(=O)N(C)[C@@H]1C(=O)N[C@@H](C)C(=O)N[C@H](C(=O)NCC#N)Cc2ccc(OC[C@H](O)CN)c(c2)-c2cc1cc(OC[C@H](O)CN)c2O] | rac-(8S,11S,14S)-N-(cyanomethyl)-18-hydroxy-11-methyl-14-[methyl-[rac-(2S)-2-[[2-(4-tert-butylphenyl)-4,6-dimethyl-pyrimidine-5-carbonyl]amino]-3-(sulfamoylamino)propanoyl]amino]-10,13-dioxo-3,17-bis[rac-(2R)-3-amino-2-hydroxy-propoxy]-9,12-diazatricyclo[13.3.1.12,6]icosa-1(18),2(20),3,5,15(19),16-hexaene-8-carboxamide |
| 586 | 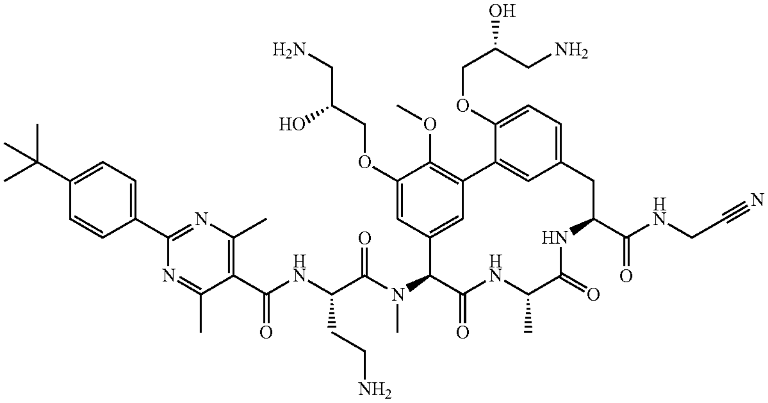 [SMILES: COc1c(OC[C@H](O)CN)cc2cc1-c1cc(ccc1OC[C@H](O)CN)C[C@@H](C(=O)NCC#N)NC(=O)[C@H](C)NC(=O)[C@H]2N(C)C(=O)[C@H](CCN)NC(=O)c1c(C)nc(-c2ccc(C(C)(C)C)cc2)nc1C] | rac-(8S,11S,14S)-N-(cyanomethyl)-18-methoxy-11-methyl-14-[methyl-[rac-(2S)-4-amino-2-[[2-(4-tert-butylphenyl)-4,6-dimethyl-pyrimidine-5-carbonyl]amino]butanoyl]amino]-10,13-dioxo-3,17-bis[rac-(2R)-3-amino-2-hydroxy-propoxy]-9,12-diazatricyclo[13.3.1.12,6]icosa-1(18),2(20),3,5,15(19),16-hexaene-8-carboxamide |

TABLE 1-continued

| Cp. # | Structure | Name |
|---|---|---|
| 633 | 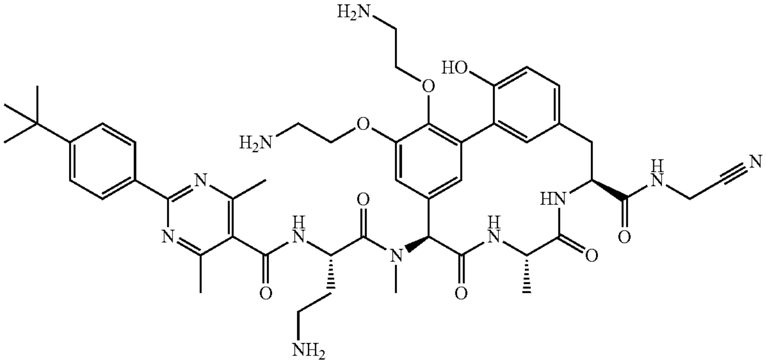 [SMILES: Cc1nc(-c2ccc(C(C)(C)C)cc2)nc(C)c1C(=O)N[C@@H](CCN)C(=O)N(C)[C@@H]1C(=O)N[C@@H](C)C(=O)N[C@H](C(=O)NCC#N)Cc2ccc(O)c(c2)-c2cc1cc(OCCN)c2OCCN] | (8S,11S,14S)-14-[[(2S)-4-amino-2-[[2-(4-tert-butylphenyl)-4,6-dimethyl-pyrimidine-5-carbonyl]amino]butanoyl]-methyl-amino]-17,18-bis(2-aminoethoxy)-N-(cyanomethyl)-3-hydroxy-11-methyl-10,13-dioxo-9,12-diazatricyclo[13.3.1.12,6]icosa-1(18),2(20),3,5,15(19),16-hexaene-8-carboxamide |
| 638 | 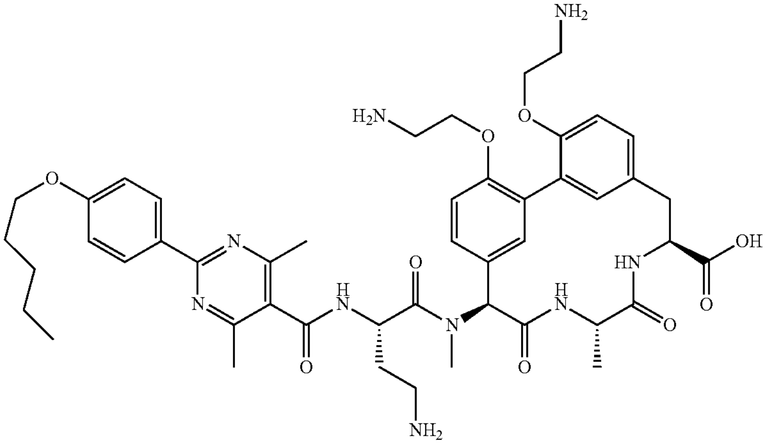 [SMILES: CCCCCOc1ccc(-c2nc(C)c(C(=O)N[C@@H](CCN)C(=O)N(C)[C@@H]3C(=O)N[C@@H](C)C(=O)N[C@H](C(=O)O)Cc4ccc(OCCN)c(c4)-c4cc3ccc4OCCN)c(C)n2)cc1] | rac-(8S,11S,14S)-3,18-bis(2-aminoethoxy)-11-methyl-14-[methyl-[rac-(2S)-4-amino-2-[[4,6-dimethyl-2-(4-pentoxyphenyl)pyrimidine-5-carbonyl]amino]butanoyl]amino]-10,13-dioxo-9,12-diazatricyclo[13.3.1.12,6]icosa-1(18),2(20),3,5,15(19),16-hexaene-8-carboxylic acid |
| 639 | 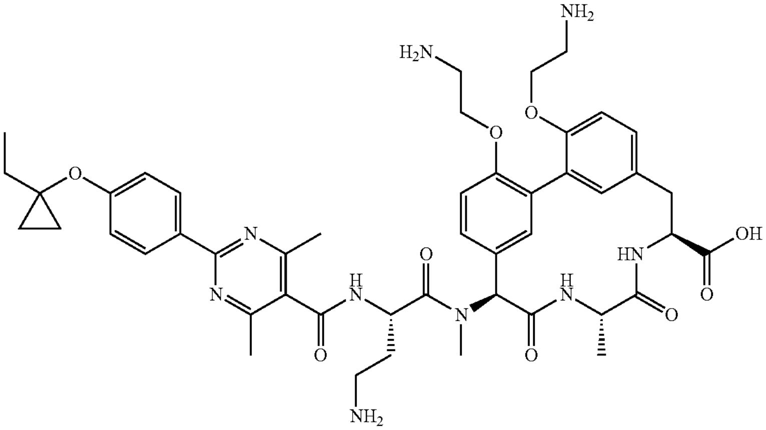 [SMILES: CCC1(Oc2ccc(-c3nc(C)c(C(=O)N[C@@H](CCN)C(=O)N(C)[C@@H]4C(=O)N[C@@H](C)C(=O)N[C@H](C(=O)O)Cc5ccc(OCCN)c(c5)-c5cc4ccc5OCCN)c(C)n3)cc2)CC1] | rac-(8S,11S,14S)-3,18-bis(2-aminoethoxy)-11-methyl-14-[methyl-[rac-(2S)-4-amino-2-[[2-[4-(1-ethylcyclopropoxy)phenyl]-4,6-dimethyl-pyrimidine-5-carbonyl]amino]butanoyl]amino]-10,13-dioxo-9,12-diazatricyclo[13.3.1.12,6]icosa-1(18),2(20),3,5,15(19),16-hexaene-8-carboxylic acid |

TABLE 1-continued

| Cp. # | Structure | Name |
|---|---|---|
| 640 | 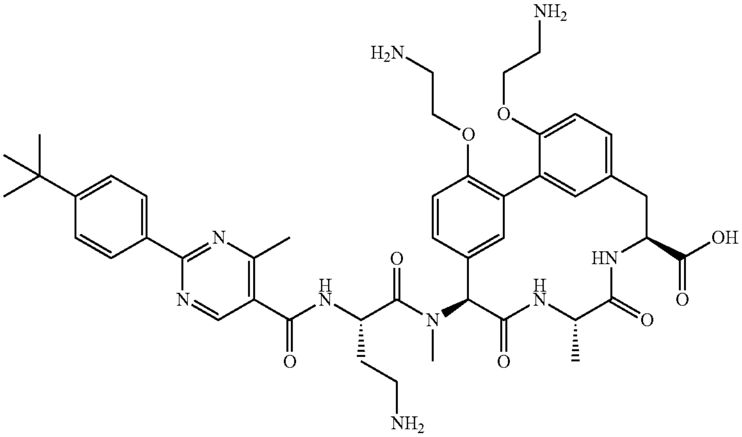 [SMILES: Cc1nc(-c2ccc(C(C)(C)C)cc2)ncc1C(=O)N[C@@H](CCN)C(=O)N(C)[C@@H]1C(=O)N[C@@H](C)C(=O)N[C@H](C(=O)O)Cc2ccc(OCCN)c(c2)-c2cc1ccc2OCCN] | rac-(8S,11S,14S)-3,18-bis(2-aminoethoxy)-11-methyl-14-[methyl-[rac-(2S)-4-amino-2-[[2-(4-tert-butylphenyl)-4-methyl-pyrimidine-5-carbonyl]amino]butanoyl]amino]-10,13-dioxo-9,12-diazatricyclo[13.3.1.12,6]icosa-1(18),2(20),3,5,15(19),16-hexaene-8-carboxylic acid |
| 641 | 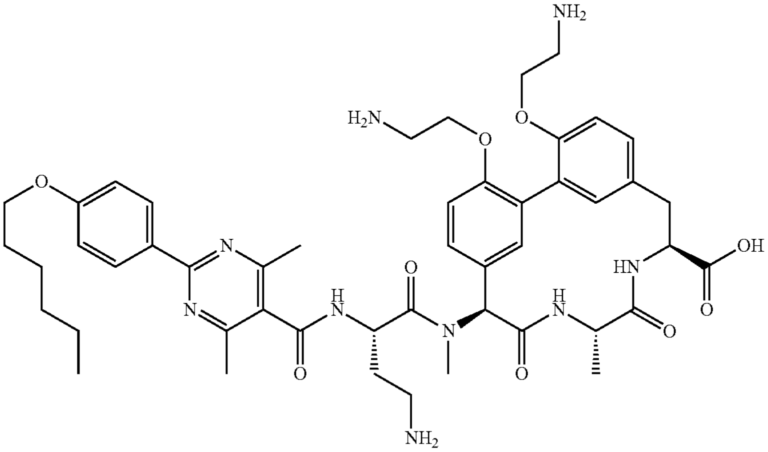 [SMILES: CCCCCCOc1ccc(-c2nc(C)c(C(=O)N[C@@H](CCN)C(=O)N(C)[C@@H]3C(=O)N[C@@H](C)C(=O)N[C@H](C(=O)O)Cc4ccc(OCCN)c(c4)-c4cc3ccc4OCCN)c(C)n2)cc1] | rac-(8S,11S,14S)-3,18-bis(2-aminoethoxy)-11-methyl-14-[methyl-[rac-(2S)-4-amino-2-[[2-(4-hexoxyphenyl)-4,6-dimethyl-pyrimidine-5-carbonyl]amino]butanoyl]amino]-10,13-dioxo-9,12-diazatricyclo[13.3.1.12,6]icosa-1(18),2(20),3,5,15(19),16-hexaene-8-carboxylic acid |
| 642 | 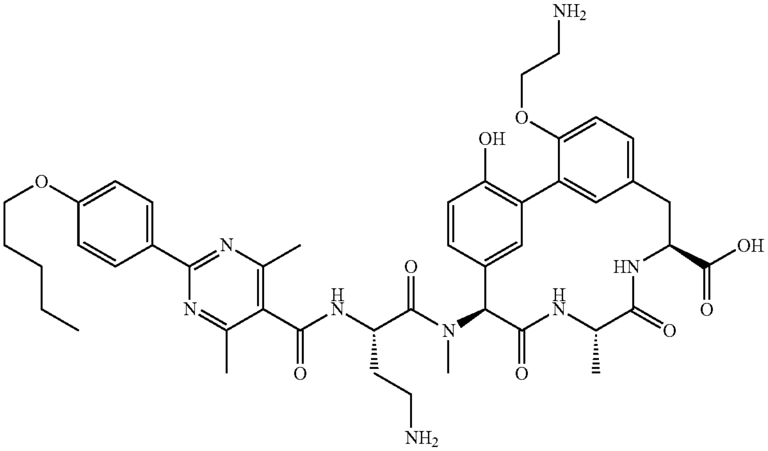 [SMILES: CCCCCOc1ccc(-c2nc(C)c(C(=O)N[C@@H](CCN)C(=O)N(C)[C@@H]3C(=O)N[C@@H](C)C(=O)N[C@H](C(=O)O)Cc4ccc(OCCN)c(c4)-c4cc3ccc4O)c(C)n2)cc1] | rac-(8S,11S,14S)-3-(2-aminoethoxy)-18-hydroxy-11-methyl-14-[methyl-[rac-(2S)-4-amino-2-[[4,6-dimethyl-2-(4-pentoxyphenyl)pyrimidine-5-carbonyl]amino]butanoyl]amino]-10,13-dioxo-9,12-diazatricyclo[13.3.1.12,6]icosa-1(18),2(20),3,5,15(19),16-hexaene-8-carboxylic acid |

TABLE 1-continued

| Cp. # | Structure | Name |
| --- | --- | --- |
| 643 | 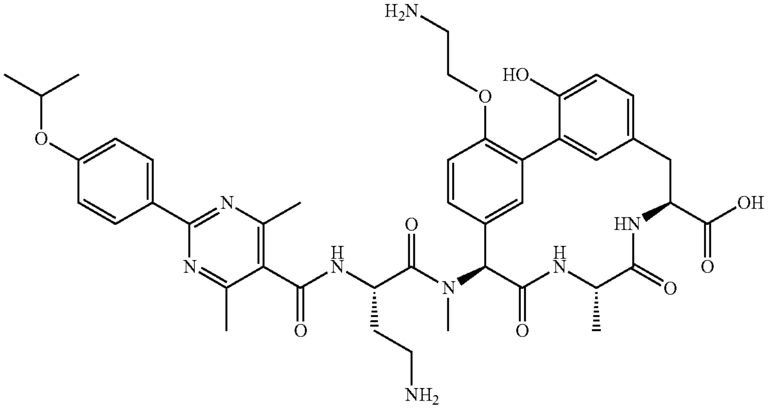 [SMILES: Cc1nc(-c2ccc(OC(C)C)cc2)nc(C)c1C(=O)N[C@@H](CCN)C(=O)N(C)[C@@H]1C(=O)N[C@@H](C)C(=O)N[C@H](C(=O)O)Cc2ccc(O)c(c2)-c2cc1ccc2OCCN] | rac-(8S,11S,14S)-18-(2-aminoethoxy)-3-hydroxy-11-methyl-14-[methyl-[rac-(2S)-4-amino-2-[[2-(4-isopropoxyphenyl)-4,6-dimethyl-pyrimidine-5-carbonyl]amino]butanoyl]amino]-10,13-dioxo-9,12-diazatricyclo[13.3.1.12,6]icosa-1(18),2(20),3,5,15(19),16-hexaene-8-carboxylic acid |
| 644 | 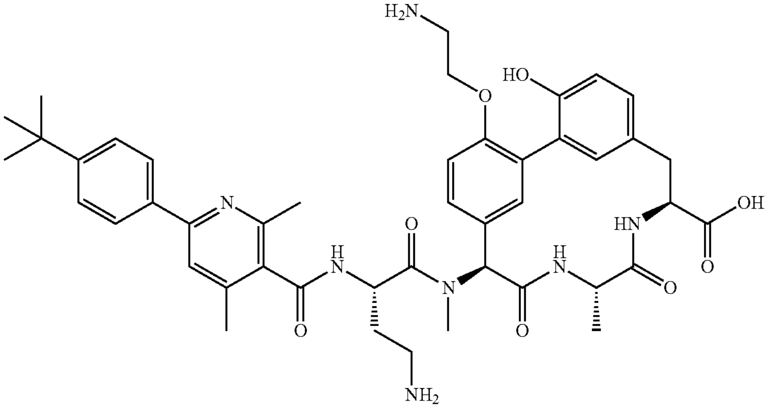 [SMILES: Cc1cc(-c2ccc(C(C)(C)C)cc2)nc(C)c1C(=O)N[C@@H](CCN)C(=O)N(C)[C@@H]1C(=O)N[C@@H](C)C(=O)N[C@H](C(=O)O)Cc2ccc(O)c(c2)-c2cc1ccc2OCCN] | rac-(8S,11S,14S)-18-(2-aminoethoxy)-3-hydroxy-11-methyl-14-[methyl-[rac-(2S)-4-amino-2-[[6-(4-tert-butylphenyl)-2,4-dimethyl-pyridine-3-carbonyl]amino]butanoyl]amino]-10,13-dioxo-9,12-diazatricyclo[13.3.1.12,6]icosa-1(18),2(20),3,5,15(19),16-hexaene-8-carboxlic acid |
| 645 | 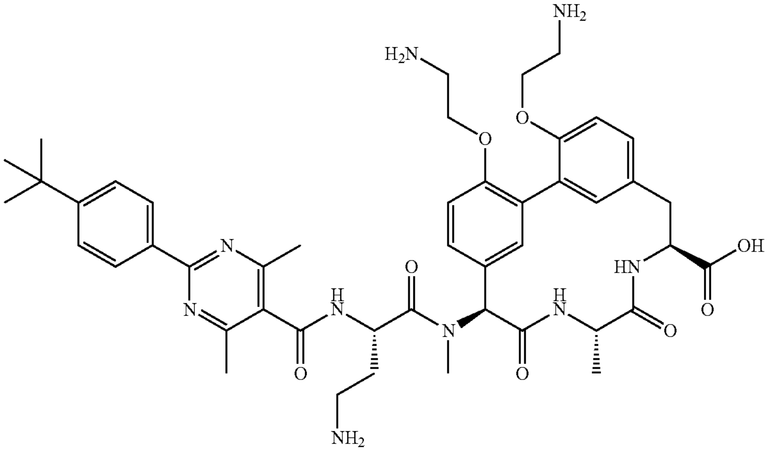 [SMILES: Cc1nc(-c2ccc(C(C)(C)C)cc2)nc(C)c1C(=O)N[C@@H](CCN)C(=O)N(C)[C@@H]1C(=O)N[C@@H](C)C(=O)N[C@H](C(=O)O)Cc2ccc(OCCN)c(c2)-c2cc1ccc2OCCN] | rac-(8S,11S,14S)-3,18-bis(2-aminoethoxy)-11-methyl-14-[methyl-[rac-(2S)-4-amino-2-[[2-(4-tert-butylphenyl)-4,6-dimethyl-pyrimidine-5-carbonyl]amino]butanoyl]amino]-10,13-dioxo-9,12-diazatricyclo[13.3.1.12,6]icosa-1(18),2(20),3,5,15(19),16-hexaene-8-carboxylic acid |

TABLE 1-continued

| Cp. # | Structure | Name |
|---|---|---|
| 646 | 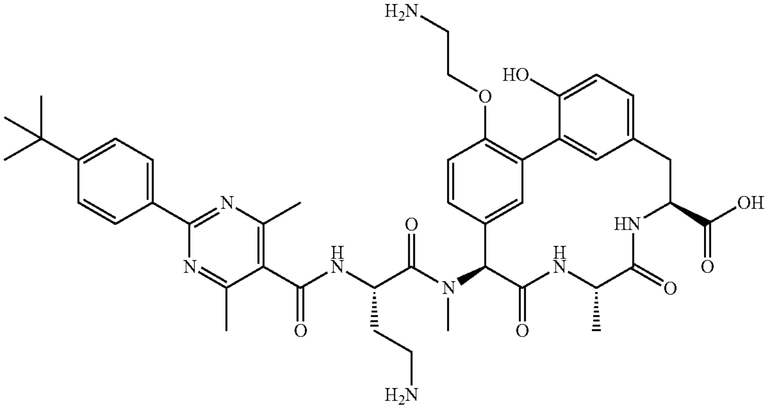 [SMILES: Cc1nc(-c2ccc(C(C)(C)C)cc2)nc(C)c1C(=O)N[C@@H](CCN)C(=O)N(C)[C@@H]1C(=O)N[C@@H](C)C(=O)N[C@H](C(=O)O)Cc2ccc(O)c(c2)-c2cc1ccc2OCCN] | rac-(8S,11S,14S)-18-(2-aminoethoxy)-3-hydroxy-11-methyl-14-[methyl-[rac-(2S)-4-amino-2-[[2-(4-tert-butylphenyl)-4,6-dimethyl-pyrimidine-5-carbonyl]amino]butanoyl]amino]-10,13-dioxo-9,12-diazatricyclo[13.3.1.12,6]icosa-1(18),2(20),3,5,15(19),16-hexaene-8-carboxylic acid |
| 647 | 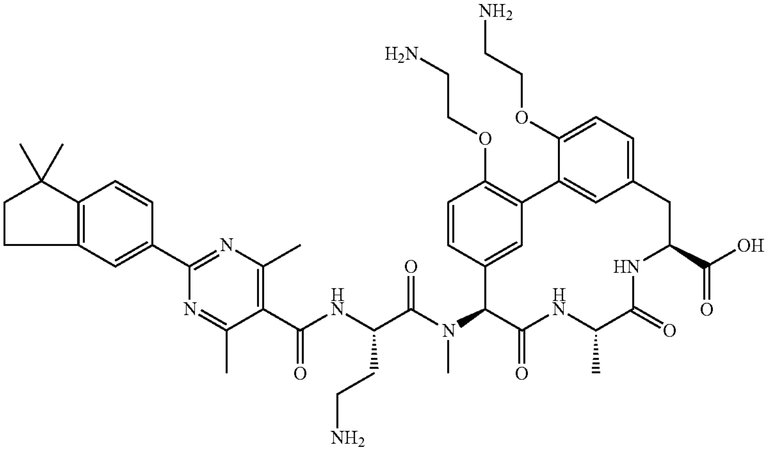 [SMILES: Cc1nc(-c2ccc3c(c2)CCC3(C)C)nc(C)c1C(=O)N[C@@H](CCN)C(=O)N(C)[C@@H]1C(=O)N[C@@H](C)C(=O)N[C@H](C(=O)O)Cc2ccc(OCCN)c(c2)-c2cc1ccc2OCCN] | rac-(8S,11S,14S)-3,18-bis(2-aminoethoxy)-11-methyl-14-[methyl-[rac-(2S)-4-amino-2-[[2-(1,1-dimethylindan-5-yl)-4,6-dimethyl-pyrimidine-5-carbonyl]amino]butanoyl]amino]-10,13-dioxo-9,12-diazatricyclo[13.3.1.12,6]icosa-1(18),2(20),3,5,15(19),16-hexaene-8-carboxylic acid |
| 648 | 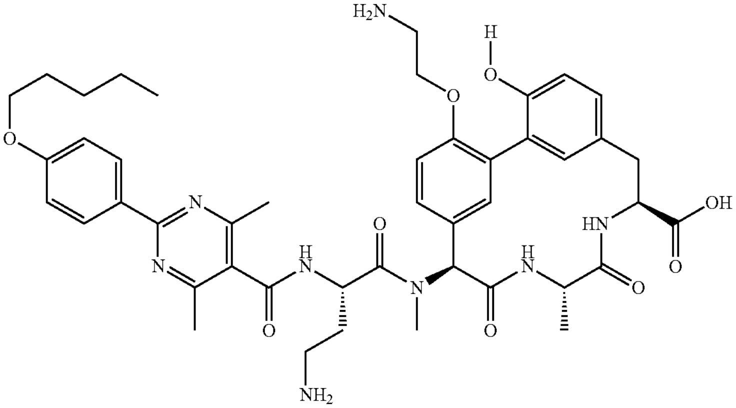 [SMILES: CCCCCOc1ccc(-c2nc(C)c(C(=O)N[C@@H](CCN)C(=O)N(C)[C@@H]3C(=O)N[C@@H](C)C(=O)N[C@H](C(=O)O)Cc4ccc(O)c(c4)-c4cc3ccc4OCCN)c(C)n2)cc1] | rac-(8S,11S,14S)-18-(2-aminoethoxy)-3-hydroxy-11-methyl-14-[methyl-[rac-(2S)-4-amino-2-[[4,6-dimethyl-2-(4-pentoxyphenyl)pyrimidine-5-carbonyl]amino]butanoyl]amino]-10,13-dioxo-9,12-diazatricyclo[13.3.1.12,6]icosa-1(18),2(20),3,5,15(19),16-hexaene-8-carboxylic acid |

TABLE 1-continued

| Cp. # | Structure | Name |
|---|---|---|
| 649 | 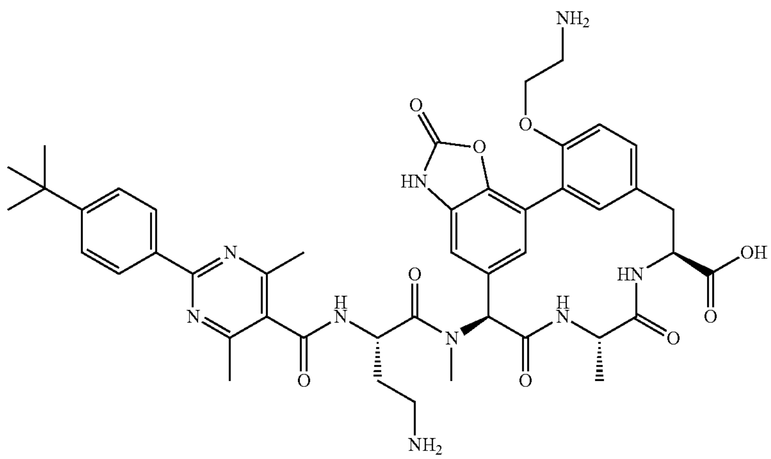 [SMILES: Cc1nc(-c2ccc(C(C)(C)C)cc2)nc(C)c1C(=O)N[C@@H](CCN)C(=O)N(C)[C@@H]1C(=O)N[C@@H](C)C(=O)N[C@H](C(=O)O)Cc2ccc(OCCN)c(c2)-c2cc1cc1[nH]c(=O)oc21] | rac-(4S,7S,10S)-10-(rac-(S)-4-amino-2-(2-(4-(tert-butyl)phenyl)-4,6-dimethylpyrimidine-5-carboxamido)-N-methylbutanamido)-$2^6$-(2-aminoethoxy)-7-methyl-$1^2$,6,9-trioxo-$1^2$,$1^3$-dihydro-5,8-diaza-1(7,5)-benzo[d]oxazola-2(1,3)-benzenacyclodecaphane-4-carboxylic acid |

However, additional novel classes of broad-spectrum antibiotics are still needed to treat particular multidrug-resistant pathogens.

SUMMARY OF THE DISCLOSURE

Described herein are novel macrocyclic compounds for the treatment of microbial infections, such as for the treatment of bacterial infections. In various embodiments, the present disclosure provides lipopeptide macrocyclic compounds for the treatment of bacterial infections. In various embodiments, the present disclosure provides classes and subclasses of chemical compounds structurally related to arylomycin for the treatment of bacterial infections. In various embodiments, the macrocyclic compounds act by inhibition of bacterial type 1 signal peptidase (SpsB), an essential protein in bacteria. In some embodiments, the signal peptidase is a Gram-negative signal peptidase. In some embodiments, the signal peptidase is LepB. The compounds of the invention are useful for the treatment of gram negative bacterial infections, and particularly useful in the treatment of infection associated with non-fermenter bacteria.

In one aspect described herein is a compound of Formula (I), or a pharmaceutically acceptable salt, solvate, or stereoisomer thereof:

Formula (I)

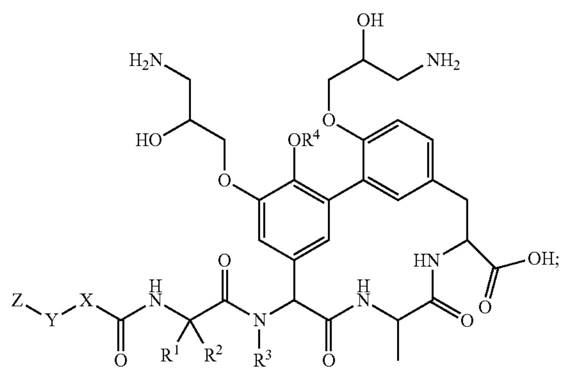

wherein:

$R^1$ is H or —($C_1$-$C_6$)alkyl optionally substituted with one, two, or three $R^{1a}$;

each $R^{1a}$ is independently halogen, —CN, —$OR^a$, —$SR^a$, —$NR^cR^d$, —$NO_2$, —C(═O)$R^b$, —$NR^a$C(═O)$R^b$, —C(═O)$OR^a$, —C(═O)$NR^cR^d$, —$NR^a$C(═O)$NR^cR^d$, —S(═O)$_2R^b$, —S(═O)$R^b$, —S(═O)$_2NR^cR^d$, —S(═O)$NR^cR^d$, —$NR^a$S(═O)$_2R^b$, —$NR^a$S(═O)$_2NR^cR^d$, —$NR^aOR^a$, —$NR^a$C(═O)$NR^aOR^a$, —O($C_1$-$C_6$)alkylene-$NR^cR^d$, —$NR^a$C(═$NR^c$)$R^a$, —C(═$NR^a$)$NR^cR^d$, —$NR^a$C(═$NR^a$)$NR^cR^d$, cycloalkyl, heterocycloalkyl, aryl, or heteroaryl; or two $R^{1a}$ on the same carbon are taken together to form an oxo;

$R^2$ is H, —$NR^cR^d$, or —($C_1$-$C_6$)alkyl optionally substituted with one, two, or three $R^{2a}$; each $R^{2a}$ is independently halogen, —CN, —$OR^a$, —$SR^a$, —$NR^cR^d$, —$NO_2$, —C(═O)$R^b$, —$NR^a$C(═O)$R^b$, —C(═O)$OR^a$, —C(═O)$NR^cR^d$, —$NR^a$C(═O)$NR^cR^d$, —S(═O)$_2R^b$, —S(═O)$R^b$, —S(═O)$_2NR^cR^d$, —S(═O)$NR^cR^d$, —$NR^a$S(═O)$_2R^b$, —$NR^a$S(═O)$_2NR^cR^d$, —$NR^aOR^a$, —$NR^a$C(═O)$NR^aOR^a$, —O($C_1$-$C_6$)alkylene-$NR^cR^d$, —$NR^a$C(═$NR^c$)$R^a$, —C(═$NR^a$)$NR^cR^d$, —$NR^a$C(═$NR^a$)$NR^cR^d$, cycloalkyl, heterocycloalkyl, aryl, or heteroaryl; or two $R^{2a}$ on the same carbon are taken together to form an oxo;

$R^3$ is H, —($C_3$-$C_6$)cycloalkyl, or —($C_1$-$C_6$)alkyl optionally substituted with one, two, or three $R^{3a}$;

each $R^{3a}$ is independently halogen, —CN, —$OR^a$, —$SR^a$, —$NR^cR^d$, —$NO_2$, —C(═O)$R^b$, —$NR^a$C(═O)$R^b$, —C(═O)$OR^a$, —C(═O)$NR^cR^d$, —$NR^a$C(═O)$NR^cR^d$, —S(═O)$_2R^b$, —S(═O)$R^b$, —S(═O)$_2NR^cR^d$, —S(═O)$NR^cR^d$, —$NR^a$S(═O)$_2R^b$, —$NR^a$S(═O)$_2NR^cR^d$, —$NR^aOR^a$, —$NR^a$C(═O)$NR^aOR^a$, —O($C_1$-$C_6$)alkylene-$NR^cR^d$, —$NR^a$C(═$NR^c$)$R^a$, —C(═$NR^a$)$NR^cR^d$, —$NR^a$C(═$NR^a$)$NR^cR^d$, cycloalkyl, heterocycloalkyl, aryl, or heteroaryl; or two $R^{3a}$ on the same carbon are taken together to form an oxo;

$R^4$ is H or —($C_1$-$C_6$)alkyl;

X is ($C_1$-$C_6$)alkylene, ($C_2$-$C_6$)alkenylene, ($C_2$-$C_6$)alkynylene, ($C_3$-$C_7$)cycloalkylene, ($C_2$-$C_7$)heterocycloalkylene, arylene, or heteroarylene; wherein the alkylene, alkenylene, alkynylene, cycloalkylene, heteroacycloalkylene, arylene, and heteroarylene is optionally substituted with one, two, or three $R^X$;

each $R^X$ is independently halogen, —CN, —$OR^a$, —$NR^cR^d$, —$NO_2$, —C(═O)$R^b$, —C(═O)$OR^a$, —C(═O)$NR^cR^d$, —($C_1$-$C_6$)alkyl, —($C_1$-$C_6$)haloalkyl, —($C_1$-$C_6$)heteroalkyl, —($C_1$-$C_6$)hydroxyalkyl, —($C_1$-$C_6$)aminoalkyl, —($C_3$-$C_7$)cycloalkyl, or —($C_2$-$C_7$)heterocycloalkyl; or two $R^X$ on the same carbon are taken together to form an oxo;

Y is bond, —O—, —S—, ($C_1$-$C_6$)alkylene, ($C_2$-$C_6$)alkenylene, ($C_2$-$C_6$)alkynylene, ($C_3$-$C_7$)cycloalkylene, ($C_2$-$C_7$)heterocycloalkylene, arylene, or heteroarylene; wherein the alkylene, alkenylene, alkynylene, cycloalkylene, heteroacycloalkylene, arylene, and heteroarylene is optionally substituted with one, two, or three $R^Y$;

each $R^Y$ is independently halogen, —CN, —$OR^a$, —$NR^cR^d$, —$NO_2$, —C(═O)$R^b$, —C(═O)$OR^a$, —C(═O)$NR^cR^d$, —($C_1$-$C_6$)alkyl, —($C_1$-$C_6$)haloalkyl, —($C_1$-$C_6$)heteroalkyl, —($C_1$-$C_6$)hydroxyalkyl, —($C_1$-$C_6$)aminoalkyl, —($C_3$-$C_7$)cycloalkyl, or —($C_2$-$C_7$)heterocycloalkyl; or two $R^Y$ on the same carbon are taken together to form an oxo;

Z is H, halogen, —CN, —$OR^{10}$, $SR^{10}$, —$NR^{12}R^{13}$, —C(═O)$R^{11}$, —C(═O)$OR^2$, —C(═O)$NR^{12}R^{13}$, —($C_1$-$C_{12}$)alkyl, —($C_1$-$C_{12}$)heteroalkyl, —($C_1$-$C_{12}$)haloalkyl, —($C_1$-$C_{12}$)hydroxyalkyl, —($C_1$-$C_{12}$)aminoalkyl, —($C_2$-$C_{12}$)alkenyl, —($C_2$-$C_{12}$)alkynyl, —($C_3$-$C_9$)cycloalkyl, —($C_2$-$C_7$)heterocycloalkyl, aryl, or heteroaryl; wherein the alkyl, alkenyl, alkynyl, cycloalkyl, heteroacycloalkyl, aryl, and heteroaryl are optionally substituted with one, two, or three $R^Z$;

each $R^Z$ is independently halogen, —CN, —$OR^{10}$, —$NR^{12}R^{13}$, —$NO_2$, —C(═O)$R^{11}$, —C(═O)$OR^{10}$, —C(═O)$NR^{12}R^{13}$, —($C_1$-$C_6$)alkyl, —($C_1$-$C_6$)haloalkyl, —($C_1$-$C_6$)heteroalkyl, —($C_1$-$C_6$)hydroxyalkyl, —($C_1$-$C_6$)aminoalkyl, —($C_2$-$C_6$)alkenyl, —($C_2$-$C_6$)alkynyl, —($C_3$-$C_7$)cycloalkyl, or —($C_2$-$C_7$)heterocycloalkyl;

or two $R^Z$ on the same carbon are taken together to form an oxo;

each $R^{10}$ is independently H, —($C_1$-$C_6$)alkyl, —($C_1$-$C_6$)haloalkyl, —($C_1$-$C_6$)heteroalkyl, —($C_1$-$C_6$)hydroxyalkyl, —($C_1$-$C_6$)aminoalkyl, —($C_2$-$C_6$)alkenyl, —($C_2$-$C_6$)alkynyl, —($C_3$-$C_7$)cycloalkyl, ($C_2$-$C_7$)heterocycloalkyl, aryl, or heteroaryl; wherein the alkyl, alkenyl, alkynyl, cycloalkyl, heterocycloalkyl, aryl, and heteroaryl are optionally independently substituted with one, two, or three $R^{10a}$;

each $R^{10a}$ is independently halogen, —CN, —$OR^a$, —$NR^cR^d$, —C(═O)$R^b$, —C(═O)$OR^a$, —C(═O)$NR^cR^d$, —($C_1$-$C_6$)alkyl, or —($C_1$-$C_6$)haloalkyl; or two $R^{10a}$ on the same carbon are taken together to form an oxo;

each $R^{11}$ is independently —($C_1$-$C_6$)alkyl, —($C_1$-$C_6$)haloalkyl, —($C_1$-$C_6$)heteroalkyl, —($C_1$-$C_6$)hydroxyalkyl, —($C_1$-$C_6$)aminoalkyl, —($C_2$-$C_6$)alkenyl, —($C_2$-$C_6$)alkynyl, —($C_3$-$C_7$)cycloalkyl, ($C_2$-$C_7$)heterocycloalkyl, aryl, or heteroaryl; wherein the alkyl, alkenyl, alkynyl, cycloalkyl, heterocycloalkyl, aryl, and heteroaryl are optionally independently substituted with one, two, or three $R^{11a}$;

each $R^{11a}$ is independently halogen, —CN, —$OR^a$, —$NR^cR^d$, —C(═O)$R^b$, —C(═O)$OR^a$, —C(═O)$NR^cR^d$, —($C_1$-$C_6$)alkyl, or —($C_1$-$C_6$)haloalkyl; or two $R^{11a}$ on the same carbon are taken together to form an oxo;

each $R^{12}$ and $R^{13}$ is independently H, —($C_1$-$C_6$)alkyl, —($C_1$-$C_6$)haloalkyl, —($C_1$-$C_6$)heteroalkyl, —($C_1$-$C_6$)hydroxyalkyl, —($C_1$-$C_6$)aminoalkyl, —($C_2$-$C_6$)alkenyl, —($C_2$-$C_6$)alkynyl, —($C_3$-$C_7$)cycloalkyl, ($C_2$-$C_7$)heterocycloalkyl, aryl, or heteroaryl; wherein the alkyl, alkenyl, alkynyl, cycloalkyl, heterocycloalkyl, aryl, and heteroaryl are optionally independently substituted with one, two, or three $R^{12a}$;

or $R^{12}$ and $R^{13}$ are taken together with the nitrogen atom to which they are attached to form a heterocycloalkyl optionally substituted with one, two, or three $R^{12b}$;

each $R^{12a}$ is independently halogen, —CN, —$OR^a$, —$NR^cR^d$, —C(═O)$R^b$, —C(═O)$OR^a$, —C(═O)$NR^cR^d$, —($C_1$-$C_6$)alkyl, or —($C_1$-$C_6$)haloalkyl; or two $R^{12a}$ on the same carbon are taken together to form an oxo;

each $R^{12b}$ is independently halogen, —CN, —$OR^a$, —$NR^cR^d$, —C(═O)$R^b$, —C(═O)$OR^a$, —C(═O)$NR^cR^d$, —($C_1$-$C_6$)alkyl, or —($C_1$-$C_6$)haloalkyl; or two $R^{12b}$ on the same carbon are taken together to form an oxo;

each $R^a$ is independently H, —($C_1$-$C_6$)alkyl, —($C_1$-$C_6$)haloalkyl, —($C_1$-$C_6$)heteroalkyl, —($C_1$-$C_6$)hydroxyalkyl, —($C_1$-$C_6$)aminoalkyl, —($C_2$-$C_6$)alkenyl, —($C_2$-$C_6$)alkynyl, —($C_3$-$C_7$)cycloalkyl, ($C_2$-$C_7$)heterocycloalkyl, aryl, or heteroaryl; wherein the alkyl, alkenyl, alkynyl, cycloalkyl, heterocycloalkyl, aryl, and heteroaryl are optionally independently substituted with one, two, or three halogen, —CN, —OH, -OMe, —$NH_2$, —C(═O)Me, —C(═O)OH, —C(═O)OMe, —C(═O)$NH_2$, or —($C_1$-$C_6$)alkyl;

each R is independently —($C_1$-$C_6$)alkyl, —($C_1$-$C_6$)haloalkyl, —($C_1$-$C_6$)heteroalkyl, —($C_1$-$C_6$)hydroxyalkyl, —($C_1$-$C_6$)aminoalkyl, —($C_2$-$C_6$)alkenyl, —($C_2$-$C_6$)alkynyl, —($C_3$-$C_7$)cycloalkyl, ($C_2$-$C_7$)heterocycloalkyl, aryl, or heteroaryl; wherein the alkyl, alkenyl, alkynyl, cycloalkyl, heterocycloalkyl, aryl, and heteroaryl are optionally independently substituted with one, two, or three halogen, —CN, —OH, -OMe, —$NH_2$, —C(═O)Me, —C(═O)OH, —C(═O)OMe, —C(═O)$NH_2$, or —($C_1$-$C_6$)alkyl; and each $R^c$ and $R^d$ is independently H, —($C_1$-$C_6$)alkyl, —($C_1$-$C_6$)haloalkyl, —($C_1$-$C_6$)heteroalkyl, —($C_1$-$C_6$)hydroxyalkyl, —($C_1$-$C_6$)aminoalkyl, —($C_2$-$C_6$)alkenyl, —($C_2$-$C_6$)alkynyl, —($C_3$-$C_7$)cycloalkyl, ($C_2$-$C_7$)heterocycloalkyl, aryl, or heteroaryl; wherein the alkyl, alkenyl, alkynyl, cycloalkyl, heterocycloalkyl, aryl, and heteroaryl are optionally independently substituted with one, two, or three halogen, —CN, —OH, -OMe, —$NH_2$, —C(═O)Me, —C(═O)OH, —C(═O)OMe, —C(═O)$NH_2$, or —($C_1$-$C_6$)alkyl;

or $R^c$ and $R^d$ are taken together with the nitrogen atom to which they are attached to form a heterocycloalkyl optionally substituted with one, two, or three oxo, halogen, —CN, —OH, -OMe, —$NH_2$, —C(═O)Me, —C(═O)OH, —C(═O)OMe, —C(═O)$NH_2$, or —($C_1$-$C_6$)alkyl.

In some embodiments of a compound of Formula (I), or a pharmaceutically acceptable salt, solvate, or stereoisomer thereof; the compound has the structure of Formula (Ia):

Formula (Ia)

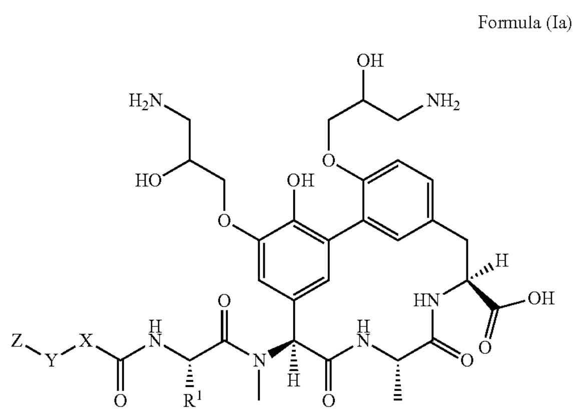

In some embodiments of a compound of Formula (I), or a pharmaceutically acceptable salt, solvate, or stereoisomer thereof; the compound has the structure of Formula (Ib):

Formula (Ib)

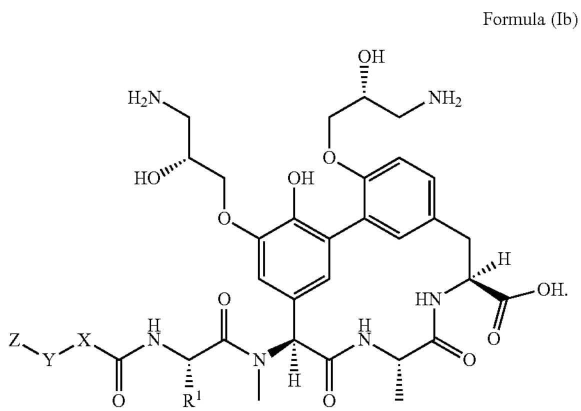

Also disclosed herein is a pharmaceutical composition comprising a compound disclosed herein, or a pharmaceutically acceptable salt, solvate, or stereoisomer thereof, and a pharmaceutically acceptable excipient.

Also disclosed herein is a method of treatment of a bacterial infection in a mammal, comprising administering to the mammal an effective amount of a compound disclosed herein, or a pharmaceutically acceptable salt, solvate, or stereoisomer thereof, to the mammal at a frequency and for a duration sufficient to provide a beneficial effect to the mammal.

Also disclosed herein is a method of treatment of a lepB-mediated infection in a mammal, comprising administering to the mammal an effective amount of a compound disclosed herein, or a pharmaceutically acceptable salt, solvate, or stereoisomer thereof, to the mammal at a frequency and for a duration sufficient to provide a beneficial effect to the mammal. In some embodiments of a method of treatment, the bacterial infection is an infection involving *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalfaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis,* Kingella, *Moraxella, Gardnerella vaginalis, Bacteroides fragilis, Bacteroides distasonis, Bacteroides* 3452A homology group, *Bacteroides vulgatus, Bacteroides ovalus, Bacteroides thetaiotaomicron, Bacteroides unformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis*, or *Staphylococcus saccharolyticus*. In some embodiments of a method of treatment, the bacterial infection is an infection involving *Acinetobacter baumannii, Klebsiella pneumoniae*, or *Pseudomonas aeruginosa*. In some embodiments of a method of treatment, the bacterial infection is an infection involving *Acinetobacter baumannii*. In some embodiments of a method of treatment, the bacterial infection is an infection involving a Gram-negative bacteria. In some embodiments of a method of treatment, the method further comprises administering a second therapeutic agent. In some embodiments of a method of treatment, the second therapeutic agent is not a SpsB or LepB inhibitor. In some embodiments of a method of treatment, the second therapeutic agent is an aminoglycoside antibiotic, fluoroquinolone antibiotic, β-lactam antibiotic, macrolide antibiotic, glycopeptide antibiotic, rifampicin, chloramphenicol, fluoramphenicol, colistin, mupirocin, bacitracin, daptomycin, or linezolid. In some embodiments of a method of treatment, the second therapeutic agent is a β-lactam antibiotic. In some embodiments of a method of treatment, wherein the β-lactam antibiotic is selected from penicillins, monobactams, cephalosporins, cephamycins, and carbapenems. In some embodiments of a method of treatment, the β-lactam antibiotic is selected from Azlocillin, Amoxicillin, Ampicillin, Doripenem, Meropenem, Biapenem, Cefamandole, Imipenem, Mezlocillin, Cefinetazole, Cefprozil, Piperacillin/tazobactam, Carbenicillin, Cefaclor, Cephalothin, Ertapenem, Cefazolin, Cefepime, Cefonicid, Cefoxitin, Ceftazidime, Oxacillin, Cefdinir, Cefixime, Cefotaxime, Cefotetan, Cefpodoxime, Ceftizoxime, Ceftriaxone, Faropenem, Mecillinam, Methicillin, Moxalactam, Ticarcillin, Tomopenem, Ceftobiprole, Ceftaroline, Flomoxef, Cefiprome, and Cefozopran. In some embodiments of a method of treatment, the method further comprises administering a β-lactamase inhibitor.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE DISCLOSURE

Definitions

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

As used in the specification and appended claims, unless specified to the contrary, the following terms have the meaning indicated below.

"Alkyl" refers to an optionally substituted straight-chain, or optionally substituted branched-chain saturated hydrocarbon monoradical having from one to about ten carbon atoms, or from one to six carbon atoms. Examples include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl, and the like. Whenever it appears herein, a numerical range such as "$C_1$-$C_6$ alkyl" means that the alkyl group consists of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. In some embodiments, the alkyl is a $C_1$-$C_{20}$ alkyl, $C_1$-$C_{10}$ alkyl, a $C_1$-$C_9$ alkyl, a $C_1$-$C_5$ alkyl, a $C_1$-$C_7$ alkyl, a $C_1$-$C_6$ alkyl, a $C_1$-$C_5$ alkyl, a $C_1$-$C_4$ alkyl, a $C_1$-$C_3$ alkyl, a $C_1$-$C_2$ alkyl, or a $C_1$ alkyl. Unless stated otherwise specifically in the specification, an alkyl group is optionally substituted as described below, for example, with oxo, halogen, amino, nitrile, nitro, hydroxyl, haloalkyl, alkoxy, aryl, cycloalkyl, heterocycloalkyl, heteroaryl, and the like. In some embodiments, the alkyl is optionally substituted with oxo, halogen, —CN, —$CF_3$, —OH, -OMe, —$NH_2$, or —$NO_2$. In some embodiments, the alkyl is optionally substituted with oxo, halogen, —CN, —$CF_3$, —OH, or -OMe. In some embodiments, the alkyl is optionally substituted with halogen.

"Alkenyl" refers to an optionally substituted straight-chain, or optionally substituted branched-chain hydrocarbon monoradical having one or more carbon-carbon double-bonds and having from two to about ten carbon atoms, more preferably two to about six carbon atoms. The group may be in either the cis or trans conformation about the double bond(s), and should be understood to include both isomers. Examples include, but are not limited to ethenyl (—CH═$CH_2$), 1-propenyl (—$CH_2$CH═$CH_2$), isopropenyl [—C($CH_3$)═$CH_2$], butenyl, 1,3-butadienyl and the like. Whenever it appears herein, a numerical range such as "$C_2$-$C_6$ alkenyl" means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated. In some embodiments, the alkenyl is a $C_2$-$C_{20}$ alkenyl, a $C_2$-$C_{10}$ alkenyl, a $C_2$-$C_9$ alkenyl, a $C_2$-$C_8$ alkenyl, a $C_2$-$C_7$ alkenyl, a $C_2$-$C_6$ alkenyl, a $C_2$-$C_5$ alkenyl, a $C_2$-$C_4$ alkenyl, a $C_2$-$C_3$ alkenyl, or a $C_2$ alkenyl. Unless stated otherwise specifically in the specification, an alkenyl group is optionally substituted as described below, for example, with oxo, halogen, amino, nitrile, nitro, hydroxyl, haloalkyl, alkoxy, aryl, cycloalkyl, heterocycloalkyl, heteroaryl, and the like. In some embodiments, an alkenyl is optionally substituted with oxo, halogen, —CN, —$CF_3$, —OH, -OMe, —$NH_2$, or —$NO_2$. In some embodiments, an alkenyl is optionally substituted with oxo, halogen, —CN, —$CF_3$, —OH, or -OMe. In some embodiments, the alkenyl is optionally substituted with halogen.

"Alkynyl" refers to an optionally substituted straight-chain or optionally substituted branched-chain hydrocarbon monoradical having one or more carbon-carbon triple-bonds and having from two to about ten carbon atoms, more preferably from two to about six carbon atoms. Examples include, but are not limited to ethynyl, 2-propynyl, 2-butynyl, 1,3-butadiynyl and the like. Whenever it appears herein, a numerical range such as "$C_2$-$C_6$ alkynyl" means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated. In some embodiments, the alkynyl is a $C_2$-$C_{20}$ alkynyl, a $C_2$-$C_{10}$ alkynyl, a $C_2$-$C_9$ alkynyl, a $C_2$-$C_8$ alkynyl, a $C_2$-$C_7$ alkynyl, a $C_2$-$C_6$ alkynyl, a $C_2$-$C_5$ alkynyl, a $C_2$-$C_4$ alkynyl, a $C_2$-$C_3$ alkynyl, or a $C_2$ alkynyl. Unless stated otherwise specifically in the specification, an alkynyl group is optionally substituted as described below, for example, with oxo, halogen, amino, nitrile, nitro, hydroxyl, haloalkyl, alkoxy, aryl, cycloalkyl, heterocycloalkyl, heteroaryl, and the like. In some embodiments, an alkynyl is optionally substituted with oxo, halogen, —CN, —$CF_3$, —OH, -OMe, —$NH_2$, or —$NO_2$. In some embodiments, an alkynyl is optionally substituted with oxo, halogen, —CN, —$CF_3$, —OH, or -OMe. In some embodiments, the alkynyl is optionally substituted with halogen.

"Alkylene" refers to a straight or branched divalent hydrocarbon chain. Unless stated otherwise specifically in the specification, an alkylene group may be optionally substituted as described below, for example, with oxo, halogen, amino, nitrile, nitro, hydroxyl, haloalkyl, alkoxy, aryl, cycloalkyl, heterocycloalkyl, heteroaryl, and the like. In some embodiments, an alkylene is optionally substituted with oxo, halogen, —CN, —$CF_3$, —OH, -OMe, —$NH_2$, or —$NO_2$. In some embodiments, an alkylene is optionally substituted with oxo, halogen, —CN, —$CF_3$, —OH, or -OMe. In some embodiments, the alkylene is optionally substituted with halogen.

"Alkoxy" refers to a radical of the formula —$OR_a$ where $R_a$ is an alkyl radical as defined. Unless stated otherwise specifically in the specification, an alkoxy group may be optionally substituted as described below, for example, with oxo, halogen, amino, nitrile, nitro, hydroxyl, haloalkyl, alkoxy, aryl, cycloalkyl, heterocycloalkyl, heteroaryl, and the like. In some embodiments, an alkoxy is optionally substituted with oxo, halogen, —CN, —$CF_3$, —OH, -OMe, —$NH_2$, or —$NO_2$. In some embodiments, an alkoxy is optionally substituted with oxo, halogen, —CN, —$CF_3$, —OH, or -OMe. In some embodiments, the alkoxy is optionally substituted with halogen.

"Aryl" refers to a radical derived from a hydrocarbon ring system comprising hydrogen, 6 to 30 carbon atoms and at least one aromatic ring. The aryl radical may be a monocyclic, bicyclic, tricyclic or tetracyclic ring system, which may include fused (when fused with a cycloalkyl or heterocycloalkyl ring, the aryl is bonded through an aromatic ring atom) or bridged ring systems. In some embodiments, the aryl is a 6- to 10-membered aryl. In some embodiments, the aryl is a 6-membered aryl. Aryl radicals include, but are not limited to, aryl radicals derived from the hydrocarbon ring systems of anthrylene, naphthylene, phenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. In some embodiments, the aryl is phenyl. Unless stated otherwise specifically in the specification, an aryl may be optionally substituted as described below, for example, with halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, an aryl is optionally substituted with halogen, methyl, ethyl, —CN, —$CF_3$, —OH, -OMe, —$NH_2$, or —$NO_2$. In some embodiments, an aryl is optionally substituted with halogen, methyl, ethyl, —CN, —$CF_3$, —OH, or -OMe. In some embodiments, the aryl is optionally substituted with halogen or methyl. In some embodiments, the aryl is optionally substituted with halogen.

"Cycloalkyl" refers to a stable, partially or fully saturated, monocyclic or polycyclic carbocyclic ring, which may include fused (when fused with an aryl or a heteroaryl ring, the cycloalkyl is bonded through a non-aromatic ring atom) or bridged ring systems. Representative cycloalkyls include, but are not limited to, cycloalkyls having from three to fifteen carbon atoms ($C_3$-$C_{15}$ cycloalkyl), from three to ten carbon atoms ($C_3$-$C_{10}$ cycloalkyl), from three to eight carbon atoms ($C_3$-$C_8$ cycloalkyl), from three to six carbon atoms ($C_3$-$C_6$ cycloalkyl), from three to five carbon atoms ($C_3$-$C_5$ cycloalkyl), or three to four carbon atoms ($C_3$-$C_4$ cycloalkyl). In some embodiments, the cycloalkyl is a 3- to 6-membered cycloalkyl. In some embodiments, the cycloalkyl is a 5- to 6-membered cycloalkyl. Monocyclic cycloalkyls include, for example, cyclopropyl, cyclobutyl, cyclopentyl, cyclohexyl, cycloheptyl, and cyclooctyl. Polycyclic cycloalkyls or carbocycles include, for example, adamantyl, norbornyl, decalinyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane, and 7,7-dimethyl-bicyclo[2.2.1]heptanyl. Partially saturated cycloalkyls include, for example cyclopentenyl, cyclohexenyl, cycloheptenyl, and cyclooctenyl. Unless stated otherwise specifically in the specification, a cycloalkyl is optionally substituted as described below, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a cycloalkyl is optionally substituted with oxo, halogen, methyl, ethyl, —CN, —$CF_3$, —OH, -OMe, —$NH_2$, or —$NO_2$. In some embodiments, a cycloalkyl is optionally substituted with oxo, halogen, methyl, ethyl, —CN, —$CF_3$, —OH, or -OMe. In some embodiments, the cycloalkyl is optionally substituted with halogen or methyl. In some embodiments, the cycloalkyl is optionally substituted with halogen.

"Halo" or "halogen" refers to bromo, chloro, fluoro, or iodo. In some embodiments, halogen is fluoro or chloro. In some embodiments, halogen is fluoro.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like.

"Aminoalkyl" refers to an alkyl radical, as defined above, that is substituted by one or more —$NH_2$, e.g., —$CH_2NH_2$, —$CH_2CH_2NH_2$, —$CH_2CH_2CH_2NH_2$, —$CH(NH_2)CH_3$, —$CH_2CH(NH_2)CH_3$, —$CH(NH_2)CH_2CH_3$, and the like.

"Hydroxyalkyl" refers to an alkyl radical, as defined above, that is substituted by one or more —OH, e.g., —$CH_2OH$, —$CH_2CH_2OH$, —$CH_2CH_2CH_2OH$, —$CH(OH)CH_3$, —$CH_2CH(OH)CH_3$, —$CH(OH)CH_2CH_3$, and the like.

"Heterocycloalkyl" refers to a stable 3- to 24-membered partially or fully saturated ring radical comprising 2 to 23 carbon atoms and from one to 8 heteroatoms selected from the group consisting of nitrogen, oxygen, phosphorous and sulfur. Unless stated otherwise specifically in the specification, the heterocycloalkyl radical may be a monocyclic, bicyclic, tricyclic or tetracyclic ring system, which may include fused (when fused with an aryl or a heteroaryl ring, the heterocycloalkyl is bonded through a non-aromatic ring atom) or bridged ring systems; and the nitrogen, carbon or sulfur atoms in the heterocycloalkyl radical may be optionally oxidized; the nitrogen atom may be optionally quaternized. In some embodiments, the heterocycloalkyl is a 3- to 6-membered heterocycloalkyl. In some embodiments, the heterocycloalkyl is a 5- to 6-membered heterocycloalkyl. In some embodiments, the heterocycloalkyl is a 6-membered heterocycloalkyl. In some embodiments, the heterocycloalkyl is a 5-membered heterocycloalkyl. In some embodiments, the heterocycloalkyl is a ($C_2$-$C_7$)heterocycloalkyl. Examples of such heterocycloalkyl radicals include, but are not limited to, aziridinyl, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, and 2-oxo-1,3-dioxol-4-yl. The term heterocycloalkyl also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl is optionally substituted as described below, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heterocycloalkyl is optionally substituted with oxo, halogen, methyl, ethyl, —CN, —$CF_3$, —OH, -OMe, —$NH_2$, or —$NO_2$. In some embodiments, a heterocycloalkyl is optionally substituted with oxo, halogen, methyl, ethyl, —CN, —$CF_3$, —OH, or -OMe. In some embodiments, the heterocycloalkyl is optionally substituted with halogen or methyl. In some embodiments, the heterocycloalkyl is optionally substituted with halogen.

"Heteroalkyl" refers to an alkyl group in which one or more skeletal atoms of the alkyl are selected from an atom other than carbon, e.g., oxygen, nitrogen (e.g., —NH—, —N(alkyl)-), sulfur, or combinations thereof. A heteroalkyl is attached to the rest of the molecule at a carbon atom of the heteroalkyl. In one aspect, a heteroalkyl is a $C_1$-$C_6$ heteroalkyl with one, two, or three heteroatoms selected from oxygen, nitrogen (e.g., —NH—, —N(alkyl)-), or sulfur. In one aspect, a heteroalkyl is a $C_1$-$C_6$ heteroalkyl with one or two heteroatoms selected from oxygen, nitrogen (e.g., —NH—, —N(alkyl)-), or sulfur. Unless stated otherwise specifically in the specification, a Heteroalkyl is optionally substituted as described below, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroalkyl is optionally substituted with oxo, halogen, methyl, ethyl, —CN, —$CF_3$, —OH, -OMe, —$NH_2$, or —$NO_2$. In some embodiments, a heteroalkyl is optionally substituted with oxo, halogen, methyl, ethyl, —CN, —$CF_3$, —OH, or -OMe. In some embodiments, the heteroalkyl is optionally substituted with halogen.

"Heteroaryl" refers to a 5- to 14-membered ring system radical comprising hydrogen atoms, one to thirteen carbon atoms, one to six heteroatoms selected from the group consisting of nitrogen, oxygen, phosphorous and sulfur, and at least one aromatic ring. The heteroaryl radical may be a monocyclic, bicyclic, tricyclic or tetracyclic ring system, which may include fused (when fused with a cycloalkyl or heterocycloalkyl ring, the heteroaryl is bonded through an aromatic ring atom) or bridged ring systems; and the nitrogen, carbon or sulfur atoms in the heteroaryl radical may be optionally oxidized; the nitrogen atom may be optionally quaternized. In some embodiments, the heteroaryl is a 5- to 10-membered heteroaryl. In some embodiments, the heteroaryl is a 5- to 6-membered heteroaryl. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl(benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl is optionally substituted as described below, for example, with halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroaryl is optionally substituted with halogen, methyl, ethyl, —CN, —$CF_3$, —OH, -OMe, —$NH_2$, or —$NO_2$. In some embodiments, a heteroaryl is optionally substituted with halogen, methyl, ethyl, —CN, —$CF_3$, —OH, or -OMe. In some embodiments, the heteroaryl is optionally substituted with halogen or methyl. In some embodiments, the heteroaryl is optionally substituted with halogen.

The term "oxo" means =O.

The terms "treat," "prevent," "ameliorate," and "inhibit," as well as words stemming therefrom, as used herein, do not necessarily imply 100% or complete treatment, prevention, amelioration, or inhibition. Rather, there are varying degrees of treatment, prevention, amelioration, and inhibition of which one of ordinary skill in the art recognizes as having a potential benefit or therapeutic effect. In this respect, the disclosed methods can provide any amount of any level of treatment, prevention, amelioration, or inhibition of the disorder in a mammal. For example, a disorder, including symptoms or conditions thereof, may be reduced by, for example, about 100%, about 90%, about 80%, about 70%, about 60%, about 50%, about 40%, about 30%, about 20%, or about 10%. Furthermore, the treatment, prevention, amelioration, or inhibition provided by the methods disclosed herein can include treatment, prevention, amelioration, or inhibition of one or more conditions or symptoms of the disorder, e.g., cancer or an inflammatory disease. Also, for purposes herein, "treatment," "prevention," "amelioration," or "inhibition" encompass delaying the onset of the disorder, or a symptom or condition thereof.

The terms "effective amount" or "therapeutically effective amount," as used herein, refer to a sufficient amount of a compound disclosed herein being administered which will relieve to some extent one or more of the symptoms of the disease or condition being treated, e.g., cancer or an inflammatory disease. In some embodiments, the result is a reduction and/or alleviation of the signs, symptoms, or causes of a disease, or any other desired alteration of a biological system. For example, an "effective amount" for therapeutic uses is the amount of the composition comprising a compound disclosed herein required to provide a clinically significant decrease in disease symptoms. In some embodiments, an appropriate "effective" amount in any individual case is determined using techniques, such as a dose escalation study.

As used herein, "individual" (as in the subject of the treatment) means both mammals and non-mammals. Mammals include, for example, humans; non-human primates, e.g. apes and monkeys; and non-primates, e.g. dogs, cats, cattle, horses, sheep, and goats. Non-mammals include, for example, fish and birds.

The term "disease" or "disorder" or "malcondition" are used interchangeably, and are used to refer to diseases or conditions wherein a bacterial SPase plays a role in the biochemical mechanisms involved in the disease or malcondition such that a therapeutically beneficial effect can be achieved by acting on the enzyme. "Acting on" SPase can include binding to SPase and/or inhibiting the bioactivity of an SPase.

"Prodrug" as the term is used herein means a compounds with one or more moieties that can be metabolized in vivo. For example, prodrugs are metabolized in vivo by esterases or by other mechanisms to active drugs. Examples of prodrugs and their uses are well known in the art (See, e.g., Berge et al. (1977) "Pharmaceutical Salts", J. Pharm. Sci. 66:1-19). Prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides.

"Substantially" as the term is used herein means completely or almost completely; for example, a composition that is "substantially free" of a component either has none of the component or contains such a trace amount that any relevant functional property of the composition is unaffected by the presence of the trace amount, or a compound is "substantially pure" is there are only negligible traces of impurities present.

Compounds

In one aspect described herein are compounds of Formula (I), or a pharmaceutically acceptable salt, solvate, or stereoisomer thereof:

Formula (I)

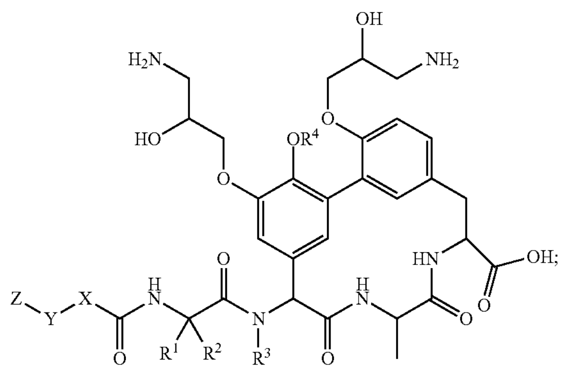

wherein:

- $R^1$ is H or —$(C_1$-$C_6)$alkyl optionally substituted with one, two, or three $R^{1a}$;
- each $R^{1a}$ is independently halogen, —CN, —$OR^a$, —$SR^a$, —$NR^cR^d$, —$NO_2$, —C(=O)$R^b$, —$NR^a$C(=O)$R^b$, —C(=O)$OR^a$, —C(=O)$NR^cR^d$, —$NR^a$C(=O)$NR^cR^d$, —S(=O)$_2R^b$, —S(=O)$R^b$, —S(=O)$_2NR^cR^d$, —S(=O)$NR^cR^d$, —$NR^a$S(=O)$_2R^b$, —$NR^a$S(=O)$_2NR^cR^d$, —$NR^aOR^a$, —$NR^a$C(=O)$NR^aOR^a$, —O($C_1$-$C_6$)alkylene-$NR^cR^d$, —$NR^a$C(=$NR^c$)$R^a$, —C(=$NR^a$)$NR^cR^d$, —$NR^a$C(=$NR^a$)$NR^cR^d$, cycloalkyl, heterocycloalkyl, aryl, or heteroaryl; or two $R^{1a}$ on the same carbon are taken together to form an oxo;
- $R^2$ is H, —$NR^cR^d$, or —$(C_1$-$C_6)$alkyl optionally substituted with one, two, or three $R^{2a}$;
- each $R^{2a}$ is independently halogen, —CN, —$OR^a$, —$SR^a$, —$NR^cR^d$, —$NO_2$, —C(=O)$R^b$, —$NR^a$C(=O)$R^b$, —C(=O)$OR^a$, —C(=O)$NR^cR^d$, —$NR^a$C(=O)$NR^cR^d$, —S(=O)$_2R^b$, —S(=O)$R^b$, —S(=O)$_2NR^cR^d$, —S(=O)$NR^cR^d$, —$NR^a$S(=O)$_2R^b$, —$NR^a$S(=O)$_2NR^cR^d$, —$NR^aOR^a$, —$NR^a$C(=O)$NR^aOR^a$, —O($C_1$-$C_6$)alkylene-$NR^cR^d$, —$NR^a$C(=$NR^c$)$R^a$, —C(=$NR^a$)$NR^cR^d$, —$NR^a$C(=$NR^a$)$NR^cR^d$, cycloalkyl, heterocycloalkyl, aryl, or heteroaryl; or two $R^{2a}$ on the same carbon are taken together to form an oxo;
- $R^3$ is H, —$(C_3$-$C_6)$cycloalkyl, or —$(C_1$-$C_6)$alkyl optionally substituted with one, two, or three $R^{3a}$;
- each $R^{3a}$ is independently halogen, —CN, —$OR^a$, —$SR^a$, —$NR^cR^d$, —$NO_2$, —C(=O)$R^b$, —$NR^a$C(=O)$R^b$, —C(=O)$OR^a$, —C(=O)$NR^cR^d$, —$NR^a$C(=O)$NR^cR^d$, —S(=O)$_2R^b$, —S(=O)$R^b$, —S(=O)$_2NR^cR^d$, —S(=O)$NR^cR^d$, —$NR^a$S(=O)$_2R^b$, —$NR^a$S(=O)$_2NR^cR^d$, —$NR^aOR^a$, —$NR^a$C(=O)$NR^aOR^a$, —O($C_1$-$C_6$)alkylene-$NR^cR^d$, —$NR^a$C(=$NR^c$)$R^a$, —C(=$NR^a$)$NR^cR^d$, —$NR^a$C(=$NR^a$)$NR^cR^d$, cycloalkyl, heterocycloalkyl, aryl, or heteroaryl; or two $R^{3a}$ on the same carbon are taken together to form an oxo;
- $R^4$ is H or —$(C_1$-$C_6)$alkyl;
- X is $(C_1$-$C_6)$alkylene, $(C_2$-$C_6)$alkenylene, $(C_2$-$C_6)$alkynylene, $(C_3$-$C_7)$cycloalkylene, $(C_2$-$C_7)$heterocycloalkylene, arylene, or heteroarylene; wherein the alkylene, alkenylene, alkynylene, cycloalkylene, heteroacycloalkylene, arylene, and heteroarylene is optionally substituted with one, two, or three $R^X$;
- each $R^X$ is independently halogen, —CN, —$OR^a$, —$NR^cR^d$, —$NO_2$, —C(=O)$R^b$, —C(=O)$OR^a$, —C(=O)$NR^cR^d$, —$(C_1$-$C_6)$alkyl, —$(C_1$-$C_6)$haloalkyl, —$(C_1$-$C_6)$heteroalkyl, —$(C_1$-$C_6)$hydroxyalkyl, —$(C_1$-$C_6)$aminoalkyl, —$(C_3$-$C_7)$cycloalkyl, or —$(C_2$-$C_7)$heterocycloalkyl; or two $R^X$ on the same carbon are taken together to form an oxo;
- Y is bond, —O—, —S—, $(C_1$-$C_6)$alkylene, $(C_2$-$C_6)$alkenylene, $(C_2$-$C_6)$alkynylene, $(C_3$-$C_7)$cycloalkylene, $(C_2$-$C_7)$heterocycloalkylene, arylene, or heteroarylene; wherein the alkylene, alkenylene, alkynylene, cycloalkylene, heteroacycloalkylene, arylene, and heteroarylene is optionally substituted with one, two, or three $R^Y$;
- each $R^Y$ is independently halogen, —CN, —$OR^a$, —$NR^cR^d$, —$NO_2$, —C(=O)$R^b$, —C(=O)$OR^a$, —C(=O)$NR^cR^d$, —$(C_1$-$C_6)$alkyl, —$(C_1$-$C_6)$haloalkyl, —$(C_1$-$C_6)$heteroalkyl, —$(C_1$-$C_6)$hydroxyalkyl, —$(C_1$-$C_6)$aminoalkyl, —$(C_3$-$C_7)$cycloalkyl, or —$(C_2$-$C_7)$heterocycloalkyl; or two $R^Y$ on the same carbon are taken together to form an oxo;
- Z is H, halogen, —CN, —$OR^{10}$, —$SR^{10}$, —$NR^{12}R^{13}$, —C(=O)$R^a$, —C(=O)$OR^2$, —C(=O)$NR^{12}R^{13}$, —$(C_1$-$C_{12})$alkyl, —$(C_1$-$C_{12})$heteroalkyl, —$(C_1$-$C_{12})$haloalkyl, —$(C_1$-$C_{12})$hydroxyalkyl, —$(C_1$-$C_{12})$aminoalkyl, —$(C_2$-$C_{12})$alkenyl, —$(C_2$-$C_{12})$alkynyl, —$(C_3$-$C_9)$cycloalkyl, —$(C_2$-$C_7)$heterocycloalkyl, aryl, or heteroaryl; wherein the alkyl, alkenyl, alkynyl, cycloalkyl, heteroacycloalkyl, aryl, and heteroaryl are optionally substituted with one, two, or three $R^Z$;
- each $R^Z$ is independently halogen, —CN, —$OR^{10}$, —$NR^{12}R^{13}$, —$NO_2$, —C(=O)$R^a$, —C(=O)$OR^{10}$, —C(=O)$NR^{12}R^{13}$, —$(C_1$-$C_6)$alkyl, —$(C_1$-$C_6)$haloalkyl, —$(C_1$-$C_6)$heteroalkyl, —$(C_1$-$C_6)$hydroxyalkyl, —$(C_1$-$C_6)$aminoalkyl, —$(C_2$-$C_6)$alkenyl, —$(C_2$-$C_6)$ alkynyl, —$(C_3$-$C_7)$cycloalkyl, or —$(C_2$-$C_7)$heterocycloalkyl; or two $R^Z$ on the same carbon are taken together to form an oxo;

each $R^{10}$ is independently H, —$(C_1$-$C_6)$alkyl, —$(C_1$-$C_6)$haloalkyl, —$(C_1$-$C_6)$heteroalkyl, —$(C_1$-$C_6)$hydroxyalkyl, —$(C_1$-$C_6)$aminoalkyl, —$(C_2$-$C_6)$alkenyl, —$(C_2$-$C_6)$alkynyl, —$(C_3$-$C_7)$cycloalkyl, $(C_2$-$C_7)$heterocycloalkyl, aryl, or heteroaryl; wherein the alkyl, alkenyl, alkynyl, cycloalkyl, heterocycloalkyl, aryl, and heteroaryl are optionally independently substituted with one, two, or three $R^{10a}$;

each $R^{10a}$ is independently halogen, —CN, —$OR^a$, —$NR^cR^d$, —C(═O)$R^b$, —C(═O)$OR^a$, —C(═O)$NR^cR^d$, —$(C_1$-$C_6)$alkyl, or —$(C_1$-$C_6)$haloalkyl; or two $R^{10a}$ on the same carbon are taken together to form an oxo;

each $R^{11}$ is independently —$(C_1$-$C_6)$alkyl, —$(C_1$-$C_6)$haloalkyl, —$(C_1$-$C_6)$heteroalkyl, —$(C_1$-$C_6)$hydroxyalkyl, —$(C_1$-$C_6)$aminoalkyl, —$(C_2$-$C_6)$alkenyl, —$(C_2$-$C_6)$alkynyl, —$(C_3$-$C_7)$cycloalkyl, $(C_2$-$C_7)$heterocycloalkyl, aryl, or heteroaryl; wherein the alkyl, alkenyl, alkynyl, cycloalkyl, heterocycloalkyl, aryl, and heteroaryl are optionally independently substituted with one, two, or three $R^{11a}$;

each $R^{11a}$ is independently halogen, —CN, —$OR^a$, —$NR^cR^d$, —C(═O)$R^b$, —C(═O)$OR^a$, —C(═O)$NR^cR^d$, —$(C_1$-$C_6)$alkyl, or —$(C_1$-$C_6)$haloalkyl; or two $R^{11a}$ on the same carbon are taken together to form an oxo;

each $R^{12}$ and $R^{13}$ is independently H, —$(C_1$-$C_6)$alkyl, —$(C_1$-$C_6)$haloalkyl, —$(C_1$-$C_6)$heteroalkyl, —$(C_1$-$C_6)$hydroxyalkyl, —$(C_1$-$C_6)$aminoalkyl, —$(C_2$-$C_6)$alkenyl, —$(C_2$-$C_6)$alkynyl, —$(C_3$-$C_7)$cycloalkyl, $(C_2$-$C_7)$heterocycloalkyl, aryl, or heteroaryl; wherein the alkyl, alkenyl, alkynyl, cycloalkyl, heterocycloalkyl, aryl, and heteroaryl are optionally independently substituted with one, two, or three $R^{12a}$;

or $R^{12}$ and $R^{13}$ are taken together with the nitrogen atom to which they are attached to form a heterocycloalkyl optionally substituted with one, two, or three $R^{12b}$;

each $R^{12a}$ is independently halogen, —CN, —$OR^a$, —$NR^cR^d$, —C(═O)$R^b$, —C(═O)$OR^a$, —C(═O)$NR^cR^d$, —$(C_1$-$C_6)$alkyl, or —$(C_1$-$C_6)$haloalkyl; or two $R^{12a}$ on the same carbon are taken together to form an oxo;

each $R^{12b}$ is independently halogen, —CN, —$OR^a$, —$NR^cR^d$, —C(═O)$R^b$, —C(═O)$OR^a$, —C(═O)$NR^cR^d$, —$(C_1$-$C_6)$alkyl, or —$(C_1$-$C_6)$haloalkyl; or two $R^{12b}$ on the same carbon are taken together to form an oxo;

each $R^a$ is independently H, —$(C_1$-$C_6)$alkyl, —$(C_1$-$C_6)$haloalkyl, —$(C_1$-$C_6)$heteroalkyl, —$(C_1$-$C_6)$hydroxyalkyl, —$(C_1$-$C_6)$aminoalkyl, —$(C_2$-$C_6)$alkenyl, —$(C_2$-$C_6)$alkynyl, —$(C_3$-$C_7)$cycloalkyl, $(C_2$-$C_7)$heterocycloalkyl, aryl, or heteroaryl; wherein the alkyl, alkenyl, alkynyl, cycloalkyl, heterocycloalkyl, aryl, and heteroaryl are optionally independently substituted with one, two, or three halogen, —CN, —OH, -OMe, —$NH_2$, —C(═O)Me, —C(═O)OH, —C(═O)OMe, —C(═O)$NH_2$, or —$(C_1$-$C_6)$alkyl;

each $R^b$ is independently —$(C_1$-$C_6)$alkyl, —$(C_1$-$C_6)$haloalkyl, —$(C_1$-$C_6)$heteroalkyl, —$(C_1$-$C_6)$hydroxyalkyl, —$(C_1$-$C_6)$aminoalkyl, —$(C_2$-$C_6)$alkenyl, —$(C_2$-$C_6)$alkynyl, —$(C_3$-$C_7)$cycloalkyl, $(C_2$-$C_7)$heterocycloalkyl, aryl, or heteroaryl; wherein the alkyl, alkenyl, alkynyl, cycloalkyl, heterocycloalkyl, aryl, and heteroaryl are optionally independently substituted with one, two, or three halogen, —CN, —OH, -OMe, —$NH_2$, —C(═O)Me, —C(═O)OH, —C(═O)OMe, —C(═O)$NH_2$, or —$(C_1$-$C_6)$alkyl; and each $R^c$ and $R^d$ is independently H, —$(C_1$-$C_6)$alkyl, —$(C_1$-$C_6)$haloalkyl, —$(C_1$-$C_6)$heteroalkyl, —$(C_1$-$C_6)$hydroxyalkyl, —$(C_1$-$C_6)$aminoalkyl, —$(C_2$-$C_6)$alkenyl, —$(C_2$-$C_6)$alkynyl, —$(C_3$-$C_7)$cycloalkyl, $(C_2$-$C_7)$heterocycloalkyl, aryl, or heteroaryl; wherein the alkyl, alkenyl, alkynyl, cycloalkyl, heterocycloalkyl, aryl, and heteroaryl are optionally independently substituted with one, two, or three halogen, —CN, —OH, -OMe, —$NH_2$, —C(═O)Me, —C(═O)OH, —C(═O)OMe, —C(═O)$NH_2$, or —$(C_1$-$C_6)$alkyl;

or $R^c$ and $R^d$ are taken together with the nitrogen atom to which they are attached to form a heterocycloalkyl optionally substituted with one, two, or three oxo, halogen, —CN, —OH, -OMe, —$NH_2$, —C(═O)Me, —C(═O)OH, —C(═O)OMe, —C(═O)$NH_2$, or —$(C_1$-$C_6)$alkyl.

In some embodiments of a compound of Formula (I), $R^2$ is H or —$(C_1$-$C_6)$alkyl optionally substituted with one, two, or three $R^{2a}$. In some embodiments of a compound of Formula (I), $R^2$ is H or —$(C_1$-$C_6)$alkyl optionally substituted with one $R^{2a}$. In some embodiments of a compound of Formula (I), $R^2$ is H or —$(C_1$-$C_6)$alkyl. In some embodiments of a compound of Formula (I), $R^2$ is H.

In some embodiments of a compound of Formula (I), each $R^{2a}$ is independently halogen, —CN, —$OR^a$, —$NR^cR^d$, —$NR^c$C(═O)$R^b$, —$NR^c$C(═O)$NR^cR^d$, —$NR^c$S(═O)$_2R^b$, or —$NR^c$S(═O)$_2NR^cR^d$. In some embodiments of a compound of Formula (I), each $R^{2a}$ is independently —$NR^cR^d$ or —$NR^c$S(═O)$_2NR^cR^d$.

In some embodiments of a compound of Formula (I), $R^3$ is H or —$(C_1$-$C_6)$alkyl optionally substituted with one, two, or three $R^{3a}$. In some embodiments of a compound of Formula (I), $R^3$ is H or —$(C_1$-$C_6)$alkyl optionally substituted with one $R^{3a}$. In some embodiments of a compound of Formula (I), $R^3$ is H or —$(C_1$-$C_6)$alkyl. In some embodiments of a compound of Formula (I), $R^3$ is H. In some embodiments of a compound of Formula (I), $R^3$ is —$(C_1$-$C_6)$alkyl. In some embodiments of a compound of Formula (I), $R^3$ is methyl.

In some embodiments of a compound of Formula (I), each $R^{3a}$ is independently halogen, —CN, —$OR^a$, —$NR^cR^d$, —$NR^c$C(═O)$R^b$, —$NR^c$C(═O)$NR^cR^d$, —$NR^c$S(═O)$_2$R, or —$NR^c$S(═O)$_2NR^cR^d$. In some embodiments of a compound of Formula (I), each $R^{3a}$ is independently —$NR^cR^d$ or —$NR^c$S(═O)$_2NR^cR^d$.

In some embodiments of a compound of Formula (I), $R^4$ is H. In some embodiments of a compound of Formula (I), $R^4$ is —$(C_1$-$C_6)$alkyl. In some embodiments of a compound of Formula (I), $R^4$ is methyl.

In some embodiments of a compound of Formula (I), or a pharmaceutically acceptable salt, solvate, or stereoisomer thereof; the compound has the structure of Formula (Ia):

Formula (Ia)

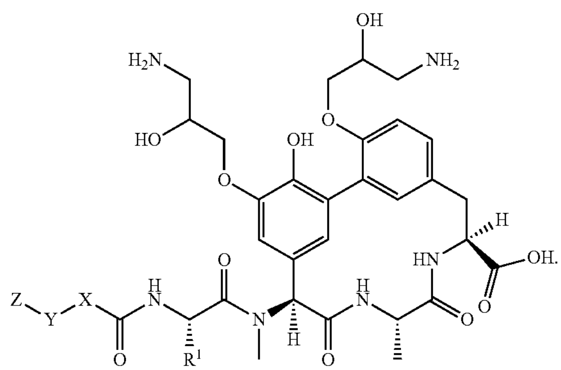

In some embodiments of a compound of Formula (I), or a pharmaceutically acceptable salt, solvate, or stereoisomer thereof; the compound has the structure of Formula (Ib):

Formula (Ib)

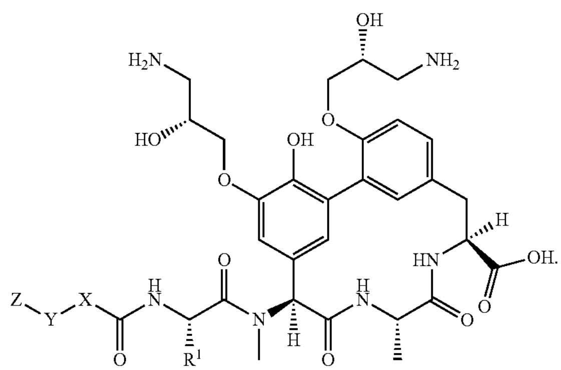

In some embodiments of a compound of Formula (I), (Ia), or (Ib), $R^1$ is —$(C_1$-$C_6)$alkyl optionally substituted with one, two, or three $R^{1a}$. In some embodiments of a compound of Formula (I), (Ia), or (Ib), $R^1$ is —$(C_1$-$C_6)$alkyl optionally substituted with one or two $R^{1a}$. In some embodiments of a compound of Formula (I), (Ia), or (Ib), $R^1$ is —$(C_1$-$C_6)$alkyl substituted with one $R^{1a}$. In some embodiments of a compound of Formula (I), (Ia), or (Ib), $R^1$ is —$CH_2CH_2NH_2$, —$CH_2CH_2NHSO_2NH_2$ or —$CH_2NHSO_2NH_2$. In some embodiments of a compound of Formula (I), (Ia), or (Ib), $R^1$ is —$CH_2CH_2NH_2$. In some embodiments of a compound of Formula (I), (Ia), or (Ib), $R^1$ is —$CH_2CH_2NHSO_2NH_2$. In some embodiments of a compound of Formula (I), (Ia), or (Ib), $R^1$ is —$CH_2NHSO_2NH_2$.

In some embodiments of a compound of Formula (I), (Ia), or (Ib), each $R^{1a}$ is independently halogen, —CN, —$OR^a$, —$NR^cR^d$, —$NR^cC(=O)R^b$, —$NR^cC(=O)NR^cR^d$, —$NRS(=O)_2R^b$, or —$NR^cS(=O)_2NR^cR^d$. In some embodiments of a compound of Formula (I), (Ia), or (Ib), each $R^{1a}$ is independently —$NR^cR^d$ or —$NR^cS(=O)_2NR^cR^d$. In some embodiments of a compound of Formula (I), (Ia), or (Ib), each $R^{1a}$ is independently —$NR^cR^d$. In some embodiments of a compound of Formula (I), (Ia), or (Ib), each $R^{1a}$ is independently —$NR^cS(=O)_2NR^cR^d$.

In some embodiments of a compound of Formula (I), (Ia), or (Ib), X is $(C_2$-$C_7)$heterocycloalkylene or heteroarylene; each optionally substituted with one, two, or three $R^X$. In some embodiments of a compound of Formula (I), (Ia), or (Ib), X is $(C_2$-$C_7)$heterocycloalkylene or heteroarylene; each optionally substituted with one or two $R^X$. In some embodiments of a compound of Formula (I), (Ia), or (Ib), X is $(C_2$-$C_7)$heterocycloalkylene or heteroarylene; each optionally substituted with one $R^X$. In some embodiments of a compound of Formula (I), (Ia), or (Ib), X is $(C_2$-$C_7)$heterocycloalkylene optionally substituted with one, two, or three $R^X$. In some embodiments of a compound of Formula (I), (Ia), or (Ib), X is $(C_2$-$C_7)$heterocycloalkylene optionally substituted with one or two $R^X$. In some embodiments of a compound of Formula (I), (Ia), or (Ib), X is $(C_2$-$C_7)$heterocycloalkylene optionally substituted with one $R^X$. In some embodiments of a compound of Formula (I), (Ia), or (Ib), X is heteroarylene optionally substituted with one, two, or three $R^X$. In some embodiments of a compound of Formula (I), (Ia), or (Ib), X is heteroarylene optionally substituted with one or two $R^X$. In some embodiments of a compound of Formula (I), (Ia), or (Ib), X is heteroarylene optionally substituted with one $R^X$. In some embodiments of a compound of Formula (I), (Ia), or (Ib), X is pyrimidinylene optionally substituted with one, or two $R^X$. In some embodiments of a compound of Formula (I), (Ia), or (Ib), X is pyridinylene optionally substituted with one, two, or three $R^X$.

In some embodiments of a compound of Formula (I), (Ia), or (Ib), each $R^X$ is independently halogen, —$OR^a$, —$NR^cR^d$, —$(C_1$-$C_6)$alkyl, or —$(C_1$-$C_6)$haloalkyl; or two $R^X$ on the same carbon are taken together to form an oxo. In some embodiments of a compound of Formula (I), (Ia), or (Ib), each $R^X$ is independently —$NR^cR^d$ or —$(C_1$-$C_6)$alkyl; or two $R^X$ on the same carbon are taken together to form an oxo. In some embodiments of a compound of Formula (I), (Ia), or (Ib), each $R^X$ is independently —$NR^cR^d$ or —$(C_1$-$C_6)$alkyl. In some embodiments of a compound of Formula (I), (Ia), or (Ib), each $R^X$ is independently Cl, —CN, methyl, ethyl, —$CF_2H$, —$CF_3$, —$CH_2NH_2$, cyclopropyl, or 3-aminoazetidin-1-yl. In some embodiments of a compound of Formula (I), (Ia), or (Ib), each $R^X$ is independently Cl, —CN, methyl, or —$CH_2NH_2$. In some embodiments of a compound of Formula (I), (Ia), or (Ib), each $R^X$ is independently Cl, methyl, or —$CH_2NH_2$. In some embodiments of a compound of Formula (I), (Ia), or (Ib), each $R^X$ is independently methyl, or —$CH_2NH_2$. In some embodiments of a compound of Formula (I), (Ia), or (Ib), one $R^X$ is 3-amino-azetidin-1-yl. In some embodiments of a compound of Formula (I), (Ia), or (Ib), each $R^X$ is independently methyl.

In some embodiments of a compound of Formula (I), (Ia), or (Ib), Y is —$(C_2$-$C_7)$heterocycloalkylene or arylene; each optionally substituted with one, two, or three $R^Y$. In some embodiments of a compound of Formula (I), (Ia), or (Ib), Y is —$(C_2$-$C_7)$heterocycloalkylene or arylene. In some embodiments of a compound of Formula (I), (Ia), or (Ib), Y is —$(C_2$-$C_7)$heterocycloalkylene or arylene; each optionally substituted with one or two $R^Y$. In some embodiments of a compound of Formula (I), (Ia), or (Ib), Y is —$(C_2$-$C_7)$ heterocycloalkylene or arylene; each optionally substituted with one $R^Y$. In some embodiments of a compound of Formula (I), (Ia), or (Ib), Y is arylene optionally substituted with one, two, or three $R^Y$. In some embodiments of a compound of Formula (I), (Ia), or (Ib), Y is arylene optionally substituted with one or two $R^Y$. In some embodiments of a compound of Formula (I), (Ia), or (Ib), Y is arylene optionally substituted with one $R^Y$. In some embodiments of a compound of Formula (I), (Ia), or (Ib), Y is arylene. In some embodiments of a compound of Formula (I), (Ia), or (Ib), Y is phenylene optionally substituted with one, two, or three $R^Y$. In some embodiments of a compound of Formula (I), (Ia), or (Ib), Y is a bond.

In some embodiments of a compound of Formula (I), (Ia), or (Ib), each $R^Y$ is independently halogen, —$OR^a$, —$NR^cR^d$, —($C_1$-$C_6$)alkyl, or —($C_1$-$C_6$)haloalkyl; or two $R^Y$ on the same carbon are taken together to form an oxo. In some embodiments of a compound of Formula (I), (Ia), or (Ib), each $R^Y$ is independently halogen, —$OR^a$, —$NR^cR^d$, —($C_1$-$C_6$)alkyl, or —($C_1$-$C_6$)haloalkyl. In some embodiments of a compound of Formula (I), (Ia), or (Ib), each $R^Y$ is independently halogen, —($C_1$-$C_6$)alkyl, or —($C_1$-$C_6$)haloalkyl. In some embodiments of a compound of Formula (I), (Ia), or (Ib), each $R^Y$ is independently F or —OH. In some embodiments of a compound of Formula (I), (Ia), or (Ib), each $R^Y$ is F.

In some embodiments of a compound of Formula (I), (Ia), or (Ib), Z is H, halogen, —CN, —$OR^{14}$, —$SR^{10}$, —$NR^{12}R^{13}$, —C(═O)$R^a$, —C(═O)$OR^2$, —C(═O)$NR^{12}R^{13}$, —($C_1$-$C_{12}$)alkyl, —($C_1$-$C_{12}$)heteroalkyl, —($C_1$-$C_{12}$)haloalkyl, —($C_1$-$C_{12}$)hydroxyalkyl, —($C_1$-$C_{12}$)aminoalkyl, —($C_2$-$C_{12}$)alkenyl, —($C_2$-$C_{12}$)alkynyl, —($C_3$-$C_7$)cycloalkyl, —($C_2$-$C_7$)heterocycloalkyl, aryl, or heteroaryl; wherein the alkyl, alkenyl, alkynyl, cycloalkyl, heteroacycloalkyl, aryl, and heteroaryl are optionally substituted with one, two, or three $R^Z$.

In some embodiments of a compound of Formula (I), (Ia), or (Ib), Z is halogen, —$OR^{10}$, —$NR^{12}R^{13}$, —($C_1$-$C_{12}$)alkyl, —($C_1$-$C_{12}$)heteroalkyl, —($C_1$-$C_{12}$)haloalkyl, —($C_1$-$C_{12}$)hydroxyalkyl, —($C_1$-$C_{12}$)aminoalkyl, —($C_3$-$C_9$)cycloalkyl, or —($C_2$-$C_7$)heterocycloalkyl; wherein the alkyl, cycloalkyl, and heteroacycloalkyl are optionally substituted with one, two, or three $R^Z$. In some embodiments of a compound of Formula (I), (Ia), or (Ib), Z is halogen, —$OR^{10}$, —$NR^{12}R^{13}$, —($C_1$-$C_{12}$)alkyl, —($C_1$-$C_{12}$)heteroalkyl, —($C_1$-$C_{12}$)haloalkyl, —($C_1$-$C_{12}$)hydroxyalkyl, —($C_1$-$C_{12}$)aminoalkyl, —($C_3$-$C_9$)cycloalkyl, or —($C_2$-$C_7$)heterocycloalkyl; wherein the alkyl, cycloalkyl, and heteroacycloalkyl are optionally substituted with one or two $R^Z$. In some embodiments of a compound of Formula (I), (Ia), or (Ib), Z is halogen, —$OR^{10}$, —$NR^{12}R^{13}$, —($C_1$-$C_{12}$)alkyl, —($C_1$-$C_{12}$)heteroalkyl, —($C_1$-$C_{12}$)haloalkyl, —($C_1$-$C_{12}$)hydroxyalkyl, —($C_1$-$C_{12}$)aminoalkyl, —($C_3$-$C_9$)cycloalkyl, or —($C_2$-$C_7$)heterocycloalkyl; wherein the alkyl, cycloalkyl, and heteroacycloalkyl are optionally substituted with one $R^Z$. In some embodiments of a compound of Formula (I), (Ia), or (Ib), Z is halogen, —$OR^{10}$, —$NR^{12}R^{13}$, —($C_1$-$C_{12}$)alkyl, —($C_1$-$C_{12}$)heteroalkyl, —($C_1$-$C_{12}$)haloalkyl, —($C_1$-$C_{12}$)hydroxyalkyl, —($C_1$-$C_{12}$)aminoalkyl, —($C_3$-$C_9$)cycloalkyl, or —($C_2$-$C_7$)heterocycloalkyl.

In some embodiments of a compound of Formula (I), (Ia), or (Ib), Z is halogen, —$OR^{10}$, —$NR^{12}R^{13}$, —($C_1$-$C_{12}$)alkyl, —($C_1$-$C_{12}$)heteroalkyl, —($C_1$-$C_{12}$)haloalkyl, —($C_1$-$C_{12}$)hydroxyalkyl, —($C_1$-$C_{12}$)aminoalkyl, —($C_3$-$C_7$)cycloalkyl, or —($C_2$-$C_7$)heterocycloalkyl; wherein the alkyl, cycloalkyl, and heteroacycloalkyl are optionally substituted with one, two, or three $R^Z$. In some embodiments of a compound of Formula (I), (Ia), or (Ib), Z is halogen, —$OR^{10}$, —$NR^{12}R^{13}$, —($C_1$-$C_{12}$)alkyl, —($C_1$-$C_{12}$)heteroalkyl, —($C_1$-$C_{12}$)haloalkyl, —($C_1$—$C_{12}$)hydroxyalkyl, —($C_1$-$C_{12}$)aminoalkyl, —($C_3$-$C_7$)cycloalkyl, or —($C_2$-$C_7$)heterocycloalkyl; wherein the alkyl, cycloalkyl, and heteroacycloalkyl are optionally substituted with one or two $R^Z$. In some embodiments of a compound of Formula (I), (Ia), or (Ib), Z is halogen, —$OR^{10}$, —$NR^{12}R^{13}$, —($C_1$-$C_{12}$)alkyl, —($C_1$-$C_{12}$)heteroalkyl, —($C_1$-$C_{12}$)haloalkyl, —($C_1$-$C_{12}$)hydroxyalkyl, —($C_1$-$C_{12}$)aminoalkyl, —($C_3$-$C_7$)cycloalkyl, or —($C_2$-$C_7$)heterocycloalkyl; wherein the alkyl, cycloalkyl, and heteroacycloalkyl are optionally substituted with one $R^Z$. In some embodiments of a compound of Formula (I), (Ia), or (Ib), Z is halogen, —$OR^{10}$, —$NR^{12}R^{13}$, —($C_1$-$C_{12}$)alkyl, —($C_1$-$C_{12}$)heteroalkyl, —($C_1$-$C_{12}$)haloalkyl, —($C_1$-$C_{12}$)hydroxyalkyl, —($C_1$-$C_{12}$)aminoalkyl, —($C_3$-$C_7$)cycloalkyl, or —($C_2$-$C_7$)heterocycloalkyl.

In some embodiments of a compound of Formula (I), (Ia), or (Ib), Z is —$OR^{10}$, —($C_1$-$C_{12}$)alkyl, —($C_1$-$C_{12}$)haloalkyl, or —($C_3$-$C_9$)cycloalkyl; wherein the alkyl and cycloalkyl are optionally substituted with one, two, or three $R^Z$. In some embodiments of a compound of Formula (I), (Ia), or (Ib), Z is —$OR^{10}$, —($C_1$-$C_{12}$)alkyl, —($C_1$-$C_{12}$)haloalkyl, or —($C_3$-$C_9$)cycloalkyl; wherein the alkyl and cycloalkyl are optionally substituted with one or two $R^Z$. In some embodiments of a compound of Formula (I), (Ia), or (Ib), Z is —$OR^{10}$, —($C_1$-$C_{12}$)alkyl, —($C_1$-$C_{12}$)haloalkyl, or —($C_3$-$C_9$)cycloalkyl; wherein the alkyl and cycloalkyl are optionally substituted with one $R^Z$. In some embodiments of a compound of Formula (I), (Ia), or (Ib), Z is —$OR^{10}$, —($C_1$-$C_{12}$)alkyl, —($C_1$-$C_{12}$)haloalkyl, or —($C_3$-$C_9$)cycloalkyl.

In some embodiments of a compound of Formula (I), (Ia), or (Ib), Z is —$OR^{10}$, —($C_1$-$C_{12}$)alkyl, —($C_1$-$C_{12}$)haloalkyl, or —($C_3$-$C_7$)cycloalkyl; wherein the alkyl and cycloalkyl are optionally substituted with one, two, or three $R^Z$. In some embodiments of a compound of Formula (I), (Ia), or (Ib), Z is —$OR^{10}$, —($C_1$-$C_{12}$)alkyl, —($C_1$-$C_{12}$)haloalkyl, or —($C_3$-$C_7$)cycloalkyl; wherein the alkyl and cycloalkyl are optionally substituted with one or two $R^Z$. In some embodiments of a compound of Formula (I), (Ia), or (Ib), Z is —$OR^{10}$, —($C_1$-$C_{12}$)alkyl, —($C_1$-$C_{12}$)haloalkyl, or —($C_3$-$C_7$)cycloalkyl; wherein the alkyl and cycloalkyl are optionally substituted with one $R^Z$. In some embodiments of a compound of Formula (I), (Ia), or (Ib), Z is —$OR^{10}$, —($C_1$-$C_{12}$)alkyl, —($C_1$-$C_{12}$)haloalkyl, or —($C_3$-$C_7$)cycloalkyl.

In some embodiments of a compound of Formula (I), (Ia), or (Ib), Z is —$OR^{10}$.

In some embodiments of a compound of Formula (I), (Ia), or (Ib), Z is —($C_1$-$C_{12}$)alkyl optionally substituted with one, two, or three $R^Z$. In some embodiments of a compound of Formula (I), (Ia), or (Ib), Z is —($C_1$-$C_{12}$)alkyl optionally substituted with one or two $R^Z$. In some embodiments of a compound of Formula (I), (Ia), or (Ib), Z is —($C_1$-$C_{12}$)alkyl optionally substituted with one $R^Z$. In some embodiments of a compound of Formula (I), (Ia), or (Ib), Z is —($C_1$-$C_{12}$)alkyl. In some embodiments of a compound of Formula (I), (Ia), or (Ib), Z is 2,2-dimethylpropyl. In some embodiments of a compound of Formula (I), (Ia), or (Ib), Z is tert-butyl. In some embodiments of a compound of Formula (I), (Ia), or (Ib), Z is isobutyl. In some embodiments of a compound of Formula (I), (Ia), or (Ib), Z substituted with one $R^Z$ is cyclopropylmethyl. In some embodiments of a compound of Formula (I), (Ia), or (Ib), Z substituted with one $R^Z$ is cyclobutylmethyl. In some embodiments of a compound of Formula (I), (Ia), or (Ib), Z substituted with one $R^Z$ is 1-fluoro-2-methylpropyl. In some embodiments of a compound of Formula (I), (Ia), or (Ib), Z substituted with two $R^Z$ is 1,1-difluoro-2-methylpropyl.

In some embodiments of a compound of Formula (I), (Ia), or (Ib), Z is —($C_1$-$C_{12}$)haloalkyl optionally substituted with one, two, or three $R^Z$. In some embodiments of a compound of Formula (I), (Ia), or (Ib), Z is —($C_1$-$C_{12}$)haloalkyl optionally substituted with one or two $R^Z$. In some embodiments of a compound of Formula (I), (Ia), or (Ib), Z is —($C_1$-$C_{12}$)haloalkyl optionally substituted with one $R^Z$. In some embodiments of a compound of Formula (I), (Ia), or (Ib), Z is —($C_1$-$C_{12}$)haloalkyl.

In some embodiments of a compound of Formula (I), (Ia), or (Ib), Z is —($C_3$-$C_9$)cycloalkyl optionally substituted with one, two, or three $R^Z$. In some embodiments of a compound of Formula (I), (Ia), or (Ib), Z is —($C_3$-$C_9$)cycloalkyl optionally substituted with one or two $R^Z$. In some embodiments of a compound of Formula (I), (Ia), or (Ib), Z is —($C_3$-$C_9$)cycloalkyl optionally substituted with one $R^Z$. In some embodiments of a compound of Formula (I), (Ia), or (Ib), Z is —($C_3$-$C_9$)cycloalkyl.

In some embodiments of a compound of Formula (I), (Ia), or (Ib), Z is —($C_3$-$C_7$)cycloalkyl optionally substituted with one, two, or three $R^Z$. In some embodiments of a compound of Formula (I), (Ia), or (Ib), Z is —($C_3$-$C_7$)cycloalkyl optionally substituted with one or two $R^Z$. In some embodiments of a compound of Formula (I), (Ia), or (Ib), Z is —($C_3$-$C_7$)cycloalkyl optionally substituted with one $R^Z$. In some embodiments of a compound of Formula (I), (Ia), or (Ib), Z is —($C_3$-$C_7$)cycloalkyl. In some embodiments of a compound of Formula (I), (Ia), or (Ib), Z is 2,3-dihyro-1H-indene-5-yl.

In some embodiments of a compound of Formula (I), (Ia), or (Ib), each $R^Z$ is independently halogen, —$OR^{10}$, —$NR^{12}R^{13}$, or —($C_1$-$C_6$)alkyl. In some embodiments of a compound of Formula (I), (Ia), or (Ib), each $R^Z$ is independently —($C_1$-$C_6$)alkyl. In some embodiments of a compound of Formula (I), (Ia), or (Ib), each $R^Z$ is independently methyl. In some embodiments of a compound of Formula (I), (Ia), or (Ib), each $R^Z$ is independently F.

In some embodiments of a compound of Formula (I), (Ia), or (Ib), $R^{10}$ is H, —($C_1$-$C_6$)alkyl, —($C_1$-$C_6$)haloalkyl, or —($C_3$-$C_7$)cycloalkyl. In some embodiments of a compound of Formula (I), (Ia), or (Ib), $R^{10}$ is —($C_1$-$C_6$)alkyl, —($C_1$-$C_6$)haloalkyl, or —($C_3$-$C_7$)cycloalkyl. In some embodiments of a compound of Formula (I), (Ia), or (Ib), $R^{10}$ is —($C_1$-$C_6$)alkyl or —($C_3$-$C_7$)cycloalkyl. In some embodiments of a compound of Formula (I), (Ia), or (Ib), $R^{10}$ is 2,2-dimethylbutyl. In some embodiments of a compound of Formula (I), (Ia), or (Ib), $R^{10}$ is isopropyl. In some embodiments of a compound of Formula (I), (Ia), or (Ib), $R^{10}$ is cyclohexyl.

In some embodiments of a compound of Formula (I), (Ia), or (Ib), $R^{11}$ is —($C_1$-$C_6$)alkyl, —($C_1$-$C_6$)haloalkyl, or —($C_3$-$C_7$)cycloalkyl. In some embodiments of a compound of Formula (I), (Ia), or (Ib), $R^{11}$ is —($C_1$-$C_6$)alkyl or —($C_3$-$C_7$)cycloalkyl.

In some embodiments of a compound of Formula (I), (Ia), or (Ib), $R^{12}$ and $R^{13}$ are independently H, —($C_1$-$C_6$)alkyl, —($C_1$-$C_6$)haloalkyl, or —($C_3$-$C_7$)cycloalkyl. In some embodiments of a compound of Formula (I), (Ia), or (Ib), $R^{12}$ and $R^{13}$ are independently H, —($C_1$-$C_6$)alkyl, or —($C_3$-$C_7$)cycloalkyl.

In some embodiments of a compound of Formula (I), (Ia), or (Ib), —X—Y—Z is

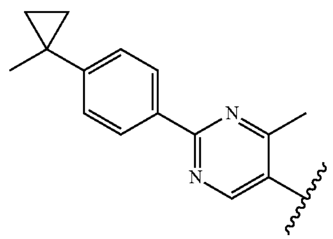

-continued

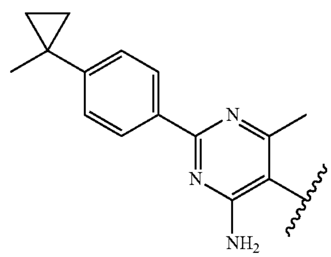

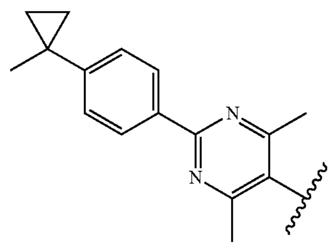

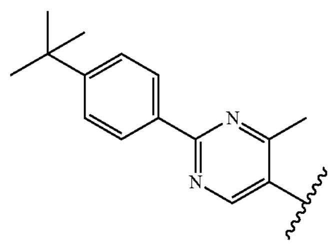

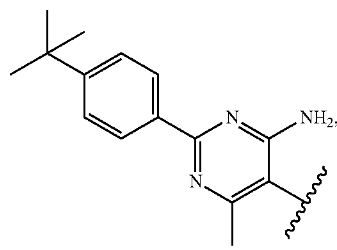

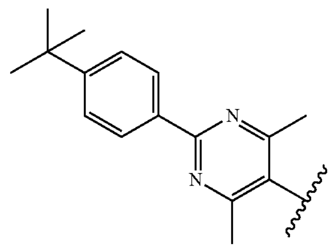

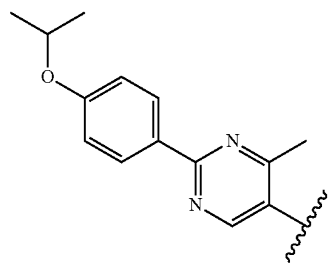

-continued
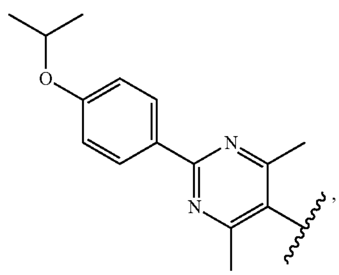
,
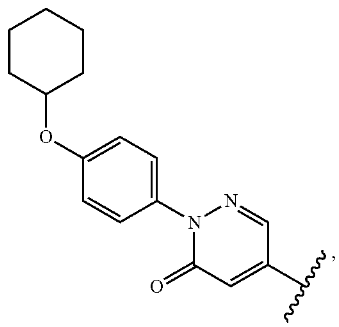
,
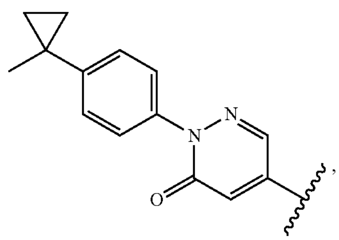
,
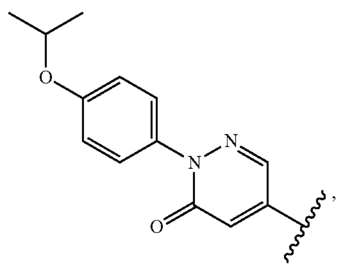
,
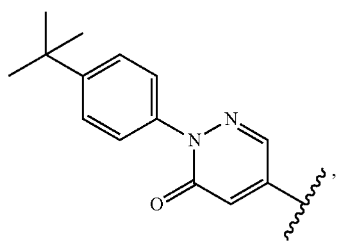
,
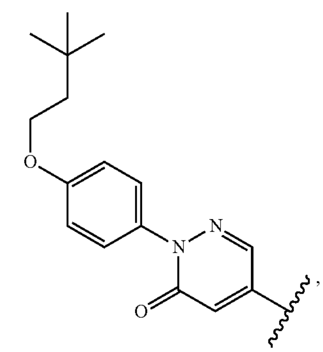
,
-continued
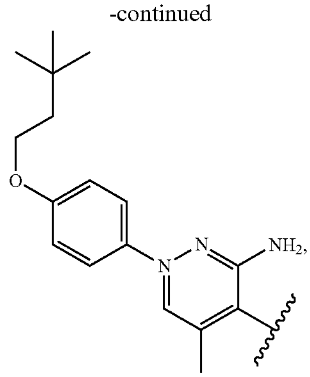
,
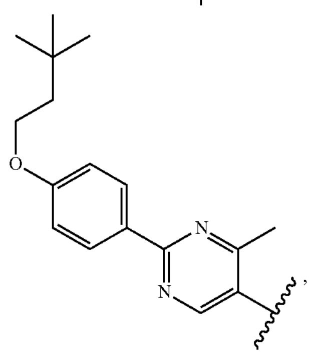
,
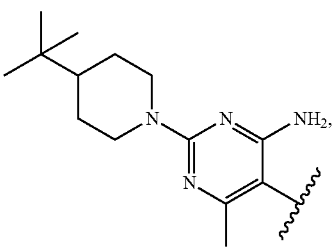
,
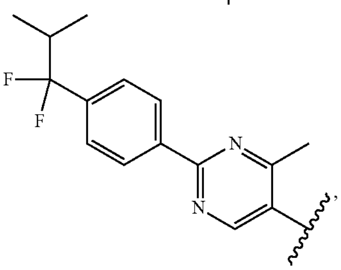
,
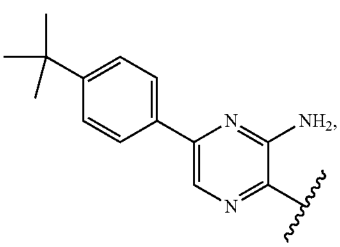
,
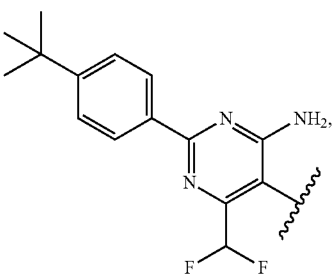
, -continued
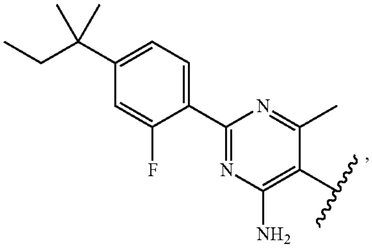
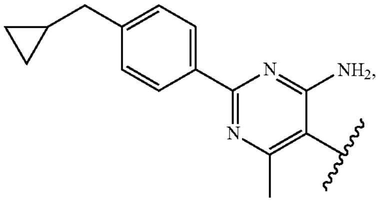
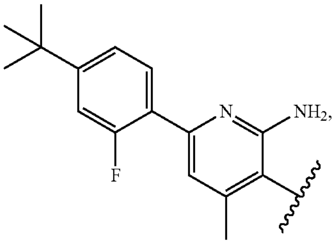
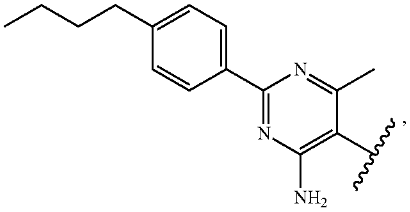
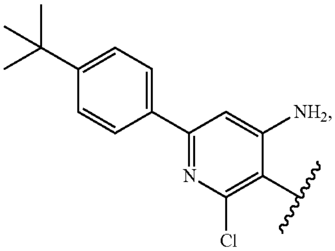
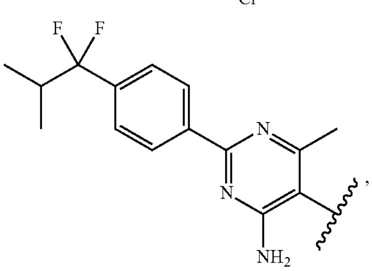
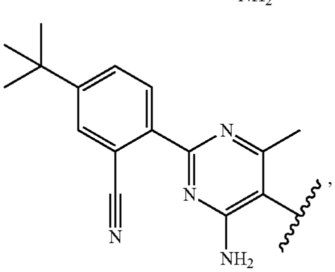
-continued
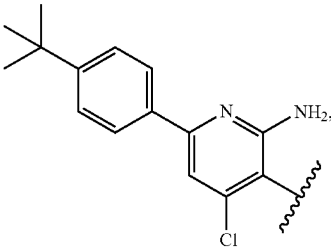
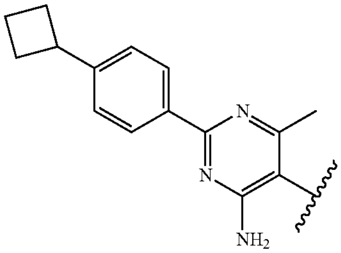
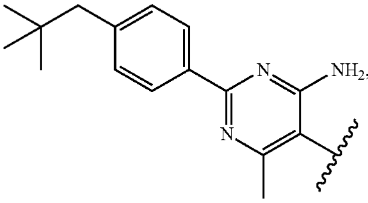
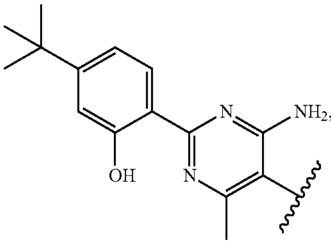
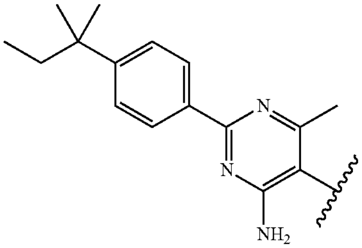
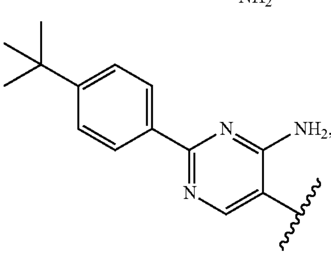
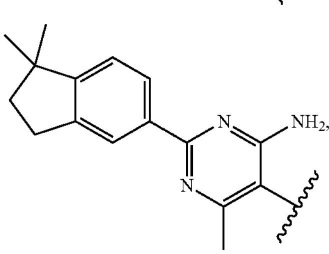

-continued
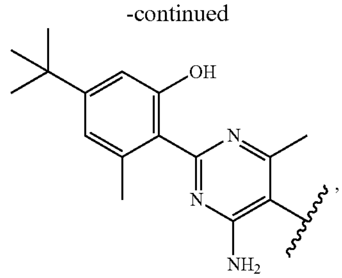
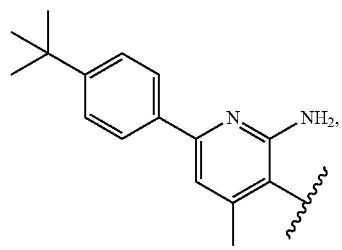
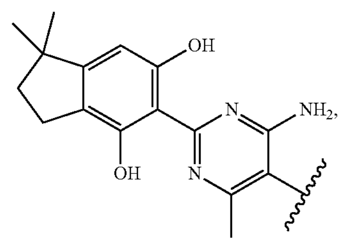
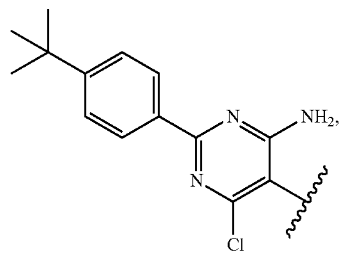
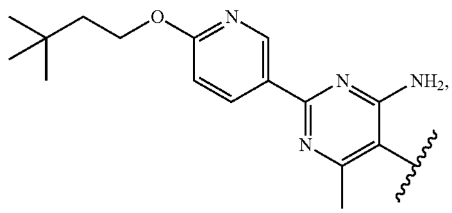
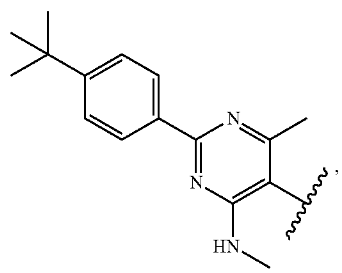
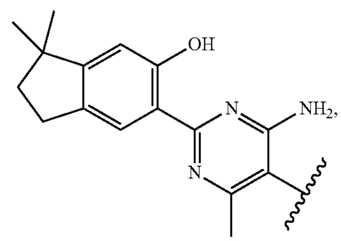
-continued
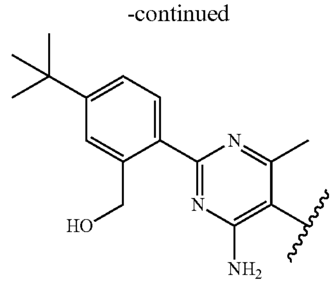
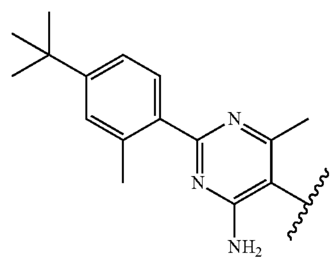
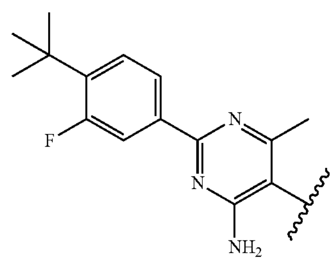
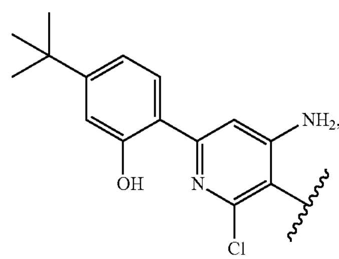
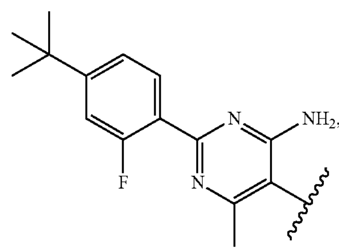
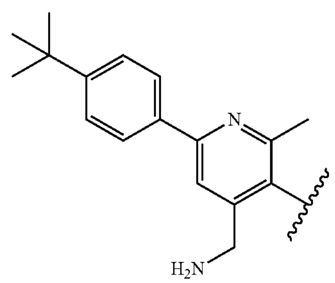

-continued
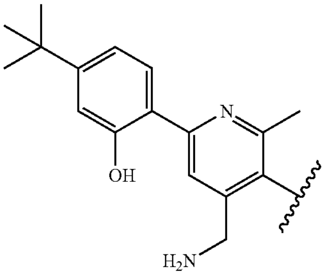
,
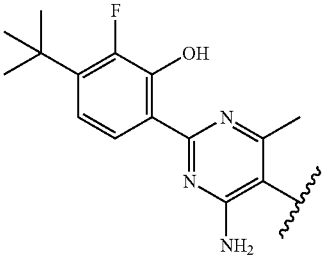
,
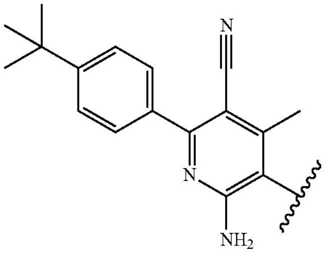
,
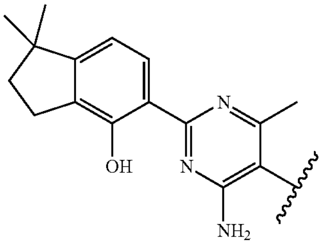
,
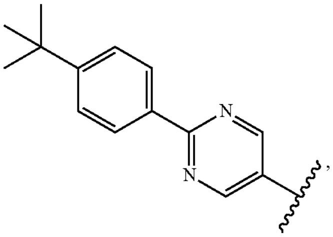
, or
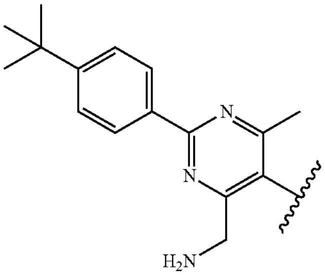
.
In some embodiments of a compound of Formula (I), (Ia), or (Ib), —X—Y—Z is
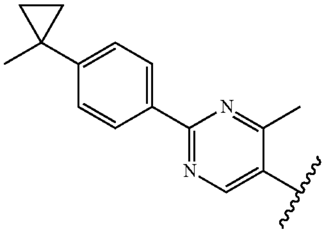
,
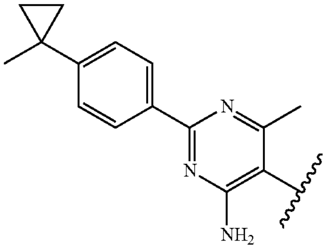
,
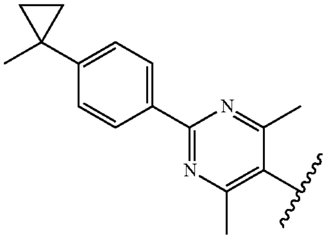
,
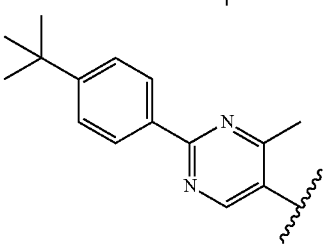
,
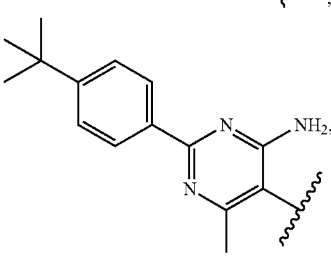
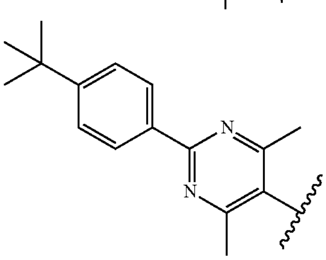
,
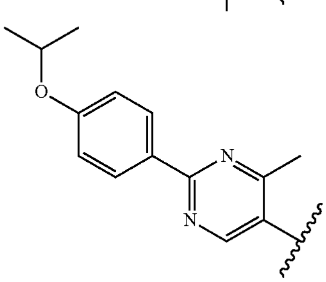
, -continued
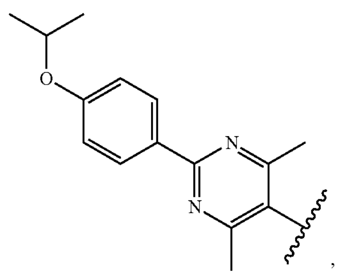
,
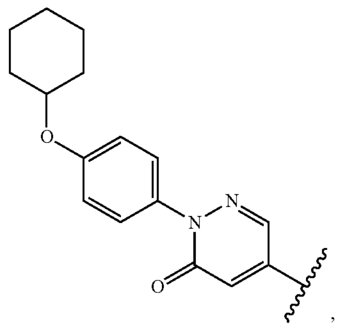
,
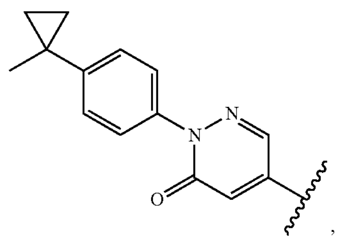
,
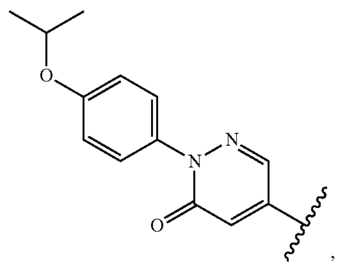
,
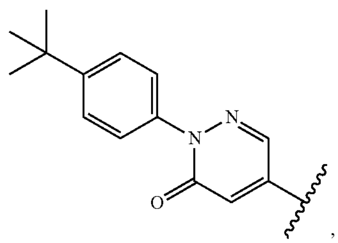
,
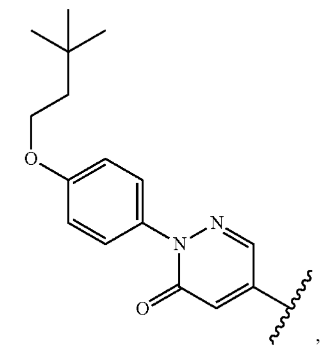
,
-continued
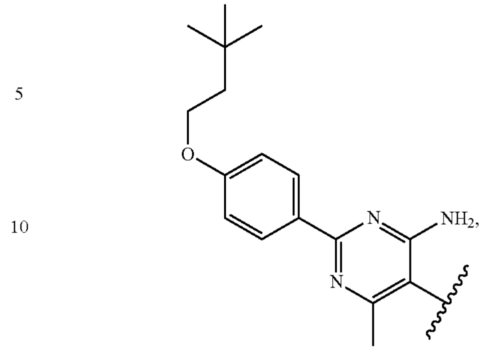
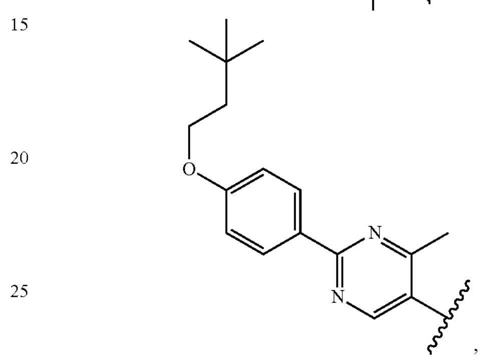
,
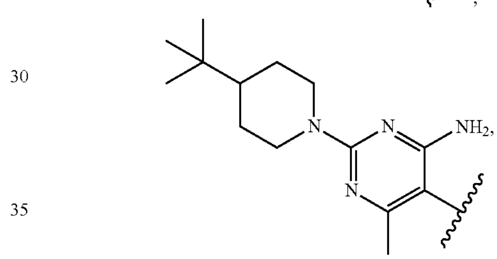
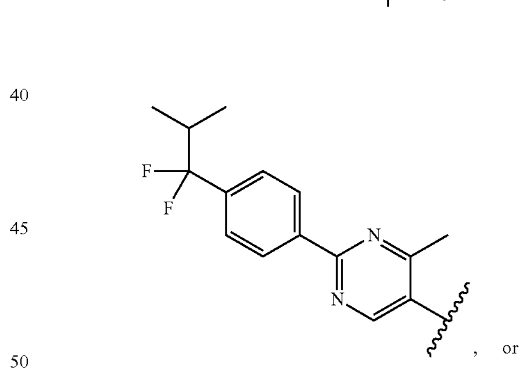
, or
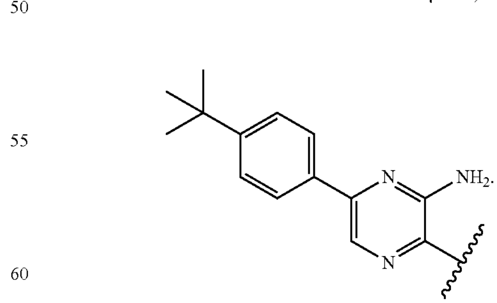
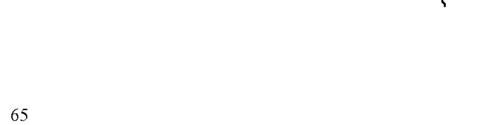
In some embodiments of a compound of Formula (I), (Ia), or (Ib), —X—Y—Z is

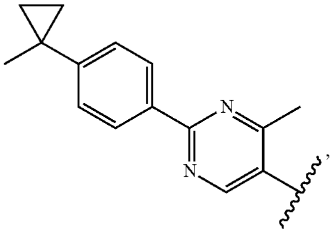
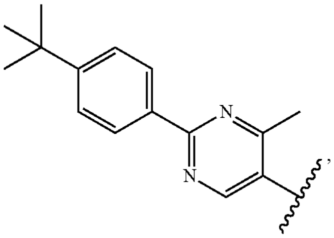
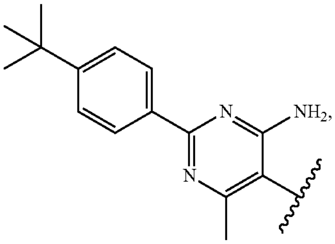
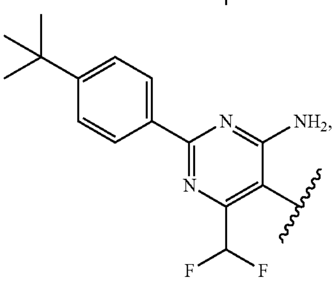
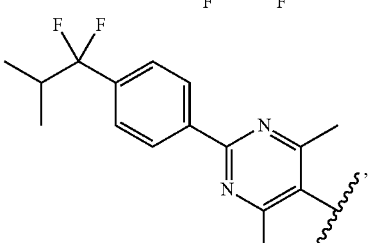
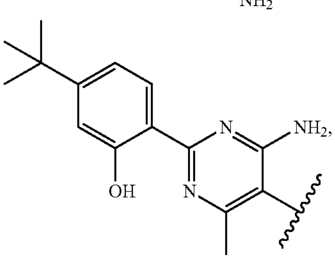
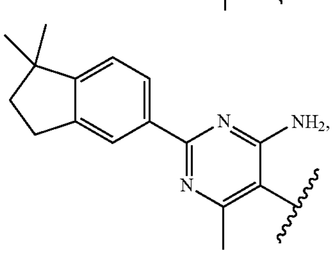
-continued
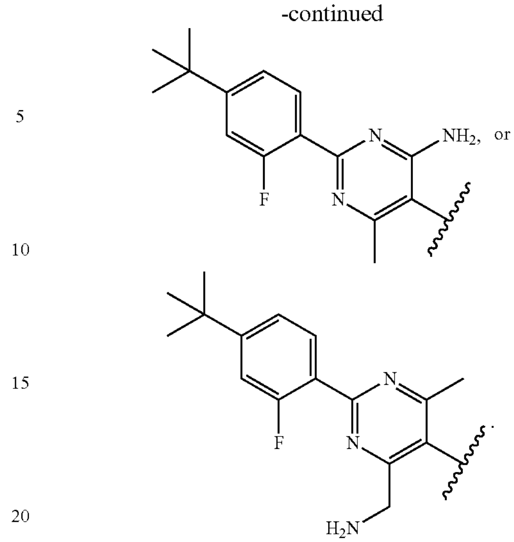
In some embodiments of a compound of Formula (I), (Ia), or (Ib), —X—Y—Z is
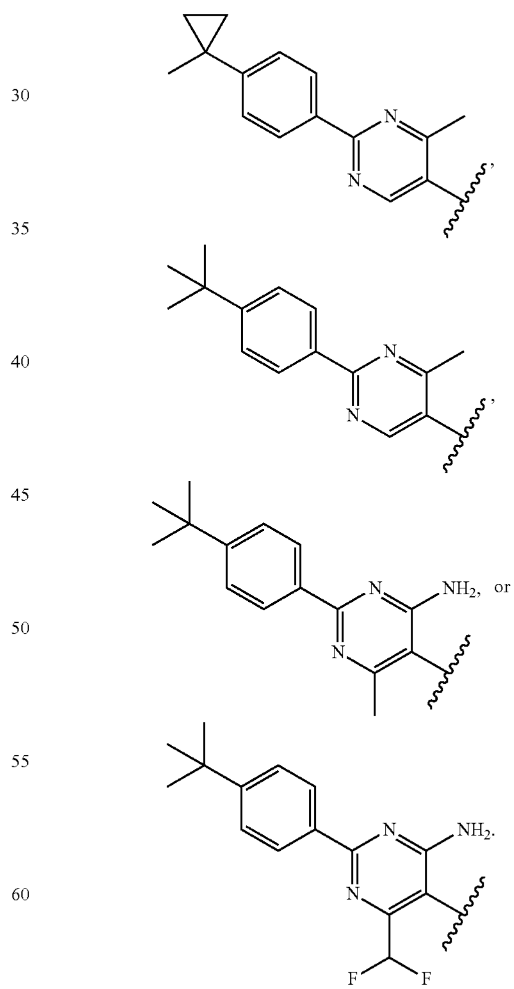
In some embodiments of a compound of Formula (I), (Ia), or (Ib), —X—Y—Z is

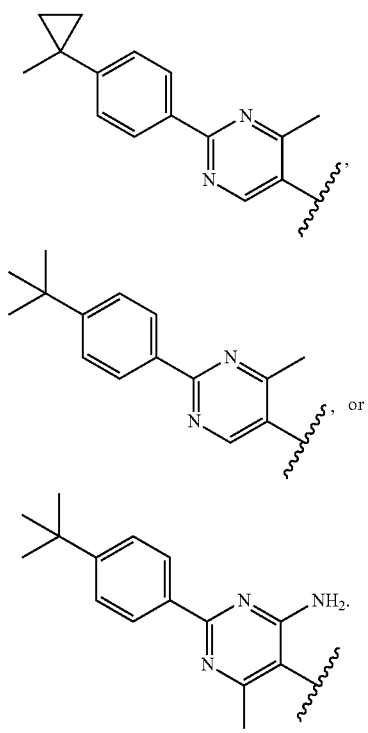

or

In some embodiments of a compound of Formula (I), (Ia), or (Ib), each $R^a$ is independently H, —$(C_1$-$C_6)$alkyl, —$(C_1$-$C_6)$haloalkyl, or —$(C_3$-$C_7)$cycloalkyl. In some embodiments of a compound of Formula (I), (Ia), or (Ib), each $R^a$ is independently H or —$(C_1$-$C_6)$alkyl. In some embodiments of a compound of Formula (I), (Ia), or (Ib), each $R^a$ is H. In some embodiments of a compound of Formula (I), (Ia), or (Ib), each $R^a$ is independently —$(C_1$-$C_6)$alkyl.

In some embodiments of a compound of Formula (I), (Ia), or (Ib), each $R^a$ is independently —$(C_1$-$C_6)$alkyl, —$(C_1$-$C_6)$haloalkyl, or —$(C_3$-$C_7)$cycloalkyl. In some embodiments of a compound of Formula (I), (Ia), or (Ib), each $R^a$ is independently —$(C_1$-$C_6)$alkyl.

In some embodiments of a compound of Formula (I), (Ia), or (Ib), each $R^c$ and $R^d$ is independently H, —$(C_1$-$C_6)$alkyl, —$(C_1$-$C_6)$haloalkyl, or —$(C_3$-$C_7)$cycloalkyl. In some embodiments of a compound of Formula (I), (Ia), or (Ib), each $R^c$ and $R^d$ is independently H or —$(C_1$-$C_6)$alkyl. In some embodiments of a compound of Formula (I), (Ia), or (Ib), each $R^c$ and $R^d$ is H. In some embodiments of a compound of Formula (I), (Ia), or (Ib), each $R^c$ and $R^d$ is independently —$(C_1$-$C_6)$alkyl.

In some embodiments, the compound of Formula (I), (Ia), or (Ib) is selected from a compound in Table 2 or a pharmaceutically acceptable salt, solvate, or stereoisomer thereof.

TABLE 2

| Ex. # | Structure | Name |
| --- | --- | --- |
| 1 | 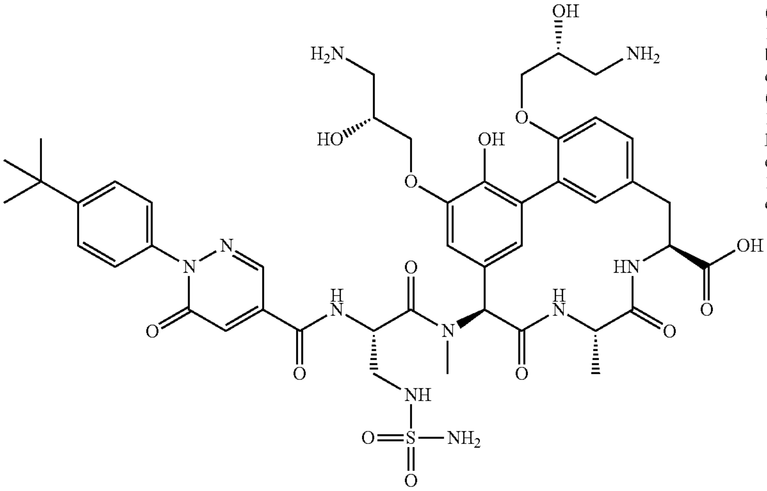 | (8S,11S,14S)-18-hydroxy-11-methyl-14-[methyl-[(2S)-2-[[1-(4-tert-butylphenyl)-6-oxo-pyridazine-4-carbonyl]amino]-3-(sulfamoylamino)propanoyl]amino]-10,13-dioxo-3,17-bis[(2R)-3-amino-2-hydroxy-propoxy]-9,12-diazatricyclo[13.3.1.12,6]icosa-1(18),2(20),3,5,15(19),16-hexaene-8-carboxylic acid |

TABLE 2-continued

| Ex. # | Structure | Name |
| --- | --- | --- |
| 2 | 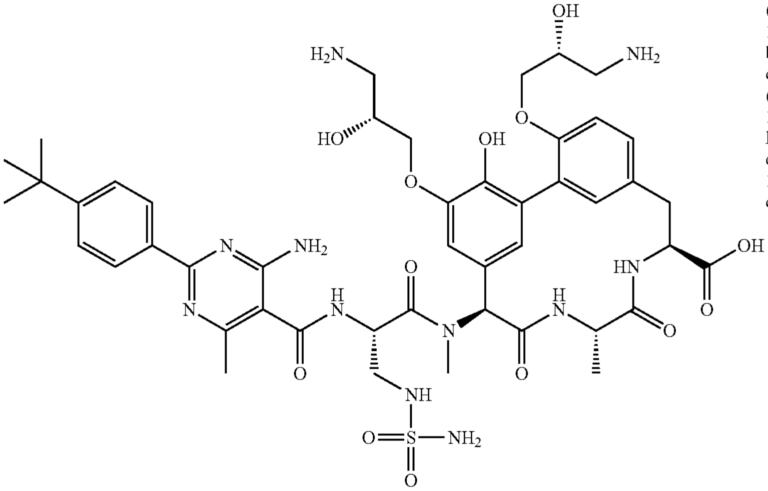 | (8S,11S,14S)-18-hydroxy-11-methyl-14-[methyl-[(2S)-2-[[4-amino-2-(4-tert-butylphenyl)-6-methyl-pyrimidine-5-carbonyl]amino]-3-(sulfamoylamino)propanoyl]amino]-10,13-dioxo-3,17-bis[(2R)-3-amino-2-hydroxy-propoxy]-9,12-diazatricyclo[13.3.1.12,6]icosa-1(18),2(20),3,5,15(19),16-hexaene-8-carboxylic acid |
| 3 | 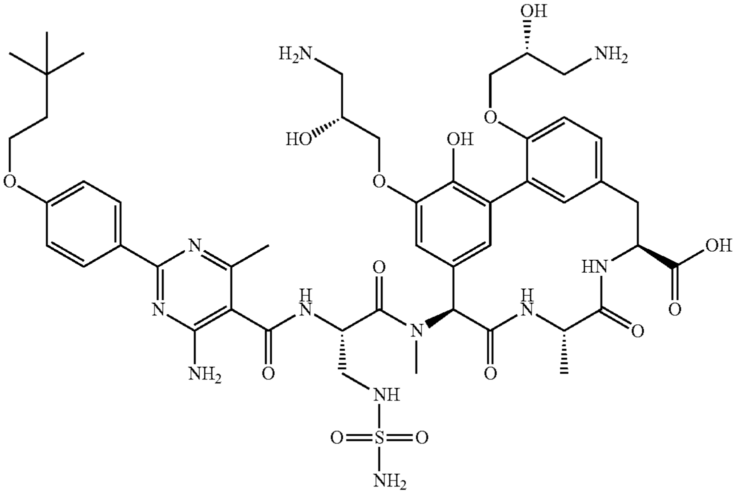 [SMILES: Cc1nc(-c2ccc(OCCC(C)(C)C)cc2)nc(N)c1C(=O)N[C@@H](CNS(N)(=O)=O)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O] | (8S,11S,14S)-18-hydroxy-11-methyl-14-[methyl-[(2S)-2-[[4-amino-2-[4-(3,3-dimethylbutoxy)phenyl]-6-methyl-pyrimidine-5-carbonyl]amino]-3-(sulfamoylamino)propanoyl]amino]-10,13-dioxo-3,17-bis[(2R)-3-amino-2-hydroxy-propoxy]-9,12-diazatricyclo[13.3.1.12,6]icosa-1(18),2(20),3,5,15(19),16-hexaene-8-carboxylic acid |
| 4 | 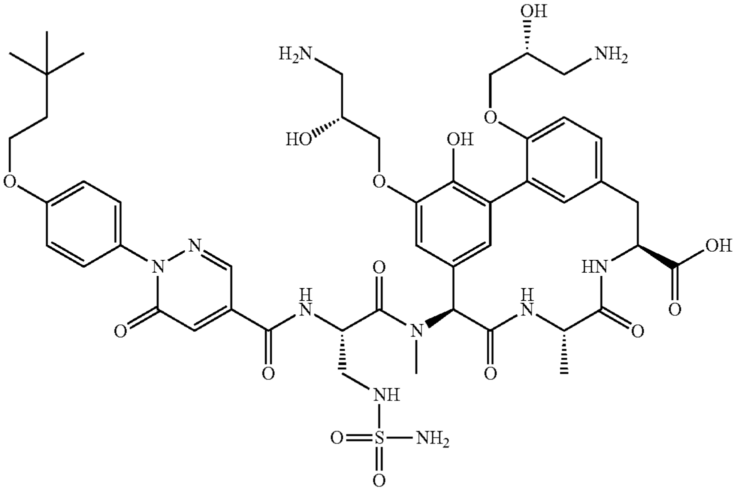 [SMILES: C[C@@H]1NC(=O)[C@@H](N(C)C(=O)[C@H](CNS(N)(=O)=O)NC(=O)c2cnn(-c3ccc(OCCC(C)(C)C)cc3)c(=O)c2)c2cc(OC[C@H](O)CN)c(O)c(c2)-c2cc(ccc2OC[C@H](O)CN)C[C@@H](C(=O)O)NC1=O] | (8S,11S,14S)-18-hydroxy-11-methyl-14-[methyl-[(2S)-2-[[1-[4-(3,3-dimethylbutoxy)phenyl]-6-oxo-pyridazine-4-carbonyl]amino]-3-(sulfamoylamino)propanoyl]amino]-10,13-dioxo-3,17-bis[(2R)-3-amino-2-hydroxy-propoxy]-9,12-diazatricyclo[13.3.1.12,6]icosa-1(18),2(20),3,5,15(19),16-hexaene-8-carboxylic acid |

TABLE 2-continued

| Ex. # | Structure | Name |
|---|---|---|
| 5 | 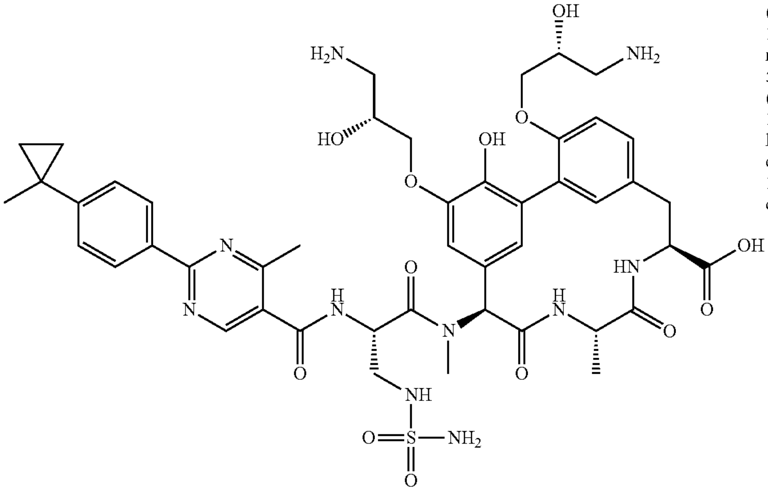 | (8S,11S,14S)-18-hydroxy-11-methyl-14-[methyl-[(2S)-2-[[4-methyl-2-[4-(1-methylcyclopropyl)phenyl]pyrimidine-5-carbonyl]amino]-3-(sulfamoylamino)propanoyl]amino]-10,13-dioxo-3,17-bis[(2R)-3-amino-2-hydroxy-propoxy]-9,12-diazatricyclo[13.3.1.12,6]icosa-1(18),2(20),3,5,15(19),16-hexaene-8-carboxylic acid |
| 6 | 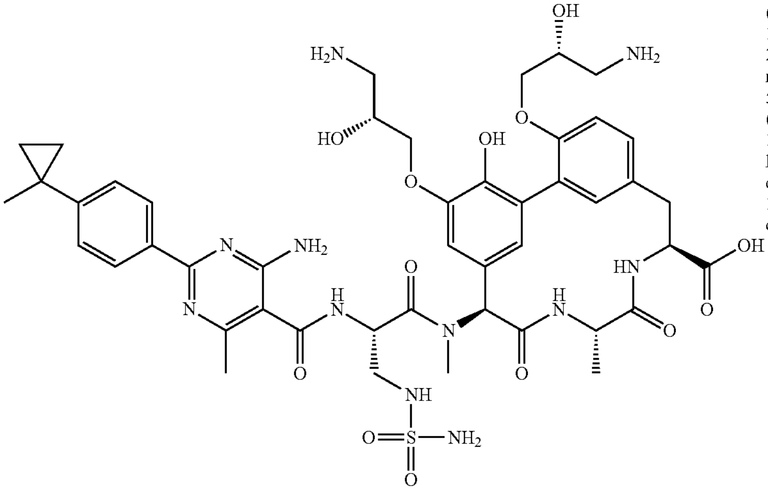 | (8S,11S,14S)-18-hydroxy-11-methyl-14-[methyl-[(2S)-2-[[4-amino-6-methyl-2-[4-(1-methylcyclopropyl)phenyl]pyrimidine-5-carbonyl]amino]-3-(sulfamoylamino)propanoyl]amino]-10,13-dioxo-3,17-bis[(2R)-3-amino-2-hydroxy-propoxy]-9,12-diazatricyclo[13.3.1.12,6]icosa-1(18),2(20),3,5,15(19),16-hexaene-8-carboxylic acid |
| 7 | 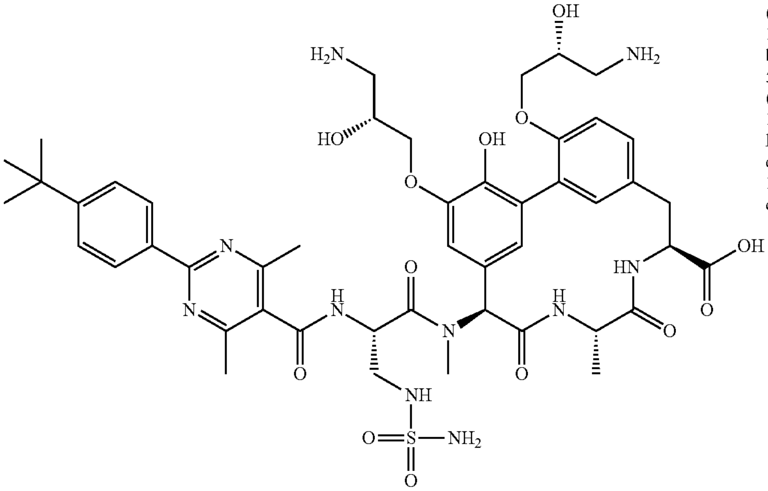 | (8S,11S,14S)-18-hydroxy-11-methyl-14-[methyl-[(2S)-2-[[2-(4-tert-butylphenyl)-4,6-dimethyl-pyrimidine-5-carbonyl]amino]-3-(sulfamoylamino)propanoyl]amino]-10,13-dioxo-3,17-bis[(2R)-3-amino-2-hydroxy-propoxy]-9,12-diazatricyclo[13.3.1.12,6]icosa-1(18),2(20),3,5,15(19),16-hexaene-8-carboxylic acid |

TABLE 2-continued

| Ex. # | Structure | Name |
| --- | --- | --- |
| 8 | 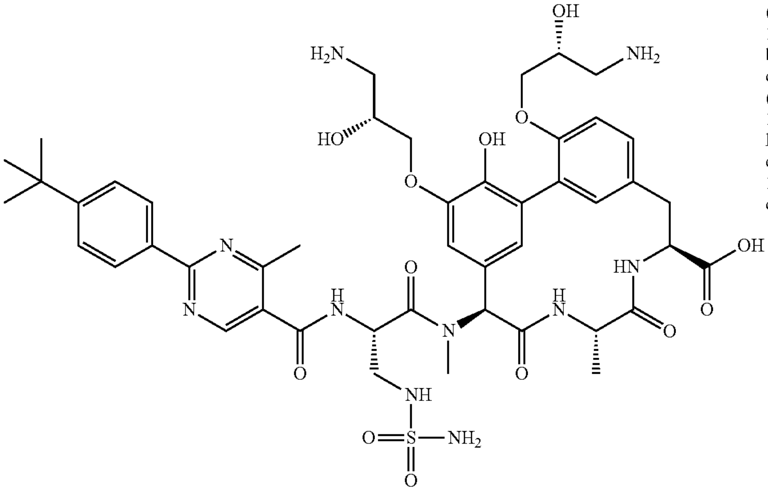 | (8S,11S,14S)-18-hydroxy-11-methyl-14-[methyl-[(2S)-2-[[2-(4-tert-butylphenyl)-4-methyl-pyrimidine-5-carbonyl]amino]-3-(sulfamoylamino)propanoyl]amino]-10,13-dioxo-3,17-bis[(2R)-3-amino-2-hydroxy-propoxy]-9,12-diazatricyclo[13.3.1.12,6]icosa-1(18),2(20),3,5,15(19),16-hexaene-8-carboxylic acid |
| 9 | 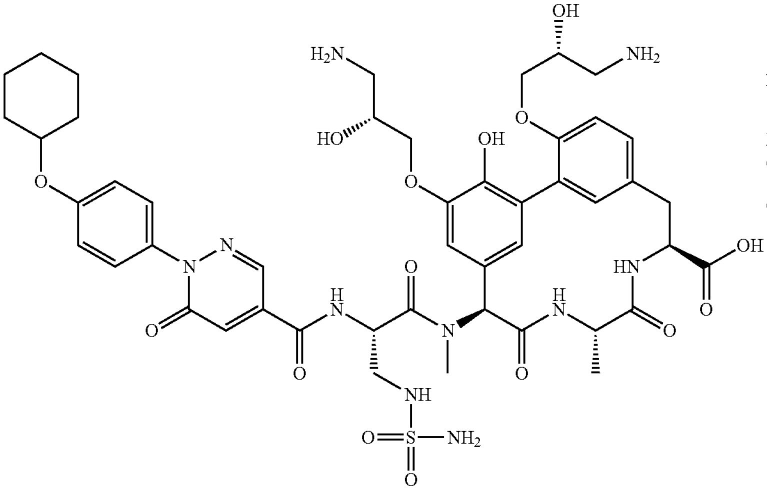 | (8S,11S,14S)-18-hydroxy-11-methyl-14-[methyl-[(2S)-2-[[1-[4-(cyclohexoxy)phenyl]-6-oxo-pyridazine-4-carbonyl]amino]-3-(sulfamoylamino)propanoyl]amino]-10,13-dioxo-3,17-bis[(2R)-3-amino-2-hydroxy-propoxy]-9,12-diazatricyclo[13.3.1.12,6]icosa-1(18),2(20),3,5,15(19),16-hexaene-8-carboxylic acid |
| 10 | 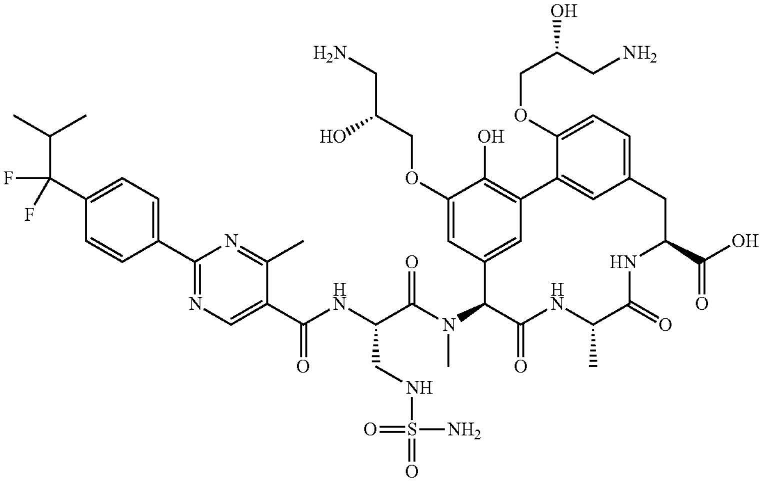 [SMILES: Cc1nc(-c2ccc(C(F)(F)C(C)C)cc2)ncc1C(=O)N[C@@H](CNS(N)(=O)=O)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O] | (8S,11S,14S)-18-hydroxy-11-methyl-14-[methyl-[(2S)-2-[[2-[4-(1,1-difluoro-2-methyl-propyl)phenyl]-4-methyl-pyrimidine-5-carbonyl]amino]-3-(sulfamoylamino)propanoyl]amino]-10,13-dioxo-3,17-bis[(2R)-3-amino-2-hydroxy-propoxy]-9,12-diazatricyclo[13.3.1.12,6]icosa-1(18),2(20),3,5,15(19),16-hexaene-8-carboxylic acid |

TABLE 2-continued

| Ex. # | Structure | Name |
|---|---|---|
| 11 | 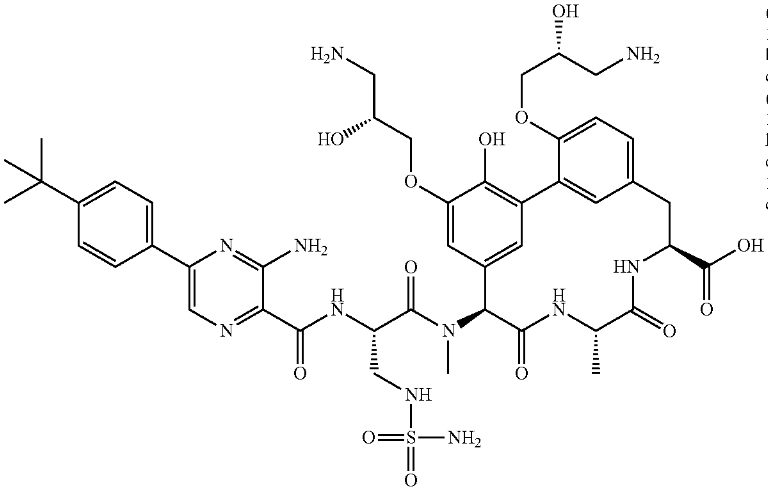 | (8S,11S,14S)-18-hydroxy-11-methyl-14-[methyl-[(2S)-2-[[3-amino-5-(4-tert-butylphenyl)pyrazine-2-carbonyl]amino]-3-(sulfamoylamino)propanoyl]amino]-10,13-dioxo-3,17-bis[(2R)-3-amino-2-hydroxy-propoxy]-9,12-diazatricyclo[13.3.1.12,6]icosa-1(18),2(20),3,5,15(19),16-hexaene-8-carboxylic acid |
| 12 | 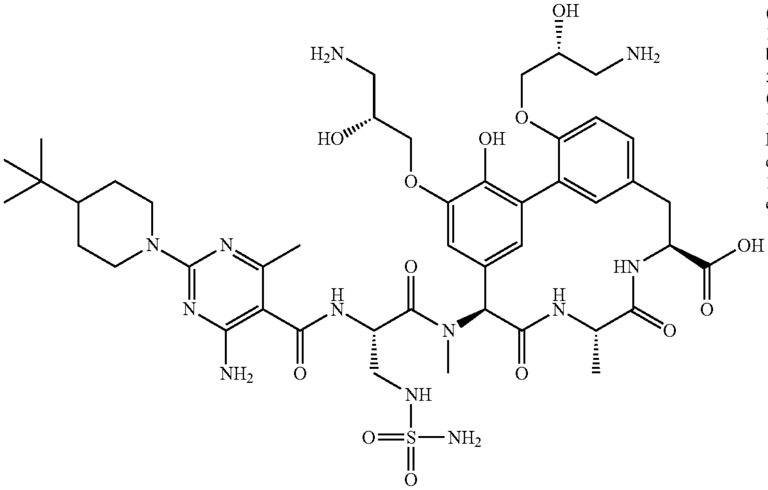 | (8S,11S,14S)-18-hydroxy-11-methyl-14-[methyl-[(2S)-2-[[4-amino-2-(4-tert-butyl-1-piperidyl)-6-methyl-pyrimidine-5-carbonyl]amino]-3-(sulfamoylamino)propanoyl]amino]-10,13-dioxo-3,17-bis[(2R)-3-amino-2-hydroxy-propoxy]-9,12-diazatricyclo[13.3.1.12,6]icosa-1(18),2(20),3,5,15(19),16-hexaene-8-carboxylic acid |
| 13 | 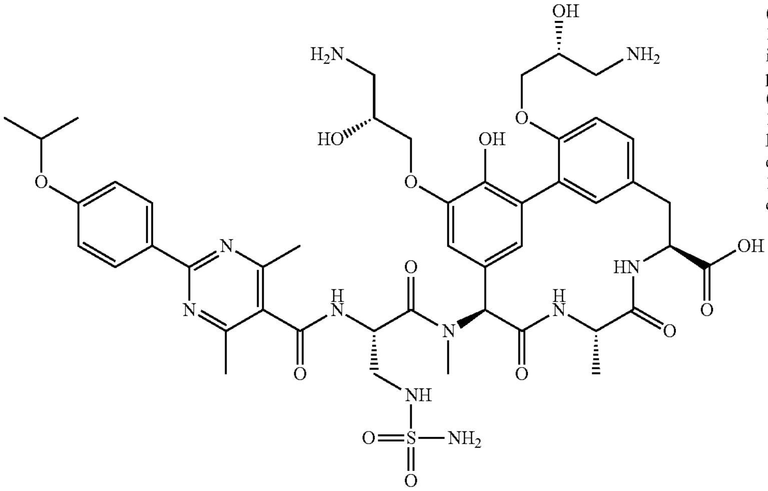 | (8S,11S,14S)-18-hydroxy-11-methyl-14-[methyl-[(2S)-2-[[2-(4-isopropoxyphenyl)-4,6-dimethyl-pyrimidine-5-carbonyl]amino]-3-(sulfamoylamino)propanoyl]amino]-10,13-dioxo-3,17-bis[(2R)-3-amino-2-hydroxy-propoxy]-9,12-diazatricyclo[13.3.1.12,6]icosa-1(18),2(20),3,5,15(19),16-hexaene-8-carboxylic acid |

TABLE 2-continued

| Ex. # | Structure | Name |
| --- | --- | --- |
| 14 | 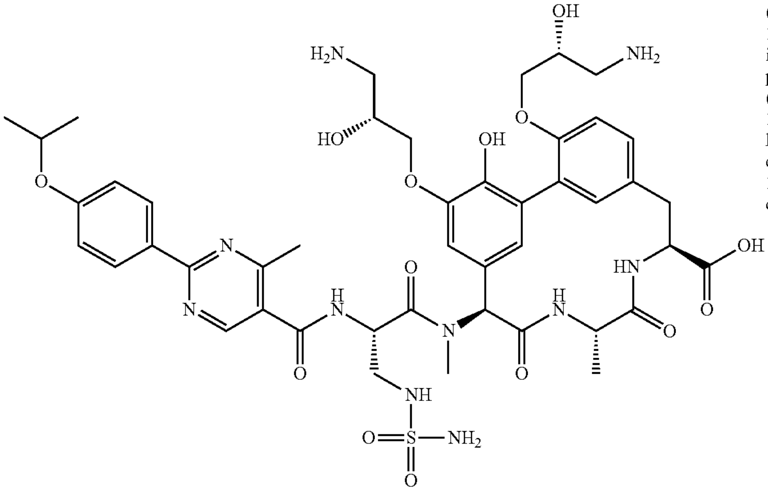 | (8S,11S,14S)-18-hydroxy-11-methyl-14-[methyl-[(2S)-2-[[2-(4-isopropoxyphenyl)-4-methyl-pyrimidine-5-carbonyl]amino]-3-(sulfamoylamino)propanoyl]amino]-10,13-dioxo-3,17-bis[(2R)-3-amino-2-hydroxy-propoxy]-9,12-diazatricyclo[13.3.1.12,6]icosa-1(18),2(20),3,5,15(19),16-hexaene-8-carboxylic acid |
| 15 | 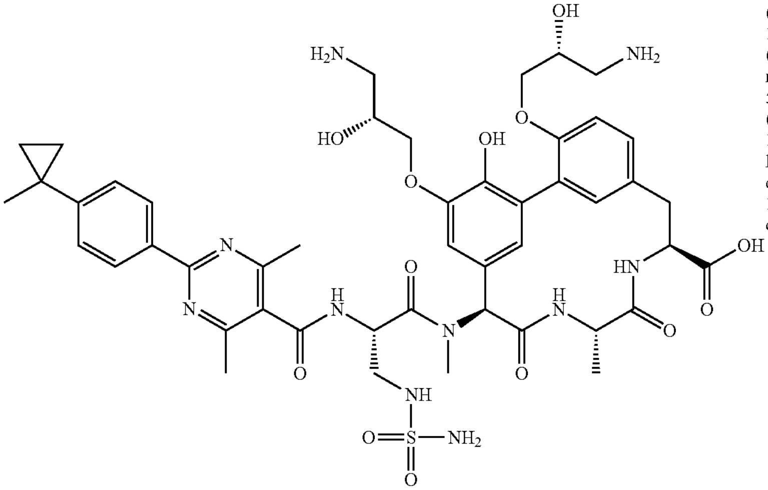 | (8S,11S,14S)-18-hydroxy-11-methyl-14-[methyl-[(2S)-2-[[4,6-dimethyl-2-[4-(1-methylcyclopropyl)phenyl]pyrimidine-5-carbonyl]amino]-3-(sulfamoylamino)propanoyl]amino]-10,13-dioxo-3,17-bis[(2R)-3-amino-2-hydroxy-propoxy]-9,12-diazatricyclo[13.3.1.12,6]icosa-1(18),2(20),3,5,15(19),16-hexaene-8-carboxylic acid |
| 16 | 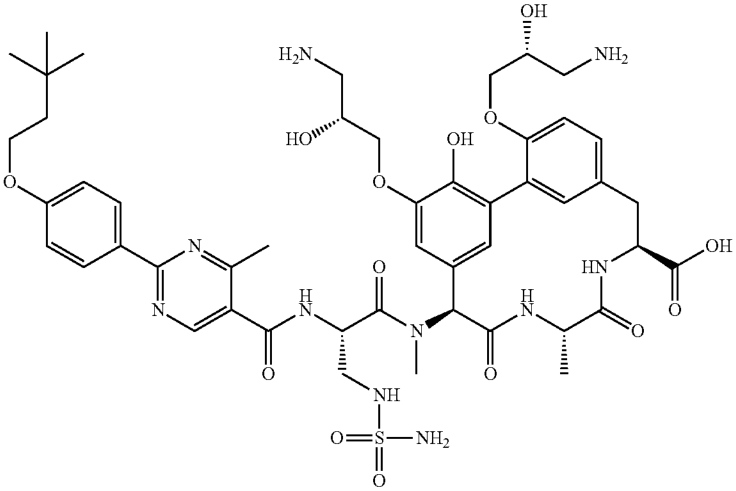 [SMILES: Cc1nc(-c2ccc(OCCC(C)(C)C)cc2)ncc1C(=O)N[C@@H](CNS(N)(=O)=O)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O] | (8S,11S,14S)-18-hydroxy-11-methyl-14-[methyl-[(2S)-2-[[2-[4-(3,3-dimethylbutoxy)phenyl]-4-methyl-pyrimidine-5-carbonyl]amino]-3-(sulfamoylamino)propanoyl]amino]-10,13-dioxo-3,17-bis[(2R)-3-amino-2-hydroxy-propoxy]-9,12-diazatricyclo[13.3.1.12,6]icosa-1(18),2(20),3,5,15(19),16-hexaene-8-carboxylic acid |

TABLE 2-continued

| Ex. # | Structure | Name |
|---|---|---|
| 17 | 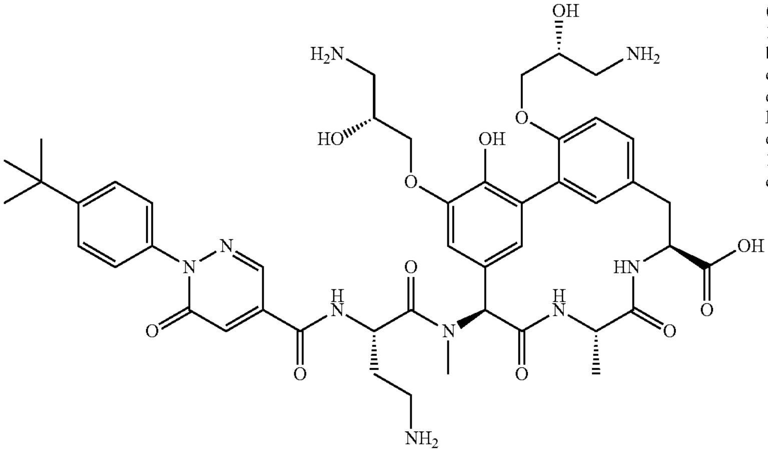 | (8S,11S,14S)-18-hydroxy-11-methyl-14-[methyl-[(2S)-4-amino-2-[[1-(4-tert-butylphenyl)-6-oxo-pyridazine-4-carbonyl]amino]butanoyl]amino]-10,13-dioxo-3,17-bis[(2R)-3-amino-2-hydroxy-propoxy]-9,12-diazatricyclo[13.3.1.12,6]icosa-1(18),2(20),3,5,15(19),16-hexaene-8-carboxylic acid |
| 18 | 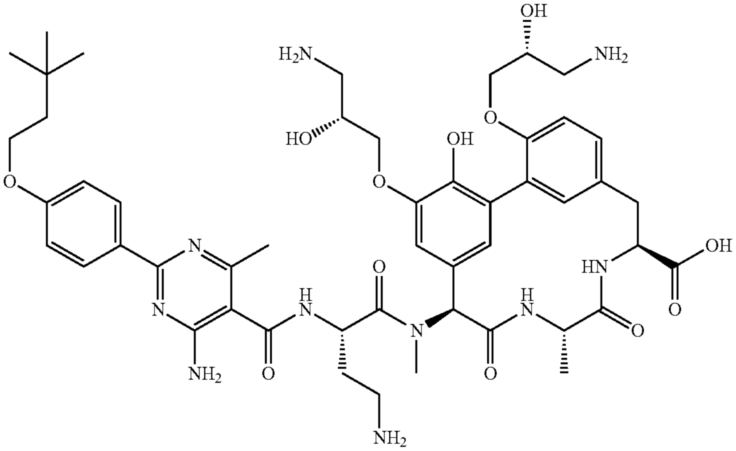 [SMILES: Cc1nc(-c2ccc(OCCC(C)(C)C)cc2)nc(N)c1C(=O)N[C@@H](CCN)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O] | (8S,11S,14S)-18-hydroxy-11-methyl-14-[methyl-[(2S)-4-amino-2-[[4-amino-2-[4-(3,3-dimethylbutoxy)phenyl]-6-methyl-pyrimidine-5-carbonyl]amino]butanoyl]amino]-10,13-dioxo-3,17-bis[(2R)-3-amino-2-hydroxy-propoxy]-9,12-diazatricyclo[13.3.1.12,6]icosa-1(18),2(20),3,5,15(19),16-hexaene-8-carboxylic acid |
| 19 | 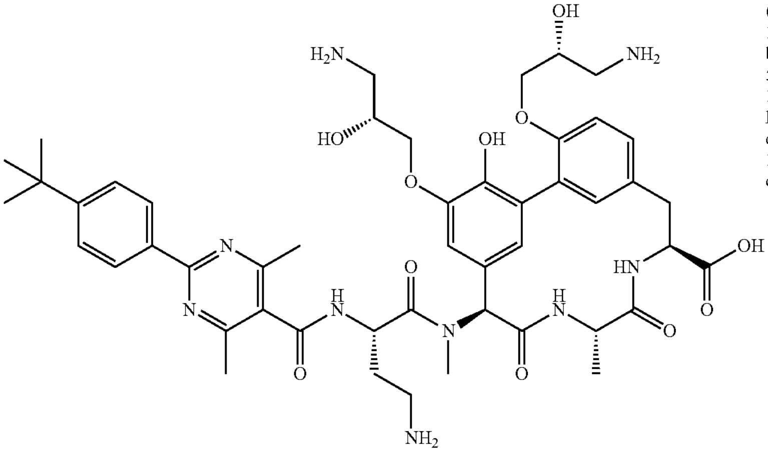 | (8S,11S,14S)-18-hydroxy-11-methyl-14-[methyl-[(2S)-4-amino-2-[[2-(4-tert-butylphenyl)-4,6-dimethyl-pyrimidine-5-carbonyl]amino]butanoyl]amino]-10,13-dioxo-3,17-bis[(2R)-3-amino-2-hydroxy-propoxy]-9,12-diazatricyclo[13.3.1.12,6]icosa-1(18),2(20),3,5,15(19),16-hexaene-8-carboxylic acid |

TABLE 2-continued

| Ex. # | Structure | Name |
|---|---|---|
| 20 | 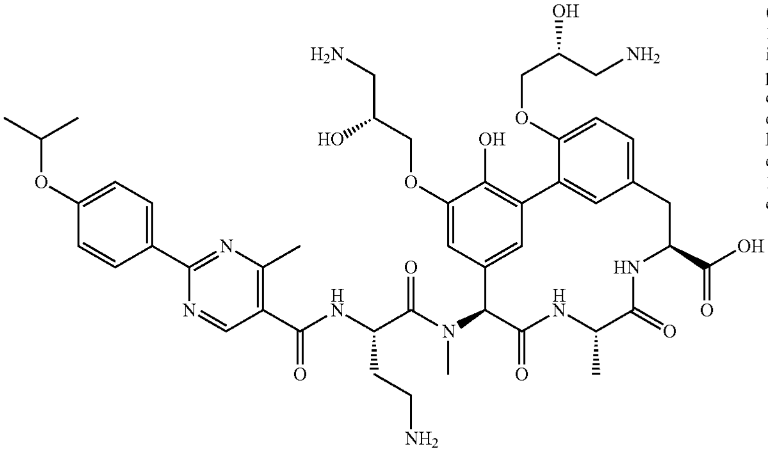 [SMILES: Cc1nc(-c2ccc(OC(C)C)cc2)ncc1C(=O)N[C@@H](CCN)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O] | (8S,11S,14S)-18-hydroxy-11-methyl-14-[methyl-[(2S)-4-amino-2-[[2-(4-isopropoxyphenyl)-4-methyl-pyrimidine-5-carbonyl]amino]butanoyl]amino]-10,13-dioxo-3,17-bis[(2R)-3-amino-2-hydroxy-propoxy]-9,12-diazatricyclo[13.3.1.12,6]icosa-1(18),2(20),3,5,15(19),16-hexaene-8-carboxylic acid |
| 21 | 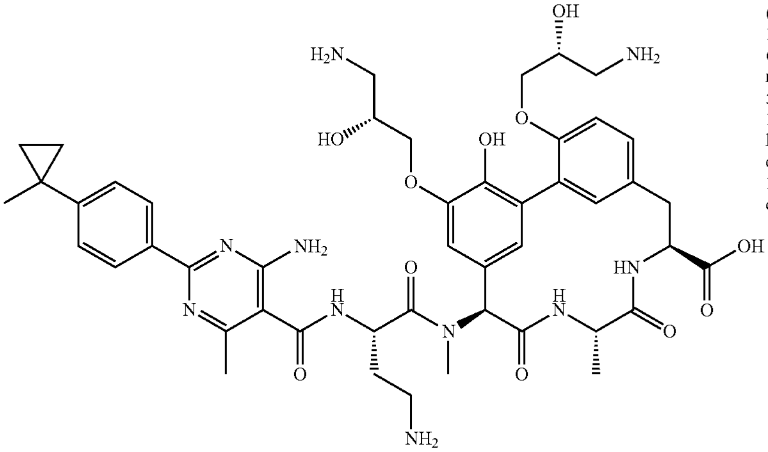 | (8S,11S,14S)-18-hydroxy-11-methyl-14-[methyl-[(2S)-4-amino-2-[[4-amino-6-methyl-2-[4-(1-methylcyclopropyl)phenyl]pyrimidine-5-carbonyl]amino]butanoyl]amino]-10,13-dioxo-3,17-bis[(2R)-3-amino-2-hydroxy-propoxy]-9,12-diazatricyclo[13.3.1.12,6]icosa-1(18),2(20),3,5,15(19),16-hexaene-8-carboxylic acid |
| 22 | 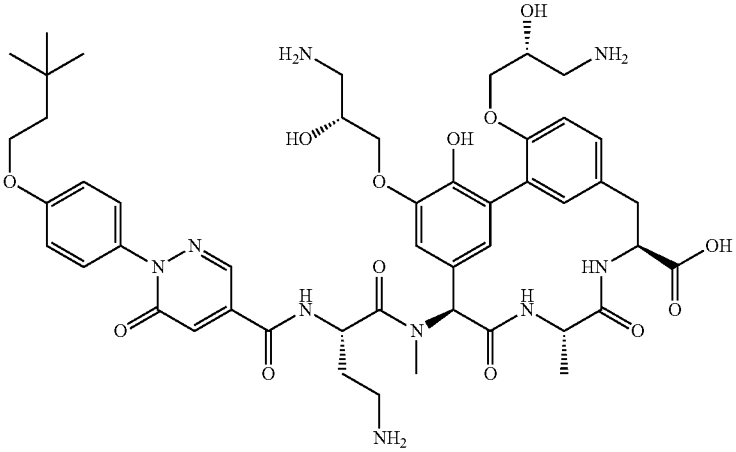 [SMILES: C[C@@H]1NC(=O)[C@@H](N(C)C(=O)[C@H](CCN)NC(=O)c2cnn(-c3ccc(OCCC(C)(C)C)cc3)c(=O)c2)c2cc(OC[C@H](O)CN)c(O)c(c2)-c2cc(ccc2OC[C@H](O)CN)C[C@@H](C(=O)O)NC1=O] | (8S,11S,14S)-18-hydroxy-11-methyl-14-[methyl-[(2S)-4-amino-2-[[1-[4-(3,3 dimethylbutoxy)phenyl]-6-oxo-pyridazine-4-carbonyl]amino]butanoyl]amino]-10,13 dioxo-3,17-bis[(2R)-3-amino-2-hydroxy-propoxy]-9,12-diazatricyclo[13.3.1.12,6]icosa-1(18),2(20),3,5,15(19),16-hexaene-8-carboxylic acid |

TABLE 2-continued

| Ex. # | Structure | Name |
| --- | --- | --- |
| 23 | 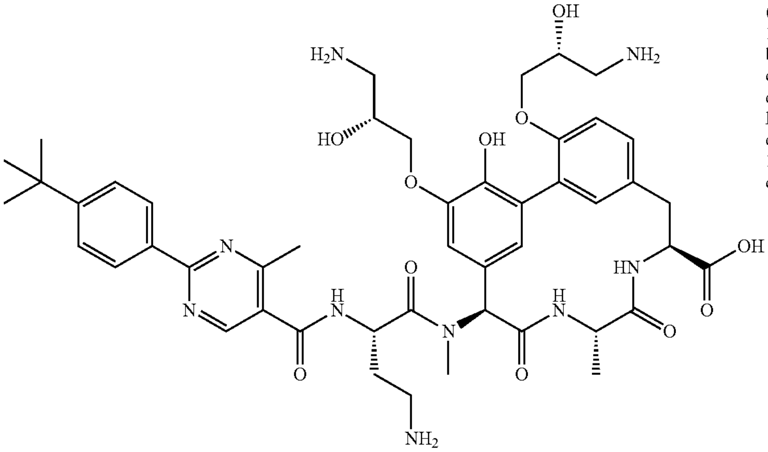 | (8S,11S,14S)-18-hydroxy-11-methyl-14-[methyl-[(2S)-4-amino-2-[[2-(4-tert-butylphenyl)-4-methyl-pyrimidine-5-carbonyl]amino]butanoyl]amino]-10,13-dioxo-3,17-bis[(2R)-3-amino-2-hydroxy-propoxy]-9,12-diazatricyclo[13.3.1.12,6]icosa-1(18),2(20),3,5,15(19),16-hexaene-8-carboxylic acid |
| 24 | 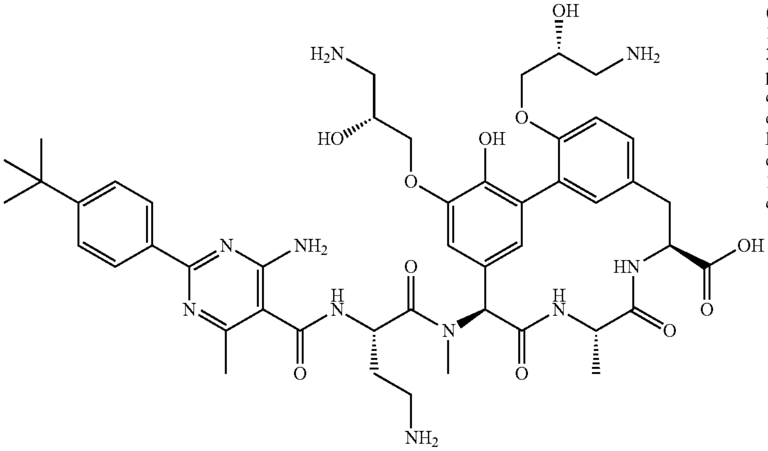 | (8S,11S,14S)-18-hydroxy-11-methyl-14-[methyl-[(2S)-4-amino-2-[[4-amino-2-(4-tert-butylphenyl)-6-methyl-pyrimidine-5-carbonyl]amino]butanoyl]amino]-10,13-dioxo-3,17-bis[(2R)-3-amino-2-hydroxy-propoxy]-9,12-diazatricyclo[13.3.1.12,6]icosa-1(18),2(20),3,5,15(19),16-hexaene-8-carboxylic acid |
| 25 | 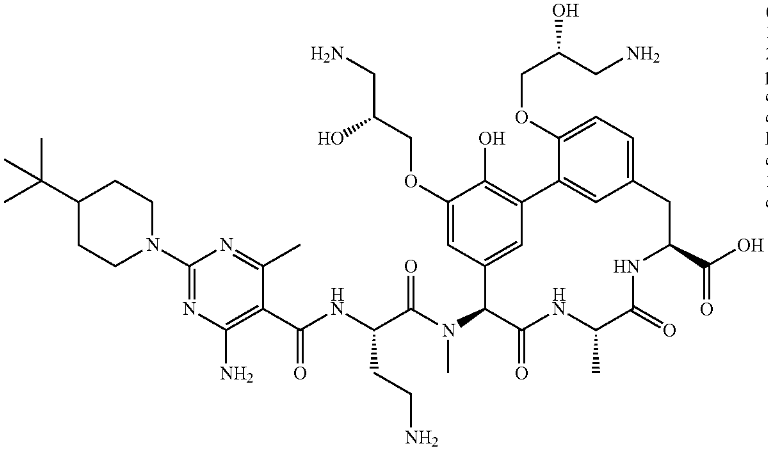 | (8S,11S,14S)-18-hydroxy-11-methyl-14-[methyl-[(2S)-4-amino-2-[[4-amino-2-(4-tert-butyl-1-piperidyl)-6-methyl-pyrimidine-5-carbonyl]amino]butanoyl]amino]-10,13-dioxo-3,17-bis[(2R)-3-amino-2-hydroxy-propoxy]-9,12-diazatricyclo[13.3.1.12,6]icosa-1(18),2(20),3,5,15(19),16-hexaene-8-carboxylic acid |

TABLE 2-continued

| Ex. # | Structure | Name |
|---|---|---|
| 26 | 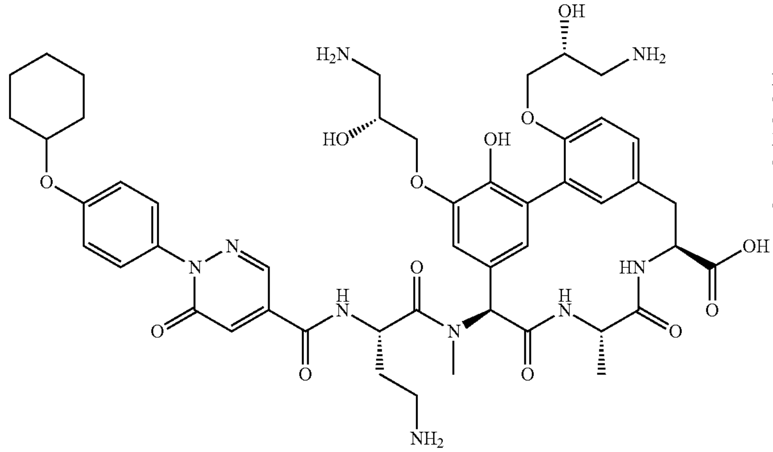 [SMILES: C[C@@H]1NC(=O)[C@@H](N(C)C(=O)[C@H](CCN)NC(=O)c2cnn(-c3ccc(OC4CCCCC4)cc3)c(=O)c2)c2cc(OC[C@H](O)CN)c(O)c(c2)-c2cc(ccc2OC[C@H](O)CN)C[C@@H](C(=O)O)NC1=O] | (8S,11S,14S)-18-hydroxy-11-methyl-14-[methyl-[(2S)-4-amino-2-[[1-[4-(cyclohexoxy)phenyl]-6-oxo-pyridazine-4-carbonyl]amino]butanoyl]amino]-10,13-dioxo-3,17-bis[(2R)-3-amino-2-hydroxy-propoxy]-9,12-diazatricyclo[13.3.1.12,6]icosa-1(18),2(20),3,5,15(19),16-hexaene-8-carboxylic acid |
| 27 | 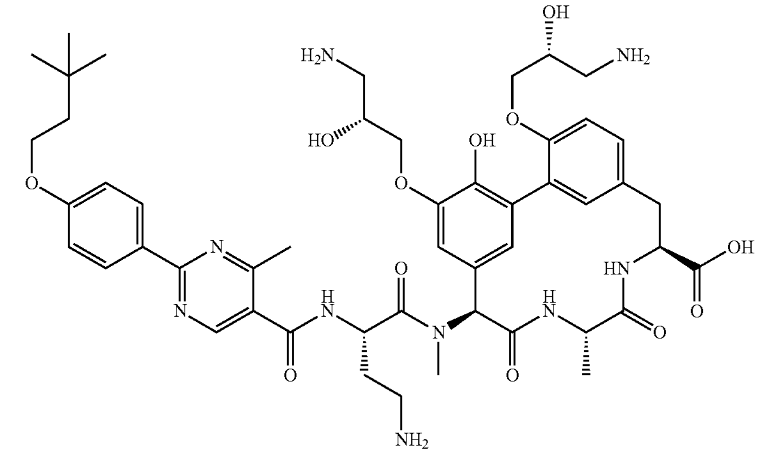 [SMILES: Cc1nc(-c2ccc(OCCC(C)(C)C)cc2)ncc1C(=O)N[C@@H](CCN)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O] | (8S,11S,14S)-18-hydroxy-11-methyl-14-[methyl-[(2S)-4-amino-2-[[2-[4-(3,3 dimethylbutoxy)phenyl]-4-methyl-pyrimidine-5-carbonyl]amino]butanoyl]amino]-10,13-dioxo-3,17-bis[(2R)-3-amino-2-hydroxy-propoxy]-9,12-diazatricyclo[13.3.1.12,6]icosa-1(18),2(20),3,5,15(19),16-hexaene-8-carboxylic acid |
| 28 | 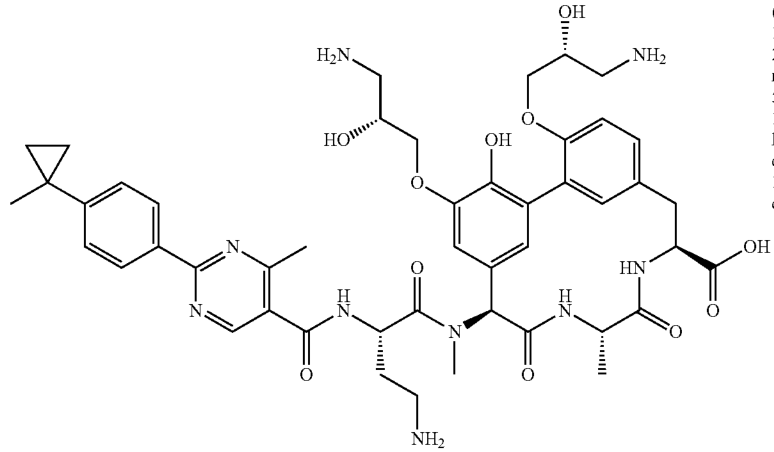 | (8S,11S,14S)-18-hydroxy-11-methyl-14-[methyl-[(2S)-4-amino-2-[[4-methyl-2-[4-(1-methylcyclopropyl)phenyl]pyrimidine-5-carbonyl]amino]butanoyl]amino]-10,13-dioxo-3,17-bis[(2R)-3-amino-2-hydroxy-propoxy]-9,12-diazatricyclo[13.3.1.12,6]icosa-1(18),2(20),3,5,15(19),16-hexaene-8-carboxylic acid |

TABLE 2-continued

| Ex. # | Structure | Name |
|---|---|---|
| 29 | 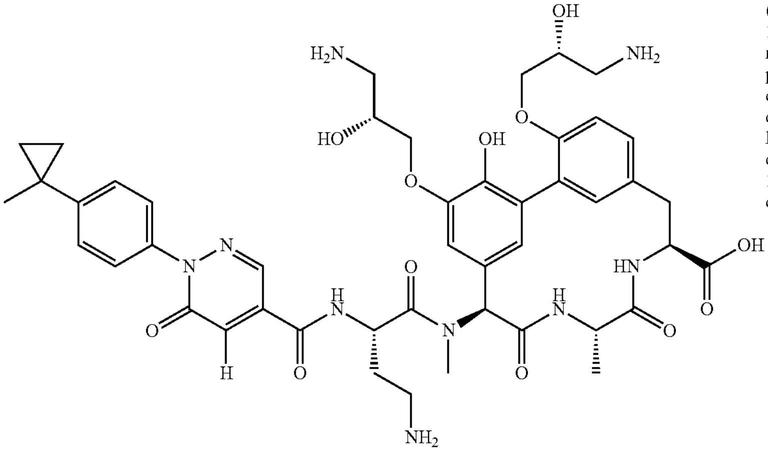 [SMILES: C[C@@H]1NC(=O)[C@@H](N(C)C(=O)[C@H](CCN)NC(=O)c2cnn(-c3ccc(C4(C)CC4)cc3)c(=O)c2)c2cc(OC[C@H](O)CN)c(O)c(c2)-c2cc(ccc2OC[C@H](O)CN)C[C@@H](C(=O)O)NC1=O] | (8S,11S,14S)-18-hydroxy-11-methyl-14-[methyl-[(2S)-4-amino-2-[[1-[4-(1-methylcyclopropyl)phenyl]-6-oxo-pyridazine-4-carbonyl]amino]butanoyl]amino]-10,13-dioxo-3,17-bis[(2R)-3-amino-2-hydroxy-propoxy]-9,12-diazatricyclo[13.3.1.12,6]icosa-1(18),2(20),3,5,15(19),16-hexaene-8-carboxylic acid |
| 30 | 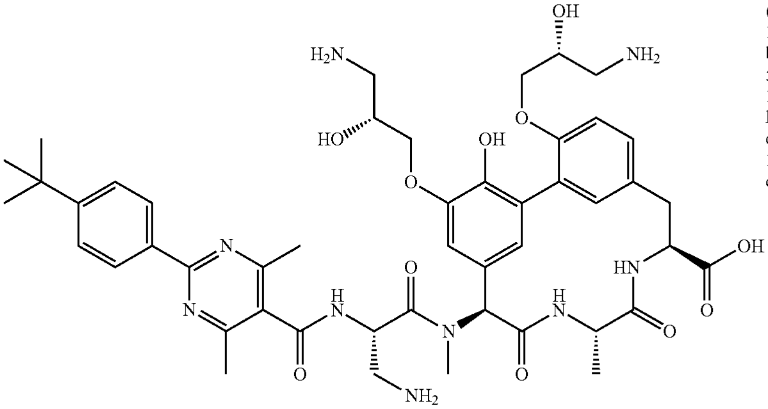 [SMILES: Cc1nc(-c2ccc(C(C)(C)C)cc2)nc(C)c1C(=O)N[C@@H](CN)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O] | (8S,11S,14S)-18-hydroxy-11-methyl-14-[methyl-[(2S)-3-amino-2-[[2-(4-tert-butylphenyl)-4,6-dimethyl-pyrimidine-5-carbonyl]amino]propanoyl]amino]-10,13-dioxo-3,17-bis[(2R)-3-amino-2-hydroxy-propoxy]-9,12-diazatricyclo[13.3.1.12,6]icosa-1(18),2(20),3,5,15(19),16-hexaene-8-carboxylic acid |
| 31 | 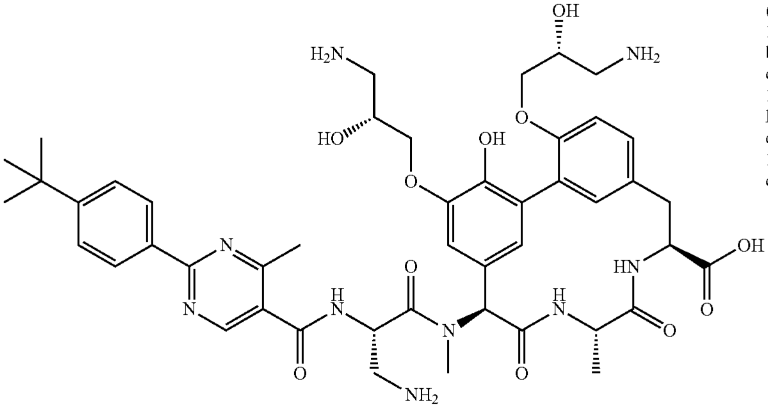 [SMILES: Cc1nc(-c2ccc(C(C)(C)C)cc2)ncc1C(=O)N[C@@H](CN)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O] | (8S,11S,14S)-18-hydroxy-11-methyl-14-[methyl-[(2S)-3-amino-2-[[2-(4-tert-butylphenyl)-4-methyl-pyrimidine-5-carbonyl]amino]propanoyl]amino]-10,13-dioxo-3,17-bis[(2R)-3-amino-2-hydroxy-propoxy]-9,12-diazatricyclo[13.3.1.12,6]icosa-1(18),2(20),3,5,15(19),16-hexaene-8-carboxylic acid |

TABLE 2-continued

| Ex. # | Structure | Name |
|---|---|---|
| 32 | 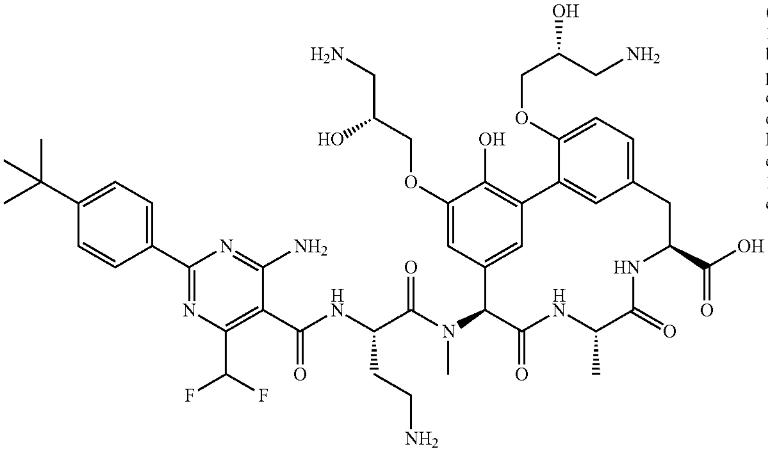 | (8S,11S,14S)-18-hydroxy-11-methyl-14-[methyl-[(2S)-4-amino-2-[[2-(4-tert-butylphenyl)-4-amino-6-difluoromethyl-pyrimidine-5-carbonyl]amino]butanoyl]amino]-10,13-dioxo-3,17-bis[(2R)-3-amino-2-hydroxy-propoxy]-9,12-diazatricyclo[13.3.1.12,6]icosa-1(18),2(20),3,5,15(19),16-hexaene-8-carboxylic acid |
| 33 | 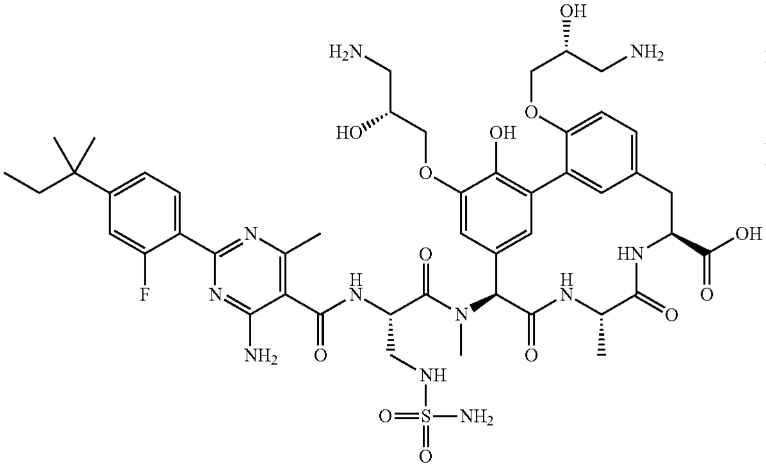 | (8S,11S,14S)-14-[[(2S)-2-[[4-amino-2-[4-(1,1-dimethylpropyl)-2-fluoro-phenyl]-6-methyl-pyrimidine-5-carbonyl]amino]-3-(sulfamoylamino)propanoyl]-methyl-amino]-3,17-bis[(2R)-3-amino-2-hydroxy-propoxy]-18-hydroxy-11-methyl-10,13-dioxo-9,12-diazatricyclo[13.3.1.12,6]icosa-1(18),2(20),3,5,15(19),16-hexaene-8-carboxylic acid |
| 34 | 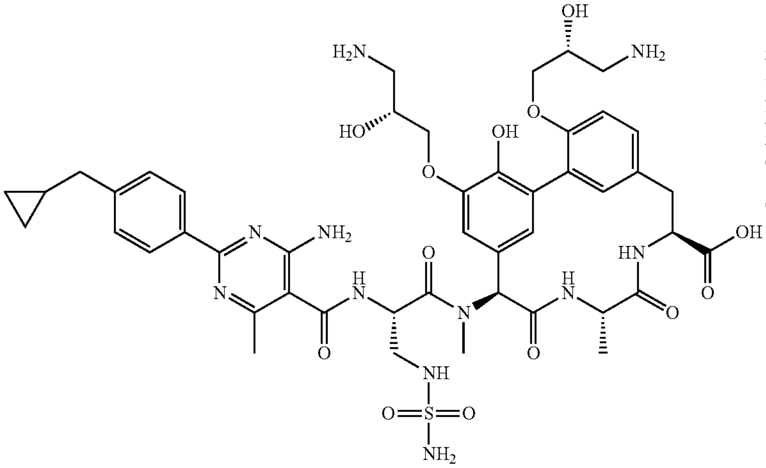 [SMILES: Cc1nc(-c2ccc(CC3CC3)cc2)nc(N)c1C(=O)N[C@@H](CNS(N)(=O)=O)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O] | (8S,11S,14S)-14-[[(2S)-2-[[4-amino-2-[4-(cyclopropylmethyl)phenyl]-6-methyl-pyrimidine-5-carbonyl]amino]-3-(sulfamoylamino)propanoyl]-methyl-amino]-3,17-bis[(2R)-3-amino-2-hydroxy-propoxy]-18-hydroxy-11-methyl-10,13-dioxo-9,12-diazatricyclo[13.3.1.12,6]icosa-1(18),2(20),3,5,15(19),16-hexaene-8-carboxylic acid |

TABLE 2-continued

| Ex. # | Structure | Name |
|---|---|---|
| 35 | 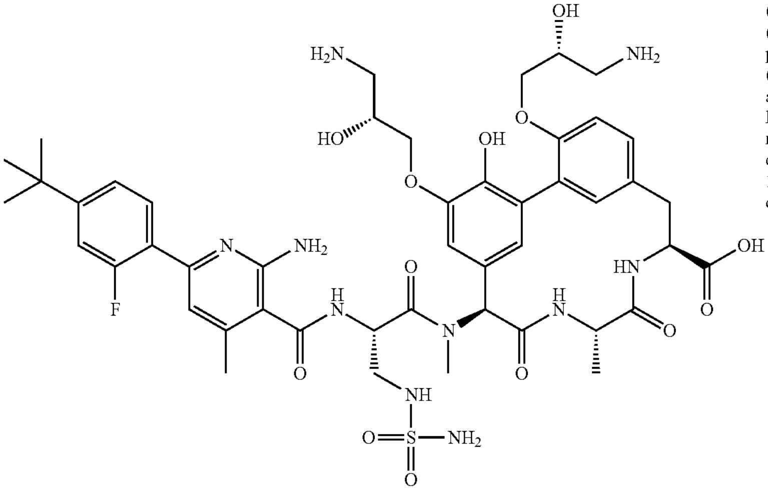 | (8S,11S,14S)-14-[[(2S)-2-[[2-amino-6-(4-tert-butyl-2-fluoro-phenyl)-4-methyl-pyridine-3-carbonyl]amino]-3-(sulfamoylamino)propanoyl]-methyl-amino]-3,17-bis[(2R)-3-amino-2-hydroxy-propoxy]-18-hydroxy-11-methyl-10,13-dioxo-9,12-diazatricyclo[13.3.1.12,6]icosa-1(18),2(20),3,5,15(19),16-hexaene-8-carboxylic acid |
| 36 | 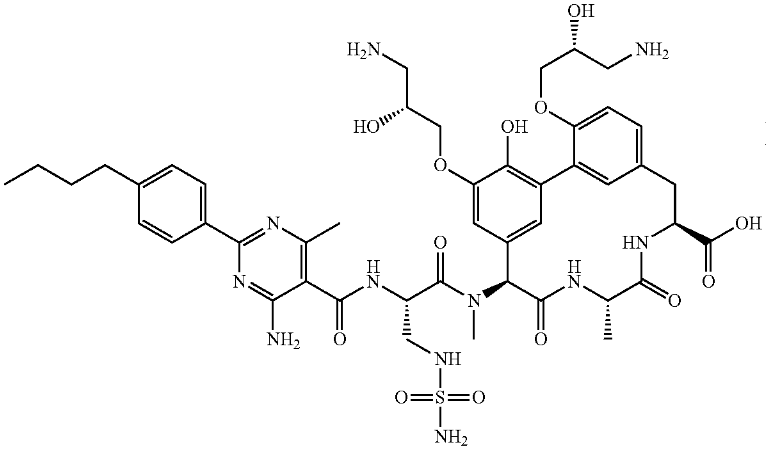 | (8S,11S,14S)-14-[[(2S)-2-[[4-amino-2-(4-butylphenyl)-6-methyl-pyrimidine-5-carbonyl]amino]-3-(sulfamoylamino)propanoyl]-methyl-amino]-3,17-bis[(2R)-3-amino-2-hydroxy-propoxy]-18-hydroxy-11-methyl-10,13-dioxo-9,12-diazatricyclo[13.3.1.12,6]icosa-1(18),2(20),3,5,15(19),16-hexaene-8-carboxylic acid |
| 37 | 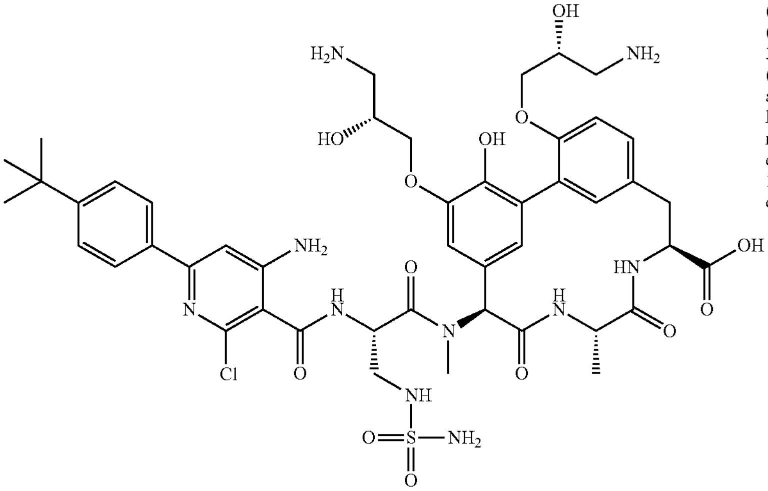 | (8S,11S,14S)-14-[[(2S)-2-[[4-amino-6-(4-tert-butylphenyl)-2-chloro-pyridine-3-carbonyl]amino]-3-(sulfamoylamino)propanoyl]-methyl-amino]-3,17-bis[(2R)-3-amino-2-hydroxy-propoxy]-18-hydroxy-11-methyl-10,13-dioxo-9,12-diazatricyclo[13.3.1.12,6]icosa-1(18),2(20),3,5,15(19),16-hexaene-8-carboxylic acid |

TABLE 2-continued

| Ex. # | Structure | Name |
|---|---|---|
| 38 | 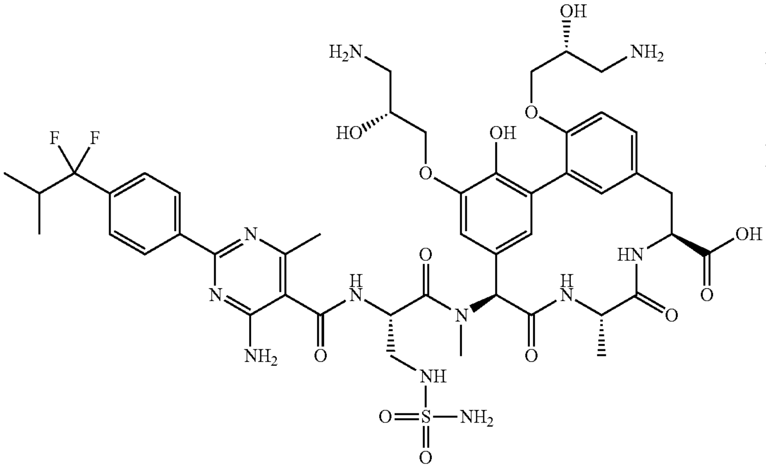 | (8S,11S,14S)-14-[[(2S)-2-[[4-amino-2-[4-(1,1-difluoro-2-methyl-propyl)phenyl]-6-methyl-pyrimidine-5-carbonyl]amino]-3-(sulfamoylamino)propanoyl]-methyl-amino]-3,17-bis[(2R)-3-amino-2-hydroxy-propoxy]-18-hydroxy-11-methyl-10,13-dioxo-9,12-diazatricyclo[13.3.1.12,6]icosa-1(18),2(20),3,5,15(19),16-hexaene-8-carboxylic acid |
| 39 | 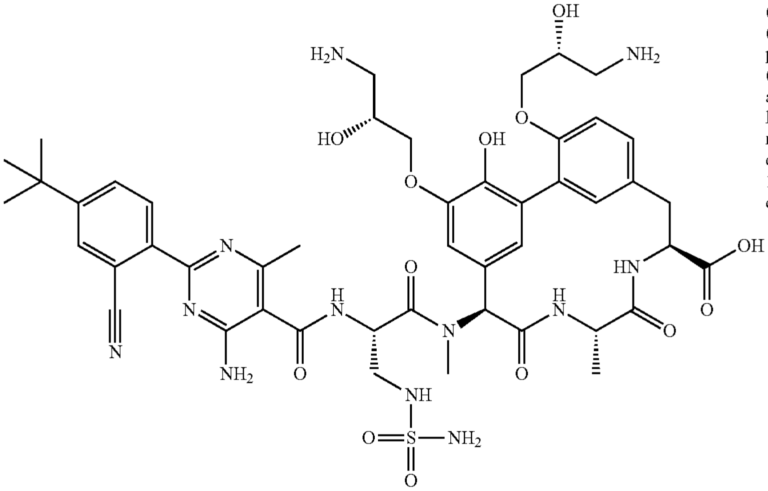 | (8S,11S,14S)-14-[[(2S)-2-[[4-amino-2-(4-tert-butyl-2-cyano-phenyl)-6-methyl-pyrimidine-5-carbonyl]amino]-3-(sulfamoylamino)propanoyl]-methyl-amino]-3,17-bis[(2R)-3-amino-2-hydroxy-propoxy]-18-hydroxy-11-methyl-10,13-dioxo-9,12-diazatricyclo[13.3.1.12,6]icosa-1(18),2(20),3,5,15(19),16-hexaene-8-carboxylic acid |
| 40 | 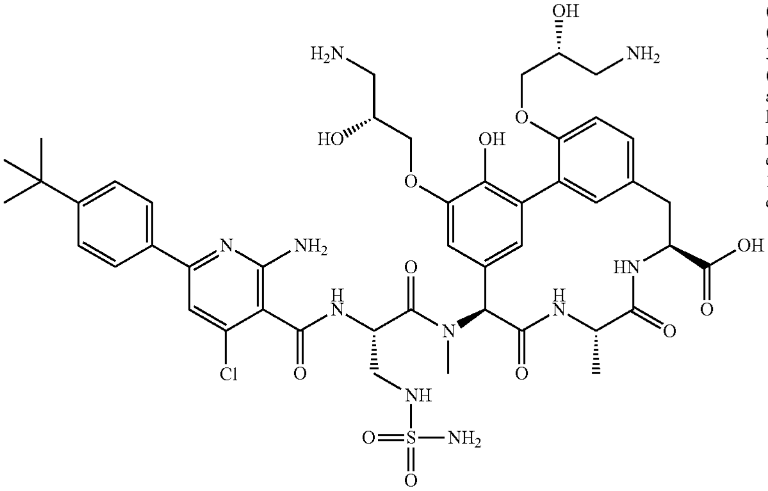 | (8S,11S,14S)-14-[[(2S)-2-[[2-amino-6-(4-tert-butylphenyl)-4-chloro-pyridine-3-carbonyl]amino]-3-(sulfamoylamino)propanoyl]-methyl-amino]-3,17-bis[(2R)-3-amino-2-hydroxy-propoxy]-18-hydroxy-11-methyl-10,13-dioxo-9,12-diazatricyclo[13.3.1.12,6]icosa-1(18),2(20),3,5,15(19),16-hexaene-8-carboxylic acid |

TABLE 2-continued

| Ex. # | Structure | Name |
| --- | --- | --- |
| 41 | 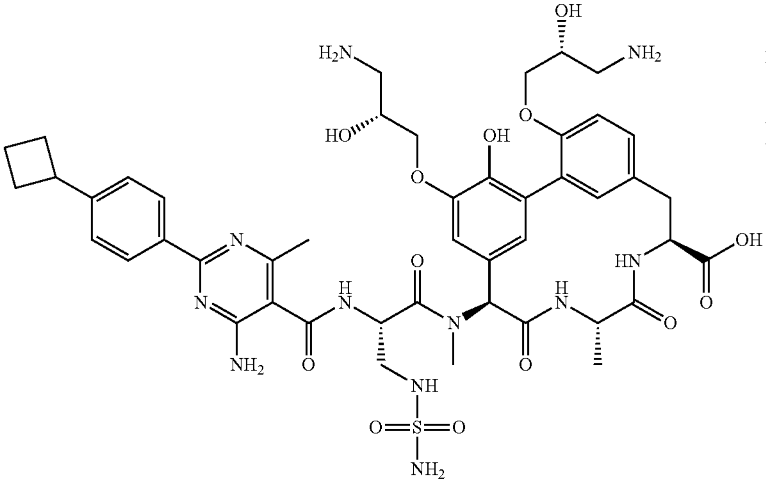 [SMILES: Cc1nc(-c2ccc(C3CCC3)cc2)nc(N)c1C(=O)N[C@@H](CNS(N)(=O)=O)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O] | (8S,11S,14S)-14-[[(2S)-2-[[4-amino-2-(4-cyclobutylphenyl)-6-methyl-pyrimidine-5-carbonyl]amino]-3-(sulfamoylamino)propanoyl]-methyl-amino]-3,17-bis[(2R)-3-amino-2-hydroxy-propoxy]-18-hydroxy-11-methyl-10,13-dioxo-9,12-diazatricyclo[13.3.1.12,6]icosa-1(18),2(20),3,5,15(19),16-hexaene-8-carboxylic acid |
| 42 | 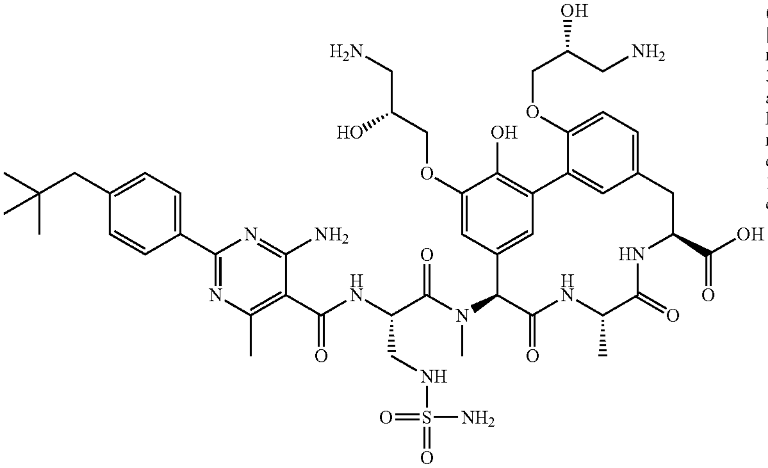 | (8S,11S,14S)-14-[[(2S)-2-[[4-amino-2-[4-(2,2-dimethylpropyl)phenyl]-6-methyl-pyrimidine-5-carbonyl]amino]-3-(sulfamoylamino)propanoyl]-methyl-amino]-3,17-bis[(2R)-3-amino-2-hydroxy-propoxy]-18-hydroxy-11-methyl-10,13-dioxo-9,12-diazatricyclo[13.3.1.12,6]icosa-1(18),2(20),3,5,15(19),16-hexaene-8-carboxylic acid |
| 43 | 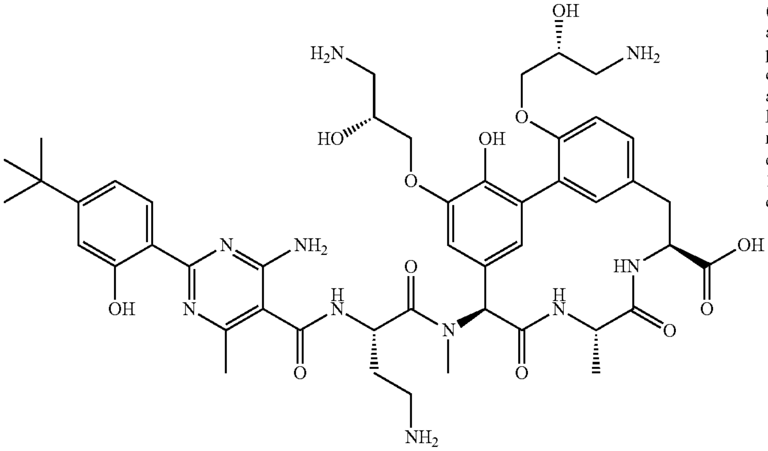 | (8S,11S,14S)-14-[[(2S)-4-amino-2-[[4-amino-2-(4-tert-butyl-2-hydroxy-phenyl)-6-methyl-pyrimidine-5-carbonyl]amino]butanoyl]-methyl-amino]-3,17-bis[(2R)-3-amino-2-hydroxy-propoxy]-18-hydroxy-11-methyl-10,13-dioxo-9,12-diazatricyclo[13.3.1.12,6]icosa-1(19),2(20),3,5,15,17-hexaene-8-carboxylic acid |

TABLE 2-continued

| Ex. # | Structure | Name |
|---|---|---|
| 44 | 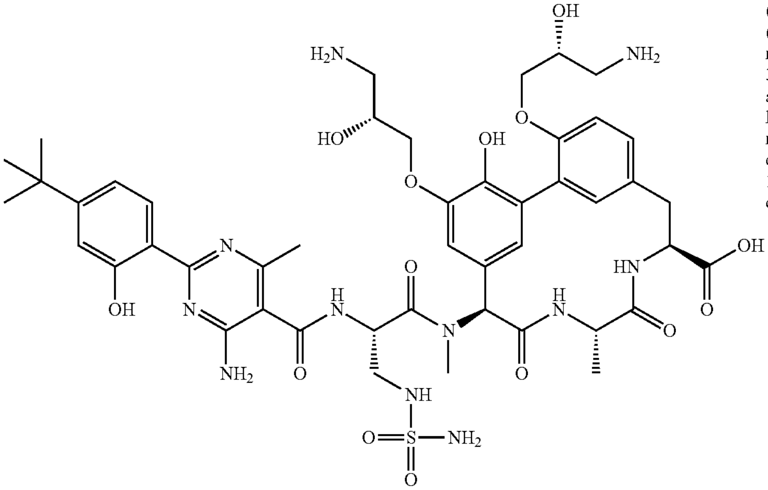 | (8S,11S,14S)-14-[[(2S)-2-[[4-amino-2-(4-tert-butyl-2-hydroxy-phenyl)-6-methyl-pyrimidine-5-carbonyl]amino]-3-(sulfamoylamino)propanoyl]-methyl-amino]-3,17-bis[(2R)-3-amino-2-hydroxy-propoxy]-18-hydroxy-11-methyl-10,13-dioxo-9,12-diazatricyclo[13.3.1.12,6]icosa-1(18),2(20),3,5,15(19),16-hexaene-8-carboxylic acid |
| 45 | 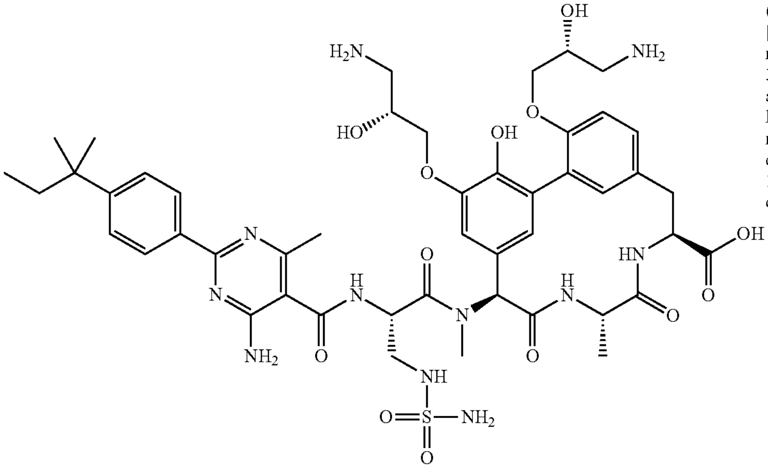 | (8S,11S,14S)-14-[[(2S)-2-[[4-amino-2-[4-(1,1-dimethylpropyl)phenyl]-6-methyl-pyrimidine-5-carbonyl]amino]-3-(sulfamoylamino)propanoyl]-methyl-amino]-3,17-bis[(2R)-3-amino-2-hydroxy-propoxy]-18-hydroxy-11-methyl-10,13-dioxo-9,12-diazatricyclo[13.3.1.12,6]icosa-1(18),2(20),3,5,15(19),16-hexaene-8-carboxylic acid |
| 46 | 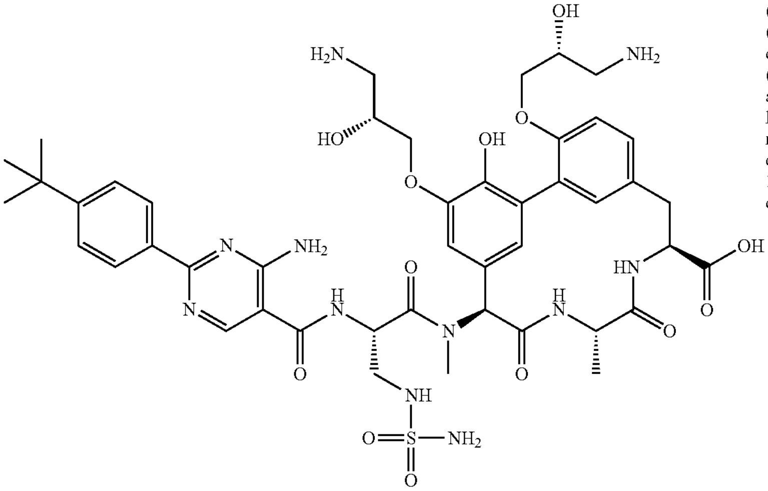 | (8S,11S,14S)-14-[[(2S)-2-[[4-amino-2-(4-tert-butylphenyl)pyrimidine-5-carbonyl]amino]-3-(sulfamoylamino)propanoyl]-methyl-amino]-3,17-bis[(2R)-3-amino-2-hydroxy-propoxy]-18-hydroxy-11-methyl-10,13-dioxo-9,12-diazatricyclo[13.3.1.12,6]icosa-1(18),2(20),3,5,15(19),16-hexaene-8-carboxylic acid |

TABLE 2-continued

| Ex. # | Structure | Name |
|---|---|---|
| 47 | 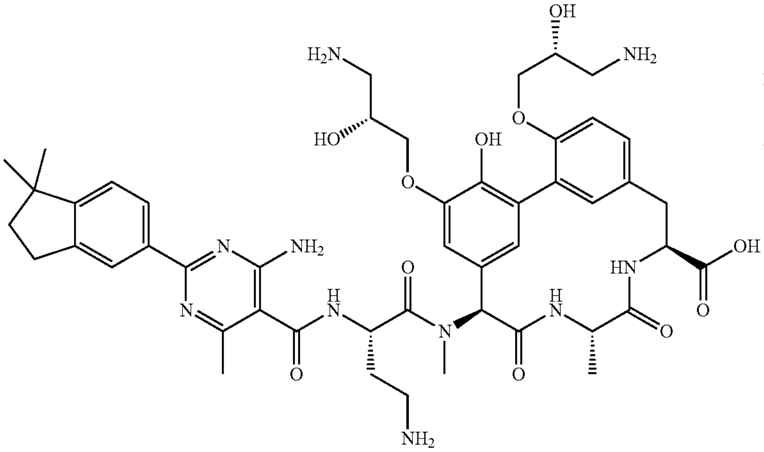 [SMILES: Cc1nc(-c2ccc3c(c2)CCC3(C)C)nc(N)c1C(=O)N[C@@H](CCN)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O] | (8S,11S,14S)-18-hydroxy-11-methyl-14-[methyl-[(2S)-4-amino-2-[[4-amino-2-(1,1-dimethylindan-5-yl)-6-methyl-pyrimidine-5-carbonyl]amino]butanoyl]amino]-10,13-dioxo-3,17-bis[(2R)-3-amino-2-hydroxy-propoxy]-9,12-diazatricyclo[13.3.1.12,6]icosa-1(18),2(20),3,5,15(19),16-hexaene-8-carboxylic acid |
| 48 | 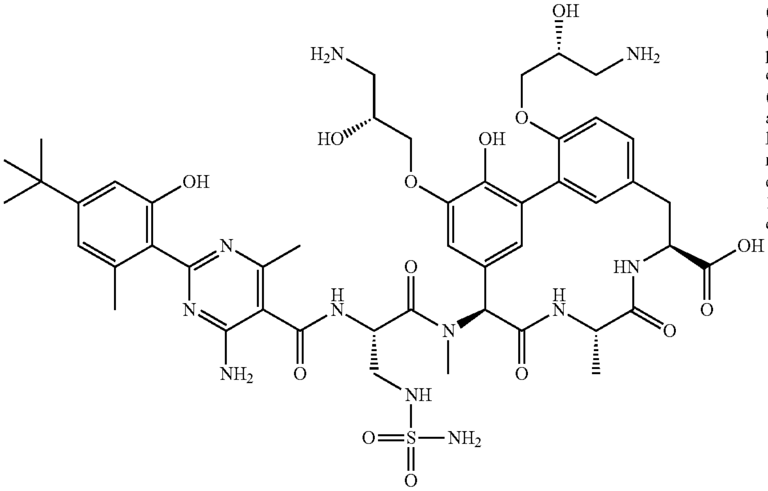 | (8S,11S,14S)-14-[[(2S)-2-[[4-amino-2-(4-tert-butyl-2-hydroxy-6-methyl-phenyl)-6-methyl-pyrimidine-5-carbonyl]amino]-3-(sulfamoylamino)propanoyl]-methyl-amino]-3,17-bis[(2R)-3-amino-2-hydroxy-propoxy]-18-hydroxy-11-methyl-10,13-dioxo-9,12-diazatricyclo[13.3.1.12,6]icosa-1(18),2(20),3,5,15(19),16-hexaene-8-carboxylic acid |
| 49 | 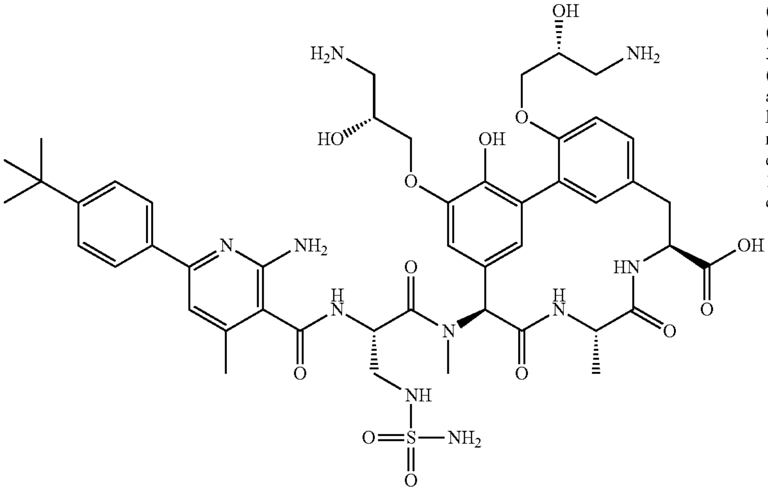 | (8S,11S,14S)-14-[[(2S)-2-[[2-amino-6-(4-tert-butylphenyl)-4-methyl-pyridine-3-carbonyl]amino]-3-(sulfamoylamino)propanoyl]-methyl-amino]-3,17-bis[(2R)-3-amino-2-hydroxy-propoxy]-18-hydroxy-11-methyl-10,13-dioxo-9,12-diazatricyclo[13.3.1.12,6]icosa-1(18),2(20),3,5,15(19),16-hexaene-8-carboxylic acid |

TABLE 2-continued

| Ex. # | Structure | Name |
|---|---|---|
| 50 | 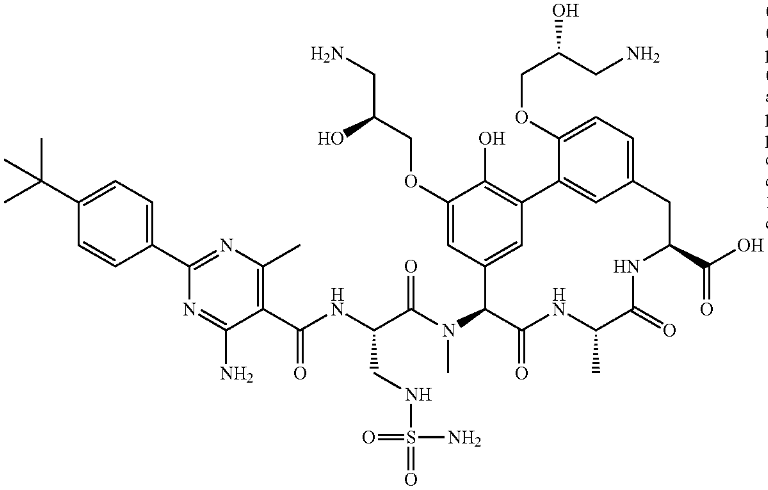 | (8S,11S,14S)-14-[[(2S)-2-[[4-amino-2-(4-tert-butylphenyl)-6-methyl-pyrimidine-5-carbonyl]amino]-3-(sulfamoylamino)propanoyl]-methyl-amino]-3-[(2R)-3-amino-2-hydroxy-propoxy]-17-[(2S)-3-amino-2-hydroxy-propoxy]-18-hydroxy-11-methyl-10,13-dioxo-9,12-diazatricyclo[13.3.1.12,6]icosa-1(19),2(20),3,5,15,17-hexaene-8-carboxylic acid |
| 51 | 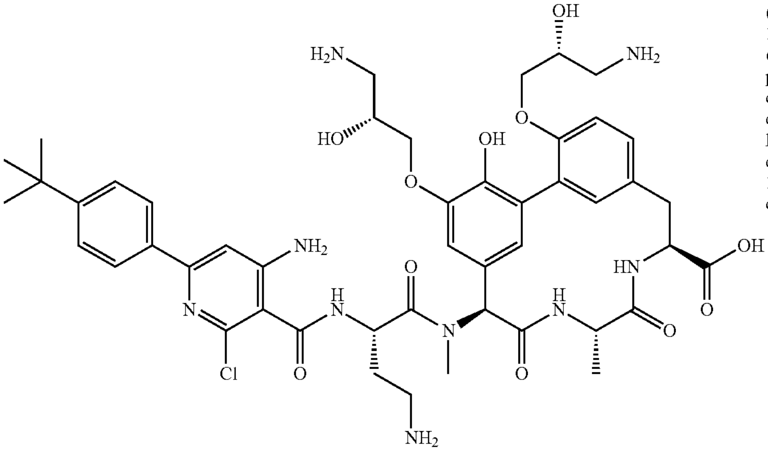 | (8S,11S,14S)-18-hydroxy-11-methyl-14-[methyl-[(2S)-4-amino-2-[[4-amino-6-(4-tert-butylphenyl)-2-chloro-pyridine-3-carbonyl]amino]butanoyl]amino]-10,13-dioxo-3,17-bis[(2R)-3-amino-2-hydroxy-propoxy]-9,12-diazatricyclo[13.3.1.12,6]icosa-1(18),2(20),3,5,15(19),16-hexaene-8-carboxylic acid |
| 52 | 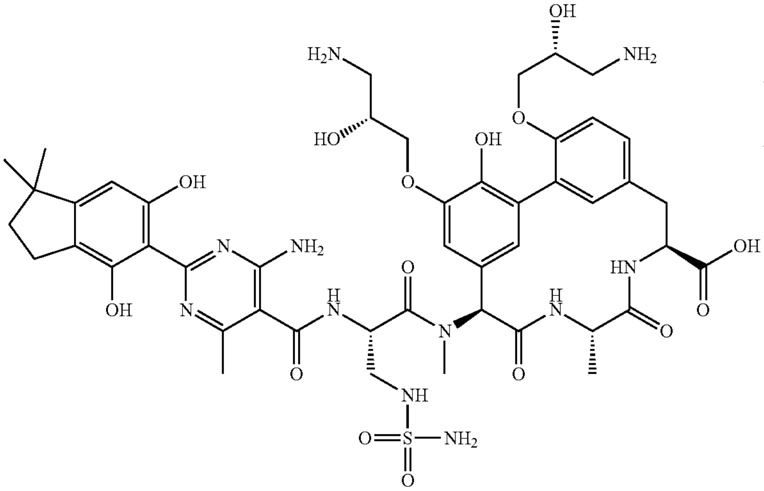 [SMILES: Cc1nc(-c2c(O)cc3c(c2O)CCC3(C)C)nc(N)c1C(=O)N[C@@H](CNS(N)(=O)=O)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O] | (8S,11S,14S)-18-hydroxy-11-methyl-14-[methyl-[(2S)-2-[[4-amino-2-(4,6-dihydroxy-1,1-dimethyl-indan-5-yl)-6-methyl-pyrimidine-5-carbonyl]amino]-3-(sulfamoylamino)propanoyl]amino]-10,13-dioxo-3,17-bis[(2R)-3-amino-2-hydroxy-propoxy]-9,12-diazatricyclo[13.3.1.12,6]icosa-1(18),2(20),3,5,15(19),16-hexaene-8-carboxylic acid |

TABLE 2-continued

| Ex. # | Structure | Name |
|---|---|---|
| 53 | 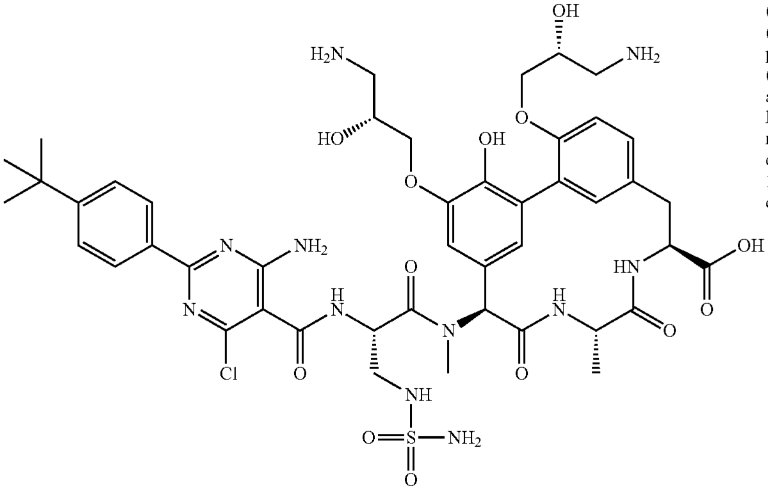 | (8S,11S,14S)-14-[[(2S)-2-[[4-amino-2-(4-tert-butylphenyl)-6-chloro-pyrimidine-5-carbonyl]amino]-3-(sulfamoylamino)propanoyl]-methyl-amino]-3,17-bis[(2R)-3-amino-2-hydroxy-propoxy]-18-hydroxy-11-methyl-10,13-dioxo-9,12-diazatricyclo[13.3.1.12,6]icosa-1(18),2(20),3,5,15(19),16-hexaene-8-carboxylic acid |
| 54 | 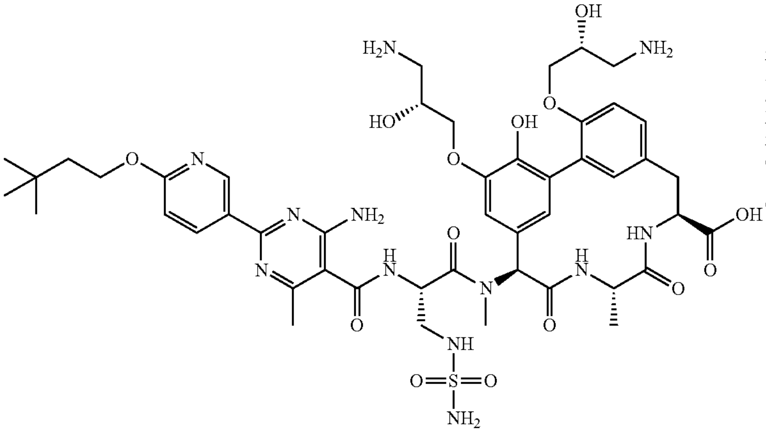 | (8S,11S,14S)-14-[[(2S)-2-[[4-amino-2-[6-(3,3-dimethylbutoxy)-3-pyridyl]-6-methyl-pyrimidine-5-carbonyl]amino]-3-(sulfamoylamino)propanoyl]-methyl-amino]-3,17-bis[(2R)-3-amino-2-hydroxy-propoxy]-18-hydroxy-11-methyl-10,13-dioxo-9,12-diazatricyclo[13.3.1.12,6]icosa-1(18),2(20),3,5,15(19),16-hexaene-8-carboxylic acid |
| 55 | 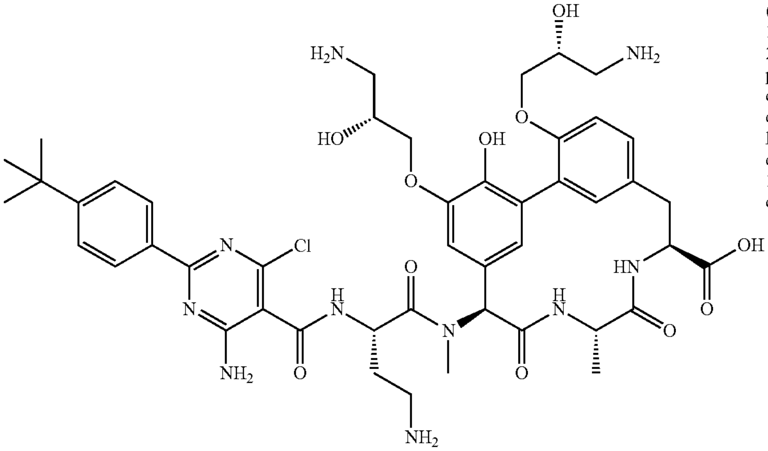 | (8S,11S,14S)-18-hydroxy-11-methyl-14-[methyl-[(2S)-4-amino-2-[[4-amino-2-(4-tert-butylphenyl)-6-chloro-pyrimidine-5-carbonyl]amino]butanoyl]amino]-10,13-dioxo-3,17-bis[(2R)-3-amino-2-hydroxy-propoxy]-9,12-diazatricyclo[13.3.1.12,6]icosa-1(18),2(20),3,5,15(19),16-hexaene-8-carboxylic acid |

TABLE 2-continued

| Ex. # | Structure | Name |
|---|---|---|
| 56 | 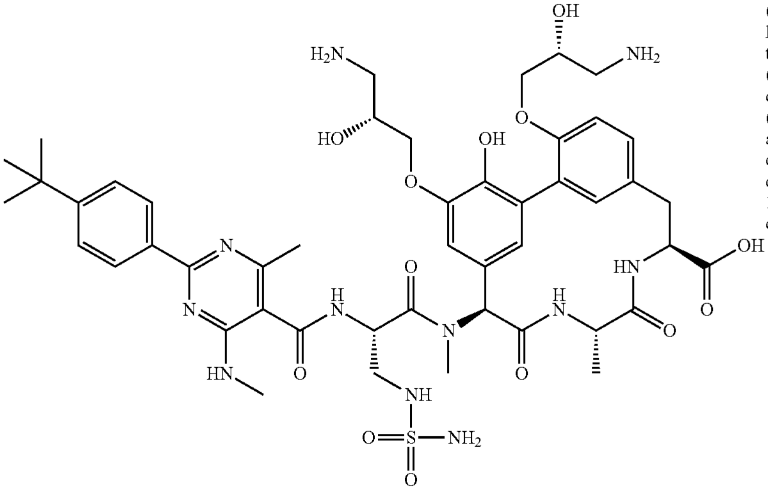 | (8S,11S,14S)-3,17-bis[(2R)-3-amino-2-hydroxy-propoxy]-14-[[(2S)-2-[[2-(4-tert-butylphenyl)-4-methyl-6-(methylamino)pyrimidine-5-carbonyl]amino]-3-(sulfamoylamino)propanoyl]-methyl-amino]-18-hydroxy-11-methyl-10,13-dioxo-9,12-diazatricyclo[13.3.1.12,6]icosa-1(18),2(20),3,5,15(19),16-hexaene-8-carboxylic acid |
| 57 | 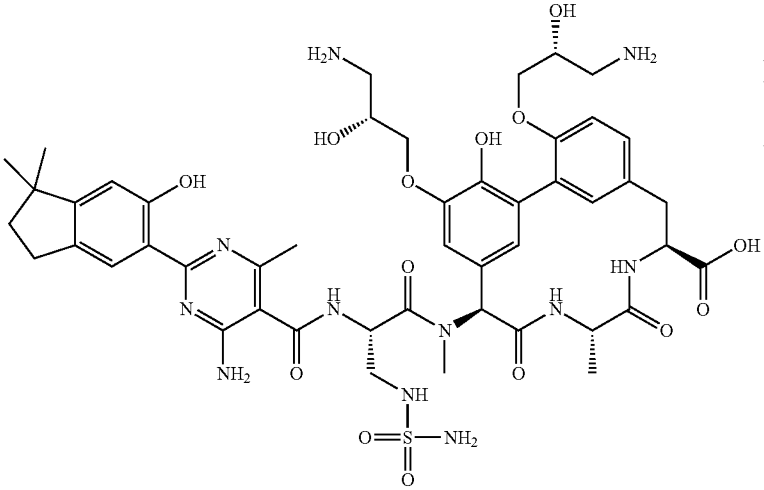 | (8S,11S,14S)-18-hydroxy-11-methyl-14-[methyl-[(2S)-2-[[4-amino-2-(6-hydroxy-1,1-dimethyl-indan-5-yl)-6-methyl-pyrimidine-5-carbonyl]amino]-3-(sulfamoylamino)propanoyl]amino]-10,13-dioxo-3,17-bis[(2R)-3-amino-2-hydroxy-propoxy]-9,12-diazatricyclo[13.3.1.12,6]icosa-1(18),2(20),3,5,15(19),16-hexaene-8-carboxylic acid |
| 58 | 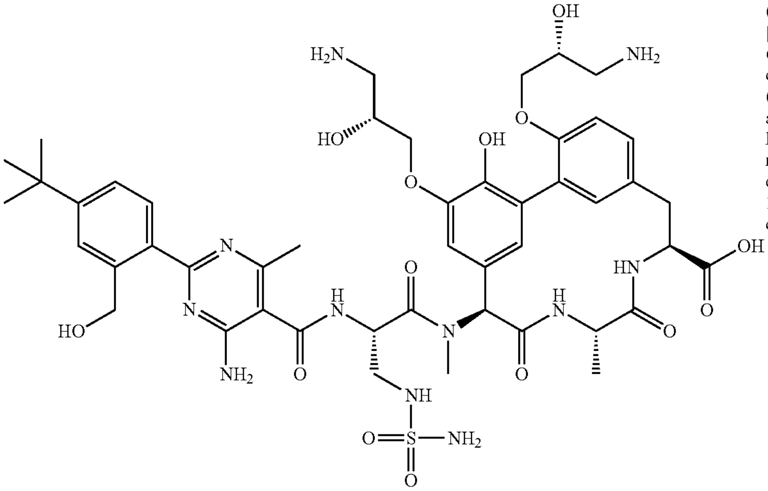 | (8S,11S,14S)-14-[[(2S)-2-[[4-amino-2-[4-tert-butyl-2-(hydroxymethyl)phenyl]-6-methyl-pyrimidine-5-carbonyl]amino]-3-(sulfamoylamino)propanoyl]-methyl-amino]-3,17-bis[(2R)-3-amino-2-hydroxy-propoxy]-18-hydroxy-11-methyl-10,13-dioxo-9,12-diazatricyclo[13.3.1.12,6]icosa-1(18),2(20),3,5,15(19),16-hexaene-8-carboxylic acid |

TABLE 2-continued

| Ex. # | Structure | Name |
| --- | --- | --- |
| 59 | 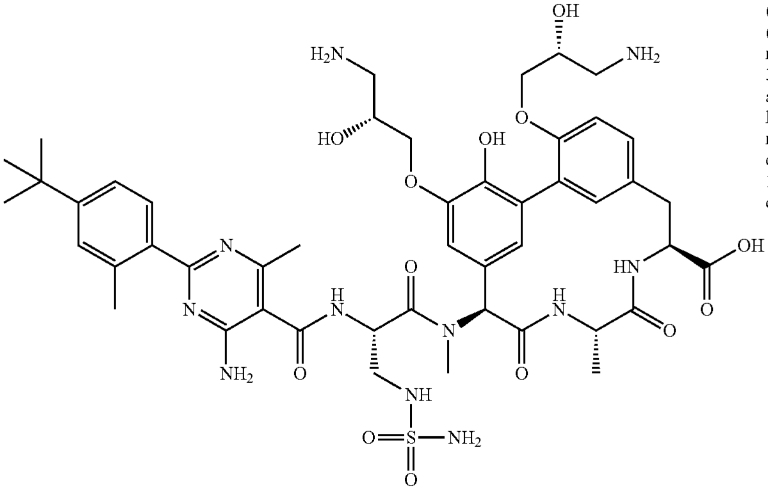 | (8S,11S,14S)-14-[[(2S)-2-[[4-amino-2-(4-tert-butyl-2-methyl-phenyl)-6-methyl-pyrimidine-5-carbonyl]amino]-3-(sulfamoylamino)propanoyl]-methyl-amino]-3,17-bis[(2R)-3-amino-2-hydroxy-propoxy]-18-hydroxy-11-methyl-10,13-dioxo-9,12-diazatricyclo[13.3.1.12,6]icosa-1(18),2(20),3,5,15(19),16-hexaene-8-carboxylic acid |
| 60 | 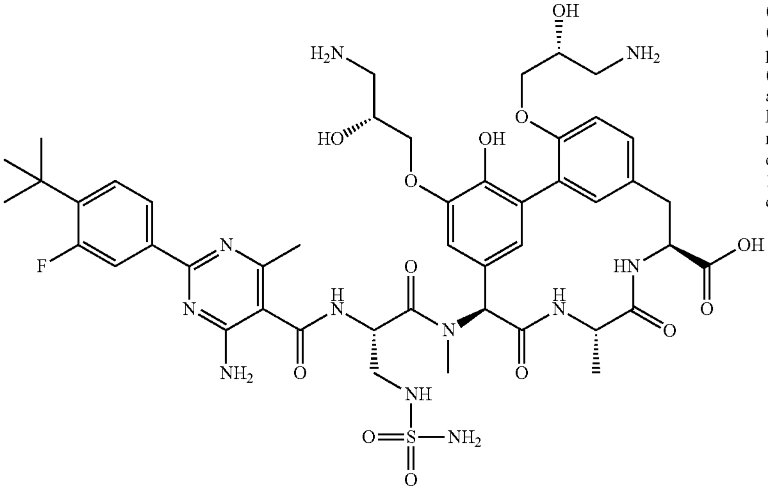 | (8S,11S,14S)-14-[[(2S)-2-[[4-amino-2-(4-tert-butyl-3-fluoro-phenyl)-6-methyl-pyrimidine-5-carbonyl]amino]-3-(sulfamoylamino)propanoyl]-methyl-amino]-3,17-bis[(2R)-3-amino-2-hydroxy-propoxy]-18-hydroxy-11-methyl-10,13-dioxo-9,12-diazatricyclo[13.3.1.12,6]icosa-1(18),2(20),3,5,15(19),16-hexaene-8-carboxylic acid |
| 61 | 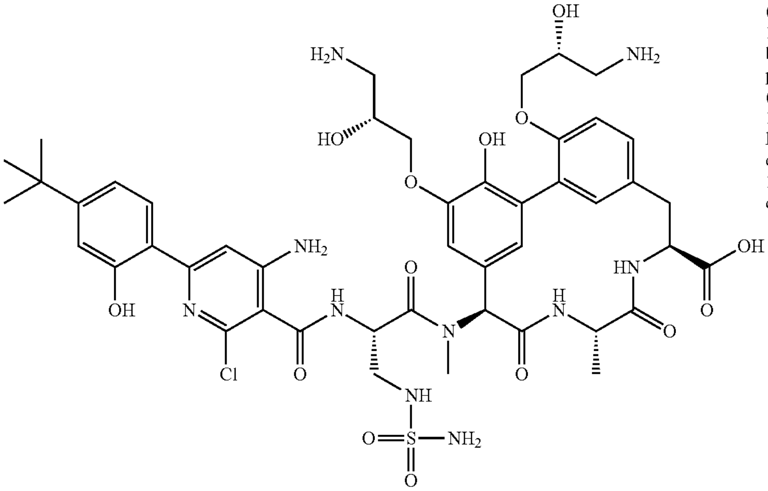 | (8S,11S,14S)-18-hydroxy-11-methyl-14-[methyl-[(2S)-2-[[4-amino-6-(4-tert-butyl-2-hydroxy-phenyl)-2-chloro-pyridine-3-carbonyl]amino]-3-(sulfamoylamino)propanoyl]amino]-10,13-dioxo-3,17-bis[(2R)-3-amino-2-hydroxy-propoxy]-9,12-diazatricyclo[13.3.1.12,6]icosa-1(18),2(20),3,5,15(19),16-hexaene-8-carboxylic acid |

TABLE 2-continued

| Ex. # | Structure | Name |
|---|---|---|
| 62 | 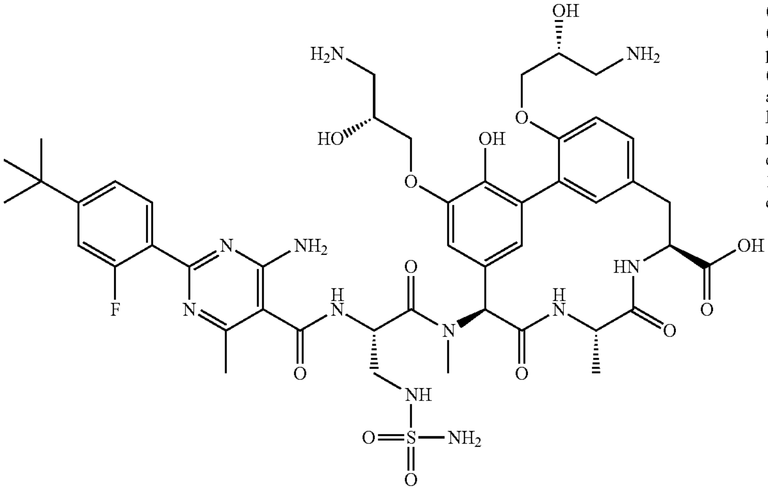 | (8S,11S,14S)-14-[[(2S)-2-[[4-amino-2-(4-tert-butyl-2-fluoro-phenyl)-6-methyl-pyrimidine-5-carbonyl]amino]-3-(sulfamoylamino)propanoyl]-methyl-amino]-3,17-bis[(2R)-3-amino-2-hydroxy-propoxy]-18-hydroxy-11-methyl-10,13-dioxo-9,12-diazatricyclo[13.3.1.12,6]icosa-1(18),2(20),3,5,15(19),16-hexaene-8-carboxylic acid |
| 63 | 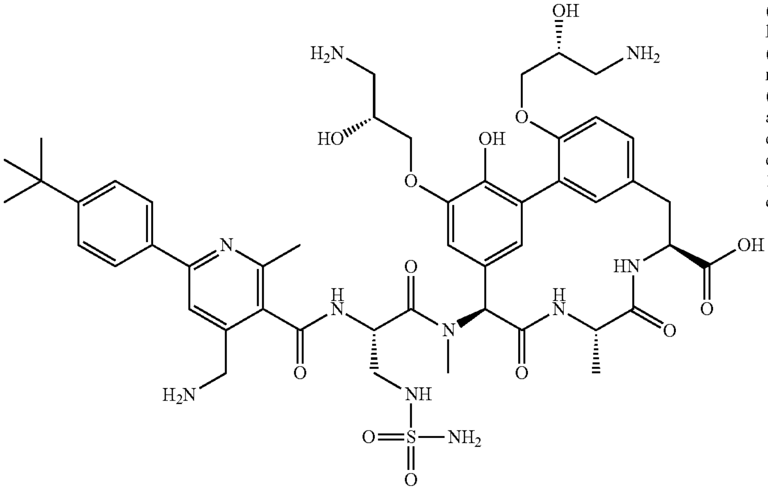 | (8S,11S,14S)-3,17-bis[(2R)-3-amino-2-hydroxy-propoxy]-14-[[(2S)-2-[[4-(aminomethyl)-6-(4-tert-butylphenyl)-2-methyl-pyridine-3-carbonyl]amino]-3-(sulfamoylamino)propanoyl]-methyl-amino]-18-hydroxy-11-methyl-10,13-dioxo-9,12-diazatricyclo[13.3.1.12,6]icosa-1(18),2(20),3,5,15(19),16-hexaene-8-carboxylic acid |
| 64 | 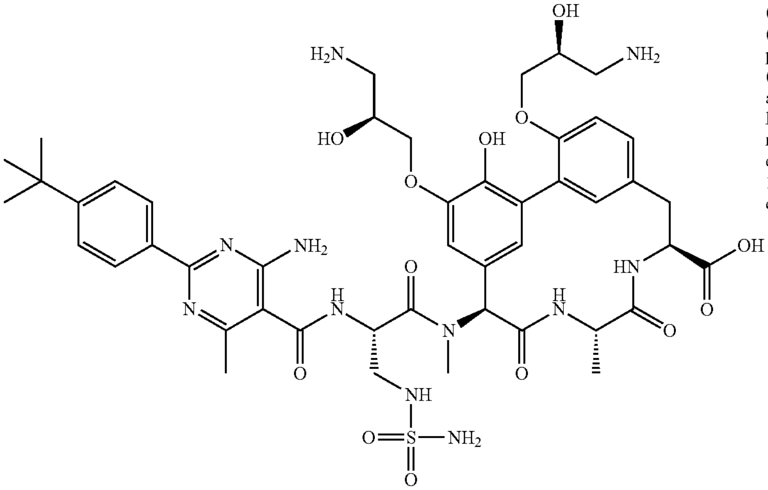 | (8S,11S,14S)-14-[[(2S)-2-[[4-amino-2-(4-tert-butylphenyl)-6-methyl-pyrimidine-5-carbonyl]amino]-3-(sulfamoylamino)propanoyl]-methyl-amino]-3,17-bis[(2S)-3-amino-2-hydroxy-propoxy]-18-hydroxy-11-methyl-10,13-dioxo-9,12-diazatricyclo[13.3.1.12,6]icosa-1(18),2(20),3,5,15(19),16-hexaene-8-carboxylic acid |

TABLE 2-continued

| Ex. # | Structure | Name |
| --- | --- | --- |
| 65 | 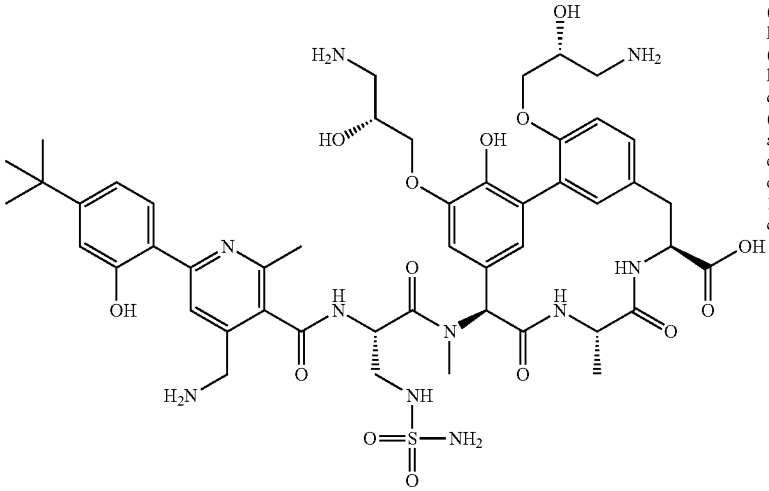 | (8S,11S,14S)-3,17-bis[(2R)-3-amino-2-hydroxy-propoxy]-14-[[(2S)-2-[[4-(aminomethyl)-6-(4-tert-butyl-2-hydroxy-phenyl)-2-methyl-pyridine-3-carbonyl]amino]-3-(sulfamoylamino)propanoyl]-methyl-amino]-18-hydroxy-11-methyl-10,13-dioxo-9,12-diazatricyclo[13.3.1.12,6]icosa-1(19),2(20),3,5,15,17-hexaene-8-carboxylic acid |
| 66 | 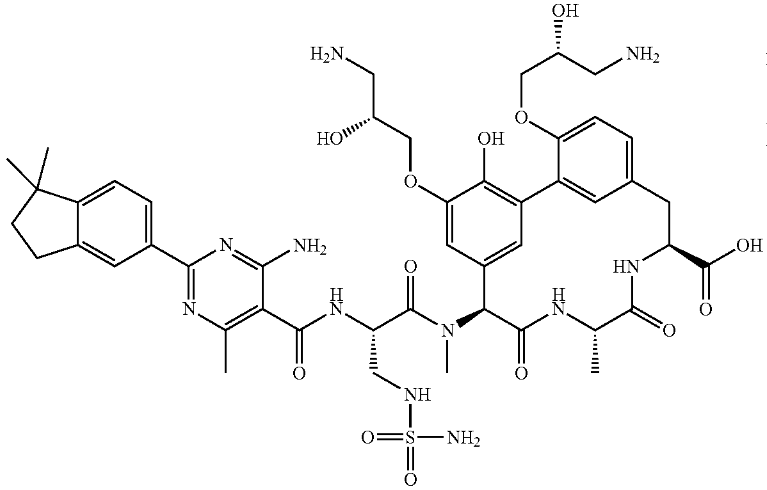 | (8S,11S,14S)-14-[[(2S)-2-[[4-amino-2-(1,1-dimethylindan-5-yl)-6-methyl-pyrimidine-5-carbonyl]amino]-3-(sulfamoylamino)propanoyl]-methyl-amino]-3,17-bis[(2R)-3-amino-2-hydroxy-propoxy]-18-hydroxy-11-methyl-10,13-dioxo-9,12-diazatricyclo[13.3.1.12,6]icosa-1(18),2(20),3,5,15(19),16-hexaene-8-carboxylic acid |
| 67 | 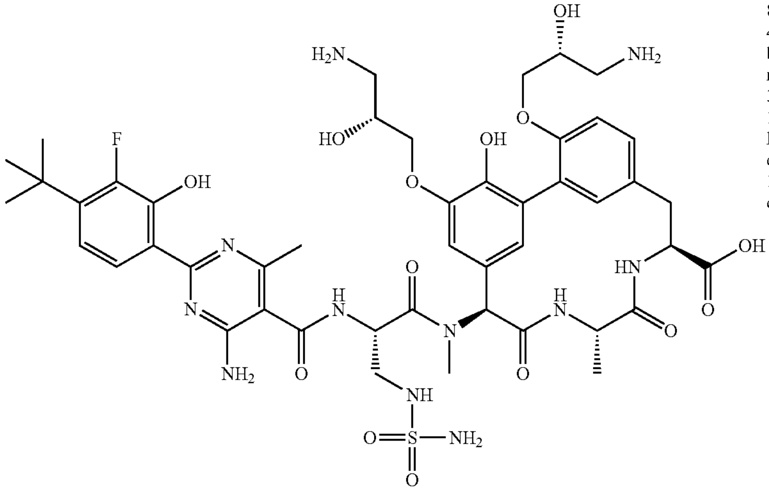 | 8S,11S,14S)-18-hydroxy-11-methyl-4-[methyl-[(2S)-2-[[4-amino-2-(4-tert-butyl-3-fluoro-2-hydroxy-phenyl)-6-methyl-pyrimidine-5-carbonyl]amino]-3-(sulfamoylamino)propanoyl]amino]-10,13-dioxo-3,17-bis[(2R)-3-amino-2-hydroxy-propoxy]-9,12-diazatricyclo[13.3.1.12,6]icosa-1(18),2(20),3,5,15(19),16-hexaene-8-carboxylic acid |

TABLE 2-continued

| Ex. # | Structure | Name |
|---|---|---|
| 68 | 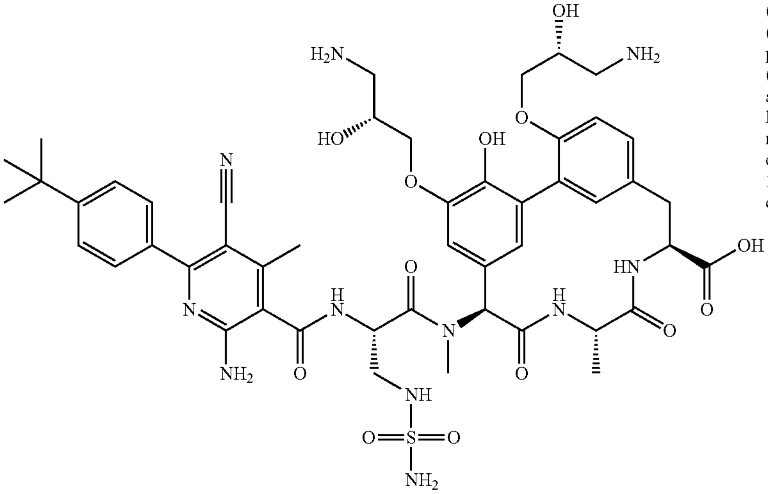 [SMILES: Cc1c(C#N)c(-c2ccc(C(C)(C)C)cc2)nc(N)c1C(=O)N[C@@H](CNS(N)(=O)=O)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O] | (8S,11S,14S)-14-[[(2S)-2-[[2-amino-6-(4-tert-butylphenyl)-5-cyano-4-methyl-pyridine-3-carbonyl]amino]-3-(sulfamoylamino)propanoyl]-methyl-amino]-3,17-bis[(2R)-3-amino-2-hydroxy-propoxy]-18-hydroxy-11-methyl-10,13-dioxo-9,12-diazatricyclo[13.3.1.12,6]icosa-1(19),2(20),3,5,15,17-hexaene-8-carboxylic acid |
| 69 | 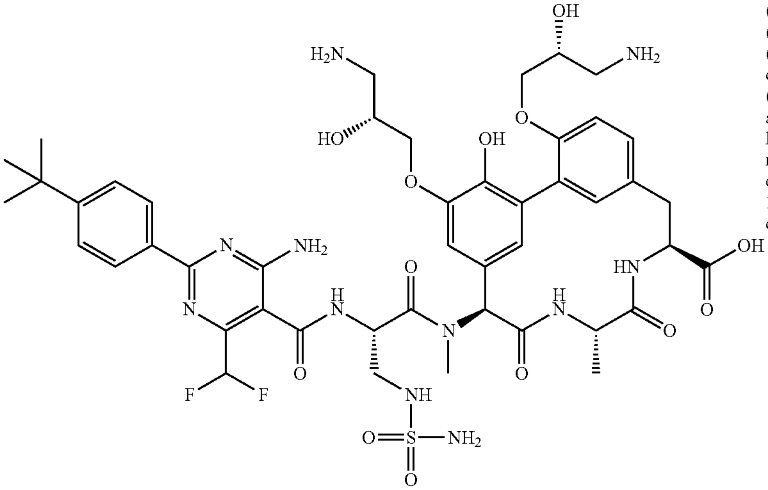 | (8S,11S,14S)-14-[[(2S)-2-[[4-amino-2-(4-tert-butylphenyl)-6-(difluoromethyl)pyrimidine-5-carbonyl]amino]-3-(sulfamoylamino)propanoyl]-methyl-amino]-3,17-bis[(2R)-3-amino-2-hydroxy-propoxy]-18-hydroxy-11-methyl-10,13-dioxo-9,12-diazatricyclo[13.3.1.12,6]icosa-1(18),2(20),3,5,15(19),16-hexaene-8-carboxylic acid |
| 70 | 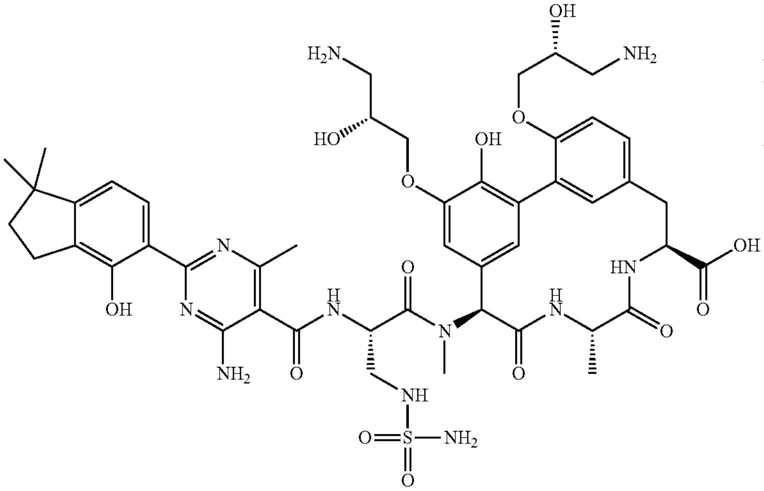 [SMILES: Cc1nc(-c2ccc3c(c2O)CCC3(C)C)nc(N)c1C(=O)N[C@@H](CNS(N)(=O)=O)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O] | (8S,11S,14S)-18-hydroxy-11-methyl-14-[methyl-[(2S)-2-[[4-amino-2-(4-hydroxy-1,1-dimethyl-indan-5-yl)-6-methyl-pyrimidine-5-carbonyl]amino]-3-(sulfamoylamino)propanoyl]amino]-10,13-dioxo-3,17-bis[(2R)-3-amino-2-hydroxy-propoxy]-9,12-diazatricyclo[13.3.1.12,6]icosa-1(18),2(20),3,5,15(19),16-hexaene-8-carboxylic acid |

TABLE 2-continued

| Ex. # | Structure | Name |
|---|---|---|
| 71 | 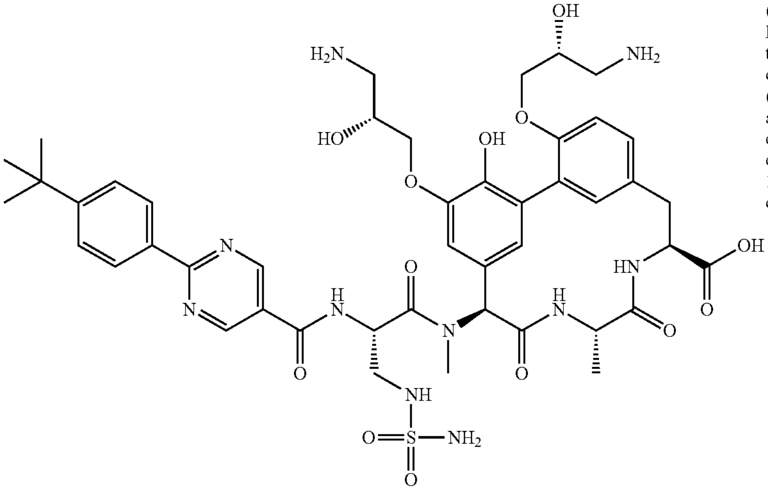 | (8S,11S,14S)-3,17-bis[(2R)-3-amino-2-hydroxy-propoxy]-14-[[(2S)-2-[[2-(4-tert-butylphenyl)pyrimidine-5-carbonyl]amino]-3-(sulfamoylamino)propanoyl]-methyl-amino]-18-hydroxy-11-methyl-10,13-dioxo-9,12-diazatricyclo[13.3.1.12,6]icosa-1(18),2(20),3,5,15(19),16-hexaene-8-carboxylic acid |
| 72 | 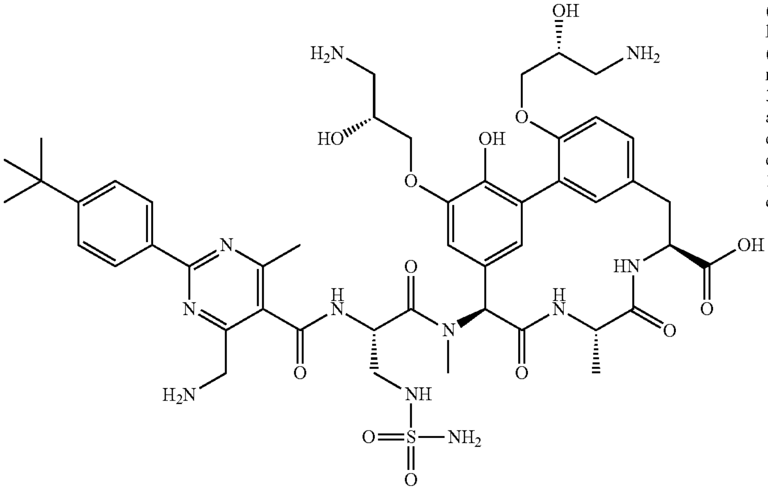 | (8S,11S,14S)-3,17-bis[(2R)-3-amino-2-hydroxy-propoxy]-14-[[(2S)-2-[[4-(aminomethyl)-2-(4-tert-butylphenyl)-6-methyl-pyrimidine-5-carbonyl]amino]-3-(sulfamoylamino)propanoyl]-methyl-amino]-18-hydroxy-11-methyl-10,13-dioxo-9,12-diazatricyclo[13.3.1.12,6]icosa-1(18),2(20),3,5,15(19),16-hexaene-8-carboxylic acid |
| 73 | 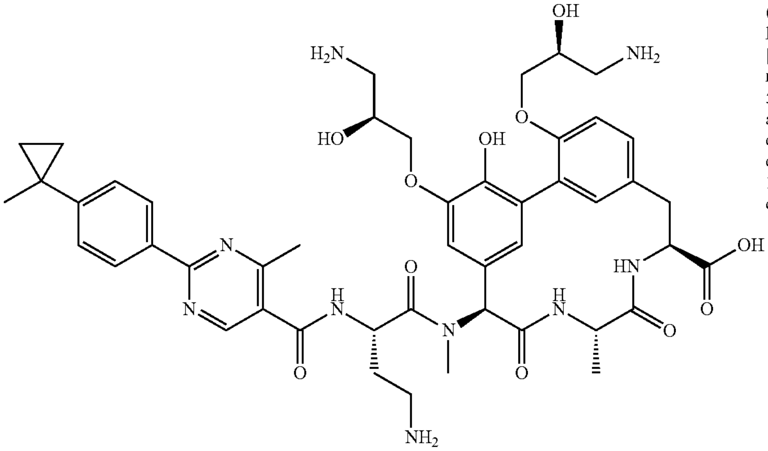 [SMILES: Cc1nc(-c2ccc(C3(C)CC3)cc2)ncc1C(=O)N[C@@H](CCN)C(=O)N(C)[C@@H]1C(=O)N[C@@H](C)C(=O)N[C@H](C(=O)O)Cc2ccc(OC[C@@H](O)CN)c(c2)-c2cc1cc(OC[C@@H](O)CN)c2O] | (8S,11S,14S)-3,17-bis[(2S)-3-amino-2-hydroxy-propoxy]-14-[[(2S)-4-amino-2-[[4-methyl-2-[4-(1-methylcyclopropyl)phenyl]pyrimidine-5-carbonyl]amino]butanoyl]-methyl-amino]-18-hydroxy-11-methyl-10,13-dioxo-9,12-diazatricyclo[13.3.1.12,6]icosa-1(19),2(20),3,5,15,17-hexaene-8-carboxylic acid |

TABLE 2-continued

| Ex. # | Structure | Name |
|---|---|---|
| 74 | 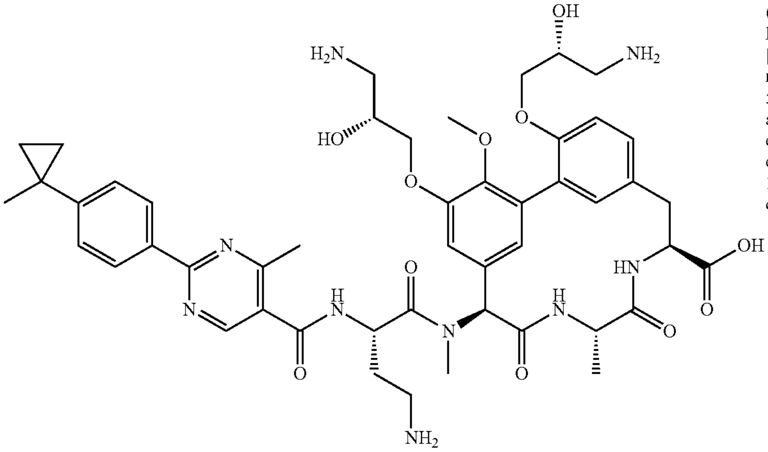 [SMILES: COc1c(OC[C@H](O)CN)cc2cc1-c1cc(ccc1OC[C@H](O)CN)C[C@@H](C(=O)O)NC(=O)[C@H](C)NC(=O)[C@H]2N(C)C(=O)[C@H](CCN)NC(=O)c1cnc(-c2ccc(C3(C)CC3)cc2)nc1C] | (8S,11S,14S)-3,17-bis[(2R)-3-amino-2-hydroxy-propoxy]-14-[[(2S)-4-amino-2-[[4-methyl-2-[4-(1-methylcyclopropyl)phenyl]pyrimidine-5-carbonyl]amino]butanoyl]-methyl-amino]-18-methoxy-11-methyl-10,13-dioxo-9,12-diazatricyclo[13.3.1.12,6]icosa-1(18),2(20),3,5,15(19),16-hexaene-8-carboxylic acid |
| 75 | 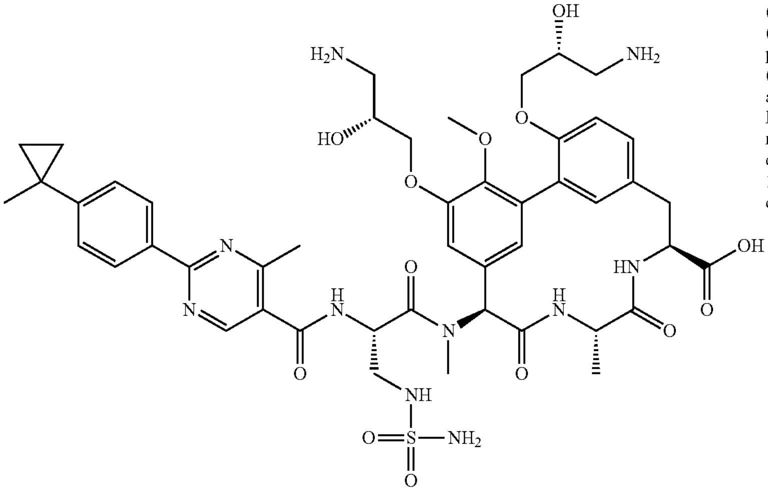 | (8S,11S,14S)-14-[[(2S)-2-[[4-amino-2-(4-tert-butylphenyl)-6-methyl-pyrimidine-5-carbonyl]amino]-3-(sulfamoylamino)propanoyl]-methyl-amino]-3,17-bis[(2R)-3-amino-2-hydroxy-propoxy]-18-methoxy-11-methyl-10,13-dioxo-9,12-diazatricyclo[13.3.1.12,6]icosa-1(18),2(20),3,5,15(19),16-hexaene-8-carboxylic acid |
| 76 | 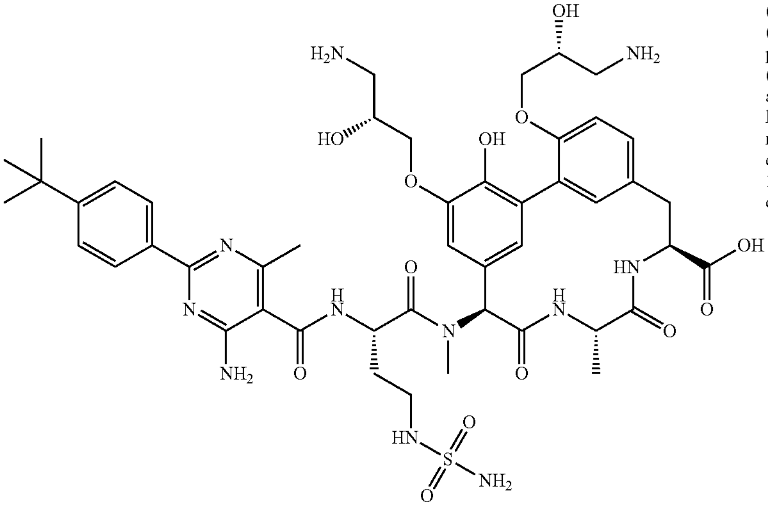 [SMILES: Cc1nc(-c2ccc(C(C)(C)C)cc2)nc(N)c1C(=O)N[C@@H](CCNS(N)(=O)=O)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O] | (8S,11S,14S)-14-[[(2S)-2-[[4-amino-2-(4-tert-butylphenyl)-6-methyl-pyrimidine-5-carbonyl]amino]-4-(sulfamoylamino)butanoyl]-methyl-amino]-3,17-bis[(2R)-3-amino-2-hydroxy-propoxy]-18-hydroxy-11-methyl-10,13-dioxo-9,12-diazatricyclo[13.3.1.12,6]icosa-1(18),2(20),3,5,15(19),16-hexaene-8-carboxylic acid |

In some embodiments, the compound of Formula (I), (Ia), or (Ib) is a compound, or a pharmaceutically acceptable salt, solvate, or stereoisomer thereof, wherein the compound is (8S,11S,14S)-18-hydroxy-11-methyl-14-[methyl-[(2S)-2-[[4-amino-2-(4-tert-butylphenyl)-6-methyl-pyrimidine-5-carbonyl]amino]-3-(sulfamoylamino)propanoyl]amino]-10,13-dioxo-3,17-bis[(2R)-3-amino-2-hydroxy-propoxy]-9,12-diazatricyclo[13.3.1.12,6]icosa-1(18),2(20),3,5,15(19),16-hexaene-8-carboxylic acid.

In some embodiments, the compound of Formula (I), (Ia), or (Ib) is a compound, or a pharmaceutically acceptable salt, solvate, or stereoisomer thereof, wherein the compound is (8S,11S,14S)-18-hydroxy-11-methyl-14-[methyl-[(2S)-2-[[4-methyl-2-[4-(1-methylcyclopropyl)phenyl]pyrimidine-5-carbonyl]amino]-3-(sulfamoylamino)propanoyl]amino]-10,13-dioxo-3,17-bis[(2R)-3-amino-2-hydroxy-propoxy]-9,12-diazatricyclo[13.3.1.12,6]icosa-1(18),2(20),3,5,15(19),16-hexaene-8-carboxylic acid.

In some embodiments, the compound of Formula (I), (Ia), or (Ib) is a compound, or a pharmaceutically acceptable salt, solvate, or stereoisomer thereof, wherein the compound is (8S,11S,14S)-18-hydroxy-11-methyl-14-[methyl-[(2S)-4-amino-2-[[4-amino-2-(4-tert-butylphenyl)-6-methyl-pyrimidine-5-carbonyl]amino]butanoyl]amino]-10,13-dioxo-3,17-bis[(2R)-3-amino-2-hydroxy-propoxy]-9,12-diazatricyclo[13.3.1.12,6]icosa-1(18),2(20),3,5,15(19),16-hexaene-8-carboxylic acid.

In some embodiments, the compound of Formula (I), (Ia), or (Ib) is a compound, or a pharmaceutically acceptable salt, solvate, or stereoisomer thereof, wherein the compound is (8S,11S,14S)-18-hydroxy-11-methyl-14-[methyl-[(2S)-4-amino-2-[[4-methyl-2-[4-(1-methylcyclopropyl)phenyl]pyrimidine-5-carbonyl]amino]butanoyl]amino]-10,13-dioxo-3,17-bis[(2R)-3-amino-2-hydroxy-propoxy]-9,12-diazatricyclo[13.3.1.12,6]icosa-1(18),2(20),3,5,15(19),16-hexaene-8-carboxylic acid.

In some embodiments, the compound of Formula (I), (Ia), or (Ib) is a compound, or a pharmaceutically acceptable salt, solvate, or stereoisomer thereof, wherein the compound is (8S,11S,14S)-18-hydroxy-11-methyl-14-[methyl-[(2S)-4-amino-2-[[2-(4-tert-butylphenyl)-4-amino-6-difluoromethyl-pyrimidine-5-carbonyl]amino]butanoyl]amino]-10,13-dioxo-3,17-bis[(2R)-3-amino-2-hydroxy-propoxy]-9,12-diazatricyclo[13.3.1.12,6]icosa-1(18),2(20),3,5,15(19),16-hexaene-8-carboxylic acid.

In some embodiments, the compound of Formula (I), (Ia), or (Ib) is a compound, or a pharmaceutically acceptable salt, solvate, or stereoisomer thereof, wherein the compound is (8S,11S,14S)-14-[[(2S)-2-[[4-amino-2-(4-tert-butylphenyl)-6-(difluoromethyl)pyrimidine-5-carbonyl]amino]-3-(sulfamoylamino)propanoyl]-methyl-amino]-3,17-bis[(2R)-3-amino-2-hydroxy-propoxy]-18-hydroxy-11-methyl-10,13-dioxo-9,12-diazatricyclo[13.3.1.12,6]icosa-1(18),2(20),3,5,15(19),16-hexaene-8-carboxylic acid.

In some embodiments, the compound of Formula (I), (Ia), or (Ib) is in the form of a prodrug. Some embodiments include a prodrug of the compound of Formula (I), (Ia), or (Ib), which is converted to an active form through other mechanisms in vivo. In some embodiments, the compounds of the invention are prodrugs of any of the formulae herein.

Further Forms of Compounds Disclosed Herein

Isomers/Stereoisomers

In some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred. In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds described herein, or a solvate, or stereoisomer thereof, include isotopes of hydrogen, carbon, nitrogen, oxygen, phosphorous, sulfur, fluorine, and chloride, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Certain isotopically-labeled compounds, for example those into which radioactive isotopes such as $^{3}H$ and $^{14}C$ are incorporated, are useful in drug and/or substrate tissue distribution assays. Tritiated, i.e., $^{3}H$ and carbon-14, i.e., $^{14}C$, isotopes are particularly preferred for their ease of preparation and detectability. Further, substitution with heavy isotopes such as deuterium, i.e., $^{2}H$, produces certain therapeutic advantages resulting from greater metabolic stability, for example increased in vivo half-life or reduced dosage requirements. In some embodiments, the isotopically labeled compound or a pharmaceutically acceptable salt, solvate, or stereoisomer thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefor react with any of a number of inorganic or organic bases, and inorganic and organic acids, to form a pharmaceutically acceptable salt. In some embodiments, these salts are prepared in situ during the final isolation and purification of the compounds disclosed herein, or by separately reacting a purified compound in its free form with a suitable acid or base, and isolating the salt thus formed.

Examples of pharmaceutically acceptable salts include those salts prepared by reaction of the compounds described herein with a mineral, organic acid, or inorganic base, such salts including acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylateundeconate, and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid.

In some embodiments, those compounds described herein which comprise a free acid group react with a suitable base, such as the hydroxide, carbonate, bicarbonate, sulfate, of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts and the like. Illustrative examples of bases include sodium hydroxide, potassium hydroxide, choline hydroxide, sodium carbonate, $N^+(C_{1-4}\text{ alkyl})_4$, and the like.

Representative organic amines useful for the formation of base addition salts include ethylamine, diethylamine, ethylenediamine, ethanolamine, diethanolamine, piperazine, and the like. It should be understood that the compounds described herein also include the quaternization of any basic nitrogen-containing groups they contain. In some embodiments, water or oil-soluble or dispersible products are obtained by such quaternization.

Solvates

In some embodiments, the compounds described herein exist as solvates. The disclosure provides for methods of treating diseases by administering such solvates. The disclosure further provides for methods of treating diseases by administering such solvates as pharmaceutical compositions. Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. By way of example only, hydrates of the compounds described herein can be conveniently prepared by recrystallization from an aqueous/organic solvent mixture, using organic solvents including, but not limited to, dioxane, tetrahydrofuran, or methanol. In addition, the compounds provided herein can exist in unsolvated as well as solvated forms. In general, the solvated forms are considered equivalent to the unsolvated forms for the purposes of the compounds and methods provided herein.

Tautomers

In some situations, compounds exist as tautomers. The compounds described herein include all possible tautomers within the formulas described herein. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH.

In another aspect are hydrates or metabolites of any of the aforementioned compounds. In another aspect are pharmaceutical compositions comprising any of the aforementioned compounds together with a pharmaceutically acceptable excipient.

In another aspect described herein is the use of a compound described herein in the manufacture of a medicament for treatment of a bacterial infection in a patient.

In another aspect are methods of treating a mammal in need of such treatment comprising administering to the mammal an antibacterial effective amount of any of the aforementioned compounds at a frequency and for a duration sufficient to provide a beneficial effect to the mammal. In one embodiment, the mammal has a bacteria-related infection that is resistant to treatment with arylomycin A2. In a further embodiment, the causative bacteria species of the bacteria infection is an infection involving *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmo-*

*nella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides* 3452A homology group, *Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis*, or *Staphylococcus* saccharolyticus.

In another embodiment the bacterial infection is an infection involving a Gram-negative bacteria. In such embodiments, the gram-negative bacteria may be, for example, *Escheria coli, Klebsiella pneumoniae, Pseudomonas aeruginosa, Acinetobacter baumanii, Neisseria gonorrhoeae, Neisseria meningitidis, Chlamydia trachomatis, Moraxella catarrhalis, Haemophilus influenzae, Proteus mirabilis, Enterobacter cloacae, Serratia marcescens, Helicobacter pylori, Salmonella enteritidis, Salmonella typhi, Legionella pneumophila, Haemophilus influenzae, Vibrio cholerae, Pseudomonas stutzeri, Ralstonia solanacearum*, or *Xylella fastidiosa.*

In certain embodiments, the bacterial infection is an infection involving non-fermenter bacteria. Such non-fermenter bacterial may be, for example, *Acinetobacter baumannii, Achromobacter xylosoxidans, Bordetella pertussis, Burkholderia cepacia* (also known as *Pseudomonas cepacia*), *Burkholderia pseudomallei* (also known as *Pseudomonas pseudomallei*), *Elizabethkingia meningoseptica* (also known as *Chryseobacterium meningosepticum*), *Moraxella catarrhalis* (also known as *Branhamella catarrhalis*), *Pseudomonas aeruginosa*, or *Stenotrophomonas maltophilia* (also known as *Pseudomonas maltophilia*).

In another embodiment the bacterial infection is a lepB-mediated infection.

In a further embodiment, the bacterial infection is an infection involving a Gram-positive bacteria.

In a further embodiment are methods of treating a mammal in need of such treatment comprising administering to the mammal a second therapeutic agent to any of the aforementioned methods of treatment. In another embodiment, the second therapeutic agent is a not an SpsB or LepB inhibitor. In another embodiment, the second therapeutic agent is an aminoglycoside antibiotic, fluoroquinolone antibiotic, β-lactam antibiotic, macrolide antibiotic, glycopeptide antibiotic, rifampicin, chloramphenicol, fluoramphenicol, colistin, mupirocin, bacitracin, daptomycin, or linezolid.

In some embodiments is a method for treating a bacterial infection in a patient, preferably a human, where the treatment includes administering a therapeutically or pharmacologically effective amount of a combination of 1) a β-lactam antibiotic; and 2) a compound disclosed herein, or a pharmaceutically acceptable salt, solvate, or stereoisomer thereof; and 3) a pharmaceutically acceptable carrier. In embodiments where a β-lactam antibiotic is used in combination with a compound disclosed herein, the β-lactam antibiotic may be a carbapenem, cephalosporin, cephamycin, monobactam or penicillin. Exemplary carbapenem antibiotics useful in the methods of the invention include ertapenem, imipenem, biapenem, and meropenem. Exemplary cephalosporin antibiotics useful in the methods of the invention include, ceftobiprole, ceftaroline, Cefiprome, Cefozopran, cefepime, Cefotaxime, and ceftriazone. Exemplary penicillin antibiotics useful in the methods of the invention include ampicillin, amoxacillin, piperacillin, oxacillin, cloxacillin, methicillin, and nafcillin. In some embodiments of the invention, the β-lactam may be administered with a β-lactamase inhibitor. In some embodiments of the invention, the carbapenem may be administered with a DHP inhibitor, e.g., cilastatin.

In various embodiments of the invention where a compound disclosed herein and a β-lactam antibiotic are used in combination, the β-lactam antibiotic and compound disclosed herein can be administered sequentially or concurrently. Preferably, the β-lactam antibiotic and compound disclosed herein are administered together. When administered concurrently, the β-lactam antibiotic and compound disclosed herein may be administered in the same formulation or in separate formulations. When administered sequentially, either the β-lactam or compound disclosed herein may be administered first. After administration of the first compound, the other compound is administered, for example, within from 1 to 60 minutes, e.g., within 1, 2, 3, 4, 5, 10, 15, 30, or 60 minutes. In one aspect of the invention, when a β-lactamase inhibitor is used, it may be administered separately, or in a formulation with the compound disclosed herein and/or β-lactam antibiotic. In one aspect of the invention, when a DHP inhibitor is used to improve the stability of a carbapenem, it may be administered separately, or in a formulation with the compound disclosed herein and/or carbapenem.

Further described herein are pharmaceutical compositions comprising a compound disclosed herein, a pharmaceutically acceptable carrier, and optionally a β-lactam antibiotic. In embodiments where a combination is used, the β-lactam antibiotic and the compound disclosed herein, are present in such amounts that their combination constitutes a therapeutically effective amount. Due to the potentiating effects of the compound disclosed herein, the amount of β-lactam antibiotic present in a combination may be less that of a β-lactam antibiotic used alone. In certain embodiments, the composition further comprises a β-lactamase antibiotic.

In further embodiments where the β-lactam antibiotic is a carbapenem, is provided a pharmaceutical composition comprising a carbapenem antibiotic, a DHP inhibitor, a compound disclosed herein, and a pharmaceutically acceptable carrier. In some embodiments where the β-lactara antibiotic is a carbepenem, the carbapenem antibiotic is preferably selected from the group consisting of ertapenem, imipenem, and meropenem.

In some embodiments is a compound disclosed herein for use in treating a bacterial infection. In some embodiments is a compound disclosed herein, in combination with one or more additional therapeutical agents including a β-lactam antibiotic, for use in treating a bacterial infection. In some embodiments is a compound disclosed herein for use as a medicament for treating a bacterial infection. In some embodiments is a compound disclosed herein, in combination with one or more additional therapeutical agents including a β-lactam antibiotic, for use as a medicament for treating a bacterial infection. In some embodiments is a compound disclosed herein for use in the preparation of a medicament for treating a bacterial infection. In some embodiments is a compound disclosed herein, in combination with one or more additional therapeutical agents including a β-lactam antibiotic, for use in the preparation of a medicament for treating a bacterial infection.

In some embodiments described herein, a compound disclosed herein can enhance the activity of a β-lactam antibacterial agent by inducing susceptibility to the antibacterial agent in a drug-resistant strain such as MRSA. In some embodiments, a compound disclosed herein can enhance the activity of a β-lactam antibacterial agent by reducing the dosage of the antibacterial agent need for a therapeutic effect in a drug-sensitive strain. For example, if a compound disclosed herein reduces the Minimum Inhibitory Concentration (MIC) of an antibacterial agent (where the MIC is the minimum concentration of antibacterial agent which will completely inhibit growth) in a susceptible strain, then such treatment may be advantageous to enable a reduction in the amount of antibacterial agent administered (could reduce side effects of an antibiotic), or to decrease the frequency of administration. In some embodiments, compounds disclosed herein can enhance the activity of an antibacterial agent such as a carbapenem to prevent the emergence of a resistant sub-population in a heterogeneous bacterial population with a resistant sub-population.

Potentiators can be used to enhance the activity of antibacterial agents whose clinical efficacy has been limited by the increasing prevalence of resistant strains. In some embodiments described herein, a compound disclosed herein is used as a potentiator wherein a compound disclosed herein can be administered together with a β-lactam antibiotic (either concurrently or sequentially) to allow effective treatment of an infection involving a resistant bacterium, or to reduce the amount of antibacterial agent necessary to treat an infection.

In one embodiment, is a compound described herein which displays antibiotic activity useful in the treatment of bacterial infections, such as by way of example only, various strains of *S. aureus, S. pneumoniae, E. faecalis, E. faecium, B. subtilis* and *E. coli* including species that are resistant to many known antibiotics such as methicillin-resistant *S. aureus* (MRSA), vancomycin-resistant *Enterococcus* sp. (VRE), multidrug-resistant *E. faecium*, macrolide-resistant *S. aureus* and *S. epidermidis*, and linezolide-resistant *S. aureus* and *E. faecium*.

Methicillin-Resistant *Staphylococcus aureus*

*Staphylococcus aureus* (*S. aureus*), a spherical bacterium, is the most common cause of staph infections. *S. aureus* has been known to cause a range of illnesses from minor skin infections, such as pimples, impetigo, boils, cellulitis folliculitis, furuncles, carbuncles, scalded skin syndrome, abscesses, to life-threatening diseases such as pneumonia, meningitis, osteomyelitis endocarditis, toxic shock syndrome, and septicemia. Further, *S. aureus* is one of the most common causes of nosocomial infections, often causing postsurgical wound infections.

Methicillin was introduced in the late 1950s to treat infections caused by penicillin-resistant *S. aureus*. It has been reported previously that *S. aureus* isolates had acquired resistance to methicillin (methicillin-resistant *S. aureus*, MRSA). The methicillin resistance gene (mecA) encodes a methicillin-resistant penicillin-binding protein that is not present in susceptible strains. mecA is carried on a mobile genetic element, the staphylococcal cassette chromosome mec (SCCmec), of which four forms have been described that differ in size and genetic composition. The methicillin-resistant penicillin-binding protein allows for resistance to β-lactam antibiotics and obviates their clinical use during MRSA infections.

In one aspect is a method for treating a subject having a resistant bacterium comprising administering to the subject a compound disclosed herein or a pharmaceutically acceptable salt, solvate, or stereoisomer thereof. In one embodiment, the bacterium is a Gram-positive bacteria. In another embodiment, the Gram-positive bacterium is *S. aureus*. In further embodiment, the *S. aureus* is resistant or refractory to a beta-lactam antibiotic. In yet a further embodiment, the beta-lactam antibiotic belongs to the class of penicillins. In a further embodiment, the beta-lactam antibiotic is methicillin. In yet another embodiment, the subject has a methicillin-resistant *S. aureus* bacteria. In one embodiment the beta-lactam antibiotic is flucloxacillin. In another embodiment is a method for treating a subject having a dicloxacillin-resistant bacteria comprising administering to the subject a compound disclosed herein or a pharmaceutically acceptable salt, solvate, or stereoisomer thereof wherein the subject is refractory to dicloxacillin. Also disclosed herein is a method for treating a subject having a methicillin-resistant bacteria comprising administering a compound disclosed herein or a pharmaceutically acceptable salt, solvate, or stereoisomer thereof wherein the subject has been determined to have a methicillin-resistant bacteria. In one embodiment the subject is screened for methicillin-resistant bacteria. In another embodiment, the subject screening is performed through a nasal culture. In a further embodiment the methicillin-resistant bacteria is detected by swabbing the nostril(s) of the subject and isolating the bacteria. In another embodiment, Real-time PCR and/or Quantitative PCR is employed to determine whether the subject has a methicillin-resistant bacteria.

In one embodiment is a method for treating a subject having a first-generation cephalosporin-resistant bacteria comprising administering a compound disclosed herein or a pharmaceutically acceptable salt, solvate, or stereoisomer thereof wherein the subject is refractory to a first-generation cephalosporin. In one embodiment, the bacteria is resistant to a first-generation cephalosporin. In a further embodiment, the bacteria is resistant to cefacetrile. In another embodiment, the bacteria is resistant to cefadroxil. In yet another embodiment, the bacteria is resistant to cefalexin. In one embodiment, the bacteria is resistant to cefaloglycin. In another embodiment, the bacteria is resistant to cefalonium. In another embodiment, the bacteria is resistant to cefaloridine. In yet another embodiment, the bacteria is resistant to cefalotin. In a further embodiment, the bacteria is resistant to cefapirin. In yet a further embodiment, the bacteria is resistant to cefatrizine. In one embodiment, the bacteria is resistant to cefazaflur. In another embodiment, the bacteria is resistant to cefazedone. In yet another embodiment, the bacteria is resistant to cefazolin. In a further embodiment, the bacteria is resistant to cefradine. In yet a further embodiment, the bacteria is resistant to cefroxadine. In one embodiment, the bacteria is resistant to ceftezole.

In one embodiment is a method for treating a subject having a second-generation cephalosporin-resistant bacteria comprising administering a compound disclosed herein or a pharmaceutically acceptable salt, solvate, or stereoisomer thereof wherein the subject is refractory to a second-generation cephalosporin. In another embodiment, the bacteria is resistant to a second-generation cephalosporin. In a further embodiment, the bacteria is resistant to cefaclor. In another embodiment, the bacteria is resistant to cefonicid. In yet another embodiment, the bacteria is resistant to cefprozil. In one embodiment, the bacteria is resistant to cefuroxime. In another embodiment, the bacteria is resistant to cefuzonam. In another embodiment, the bacteria is resistant to cefmetazole. In yet another embodiment, the bacteria is resistant to cefotetan. In a further embodiment, the bacteria is resistant to cefoxitin.

In one embodiment is a method for treating a subject having a third-generation cephalosporin-resistant bacteria comprising administering a compound disclosed herein or a pharmaceutically acceptable salt, solvate, or stereoisomer thereof wherein the subject is refractory to a third-generation cephalosporin. In another embodiment, the bacteria is resistant to a third-generation cephalosporin. In a further embodiment, the bacteria is resistant to cefcapene. In another embodiment, the bacteria is resistant to cefdaloxime. In yet another embodiment, the bacteria is resistant to cefdinir. In one embodiment, the bacteria is resistant to cefditoren. In another embodiment, the bacteria is resistant to cefixime. In another embodiment, the bacteria is resistant to cefinenoxime. In yet another embodiment, the bacteria is resistant to cefodizime. In a further embodiment, the bacteria is resistant to cefotaxime. In yet a further embodiment, the bacteria is resistant to cefpimizole. In one embodiment, the bacteria is resistant to cefpodoxime. In another embodiment, the bacteria is resistant to cefteram. In yet another embodiment, the bacteria is resistant to ceftibuten. In a further embodiment, the bacteria is resistant to ceftiofur. In yet a further embodiment, the bacteria is resistant to ceftiolene. In one embodiment, the bacteria is resistant to ceftizoxime. In another embodiment, the bacteria is resistant to ceftriaxone. In yet another embodiment, the bacteria is resistant to cefoperazone. In yet a further embodiment, the bacteria is resistant to ceftazidime.

In one embodiment is a method for treating a subject having a fourth-generation cephalosporin-resistant bacteria comprising administering a compound disclosed herein or a pharmaceutically acceptable salt, solvate, or stereoisomer thereof wherein the subject is refractory to a fourth-generation cephalosporin. In another embodiment, the bacteria is resistant to a fourth-generation cephalosporin. In a further embodiment, the bacteria is resistant to cefclidine. In another embodiment, the bacteria is resistant to cefepime. In yet another embodiment, the bacteria is resistant to cefluprenam. In one embodiment, the bacteria is resistant to cefoselis. In another embodiment, the bacteria is resistant to cefozopran. In another embodiment, the bacteria is resistant to cefpirome. In yet another embodiment, the bacteria is refractory to cefquinome.

In one embodiment is a method for treating a subject having a carbapenem-resistant bacteria comprising administering a compound disclosed herein or a pharmaceutically acceptable salt, solvate, or stereoisomer thereof wherein the subject is refractory to a carbapenem. In another embodiment, the bacteria is resistant to a carbapenem. In a further embodiment, the bacteria is resistant to imipenem. In another embodiment, the bacteria is resistant to meropenem. In yet another embodiment, the bacteria is resistant to ertapenem. In one embodiment, the bacteria is resistant to faropenem. In another embodiment, the bacteria is resistant to doripenem. In another embodiment, the bacteria is resistant to panipenem. In yet another embodiment, the bacteria is resistant to biapenem,

Vancomycin-Intermediate and Vancomycin-Resistant *Staphylococcus aureus*

Vancomycin-intermediate *Staphylococcus aureus* and vancomycin-resistant *Staphylococcus aureus* are specific types of antimicrobial-resistant Staph bacteria that are refractory to vancomycin treatment. *S. aureus* isolates for which vancomycin MICs are 4-8 μg/mL are classified as vancomycin-intermediate and isolates for which vancomycin MICs are ≥16 μg/mL are classified as vancomycin-resistant (Clinical and Laboratory Standards Institute/NCCLS. Performance Standards for Antimicrobial Susceptibility Testing. Sixteenth informational supplement. M100-S16. Wayne, PA: CLSI, 2006).

As used herein, the term "minimum inhibitory concentration" (MIC) refers to the lowest concentration of an antibiotic that is needed to inhibit growth of a bacterial isolate in vitro. A common method for determining the MIC of an antibiotic is to prepare several tubes containing serial dilutions of the antibiotic, that are then inoculated with the bacterial isolate of interest. The MIC of an antibiotic is determined from the tube with the lowest concentration that shows no turbidity (no growth).

In one aspect is a method of treating a subject having a bacterial infection comprising administering to the subject a compound disclosed herein or a pharmaceutically acceptable salt, solvate, or stereoisomer thereof wherein the bacterial infection comprises a vancomycin-intermediate *Staphylococcus aureus* bacterium. In one embodiment, the vancomycin-intermediate *Staphylococcus aureus* bacterium has a MIC of between about 4 to about 8 μg/mL. In another embodiment, the vancomycin-intermediate *Staphylococcus aureus* bacterium has a MIC of about 4 μg/mL. In yet another embodiment, the vancomycin-intermediate *Staphylococcus aureus* bacterium has a MIC of about 5 μg/mL. In a further embodiment, the vancomycin-intermediate *Staphylococcus aureus* bacterium has a MIC of about 6 μg/mL. In yet a further embodiment, the vancomycin-intermediate *Staphylococcus aureus* bacterium has a MIC of about 7 μg/mL. In one embodiment, the vancomycin-intermediate *Staphylococcus aureus* bacterium has a MIC of about 8 μg/mL.

In another aspect is a method of treating a subject having a bacterial infection comprising administering to the subject a compound disclosed herein or a pharmaceutically acceptable salt, solvate, or stereoisomer thereof wherein the bacterial infection comprises a vancomycin-resistant *Staphylococcus aureus* bacterium. In one embodiment, the vancomycin-resistant *Staphylococcus aureus* bacterium has a MIC of between about 16 μg/mL. In another embodiment, the vancomycin-resistant *Staphylococcus aureus* bacterium has a MIC of about >16 μg/mL. In yet another embodiment, the vancomycin-resistant *Staphylococcus aureus* bacterium has a MIC of about 20 μg/mL. In a further embodiment, the vancomycin-resistant *Staphylococcus aureus* bacterium has a MIC of about 25 μg/mL.

In one embodiment, conditions treated by the compounds described herein include, but are not limited to, endocarditis, osteomyelitis, meningitis, skin and skin structure infections, genitourinary tract infections, abscesses, and necrotizing infections. In another embodiment, the compounds disclosed herein are used to treat conditions, such as, but not limited to, diabetic foot infections, decubitus ulcers, burn infections, animal or human bite wound infections, synergistic-necrotizing gangrene, necrotizing fascilitis, intra-abdominal infection associated with breeching of the intestinal barrier, pelvic infection associated with breeching of the intestinal barrier, aspiration pneumonia, and post-operative wound infections. In another embodiment, the conditions listed herein are caused by, contain, or result in the presence of VISA and/or VRSA.

Vancomycin-Resistant Enterococci

Enterococci are bacteria that are normally present in the human intestines and in the female genital tract and are often found in the environment. These bacteria sometimes cause infections. In some cases, enterococci have become resistant to vancomycin (also known as vancomycin-resistant enterococci or VRE.) Common forms of resistance to vancomycin occur in enterococcal strains that involve the acquisition of a set of genes endoding proteins that direct peptidoglycan precursors to incorporate D-Ala-D-Lac instead of D-Ala-D-Ala. The six different types of vancomycin resistance shown by *enterococcus* are: Van-A, Van-B, Van-C, Van-D, Van-E and Van-F. In some cases, Van-A VRE is resistant to both vancomycin and teicoplanin, while in other cases, Van-B VRE is resistant to vancomycin but sensitive to teicoplanin; in further cases Van-C is partly resistant to vancomycin, and sensitive to teicoplanin.

In one aspect, is a method of treating a subject having a vancomycin-resistant enterococci comprising administering to the subject a compound disclosed herein or a pharmaceutically acceptable salt, solvate, or stereoisomer thereof wherein the enterococci has developed resistance to vancomycin. In one embodiment, the subject has been previously treated with vancomycin for a sustained period of time. In another embodiment, the subject has been hospitalized. In yet another embodiment, the subject has a weakened immune system such as patients in Intensive Care Units or in cancer or transplant wards. In a further embodiment, the subject has undergone surgical procedures such as, for example, abdominal or chest surgery. In yet a further embodiment, the subject has been colonized with VRE. In one embodiment, the subject has a medical device such that an infection has developed. In another embodiment, the medical device is a urinary catheter or central intravenous (IV) catheter.

In another embodiment, is a method of treating a subject having a vancomycin-resistant enterococci comprising administering to the subject a compound disclosed herein or a pharmaceutically acceptable salt, solvate, or stereoisomer thereof wherein the *enterococcus* has Van-A resistance.

In another embodiment, is a method of treating a subject having a vancomycin-resistant enterococci comprising administering to the subject a compound disclosed herein or a pharmaceutically acceptable salt, solvate, or stereoisomer thereof wherein the *enterococcus* has Van-B resistance.

In another embodiment, is a method of treating a subject having a vancomycin-resistant enterococci comprising administering to the subject a compound disclosed herein or a pharmaceutically acceptable salt, solvate, or stereoisomer thereof wherein the *enterococcus* has Van-C resistance.

Administration and Pharmaceutical Composition

Pharmaceutical compositions described herein comprise a therapeutically effective amount of a compound described herein (i.e., a compound disclosed herein) formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions described herein can be administered to humans and other animals orally, rectally, parenterally, intracisternally, intravaginally, intraperitoneally, topically (as by powders, ointments, or drops), bucally, or as an oral or nasal spray, or a liquid aerosol or dry powder formulation for inhalation.

Liquid dosage forms for oral administration include pharmaceutically acceptable emulsions, microemulsions, solutions, suspensions, syrups and elixirs. In addition to the active compounds, the liquid dosage forms optionally contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions are optionally formulated according to the known art using suitable dispersing or wetting agents and suspending agents. The sterile injectable preparation is optionally a sterile injectable solution, suspension or emulsion in a nontoxic parenterally acceptable diluent or solvent, for example, as a solution in 1,3-butanediol. Among the acceptable vehicles and solvents that are optionally employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This is optionally accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is optionally accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are optionally prepared by entrapping the drug in liposomes or microemulsions which are compatible with body tissues.

Compositions for rectal or vaginal administration are preferably suppositories which can be prepared by mixing the compound described herein (i.e., a compound disclosed herein) with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form optionally comprise buffering agents.

Solid compositions of a similar type are optionally employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings known in the pharmaceutical formulating art. They optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type are optionally employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings known in the pharmaceutical formulating art. In such solid dosage forms the active compound is optionally admixed with at least one inert diluent such as sucrose, lactose or starch. Such dosage forms optionally comprise, as is normal practice, additional substances other than inert diluents, e.g., tableting lubricants and other tableting aids such a magnesium stearate and microcrystalline cellulose. In the case of capsules, tablets and pills, the dosage forms optionally comprise buffering agents. They optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound described herein include ointments, pastes, creams, lotions, gels, powders, solutions, sprays, inhalants or patches. The active component is admixed under sterile conditions with a pharmaceutically acceptable carrier and any needed preservatives or buffers as are optionally required. Ophthalmic formulations, ear drops, and the like are also contemplated.

The ointments, pastes, creams and gels may contain, in addition to an active compound described herein, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Compositions described herein are optionally formulated for delivery as a liquid aerosol or inhalable dry powder. Liquid aerosol formulations are optionally nebulized predominantly into particle sizes that can be delivered to the terminal and respiratory bronchioles where bacteria reside in patients with bronchial infections, such as chronic bronchitis and pneumonia. Pathogenic bacteria are commonly present throughout airways down to bronchi, bronchioli and lung parenchema, particularly in terminal and respiratory bronchioles. During exacerbation of infection, bacteria can also be present in alveoli. Liquid aerosol and inhalable dry powder formulations are preferably delivered throughout the endobronchial tree to the terminal bronchioles and eventually to the parenchymal tissue.

Aerosolized formulations described herein are optionally delivered using an aerosol forming device, such as a jet, vibrating porous plate or ultrasonic nebulizer, preferably selected to allow the formation of an aerosol particles having with a mass medium average diameter predominantly between 1 to 5 micron. Further, the formulation preferably has balanced osmolarity ionic strength and chloride concentration, and the smallest aerosolizable volume able to deliver effective dose of the compounds described herein compound described herein (i.e., a compound disclosed herein) to the site of the infection. Additionally, the aerosolized formulation preferably does not impair negatively the functionality of the airways and does not cause undesirable side effects.

Aerosolization devices suitable for administration of aerosol formulations described herein include, for example, jet, vibrating porous plate, ultrasonic nebulizers and energized dry powder inhalers, that are able to nebulize the formulation into aerosol particle size predominantly in the size range from 1-5p. Predominantly in this application means that at least 70% but preferably more than 90% of all generated aerosol particles are within 1-5p range. A jet nebulizer works by air pressure to break a liquid solution into aerosol droplets. Vibrating porous plate nebulizers work by using a sonic vacuum produced by a rapidly vibrating porous plate to extrude a solvent droplet through a porous plate. An ultrasonic nebulizer works by a piezoelectric crystal that shears a liquid into small aerosol droplets. A variety of suitable devices are available, including, for example, AeroNeb™ and AeroDose™ vibrating porous plate nebulizers (AeroGen, Inc., Sunnyvale, California), Sidestream® nebulizers (Medic-Aid Ltd., West Sussex, England), Pari LC® and Pari LC Star® jet nebulizers (Pari Respiratory Equipment, Inc., Richmond, Virginia), and Aerosonic™ (DeVilbiss Medizinische Produkte (Deutschland) GmbH, Heiden, Germany) and UltraAire® (Omron Healthcare, Inc., Vernon Hills, Illinois) ultrasonic nebulizers.

In some embodiments, compounds described herein compound described herein (i.e., a compound disclosed herein) are formulated for use as topical powders and sprays that contain, in addition to the compounds described herein, excipients such as lactose, talc, silicic acid, aluminum hydroxide, calcium silicates and polyamide powder, or mixtures of these substances. Sprays optionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment described herein, bacterial infections are treated or prevented in a patient such as a human or lower mammal by administering to the patient a therapeutically effective amount of a compound described herein, in such amounts and for such time as is necessary to achieve the desired result. By a "therapeutically effective amount" of a compound described herein is meant a sufficient amount of the compound to treat bacterial infections, at a reasonable benefit/risk ratio applicable to any medical treatment. It will be understood, however, that the total daily usage of the compounds and compositions described herein will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors known in the medical arts.

The total daily dose of the compounds described herein compound described herein (i.e., a compound disclosed herein) administered to a human or other mammal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens described herein comprise administration to a patient in need of such treatment from about 10 mg to about 2000 mg of the compound (s) described herein per day in single or multiple doses.

EXAMPLES

Compounds disclosed herein are made by the methods depicted in the reaction schemes shown below. Procedures are provided herein that, in combination with the knowledge of the synthetic organic chemist of ordinary skill in the art, are in some embodiments used to prepare the full range of compounds as disclosed and claimed herein.

General Procedure A:

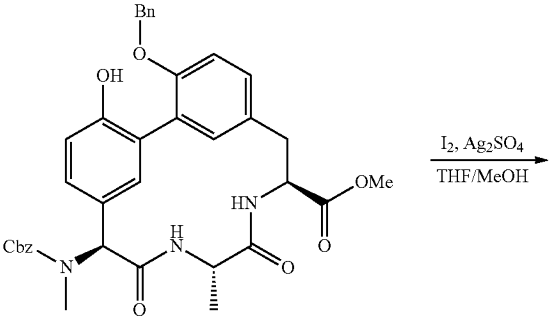

1

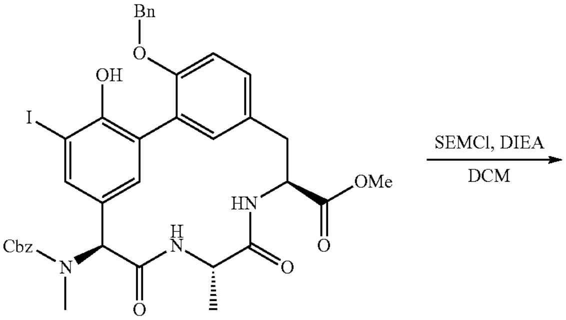

2

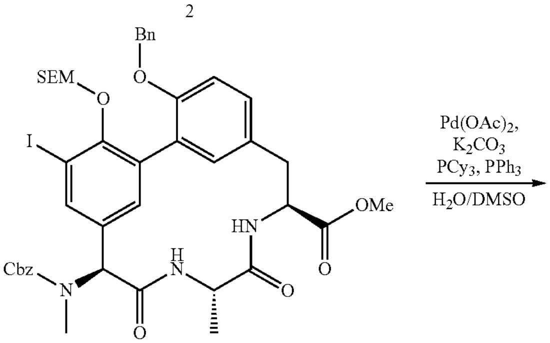

3

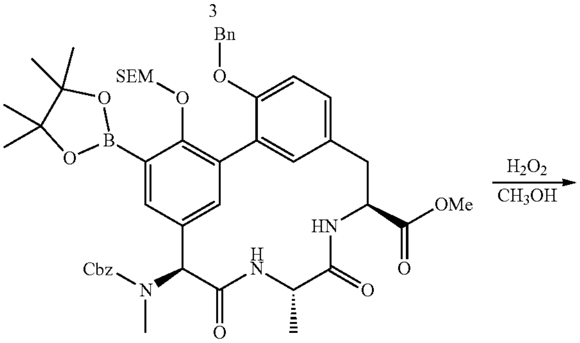

4

-continued

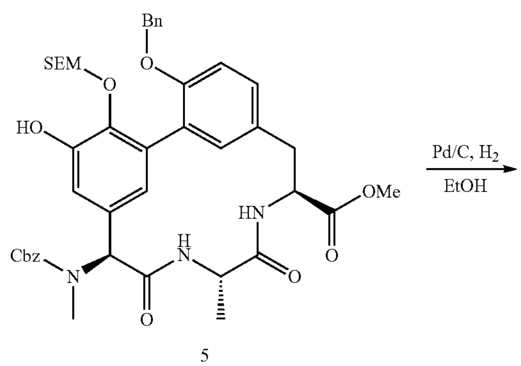

5

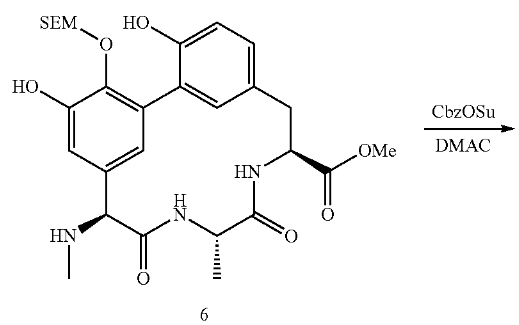

6

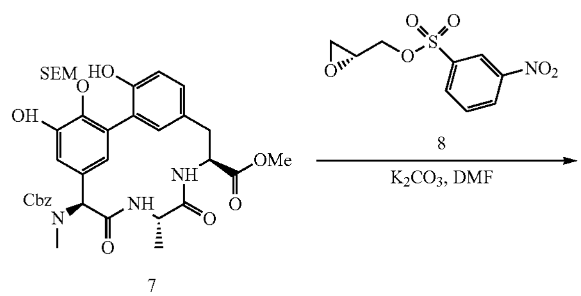

7

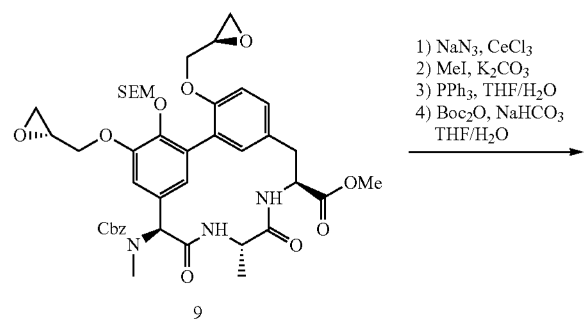

9

-continued

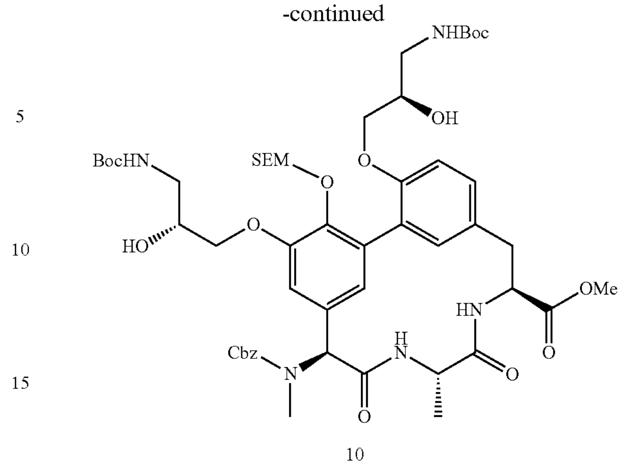

10

Step 1: To a solution of compound 1 (51.0 g, 78.3 mmol), $Ag_2SO_4$ (17.1 g, 54.8 mmol) in MeOH (250 mL) and THF (250 mL) was added $I_2$ (21.8 g, 86.1 mmol) at 25° C. The reaction mixture was stirred for 2 h at 25° C. and filtered. The filtrate was concentrated to dryness. The residue was partitioned between ethyl acetate (300 mL) and saturated aqueous $Na_2S_2O_3$ solution (300 mL). The organic phase was separated and washed with brine (2×300 mL), dried over $Na_2SO_4$ and concentrated to dryness to afford crude compound 2 (60.0 g, 98.6% yield) as a yellow solid.

Step 2: To a solution of compound 2 (60.0 g, 77.2 mmol) and DIEA (38.3 mL, 231.0 mmol) in $CH_2C_{12}$ (600 mL) was added SEMCl (27.1 mL, 154.0 mmol). The reaction was stirred at 25° C. for 2 h and concentrated to dryness. The residue was diluted with ethyl acetate (500 mL), washed with water (2×500 mL) and brine (2×500 mL), dried over $Na_2SO_4$ and concentrated to dryness. The crude product was purified by column chromatography (silica gel, 100-200 mesh, 10-40% ethyl acetate in petroleum ether) to give compound 3 (65.0 g, 92.8% yield) as a yellow solid.

Step 3: A mixture of compound 3 (20.00 g, 22.0 mmol), bis(pinacolato)diboron (8.39 g, 33.0 mmol), triphenylphosphine (1.16 g, 4.4 mmol), tricyclohexylphosphine (1.24 g, 4.4 mmol), $Pd(OAc)_2$ (0.49 g, 2.2 mmol) and $K_2OAc$ (8.65 g, 88.1 mmol) in DMSO (200 mL) and water (20 mL) was stirred at 80° C. for 1 h under nitrogen atmosphere. After cooling to room temperature, the reaction mixture was diluted with ethyl acetate (200 mL) and filtered. The filtrate was washed with water (2×200 mL) and brine (200 mL), dried over $Na_2SO_4$ and concentrated to give crude compound 4 (20.00 g, 97% yield) as a gray solid (three parallel batches were combined at this stage).

Step 4: To a solution of compound 4 (60.0 g, 66.0 mmol) in MeOH (600 mL) was added $H_2O_2$ (135 mL, 1.3 mol). The mixture was stirred at 0° C. for 2 h and diluted with ethyl acetate (700 mL). The mixture was washed with saturated aqueous $NaHCO_3$ (2×200 mL), saturated aqueous $Na_2S_2O_3$ (500 mL), brine (2×200 mL), dried over $Na_2SO_4$ and concentrated under reduced pressure. The residue was purified by column chromatography (silica gel, 100-200 mesh, 10-50% ethyl acetate in petroleum ether) to give a crude product, which was further purified by preparative HPLC (water (0.04% $NH_3H_2O$+10 mM $NH_4HCO_3$)-ACN) to give compound 5 (37.0 g, 70.1% yield) as a white solid.

Step 5: To a solution of compound 5 (50.0 g, 62.7 mmol) in ethanol (700 mL) was added 10% Pd/C (14.7 g, 13.8 mmol) and a drop of ammonia. The mixture was stirred under hydrogen (50 psi) at 40° C. for 5 h and filtered. The filtrate was concentrated to obtain crude compound 6 (35.0 g, 97.4% yield) as a white solid.

Step 6: To a solution of compound 6 (35.0 g, 61.0 mmol) in DMA (400 mL) was added CbzOSu (15.2 g, 60.9 mmol) in DMA (20.0 mL) dropwise at 0° C. After addition, the mixture was stirred at 15° C. for 14 h and then diluted with ethyl acetate (500 mL). The separated organic phase was washed with brine (3×200 mL), dried over $Na_2SO_4$ and concentrated. The residue was purified by column chromatography (silica gel, 100-200 mesh, 55% ethyl acetate in petroleum ether) to give compound 7 (21.0 g, 97.0% yield) as a white solid.

Step 7: To a solution of compound 7 (21.0 g, 29.7 mmol) in DMF (84.0 mL) was added compound 8 (23.1 g, 89.0 mmol) and $K_2CO_3$ (24.6 g, 178.0 mmol). The mixture was stirred at 50° C. for 16 h, and another portion of compound 8 (23.1 g, 89.0 mmol) and $K_2CO_3$ (24.6 g, 178 mmol) was added. The reaction mixture was stirred at 50° C. for 1 h, diluted with ethyl acetate (500 mL) and filtered. The filtrate was washed with brine (2×300 mL), dried over $Na_2SO_4$ and concentrated to dryness. The crude was purified by column chromatography (silica gel, 100-200 mesh, 55% ethyl acetate in petroleum ether) to give compound 9 (20.0 g, 83.3% yield) as a white solid.

Step 8: To a solution of compound 9 (24.0 g, 29.3 mmol) in MeCN (200 mL) and water (100 mL) was added $NaN_3$ (27.3 g, 420 mmol) and $CeCl_3$ (3.6 g, 14.6 mmol). The mixture was stirred at 75° C. for 16 h. The reaction mixture was diluted with ethyl acetate (700 mL) and filtered. The filtrate was washed with brine (2×200 mL), dried over $Na_2SO_4$ and concentrated to dryness. The residue was dissolved in DMF (200 mL) were added $K_2CO_3$ (16.2 g, 117 mmol) and MeI (12.5 g, 87.8 mmol). The reaction was stirred at 25° C. for 1 h, diluted with ethyl acetate (600 mL) and filtered. The filtrate was washed with brine (3×300 mL), dried over $Na_2SO_4$ and concentrated to dryness.

The residue was dissolved in THF (480 mL) and added $PPh_3$ (46.1 g, 176 mmol) and $H_2O$ (6.33 g, 351 mmol). The solution was stirred at 35° C. for 16 h.

$Boc_2O$ (14.7 g, 67.3 mmol) was added to the reaction mixture mentioned above. The reaction was stirred at 30° C. for another 1 h and concentrated to dryness. The residue was diluted with ethyl acetate (700 mL), washed with brine (2×300 mL), dried over $Na_2SO_4$ and concentrated. The crude was purified by column chromatography (silica gel, 100-200 mesh, 17% acetone in petroleum ether and then 85% ethyl acetate in petroleum ether) to obtain compound 10 (24.4 g, 79.2% yield) as a white solid.

General Procedure B:

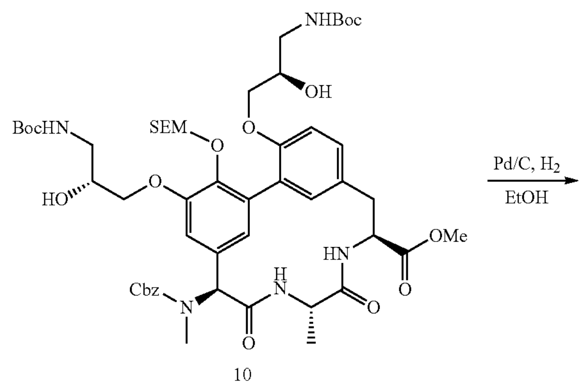

10

-continued

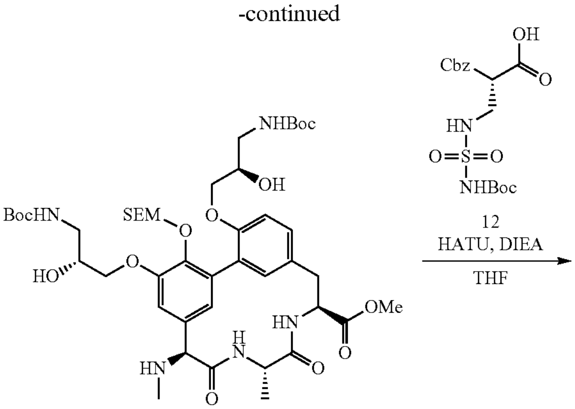

11

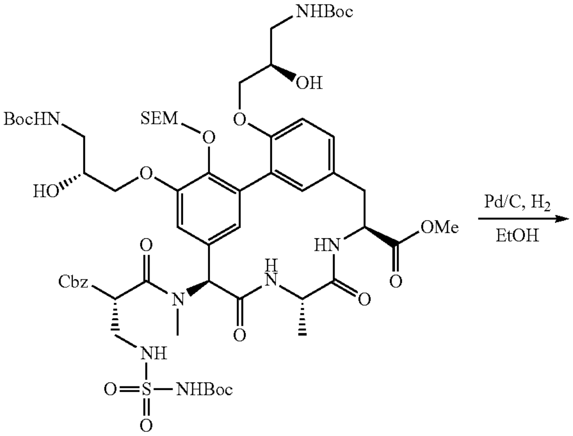

13

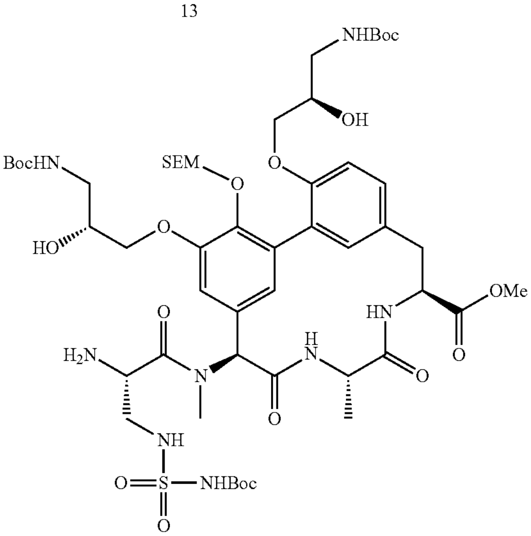

14

Step 1: A mixture of compound 10 (5.00 g, 4.74 mmol) and 10% palladium on carbon (1.51 g, 1.42 mmol) in ethanol (100 mL) was stirred under hydrogen (50 psi) at 35° C. for 2 h and filtered. The filtrate was concentrated to give the crude compound 11 (4.30 g, 98.5% yield) as a white solid.

Step 2: To a solution of compound 11 (4.30 g, 4.67 mmol) and compound 12 (2.54 g, 6.08 mmol) in THF (43 mL) was added DIEA and HATU (2.13 g, 5.61 mmol) at 0° C. After addition, the reaction mixture was stirred at 25° C. for 3 h and quenched by addition of methanol (1 mL). The reaction mixture was concentrated and then diluted with ethyl acetate (100 mL). The solution was washed with saturated aqueous $Na_2CO_3$ (150 mL), brine (150 mL×2), dried over $Na_2SO_4$ and concentrated. The residue was purified by column chromatography (silica gel, 100-200 mesh, 50-70% ethyl acetate in petroleum ether) to give compound 13 (6.00 g, 97.3% yield) as a white solid.

Step 3: To a solution of compound 13 (150 mg, 0.11 mmol) and a drop of $NH_3.H_2O$ in ethanol (15.0 mL) was added 10% Pd/C (36.3 mg, 0.03 mmol). The reaction was stirred at 30° C. under $H_2$ atmosphere (15 psi) for 2 h and filtered. The filtrate was concentrated to give compound 14 (135 mg, 63.0% yield) as a white solid.

The methods for LCMS analysis are as follows: LCMS (Method 5-95 AB, ESI): ESI, Compounds were eluted using a gradient from 5% AcCN/$H_2O$ over 0.7 min to 95% AcCN/$H_2O$. This concentration was held for 0.4 min. Flow rate 1.5 mL/min, using a Merck RP-18e, 2×25 mm column. TFA was present at 0.05% in all chromatographic solvents; LCMS (Method 5-100 AB, 7 min): Instrument: Waters Acquity UPLC using a 2.1×30 mm CSH 1.8 um C18 column held at 40° C. and ESI ionization. Compounds were eluted using a gradient from 5% B in eluant A over 5.2 min to 100% B. This concentration was held for 1.8 min and the total run time was 7 minutes. The flow rate was 0.9 mL/min, and the eluants were: (A) Milli-Q water+10 mM ammonium formate at pH=3.8 and (B) MeCN.

Example 1

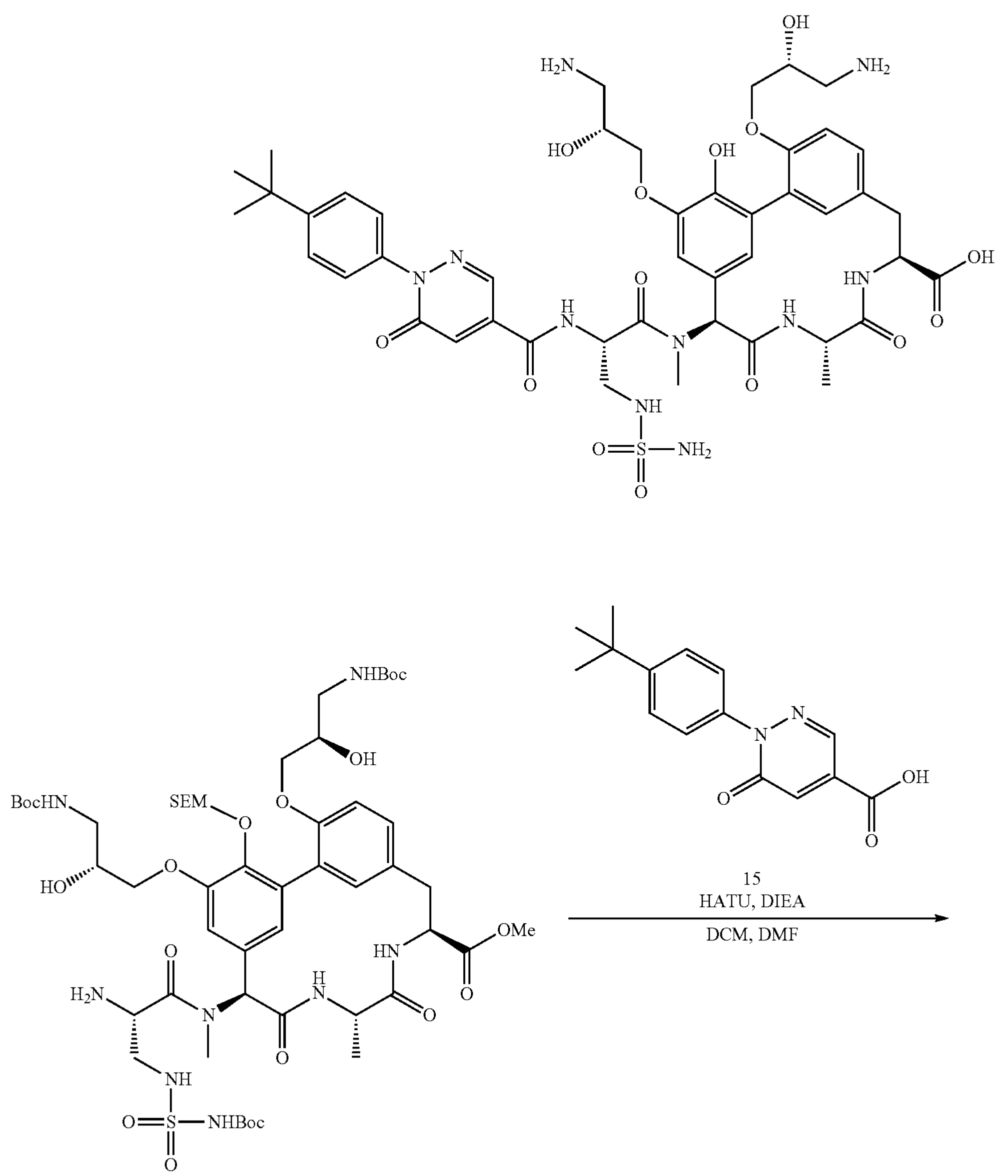

14

-continued
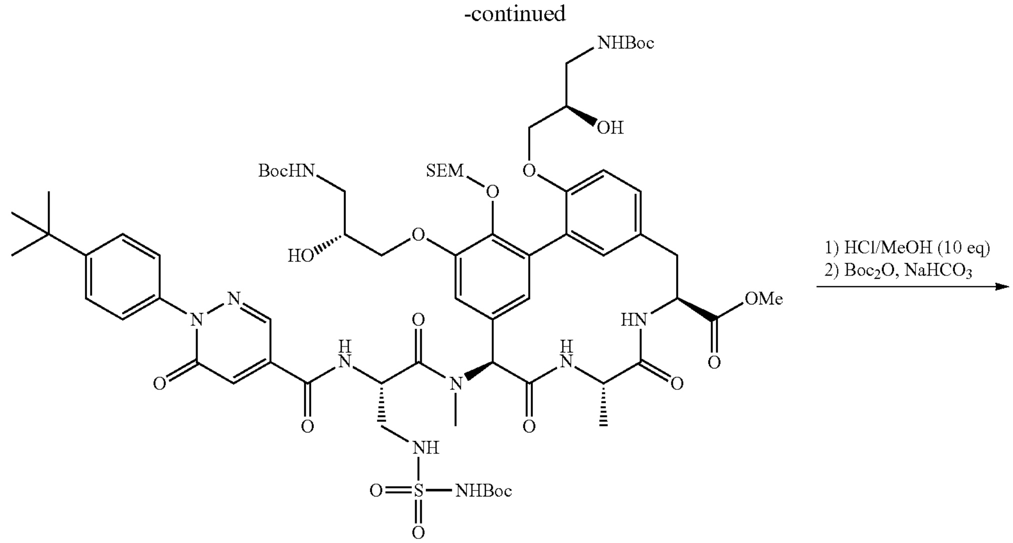
16
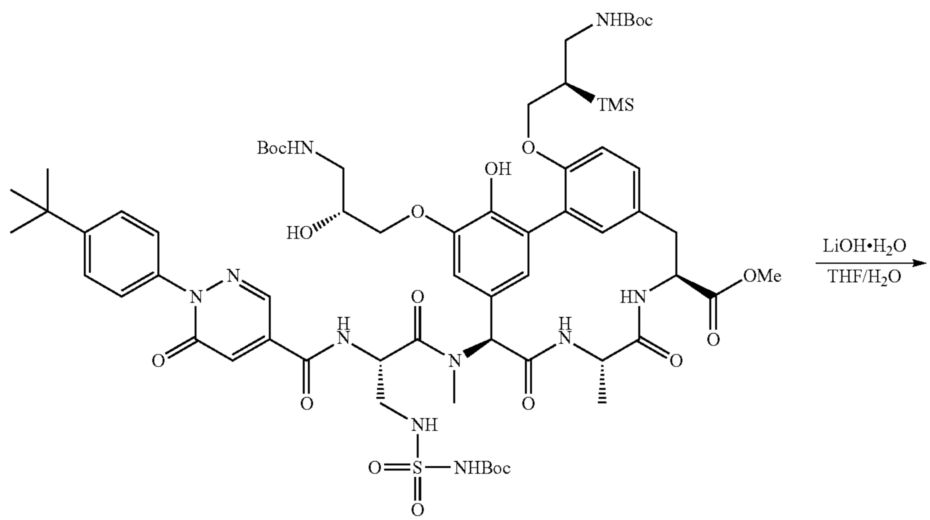
17
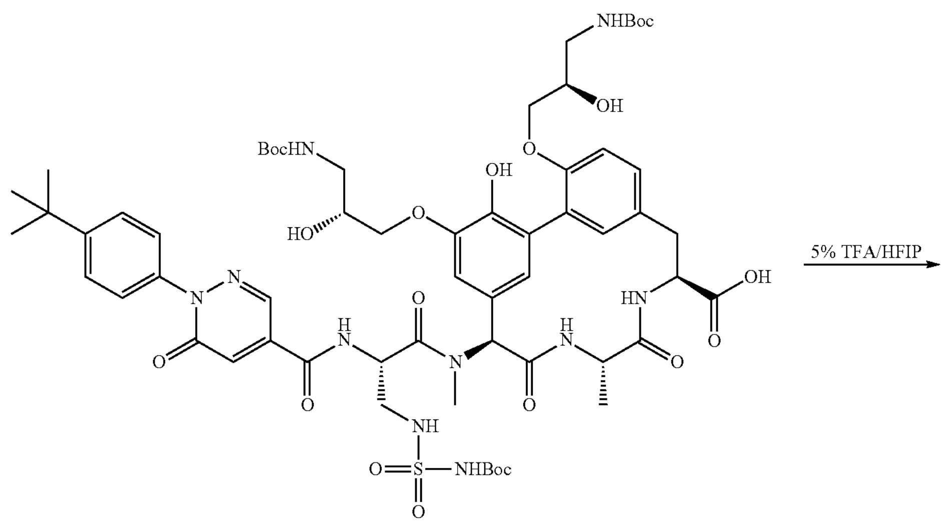
18

-continued

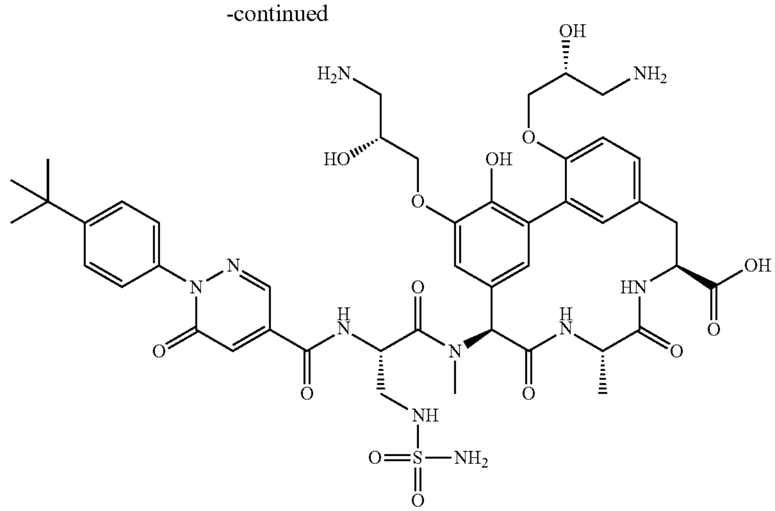

Step 1: To a solution of 1-(4-(tert-butyl)phenyl)-6-oxo-1,6-dihydropyridazine-4-carboxylic acid (46.5 mg, 0.17 mmol) (synthesis provided in Example 17) in DMF (1.00 mL) and dichloromethane (8.00 mL) was added DIEA (159 uL, 0.91 mmol) and HATU (104 mg, 0.27 mmol) at 0° C. After 5 min, compound 14 (135 mg, 0.11 mmol) was added. The reaction was stirred at 20° C. for 2 h and quenched by addition of methanol (0.50 mL). The reaction mixture was concentrated to dryness. The residue was partitioned between ethyl acetate (30 mL) and water (20 mL). The aqueous phase was extracted with ethyl acetate (2×30 mL). The combined organic layers were washed with brine (3×80 mL), dried over $Na_2SO_4$ and concentrated to dryness. The crude was purified by preparative TLC (10% methanol in dichloromethane) to obtain compound 16 (80.0 mg, 48.8% yield) as a yellow solid.

Step 5: To a solution of compound 16 (80.0 mg, 0.06 mmol) in methanol (1.00 mL) was added HCl (4 N in methanol, 0.08 mL, 0.32 mmol). The mixture was stirred at 30° C. for 0.5 h and quenched by addition of $NaHCO_3$ (70.0 mg, 0.83 mmol). The mixture was concentrated, and then THF (5 mL), water (1 mL) and $Boc_2O$ (0.01 mL, 0.06 mmol) was added. The mixture was stirred at 30° C. for 0.5 h and diluted with water (10 mL) and ethyl acetate (20 mL). The separated aqueous phase was washed with ethyl acetate (2×20 mL). The combined organic layers were washed with brine (60 mL), dried over $Na_2SO_4$ and concentrated. The residue was purified by preparative TLC (10% methanol in dichloromethane) to give compound 17 (50.0 mg, 68.7% yield) as a yellow solid.

Step 6: To a solution of compound 17 (50.0 mg, 0.04 mmol) in THF (4.00 mL) was added a solution of $LiOH.H_2O$ (4.8 mg, 0.11 mmol) in water (1 mL). The reaction was stirred at 20° C. for 1 h and concentrated. The residue was diluted with water (20 mL) and adjusted to pH=4 by addition of 5% aqueous $KHSO_4$. The mixture was extracted with ethyl acetate (3×30 mL). The combined organic layers were dried over $Na_2SO_4$ and concentrated to obtain crude compound 18 (49.0 mg, 99.1% yield) as a white solid.

Step 7: A mixture of compound 18 (49 mg, 0.04 mmol) in 5% TFA in HFIP (3 mL, 2.01 mmol) was stirred at 35° C. for 3 h and concentrated. The residue was diluted with methanol (5 mL) and neutralized with $NaHCO_3$. After filtration, the filtrate was purified by preparative HPLC (acetonitrile 19-29%/0.2% formic acid in water) to give the title compound (12.6 mg, 32.9% yield) as a white solid. $^1H$ NMR (400 MHz, DMSO-$d_6$) δ (ppm) 9.39 (s, 1H), 8.47-8.30 (m, 2H), 7.57-7.50 (m, 5H), 7.05-6.73 (m, 5H), 6.36-6.22 (m, 2H), 5.13-5.01 (m, 1H), 4.64 (s, 1H), 4.22-3.99 (m, 10H), 3.25-2.67 (m, 12H), 1.32-1.06 (m, 12H). LCMS (Method 5-95 AB, ESI): $R_T$=0.789 min, $[M+H]^+$=995.8.

Example 2

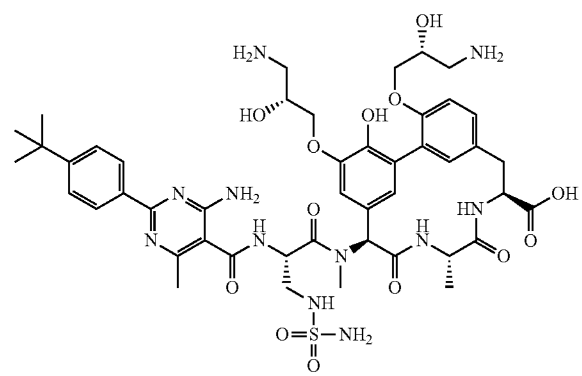 [SMILES: Cc1nc(-c2ccc(C(C)(C)C)cc2)nc(N)c1C(=O)N[C@@H](CNS(N)(=O)=O)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O]

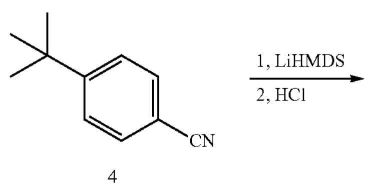

4

-continued

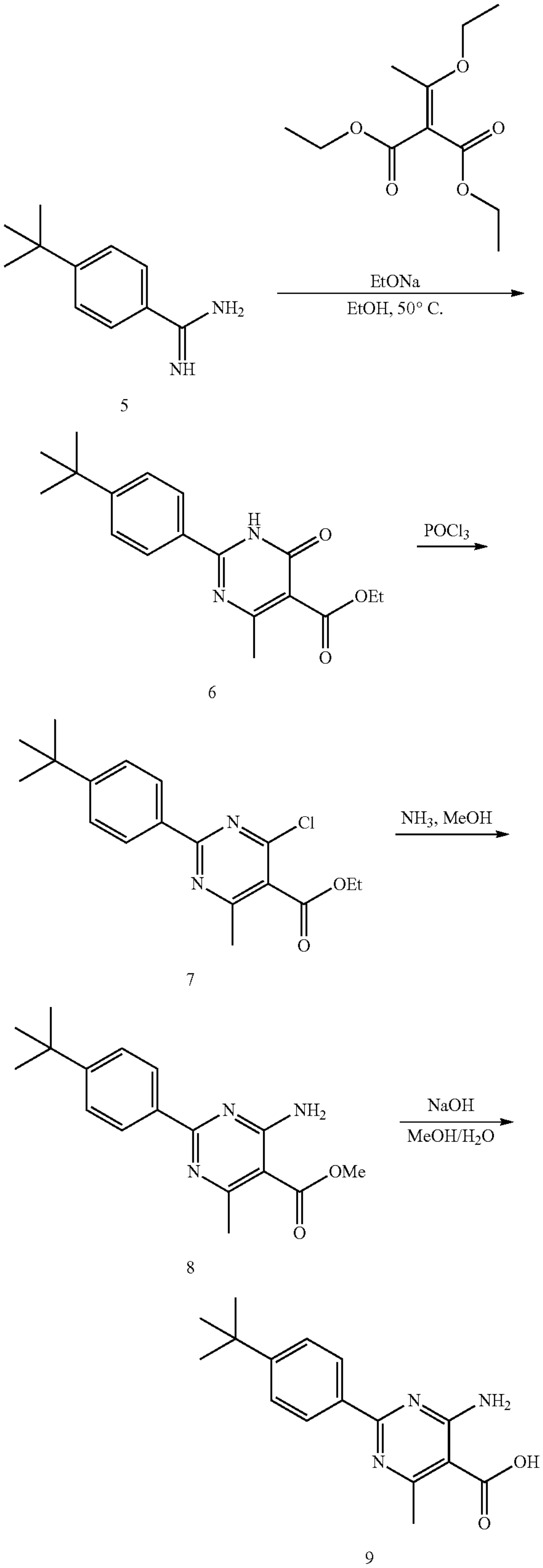

5

6

7

8

9

-continued

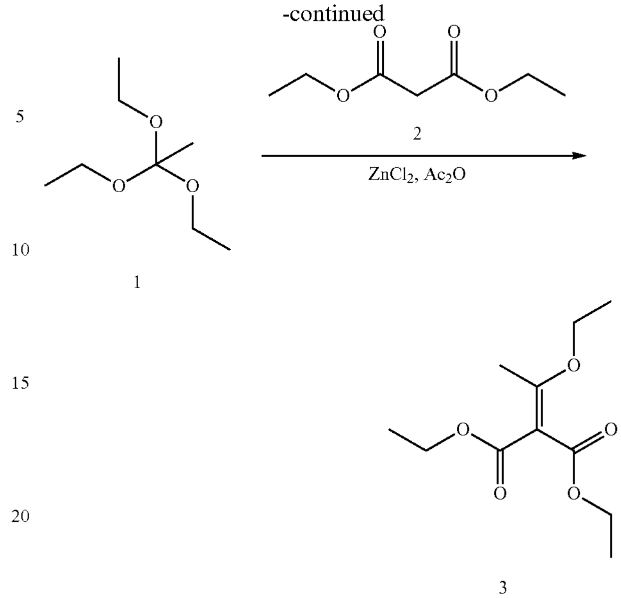

1

2

3

Step 1: A solution of diethyl malonate (8.00 g, 50.00 mmol), triethylorthoacetate (24.30 g, 150.00 mmol), $ZnCl_2$ (2.01 mg, 0.01 mmol) and $Ac_2O$ (1.00 mL, 4.32 mmol) was heated at 135° C. for 6 h, while additional $Ac_2O$ (1.00 mL, 4.32 mmol) was added every 30 min. The reaction mixture was cooled to room temperature and partitioned between (200 mL) and ethyl acetate (200 mL). The organic layer was dried with $Na_2SO_4$ and concentrated to dryness. The residue was purified by column chromatography (silica gel, 100-200 mesh, 10-20% ethyl acetate in petroleum ether) to afford diethyl 2-(1-ethoxyethylidene)malonate (9.00 g, 78.3% yield) as a yellow solid.

Step 2: LHMDS (1N in THF, 50.2 mL, 50.2 mmol) was added to a solution of 4-(tert-butyl)benzonitrile (4.00 g, 25.1 mmol) in THF (30 mL) at 0° C. The reaction was stirred for 16 h at 20° C. The mixture was quenched by addition of aqueous HCl (4 M, 20 mL) at 0° C., and then adjusted to pH>8 by addition of aqueous NaOH (4 M). The separated aqueous layer was extracted with dicloromethane (3×30 mL). The combined organic layers were dried with $Na_2SO_4$ and concentrated to dryness to give crude 4-(tert-butyl)benzimidamide (3.30 g, 74.5% yield) as brown solid.

Step 3: Sodium (470 mg, 20.4 mmol) was added to ethanol (10 mL) and stirred for 30 min. This freshly prepared sodium ethoxide solution was added to a solution of diethyl 2-(1-ethoxyethylidene)malonate (4.23 g, 18.4 mmol) and 4-(tert-butyl)benzimidamide (1.80 g, 10.2 mmol) in ethanol (30 mL). The reaction mixture was stirred at 50° C. for 16 h and quenched with saturated aqueous $NH_4Cl$ (30 mL). The mixture was extracted with ethyl acetate (100 mL). The organic layer was washed with brine (30 mL) and concentrated. The residue was purified by column chromatography (silica gel, 100-200 mesh, 0-5% ethyl acetate in petroleum ether) to afford ethyl 2-(4-(tert-butyl)phenyl)-4-methyl-6-oxo-1,6-dihydropyrimidine-5-carboxylate (1.00 g, 31.1% yield) as white solid.

Step 4: A mixture of $POCl_3$ (5.00 mL, 50.6 mmol) and ethyl 2-(4-(tert-butyl)phenyl)-4-methyl-6-oxo-1,6-dihydropyrimidine-5-carboxylate (1.00 g, 3.2 mmol) was stirred at 110° C. for 2 h. The mixture was concentrated in vacuo and diluted with ethyl acetate (100 mL). The solution was washed with saturated aqueous $NaHCO_3$ (50 mL), dried over $Na_2SO_4$ and concentrated to dryness. The residue was purified by column chromatography (silica gel, 100-200 mesh, 0-10% ethyl acetate in petroleum) to give ethyl 2-(4-(tert-butyl)phenyl)-4-chloro-6-methylpyrimidine-5-carboxylate (0.90 g, 85.0% yield) as a pale yellow solid.

Step 5: A mixture of ethyl 2-(4-(tert-butyl)phenyl)-4-chloro-6-methylpyrimidine-5-carboxylate (1.00 g, 3.00 mmol) and ammonia (4 M in MeOH, 25.0 mL, 100.0 mmol) was stirred for 16 h at 70° C. The reaction was concentrated to dryness and diluted with ethyl acetate (100 mL). The solution was washed with water (2×30 mL), brine (30 mL), dried with $Na_2SO_4$ and concentration to dryness. The crude was purified by column chromatography (silica gel, 100-200 mesh, 0-5% ethyl acetate in petroleum ether) to give methyl 4-amino-2-(4-(tert-butyl)phenyl)-6-methylpyrimidine-5-carboxylate (900 mg, 95.6% yield) as white solid.

Step 6: A mixture of methyl 4-amino-2-(4-(tert-butyl)phenyl)-6-methylpyrimidine-5-carboxylatet (900 mg, 3.0 mmol) and NaOH (601 mg, 15.0 mmol) in water (5 mL) and MeOH (15 mL) was stirred at 80° C. for 3 h and concentrated under reduced pressure. The residue was acidified to pH<5 by addition of 1 M HCl and extracted with ethyl acetate (2×80 mL). The combined organic layers were concentrated under reduced pressure to give crude 4-amino-2-(4-(tert-butyl)phenyl)-6-methylpyrimidine-5-carboxylic acid (850 mg, 99.1% yield) as white solid.

The (formic acid salt) was prepared as described in Example 1, replacing 1-(4-(tert-butyl)phenyl)-6-oxo-1,6-dihydropyridazine-4-carboxylic acid with 4-amino-2-(4-(tert-butyl)phenyl)-6-methylpyrimidine-5-carboxylic acid in the first step. $^1$H NMR (400 MHz, MeOH-$d_4$) δ (ppm) 8.36-8.10 (m, 3H), 7.63-7.34 (m, 2H), 7.27-6.28 (m, 6H), 5.28-5.10 (m, 1H), 4.74-4.45 (m, 2H), 4.42-3.90 (m, 6H), 3.87-3.35 (m, 3H), 3.29-2.89 (m, 8H), 2.87-2.37 (m, 3H), 1.49-1.15 (m, 12H). LCMS (Method 5-95 AB, ESI): $R_T$=0.610 min, $[M+H]^+$=1008.4.

Example 3

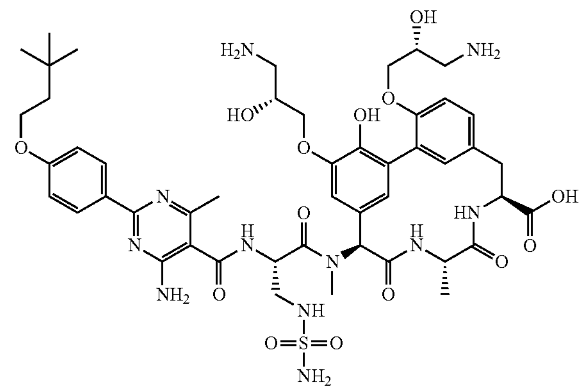 [SMILES: Cc1nc(-c2ccc(OCCC(C)(C)C)cc2)nc(N)c1C(=O)N[C@@H](CNS(N)(=O)=O)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O]

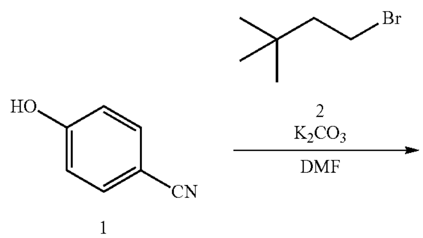

1

2

-continued

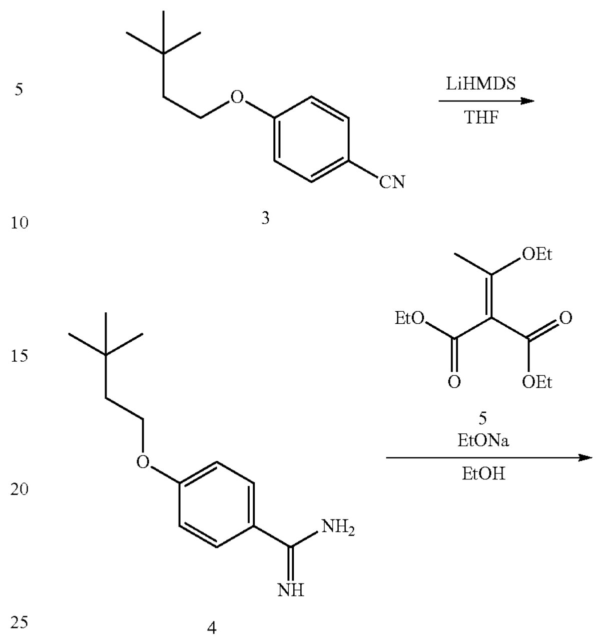

3

4

5

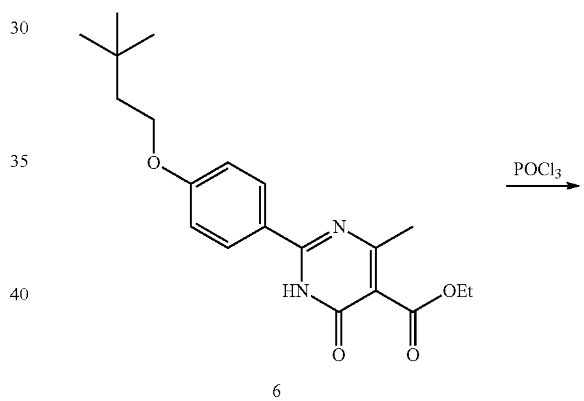

6

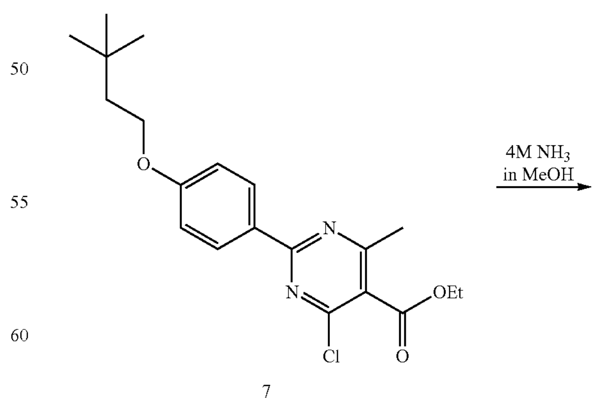

7

-continued

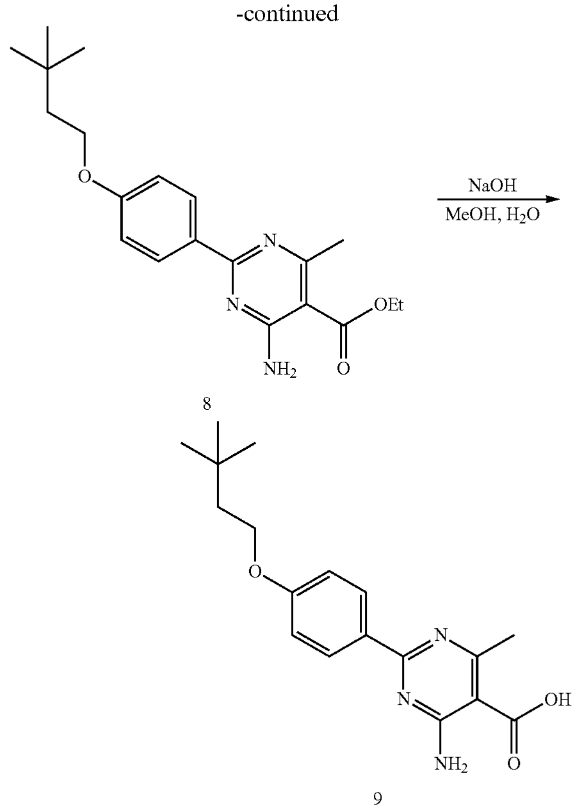

8

9

Step 1: A mixture of 4-hydroxybenzonitrile (5.0 g, 42.0 mmol), 1-bromo-3,3-dimethylbutane (10.4 g, 63.0 mmol) and $K_2CO_3$ (17.4 g, 126 mmol) in DMF (20 mL) was stirred at 80° C. for 2 h. After cooling to room temperature, the reaction mixture was diluted with water (500 mL) and extracted with ethyl acetate (3×300 mL). The combined organic layers were washed with water (2×300 mL), brine (200 mL), dried over $MgSO_4$ and concentrated to dryness. The residue was purified by column chromatography (silica gel, 100-200 mesh, 10% ethyl acetate in petroleum ether) to obtain 4-(3,3-dimethylbutoxy)benzonitrile (8.0 g, 93.8% yield) as a colorless oil.

Step 2: LHMDS (1 N in THF, 30.0 mL, 30.0 mmol) was added to 4-(3,3-dimethylbutoxy)benzonitrile (3.0 g, 14.8 mmol) in THF (30 mL) at 0° C. The reaction was stirred for 16 h at 20° C. and quenched by addition of 4 M HCl until pH=2. The mixture was then adjusted to pH=12 by addition of 4 M NaOH and extracted with chloroform (3×100 mL). The combined organic layers were dried over $Na_2SO_4$ and concentrated to dryness to give crude 4-(3,3-dimethylbutoxy)benzimidamide (3.0 g, 92.3% yield) as a yellow solid.

Step 3: To a solution of 4-(3,3-dimethylbutoxy)benzimidamide (4.70 g, 20.4 mmol) and EtONa (1.85 g, 27.2 mmol) in ethanol (20 mL) was added 2-(1-ethoxyethylidene)malonate (3.00 g, 13.6 mmol). The reaction mixture was stirred for 3 h at 50° C. and concentrated to dryness. The residue was partitioned between ethyl acetate (100 mL) and water (100 mL). The separated organic layer was washed with brine (50 mL), dried over $MgSO_4$ and concentration to dryness. The residue was purified by column chromatography (silica gel, 100-200 mesh, 30% ethyl acetate in petroleum ether) to give ethyl 2-(4-(3,3-dimethylbutoxy)phenyl)-4-methyl-6-oxo-1,6-dihydropyrimidine-5-carboxylate (1.70 g, 34.8% yield) as white solid.

Step 4: A mixture of ethyl 2-(4-(3,3-dimethylbutoxy)phenyl)-4-methyl-6-oxo-1,6-dihydropyrimidine-5-carboxylate (1.70 g, 4.74 mmol) in $POCl_3$ (30.0 mL, 325 mmol) was stirred at 110° C. for 3 h and concentrated to dryness. The crude was purified by column chromatography (silica gel, 100-200 mesh, 0-10% ethyl acetate in petroleum ether) to give ethyl 4-chloro-2-(4-(3,3-dimethylbutoxy)phenyl)-6-methylpyrimidine-5-carboxylate (1.40 g, 78.3% yield) as a white solid.

Step 5: A mixture of ethyl 4-chloro-2-(4-(3,3-dimethylbutoxy)phenyl)-6-methylpyrimidine-5-carboxylate (1.20 g, 3.18 mmol) and ammonia (4 M in MeOH, 30.0 mL, 120 mmol) was stirred for 16 h at 70° C. and concentrated to dryness. The residue was partitioned between ethyl acetate (200 mL) and water (100 mL). The separated organic layer was washed with brine (100 mL), dried over $Na_2SO_4$ and concentration to dryness. The crude was purified by column chromatography (silica gel, 100-200 mesh, 0-20% ethyl acetate in petroleum ether) to give ethyl 4-amino-2-(4-(3,3-dimethylbutoxy)phenyl)-6-methylpyrimidine-5-carboxylate (1.00 g, 87.9% yield) as white solid.

Step 6: A mixture of ethyl 4-amino-2-(4-(3,3-dimethylbutoxy)phenyl)-6-methylpyrimidine-5-carboxylate (1.00 g, 2.80 mmol) and NaOH (560 mg, 14.0 mmol) in MeOH (15 mL) and water (10 mL) was stirred at 80° C. for 22 h and concentrated. The residue was adjusted to pH=5 by addition of 1M HCl. The solid was collected by filtration and dried to give 4-amino-2-(4-(3,3-dimethylbutoxy)phenyl)-6-methylpyrimidine-5-carboxylic acid (800 mg, 86.8% yield) as a white solid.

The title compound was prepared as described in Example 1, replacing 1-(4-(tert-butyl)phenyl)-6-oxo-1,6-dihydropyridazine-4-carboxylic acid with 4-amino-2-(4-(3,3-dimethylbutoxy)phenyl)-6-methylpyrimidine-5-carboxylic acid. $^1H$ NMR (400 MHz, DMSO-$d_6$) δ (ppm) 8.34 (s, 1H), 8.20 (d, J=8.4 Hz, 2H), 7.12-7.04 (m, 1H), 6.95 (d, J=8.8 Hz, 2H), 6.92-6.84 (m 1H), 6.84-6.74 (m, 2H), 8.56 (s, 1H), 6.44 (s, 1H), 5.23-5.13 (m, 1H), 4.83-4.79 (m, 2H), 4.54-4.42 (m, 1H), 4.26-4.20 (m, 1H), 4.18-3.97 (m, 7H), 3.65-3.56 (m, 1H), 3.40-3.33 (m, 4H), 3.28-3.13 (m, 3H), 3.12-2.94 (m, 5H), 2.45 (s, 3H), 1.80-1.68 (m, 3H), 1.34 (d, J=6.0 Hz, 3H), 1.01 (s, 9H); LCMS (Method 5-95 AB): $R_T$=0.823 min, $[M+H]^+$=1052.4

Example 4

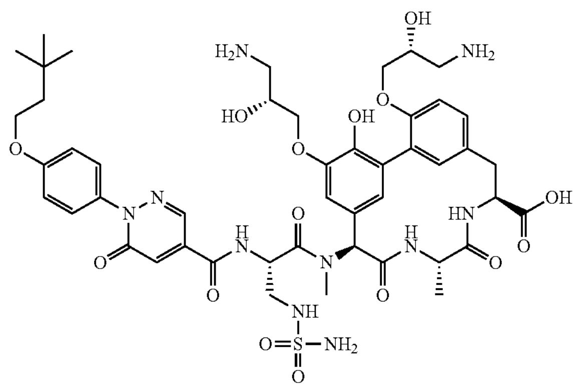 [SMILES: C[C@@H]1NC(=O)[C@@H](N(C)C(=O)[C@H](CNS(N)(=O)=O)NC(=O)c2cnn(-c3ccc(OCCC(C)(C)C)cc3)c(=O)c2)c2cc(OC[C@H](O)CN)c(O)c(c2)-c2cc(ccc2OC[C@H](O)CN)C[C@@H](C(=O)O)NC1=O]

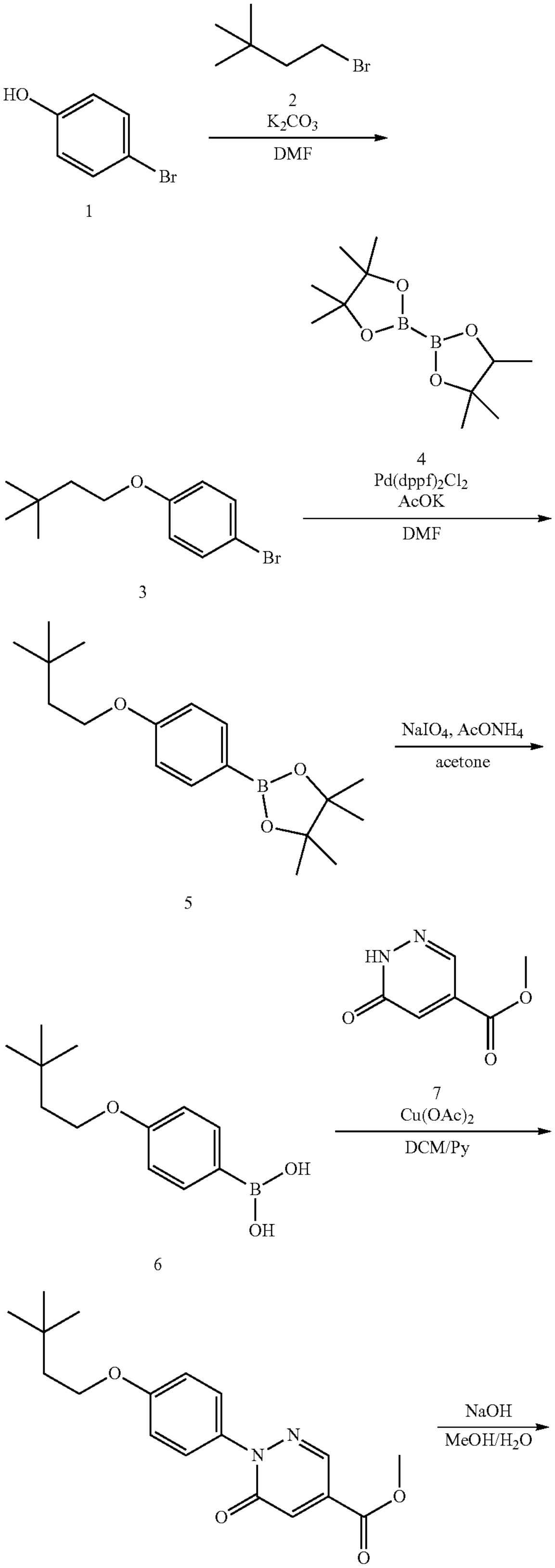

1 3 5 6 8

-continued

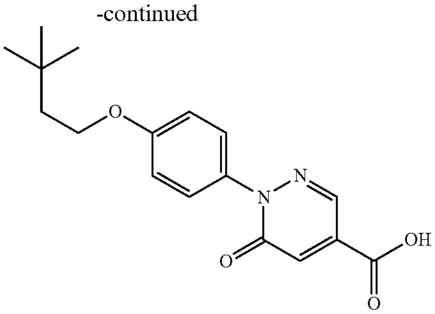

9

Step 1: To a solution of 4-bromophenol (7.16 g, 43.4 mmol) in DMF (30.0 mL) was added 1-bromo-3,3-dimethylbutane (5.00 g, 28.9 mmol) and $K_2CO_3$ (10.0 g, 72.2 mmol). The reaction mixture was stirred at 50° C. for 16 h and cooled to room temperature. The mixture was filtered and the filtrate was diluted with ethyl acetate (80 mL) and water (80 mL). The separated organic layer was washed with brine (3×80 mL), dried over $Na_2SO_4$ and concentrated to dryness. The residue was purified by column chromatography (silica gel, 100-200 mesh, 5% methanol in dichloromethane) to afford 1-bromo-4-(3,3-dimethylbutoxy)benzene (6.10 g, 82.1% yield) as a white solid.

Step 2: A mixture of 1-bromo-4-(3,3-dimethylbutoxy) benzene (6.10 g, 23.7 mmol), Pd (dppf)$Cl_2$ (1.74 g, 2.37 mmol), bis(pinacolato)diboron (9.04 g, 35.6 mmol) and potassium acetate (7.00 g, 71.2 mmol) in DMF (60 mL) was heated at 80° C. for 4 h under $N_2$ atmosphere and then filtered. The filtrate was partitioned between ethyl acetate (100 mL) and water (100 mL). The separated organic layer was washed with brine (3×150 mL), dried over $Na_2SO_4$ and concentrated. The residue was purified by column chromatography (silica gel, 100-200 mesh, 2% ethyl acetate in petroleum ether) to give 2-(4-(3,3-dimethylbutoxy)phenyl)-4,4,5,5-tetramethyl-1,3,2-dioxaborolane (6.30 g, 87.3% yield) as a white solid.

Step 3: To a solution of 2-(4-(3,3-dimethylbutoxy)phenyl)-4,4,5,5-tetramethyl-1,3,2-dioxaborolane (6.30 g, 20.7 mmol) in acetone (60 mL) was added ammonium acetate (83 mL, 82.7 mmol) and $NaIO_4$ (13.3 g, 62.0 mmol). The reaction was stirred at 40° C. for 16 h and concentrated to dryness. The residue diluted with water (100 mL) and extracted with ethyl acetate (3×100 mL). The combined organic layers were washed with brine (50 mL), dried over $Na_2SO_4$ and concentrated to dryness. The residue was purified by column chromatography (silica gel, 100-200 mesh, 2% methanol in dichloromethane to obtain (4-(3,3-dimethylbutoxy)phenyl)boronic acid (4.50 g, 20.3 mmol, 98.0% yield) as a yellow solid.

Step 4: A mixture of (4-(3,3-dimethylbutoxy)phenyl)boronic acid (200 mg, 0.90 mmol), copper diacetate (32.7 mg, 0.18 mmol) and methyl 6-oxo-1,6-dihydropyridazine-4-carboxylate (146 mg, 0.95 mmol) in dichloromethane (6 mL) and pyridine (1 mL) was stirred at 20° C. for 16 h. The reaction mixture was diluted with ethyl acetate (80 mL) and filtered. The filtrate was washed with brine (50 mL) and concentration to dryness. The residue was purified by preparative TLC (33% ethyl acetate in petroleum ether, $R_f$=0.3) to give methyl 1-(4-(3,3-dimethylbutoxy)phenyl)-6-oxo-1,6-dihydropyridazine-4-carboxylate (235 mg, 79.0% yield) as a green solid.

Step 5: A mixture of methyl 1-(4-(3,3-dimethylbutoxy) phenyl)-6-oxo-1,6-dihydropyridazine-4-carboxylate (235 mg, 0.71 mmol) and NaOH (71.1 mg, 1.78 mmol) in MeOH (10 mL) and water (3 mL) was stirred for 1 h at 80° C. The reaction mixture was adjusted pH=5 with HCl (1M in water) and extracted with ethyl acetate (2×50 mL). The combined organic layers were dried over $Na_2SO_4$ and concentrated to dryness to give crude 1-(4-(3,3-dimethylbutoxy)phenyl)-6-oxo-1,6-dihydropyridazine-4-carboxylic acid (220 mg, 97.8% yield) as a yellow solid.

The title compound was prepared as described in Example 1, replacing 1-(4-(tert-butyl)phenyl)-6-oxo-1,6-dihydropyridazine-4-carboxylic acid with 1-(4-(3,3-dimethylbutoxy)phenyl)-6-oxo-1,6-dihydropyridazine-4-carboxylic acid. $^1H$ NMR (400 MHz, DMSO-$d_6$): δ (ppm) 9.33 (s, 1H), 8.46 (s, 1H), 8.35-8.34 (m, 2H), 8.02 (s, 1H), 7.57 (s, 1H), 7.50-7.47 (m, 2H), 7.07-7.05 (m, 3H), 6.90-6.66 (m, 8H), 6.36 (s, 1H), 6.22 (s, 1H), 5.05-5.02 (m, 2H), 4.67-4.64 (m, 2H), 4.10-3.92 (m, 8H), 3.25-3.23 (m, 6H), 3.08-3.07 (m, 3H), 2.97-2.95 (m, 3H), 2.85-2.83 (m, 4H), 2.68 (s, 1H), 1.68 (t, J=6.8 Hz, 2H). 1.16 (d, J=6.4 Hz, 3H), 0.98 (s, 9H). LCMS (Method 5-95 AB, ESI), $R_T$=0.830 min, $[M+H]^+$ =1039.3.

Example 5

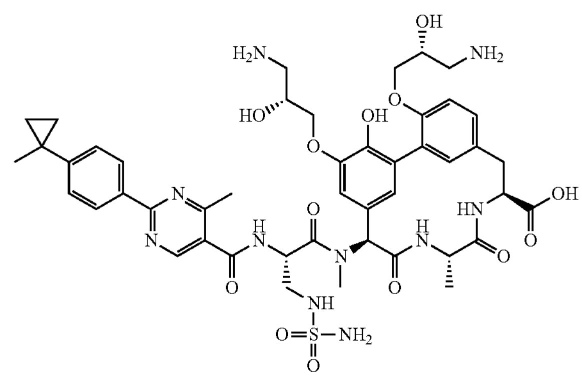 [SMILES: Cc1nc(-c2ccc(C3(C)CC3)cc2)ncc1C(=O)N[C@@H](CNS(N)(=O)=O)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O]

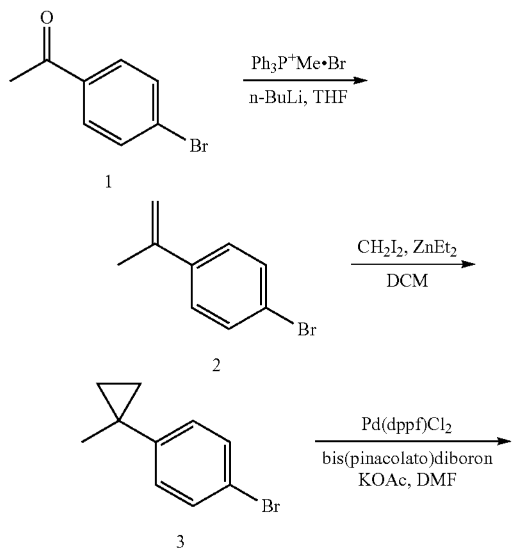

1

2

3

-continued

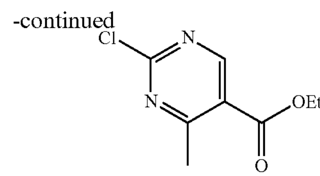

5

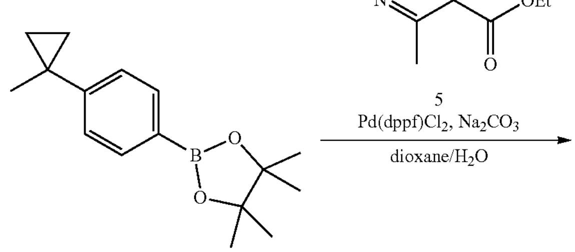

4

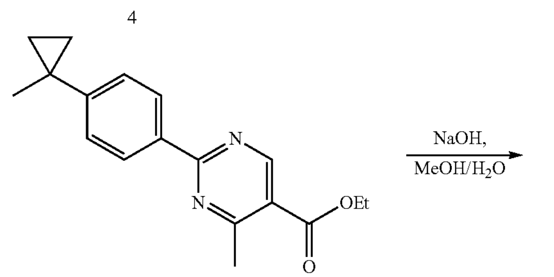

6

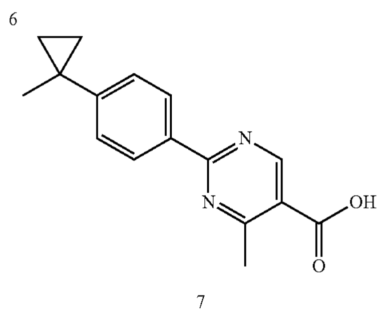

7

Step 1: To a solution of $Ph_3P^+MeBr^-$ (201 g, 563 mmol) in THF (500 mL) was added n-BuLi (2.5 N in hexanes, 225 mL, 563 mmol) under $N_2$ at 0° C. The mixture was stirred at room temperature until the solution turned clear, then a solution of 1-(4-bromophenyl)ethan-1-one (70 g, 352 mmol) in THF (200 mL) was added dropwise. After addition, the mixture was heated at 70° C. for 20 h and quenched by addition of saturated aqueous $NH_4Cl$ (1000 mL). The resulting solution was extracted with ethyl acetate (2×1000 mL). The combined organics layers were dried over $Na_2SO_4$ and concentrated. The residue was purified by column chromatography (silica gel, 100-200 mesh, petroleum ether) to give 1-bromo-4-(prop-1-en-2-yl)benzene (50 g, 72.1% yield) as colorless oil.

Step 2: To a solution of 1-bromo-4-(prop-1-en-2-yl)benzene (20.0 g, 101 mmol) in dichloromethane (100 mL) was added $ZnEt_2$ (1 M in toluene, 507 mL, 507 mmol) and $CH_2I_2$ (81.9 mL, 1010 mmol) at 0° C. under $N_2$ atmosphere. The was heated to 70° C. for 72 h and concentrated to dryness. The residue was partitioned between water (500 mL) and petroleum ether (500 mL). The organic layer was washed with brine (3×100 mL), dried over $Na_2SO_4$ and concentration to dryness. The residue was then purified by preparative HPLC (acetonitrile 55-85%/0.225% FA in water) to give 1-bromo-4-(1-methylcyclopropyl)benzene (201 g, 60.7% yield) as colorless oil.

Step 3: A mixture of 1-bromo-4-(1-methylcyclopropyl)benzene (28.8 g, 136 mmol), bis(pinacolato)diboron (36.3 g, 143 mmol), KOAc (40.1 g, 408 mmol) and $Pd(dppf)_2Cl_2$ (9.97 g, 13.6 mmol) in DMF (200 mL) was heated at 80° C. for 6 h under $N_2$ atmosphere. The reaction was diluted with ethyl acetate (600 mL) and filtered. The filtrate was washed with water (2×200 mL), brine (3×200 mL), dried over $Na_2SO_4$ and concentrated to dryness. The residue was purified by column chromatography (silica gel, 100-200 mesh, 0%-10% ethyl acetate in petroleum ether) to give 4,4,5,5-tetramethyl-2-(4-(1-methylcyclopropyl)phenyl)-1,3,2-dioxaborolane (30 g, 85.2%) as a white solid.

Step 4: A mixture of 4,4,5,5-tetramethyl-2-(4-(1-methylcyclopropyl)phenyl)-1,3,2-dioxaborolane (20.0 g, 77.5 mmol), ethyl 2-chloro-4-methylpyrimidine-5-carboxylate (15.4 g, 77.5 mmol), $Na_2CO_3$ (24.6 g, 232 mmol) and $Pd(dppf)_2Cl_2$ (5.67 g, 7.75 mmol) in 1,4-dioxane (400 mL) and water (20.0 mL) was heated at 100° C. for 16 h under $N_2$ and filtered. The filtrate was concentrated to dryness. The residue was purified by column chromatography (silica gel, 100-200 mesh, 0%-5% ethyl acetate in petroleum) to give ethyl 4-methyl-2-(4-(1-methylcyclopropyl)phenyl)pyrimidine-5-carboxylate (26.0 g, 56.4% yield) as a white solid.

Step 5: A mixture of ethyl 4-methyl-2-(4-(1-methylcyclopropyl)phenyl)pyrimidine-5-carboxylate (26.0 g, 79.0 mmol) and NaOH (9.47 g, 237 mmol) in MeOH (260 mL) and water (26 mL) was stirred at 80° C. for 16 h and concentrated. The residue was diluted with water (100 mL) and adjusted to pH=4 with HCl (1M). The mixture was filtered and the filtrate was concentrated to dryness to give crude 4-methyl-2-(4-(1-methylcyclopropyl)phenyl)pyrimidine-5-carboxylic acid (28.0 g, 100% yield) as a white solid.

The title compound was prepared as described in Example 1, replacing 1-(4-(tert-butyl)phenyl)-6-oxo-1,6-dihydropyridazine-4-carboxylic acid with compound 4-methyl-2-(4-(1-methylcyclopropyl)phenyl)pyrimidine-5-carboxylic acid. $^1H$ NMR (400 MHz, MeOH-$d_4$) δ (ppm) 8.86 (s, 1H), 8.18 (d, J=8.4 Hz, 2H), 7.32 (d, J=8.4 Hz, 2H), 6.90-6.87 (m, 2H), 6.78 (m, 2H), 6.39 (s, 2H), 5.29-5.26 (m, 1H), 4.80-4.75 (m, 1H), 4.60 (d, J=9.2 Hz, 1H), 4.36-4.32 (m, 1H), 4.27-4.19 (m, 2H), 4.11-4.05 (m, 3H), 3.65-3.60 (m, 1H), 3.45-3.34 (m, 1H), 3.28-3.13 (m, 4H), 3.06 (s, 3H), 3.00-2.86 (m, 1H), 2.77-2.72 (m, 10H) 2.65 (m, 3H), 1.48 (s, 3H), 1.37 (d, J=6.8 Hz, 3H), 0.97-0.95 (m, 2H), 0.89-0.88 (m, 2H). LCMS (Method 5-95 AB, ESI), $R_T$=0.802 min, $[M+H]^+$=991.2.

Example 6

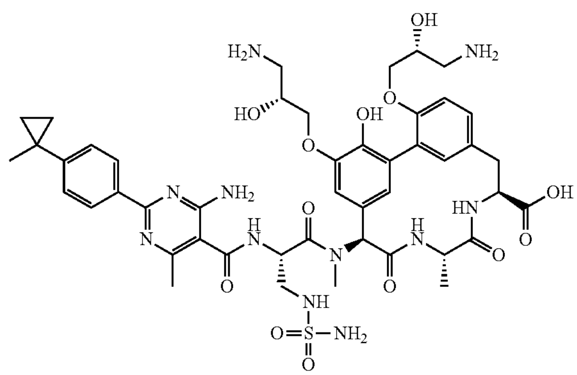 [SMILES: Cc1nc(-c2ccc(C3(C)CC3)cc2)nc(N)c1C(=O)N[C@@H](CNS(N)(=O)=O)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O]

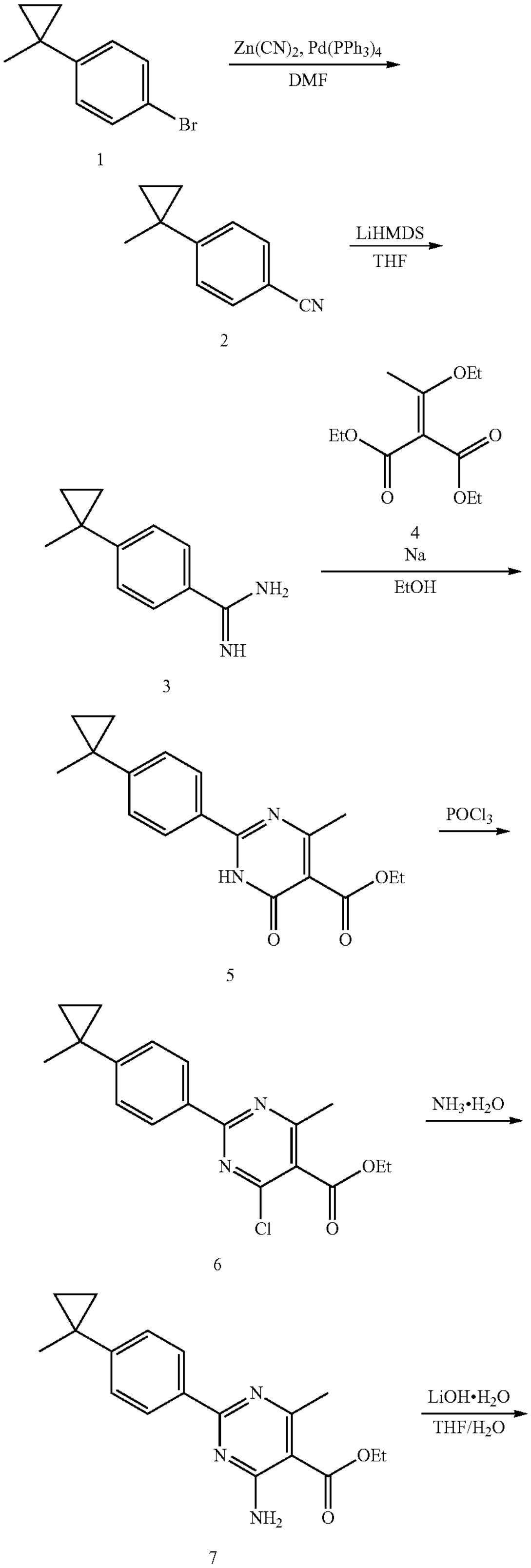

-continued

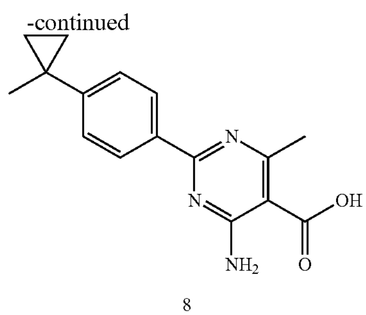

8

Step 1: A mixture of 1-bromo-4-(1-methylcyclopropyl) benzene (5.20 g, 24.6 mmol), $Pd(PPh_3)_4$ (2.80 g, 2.46 mmol) and $Zn(CN)_2$ (6.47 g, 55.1 mmol) in DMF (50 mL) was heated at 120° C. for 16 h under $N_2$ atmosphere. After cooling to room temperature, the mixture was diluted with ethyl acetate (500 mL) and filtered. The filtrate was washed with brine (2×200 mL), dried over $Na_2SO_4$ and concentrated. The residue was purified by column chromatography (silica gel, 100-200 mesh, 0-0.5% ethyl acetate in petroleum ether) to give 4-(1-methylcyclopropyl)benzonitrile (14.0 g, 92.1% yield) as a light yellow oil.

Step 2: A mixture of 4-(1-methylcyclopropyl)benzonitrile (5.00 g, 31.8 mmol) and LHMDS (1 N in THF, 63.6 mL, 63.6 mmol) in THF (50 mL) was stirred at 30° C. for 16 h and quenched by addition of 1M HCl (50 mL). The separated aqueous layer was adjusted to pH=8 by addition of 1M NaOH and extracted with ethyl acetate (5×100 mL). The combined organic layers were dried and concentrated to give crude 4-(1-methylcyclopropyl)benzimidamide (4.80 g, 86.6% yield) as a yellow solid.

Step 3: A mixture of 4-(1-methylcyclopropyl)benzimidamide (1.80 g, 10.3 mmol), 2-(1-ethoxyethylidene)malonate (12.0 mL, 18.6 mmol) and freshly made sodium ethoxide (20.7 mmol) in ethanol (40 mL) was heated at 50° C. for 16 h. After cooling to room temperature, the reaction mixture was quenched with HCl (1 M, 100 mL) and extracted with ethyl aceate (4×100 mL). The combined organic layers were washed with brine (100 mL), dried and concentrated. The residue was purified by column chromatography (silica gel, 100-200 mesh, 30% ethyl acetate in petroleum ether) to obtain ethyl 4-methyl-2-(4-(1-methylcyclopropyl)phenyl)-6-oxo-1,6-dihydropyrimidine-5-carboxylate (2.50 g, 77.5% yield) as a yellow solid.

Step 4: A mixture of ethyl 4-methyl-2-(4-(1-methylcyclopropyl)phenyl)-6-oxo-1,6-dihydropyrimidine-5-carboxylate (6.5 g, 20.8 mmol) in $POCl_3$ (69.3 mL, 743 mmol) was heated at 110° C. for 2 h and concentrated to dryness. The residue was purified by column chromatography (silica gel, 100-200 mesh, 5% ethyl acetate in petroleum ether) to obtain ethyl 4-chloro-6-methyl-2-(4-(1-methylcyclopropyl) phenyl)pyrimidine-5-carboxylate (6.1 g, 88.6% yield) as a yellow oil.

Step 5: A mixture of ethyl 4-chloro-6-methyl-2-(4-(1-methylcyclopropyl)phenyl)pyrimidine-5-carboxylate (6.10 g, 18.4 mmol) in ammonia (10 N in MeOH, 60 mL, 600 mmol) was heated at 50° C. for 16 h and concentrated to dryness. The residue was purified by column chromatography (silica gel, 100-200 mesh, 20% ethyl acetate in petroleum ether) to give ethyl 4-amino-6-methyl-2-(4-(1-methylcyclopropyl)phenyl)pyrimidine-5-carboxylate (3.00 g, 52.2% yield) as a white solid.

Step 6: A mixture of ethyl 4-amino-6-methyl-2-(4-(1-methylcyclopropyl)phenyl)pyrimidine-5-carboxylate (1.85 g, 5.94 mmol) and NaOH (0.95 g, 23.8 mmol) in MeOH (20 mL) and water (10 mL) was heated at 80° C. for 2 h. After cooling to room temperature, the mixture was filtered. The filter cake was dried to give crude 4-amino-6-methyl-2-(4-(1-methylcyclopropyl)phenyl)pyrimidine-5-carboxylic acid (1.68 g, 100% yield) as a white solid.

The title compound was prepared as described in Example 1, replacing 1-(4-(tert-butyl)phenyl)-6-oxo-1,6-dihydropyridazine-4-carboxylic acid with 4-amino-6-methyl-2-(4-(1-methylcyclopropyl)phenyl)pyrimidine-5-carboxylic acid. $^1$H NMR (400 MHz, MeOH-$d_4$) δ (ppm) 8.12 (d, J=8.4 Hz, 2H), 7.47 (d, J=8.4 Hz, 2H), 7.21-7.15 (m, 1H), 7.02 (d, J=8.4 Hz, 1H), 6.93-6.86 (m, 1H), 6.85-6.80 (m, 1H), 6.5 (s, 1H), 6.4 (s, 1H), 5.25-5.17 (m, 1H), 4.85-4.77 (m, 2H), 4.32-4.25 (m, 1H), 4.24-4.14 (m, 3H), 4.12-4.04 (m, 2H), 3.66-3.59 (m 1H), 3.58-3.43 (m, 1H), 3.41-3.38 (m, 1H), 3.37-3.31 (m, 2H), 3.29-3.28 (m, 1H), 3.28-3.20 (m, 1H), 3.19-3.14 (m, 1H), 3.13-3.07 (m, 2H), 3.1 (s, 3H), 2.75 (s, 1H), 2.7 (s, 12H), 2.63 (s, 3H), 1.48 (s, 3H), 1.42-1.28 (m, 3H), 1.03-0.97 (m, 2H), 0.94-0.90 (m, 2H). LCMS (Method 10-80 AB, ELSD), $R_T$=1.412 min, $[M+H]^+$=1006.7.

Example 7

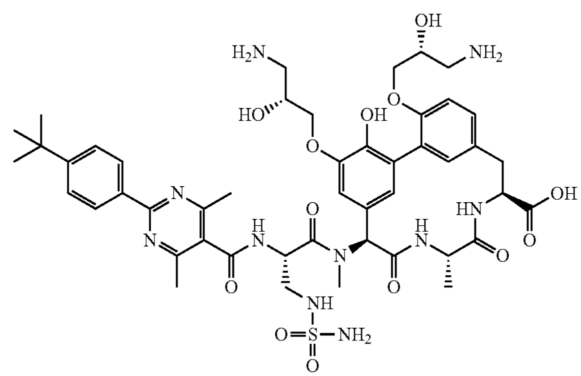 [SMILES: Cc1nc(-c2ccc(C(C)(C)C)cc2)nc(C)c1C(=O)N[C@@H](CNS(N)(=O)=O)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O]

The title compound was prepared as described in Example 1, replacing 1-(4-(tert-butyl)phenyl)-6-oxo-1,6-dihydropyridazine-4-carboxylic acid with 2-(4-(tert-butyl)phenyl)-4,6-dimethylpyrimidine-5-carboxylic acid. $^1$H NMR (400 MHz, MeOH-$d_4$) δ (ppm) 8.89 (d, J=7.6 Hz, 1H), 8.55 (d, J=8.8 Hz, 1H), 8.21 (d, J=8.0 Hz, 2H), 7.43 (d, J=8.0 Hz, 2H), 7.05-6.97 (m, 2H), 6.77 (s, 1H), 6.45 (s, 1H), 5.43-5.39 (m, 1H), 4.81-4.76 (m, 2H), 4.27-4.21 (m, 3H), 4.10-4.05 (m, 3H), 3.63-3.59 (m, 1H), 3.37-3.33 (m, 1H), 3.28-3.20 (m, 2H), 3.12-3.07 (m, 6H), 2.97-2.90 (m, 1H), 2.46 (s, 6H), 1.38 (s, 9H), 1.37 (s, 3H). LCMS (Method 10-80 AB, ELSD), $R_T$=0.652 min, $[M+H]^+$=1007.5.

Example 8

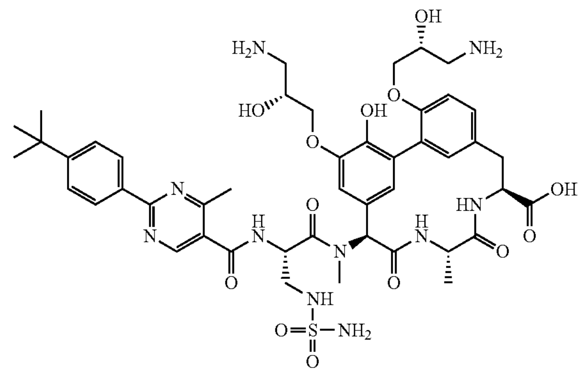 [SMILES: Cc1nc(-c2ccc(C(C)(C)C)cc2)ncc1C(=O)N[C@@H](CNS(N)(=O)=O)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O]

The title compound was prepared as described in Example 1, replacing 1-(4-(tert-butyl)phenyl)-6-oxo-1,6-dihydropyridazine-4-carboxylic acid with 2-(4-(tert-butyl)phenyl)-4-methylpyrimidine-5-carboxylic acid. $^{1}H$ NMR (400 MHz, MeOH-$d_4$) δ (ppm) 8.84 (s, 1H), 8.381 (s, 1H), 8.34-8.25 (m, 2H), 7.55-7.47 (m, 1H), 7.07-6.93 (m, 1H), 6.89-6.74 (m, 2H), 6.66-6.56 (m, 1H), 6.51 (s, 1H), 5.33-5.03 (m, 1H), 4.83-4.81 (m, 2H), 4.47 (s, 1H), 4.37-3.95 (m, 6H), 3.65-3.50 (m, 1H), 3.49-3.34 (m, 1H), 3.28-3.07 (m, 4H), 3.07-2.94 (m, 4H), 2.66 (s, 3H), 1.40-1.32 (m, 12H). LCMS (Method 5-95 AB, ELSD), $R_T$=0.667 min, $[M+H]^+$=993.4.

Example 9

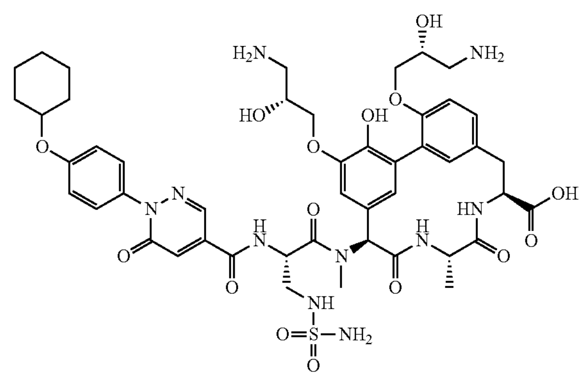 [SMILES: C[C@@H]1NC(=O)[C@@H](N(C)C(=O)[C@H](CNS(N)(=O)=O)NC(=O)c2cnn(-c3ccc(OC4CCCCC4)cc3)c(=O)c2)c2cc(OC[C@H](O)CN)c(O)c(c2)-c2cc(ccc2OC[C@H](O)CN)C[C@@H](C(=O)O)NC1=O]

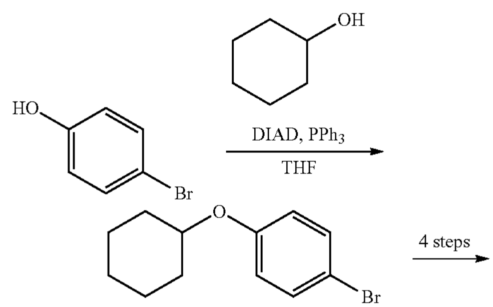

-continued

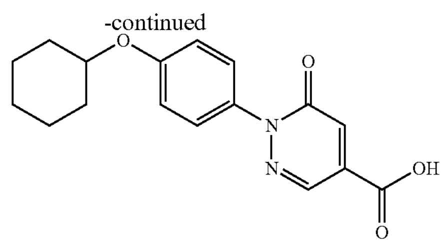

Step 1: To a solution of 4-bromophenol (5.00 g, 28.9 mmol), $PPh_3$ (22.7 g, 86.7 mmol) and cyclohexanol (8.68 g, 86.7 mmol) in THF (75.0 mL) was added DIAD (17.2 mL, 86.7 mmol) slowly at 0° C. The reaction mixture was stirred for 3 h at 20° C. and concentrated. The residue was diluted with water (70 mL) and then extracted with ethyl acetate (3×60 mL). The combined organic layers were washed with brine (40 mL), dried over $Na_2SO_4$ and concentrated to dryness. The residue was purified by column chromatography (silica gel, 100-200 mesh, 100% petroleum ether to obtain 1-bromo-4-(cyclohexyloxy)benzene (6.24 g, 85.0% yield) as a white solid. This was then converted to 1-(4-(cyclohexyloxy)phenyl)-6-oxo-1,6-dihydropyridazine-4-carboxylic acid using procedures analogous to those used in Example 4.

The title compound was prepared as described in Example 1, replacing 1-(4-(tert-butyl)phenyl)-6-oxo-1,6-dihydropyridazine-4-carboxylic acid with 1-(4-(cyclohexyloxy)phenyl)-6-oxo-1,6-dihydropyridazine-4-carboxylic acid. $^{1}H$ NMR (400 MHz, DMSO-$d_6$): δ (ppm) 9.33 (s, 1H), 8.44-8.34 (m, 2H), 8.06 (s, 1H), 7.55 (d, J=1.6 HZ, 1H), 7.47-7.43 (m, 1H), 7.06-7.04 (m, 2H), 6.89-6.67 (m, 6H), 6.36 (s, 1H), 6.22 (s 1H), 5.02 (s, 1H), 4.66 (s, 1H), 4.40 (s, 1H), 4.05-3.98 (m, 7H), 3.25 (s, 2H), 3.12-2.97 (m, 6H), 2.83 (s, 3H), 1.98-1.93 (m, 2H), 1.73-1.72 (m, 2H), 1.53-1.15 (m, 9H). LCMS (Method 5-95 AB, ELSD), $R_T$=0.815 min, $[M+H]^+$=1037.5.

Example 10

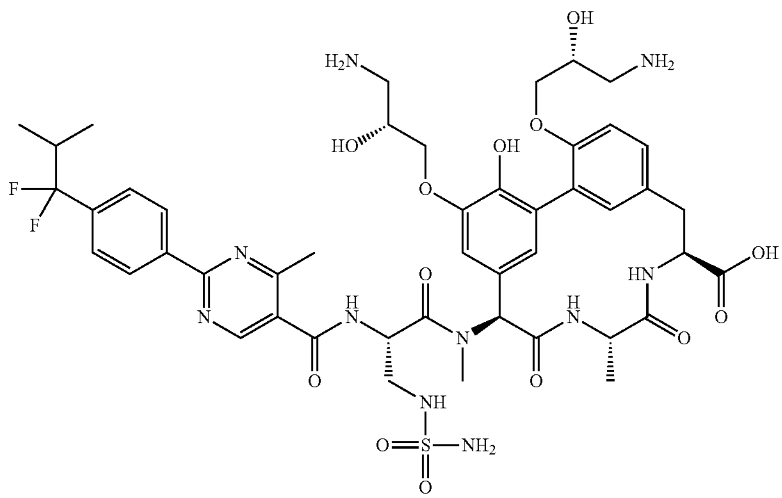 [SMILES: Cc1nc(-c2ccc(C(F)(F)C(C)C)cc2)ncc1C(=O)N[C@@H](CNS(N)(=O)=O)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O]

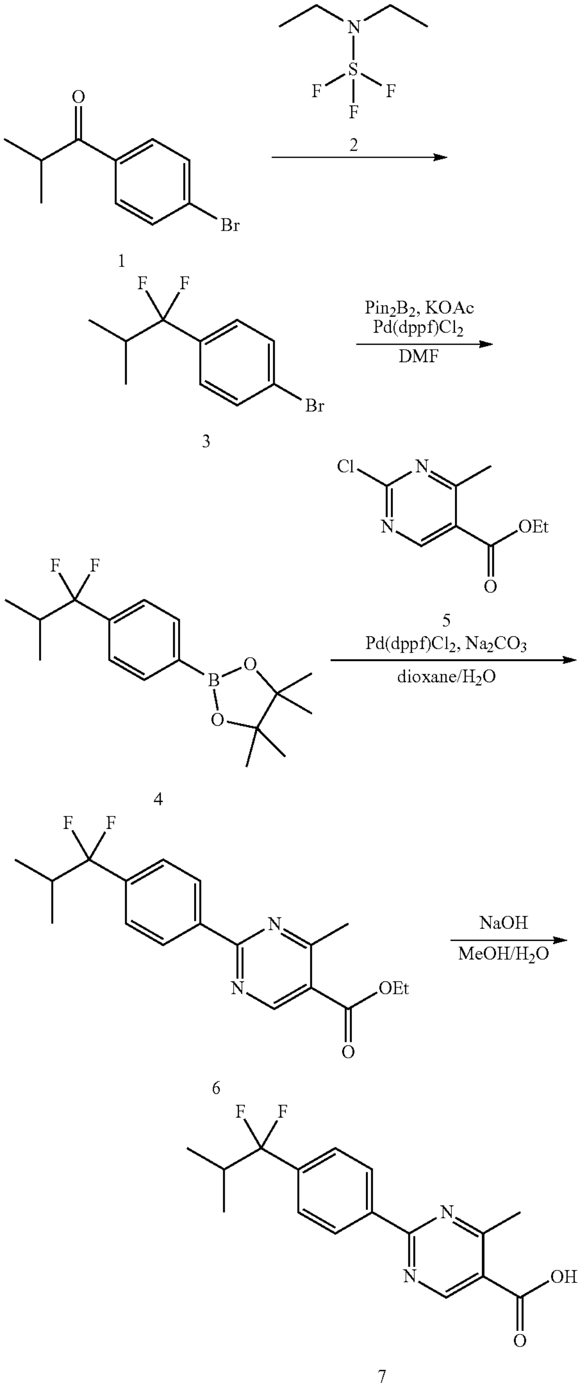

Step 1: A mixture of compound 1 (2.50 g, 11.0 mmol) and compound 2 (4.20 g, 26.0 mmol) was stirred at 50° C. for 48 h. The reaction mixture was warmed to 70° C. for another 1 h to complete the reaction. Then the mixture was poured into ice water (100 mL) and extracted with dichloromethane (3×50 mL). The combined organic layers were washed with water (50 mL), dried with $Na_2SO_4$ and concentrated. The residue was purified by column chromatography (silica gel, 100-200 mesh, 0%-5% ethyl acetate in petroleum ether) to obtain compound 3 (177 mg, 5.8% yield) as a yellow oil.

Step 2: A mixture of bis(pinacolato)diboron (177 mg, 0.70 mmol), potassium acetate (125 mg, 1.27 mmol) and compound 3 (158 mg, 0.63 mmol) in DMF (3.00 mL) was stirred at 80° C. for 14 h under $N_2$ atmosphere. The reaction mixture was diluted with ethyl acetate (20 mL) and filtered. The filtrate was concentrated in vacuo to give crude compound 4 (138 mg, 0.47 mmol) as brown oil.

Step 3: A mixture of compound 4 (138 mg, 0.47 mmol), compound 5 (102 mg, 0.51 mmol), sodium carbonate (98.8 mg, 0.93 mmol) and 1,1'-bis(diphenylphosphino)ferrocene palladium dichloride (34.1 mg, 0.05 mmol) in water (0.5 mL) and 1,4-dioxane (5 mL) was heated at 100° C. under $N_2$ for 16 h. After cooling to room temperature, the reaction mixture was diluted with ethyl acetate (80 mL). The solution was washed with water (40 mL), brine (40 mL), dried and concentrated to dryness. The residue was purified by column chromatography (silica gel, 100-200 mesh, 0-10% ethyl acetate in petroleum ether) to obtain compound 6 (60.0 mg, 38.5% yield) as a pale oil.

Step 4: A mixture of compound 6 (60.0 mg, 0.18 mmol) and sodium hydroxide (14.4 mg, 0.36 mmol) in methanol (1.5 mL) and water (1.5 mL) was stirred at 80° C. for 2 h and concentrated. The aqueous residue was adjusted to pH=5 with 5% $KHSO_4$ and extracted with ethyl acetate (2×30 mL). The combined organic layers were washed with brine (40 mL), dried and concentrated to obtain crude compound 7 (45.8 mg, 83.3% yield) as a white solid.

The title compound was prepared as described in Example 1, replacing 1-(4-(tert-butyl)phenyl)-6-oxo-1,6-dihydropyridazine-4-carboxylic acid with compound 7. $^1H$ NMR (400 MHz, MeOH-$d_4$) δ (ppm) 8.88 (s, 1H), 8.50-8.43 (m, 2H), 8.40 (s, 1H), 7.58-7.52 (m, 2H), 7.02 (s, 1H), 6.89-6.79 (m, 2H), 6.60-6.48 (m, 2H), 5.29-5.16 (m, 1H), 4.81-4.75 (m, 3H), 4.46 (s, 1H), 4.28-3.91 (m, 6H), 3.69-3.53 (m, 1H), 3.43-3.35 (m, 1H), 3.28-3.11 (m, 4H), 3.07 (s, 3H), 3.01-2.98 (m, 1H), 2.81-2.60 (m, 4H), 2.49-2.34 (m, 1H), 1.41-1.30 (m, 3H), 1.04-1.00 (m, 6H). LCMS (Method 5-95 AB, ESI), $R_T$=0.771 min, $[M+H]^+$=1029.7.

Example 11

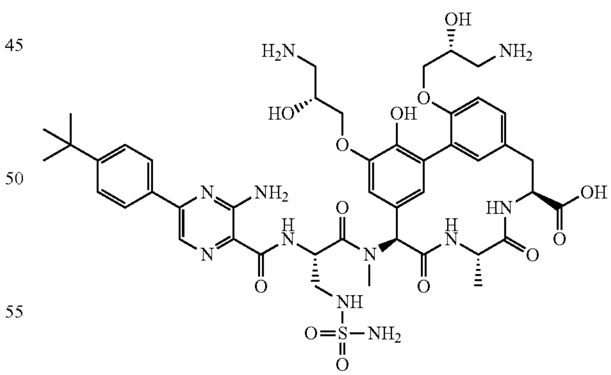

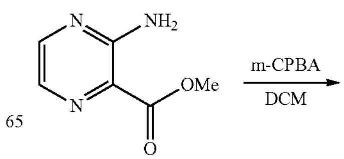

-continued

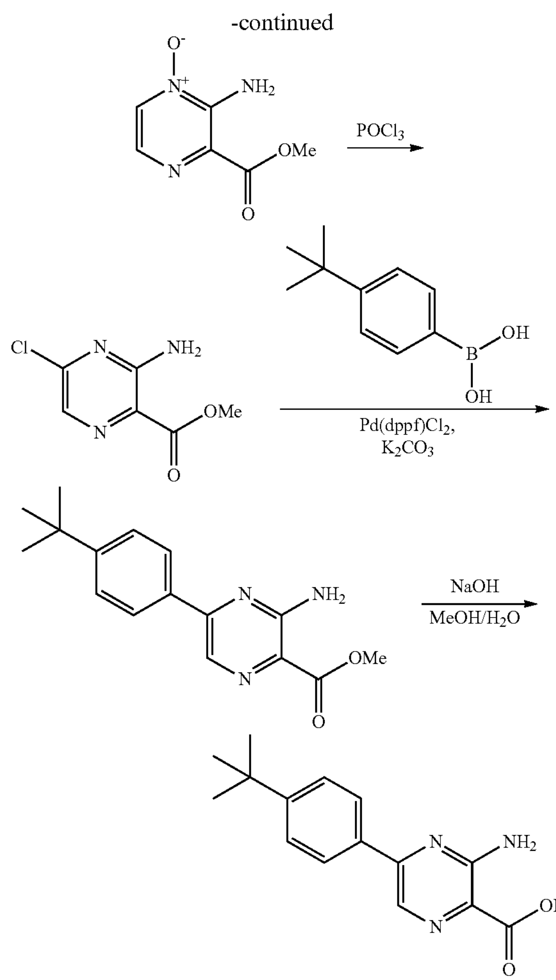

Step 1: A solution of methyl 3-aminopyrazine-2-carboxylate (5.0 g, 32.7 mmol) and m-CPBA (10.6 g, 49.0 mmol) in dichloromethane (50 mL) was stirred at 60° C. for 16 h. After cooling to room temperature, the reaction mixture was diluted with dichloromethane (250 mL) and filtered. The filtrate was concentrated to dryness and the residue was taken up to 10% ethyl acetate in petroleum ether (200 mL). The resulting mixture was stirred at 25° C. for 1 h and filtered. The solid was collected and dried to give crude 2-amino-3-(methoxycarbonyl)pyrazine 1-oxide (5.5 g, 99.6% yield) as a yellow solid.

Step 2: A mixture of 2-amino-3-(methoxycarbonyl)pyrazine 1-oxide (5.50 g, 32.5 mmol) and $POCl_3$ (15.2 mL, 163 mmol) in DMF (30 mL) was heated at 100° C. for 16 h. After cooling to room temperature, the mixture was diluted with $H_2O$ (300 mL) and adjust to pH=7 with solid $NaHCO_3$. The resulting mixture was extracted with ethyl acetate (2×200 mL). The combined organic layers were washed with brine (100 mL), dried and concentrated to dryness. The residue was purified by column chromatography (silica gel, 100-200 mesh, 10% ethyl acetate in petroleum ether) to obtain methyl 3-amino-5-chloropyrazine-2-carboxylate (940 mg, 15.4% yield).

Step 3: A mixture of (4-(tert-butyl)phenyl)boronic acid (937 mg, 5.26 mmol), methyl 3-amino-5-chloropyrazine-2-carboxylate (940 mg, 5.01 mmol), $K_3PO_4$ (2.08 g, 15.0 mmol) and Pd(dppf)$Cl_2$ (367 mg, 0.50 mmol) in DMF (10.0 mL) was heated at 90° C. for 16 h under an atmosphere of $N_2$. After cooling to room temperature, the reaction mixture was diluted with ethyl acetate (100 mL) and filtered. The filtrate was washed with brine (2×100 mL), dried and concentrated to dryness. The residue was purified by column chromatography (silica gel, 100-200 mesh, 15% ethyl acetate in petroleum ether) to obtain the crude (two isomers). The crude was further separated by SFC to give methyl 3-amino-5-(4-(tert-butyl)phenyl)pyrazine-2-carboxylate (120 mg, 8.4% yield) as a yellow solid.

Step 4: A mixture of methyl 3-amino-5-(4-(tert-butyl)phenyl)pyrazine-2-carboxylate (120 mg, 0.42 mmol) and NaOH (42.1 mg, 1.05 mmol) in methanol (5 mL) and water (1 mL) was heated at 80° C. for 16 h. The mixture was concentrated and the aqueous residue was adjusted to pH=2 by addition of 1 M HCl. The resulting mixture was extracted with ethyl acetate (3×10 mL). The combined organic layers were dried and concentrated to give crude 3-amino-5-(4-(tert-butyl)phenyl)pyrazine-2-carboxylic acid (110 mg, 96.4% yield) as a yellow solid.

The title compound was prepared as described in Example 1, replacing 1-(4-(tert-butyl)phenyl)-6-oxo-1,6-dihydropyridazine-4-carboxylic acid with 3-amino-5-(4-(tert-butyl)phenyl)pyrazine-2-carboxylic acid. $^1$H NMR (400 MHz, DMSO-$d_6$) δ (ppm) 8.55-8.42 (m, 1H), 8.37 (br s, 1H), 8.09-7.91 (m, 2H), 7.63-7.46 (m, 2H), 7.12-6.99 (m, 1H), 6.95-6.62 (m, 3H), 6.48-5.93 (m, 2H), 5.19-4.89 (m, 1H), 4.70-4.51 (m, 1H), 4.32-3.85 (m, 5H), 3.41-3.12 (m, 5H), 3.07-2.63 (m, 8H), 1.39-1.25 (m, 9H), 1.24-1.04 (m, 3H). (Method 5-95 AB, ESI): $R_T$=0.689 min, $[M+H]^+$=994.4.

Example 12

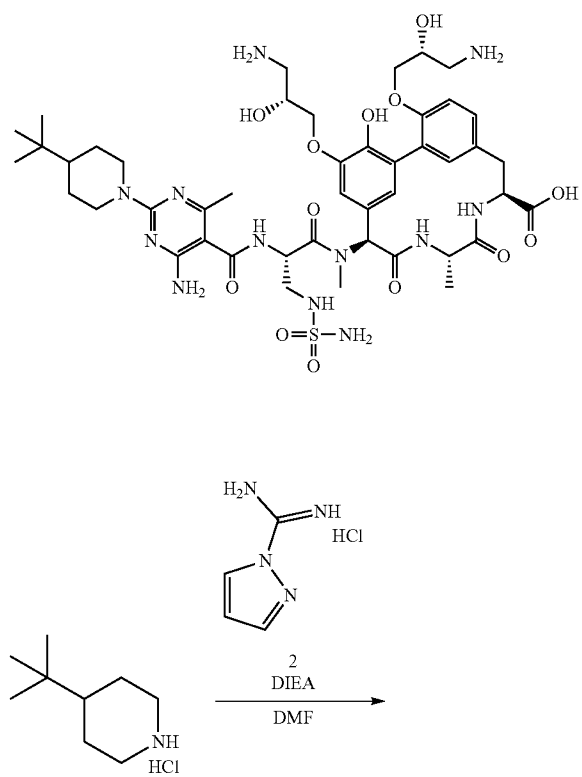

-continued

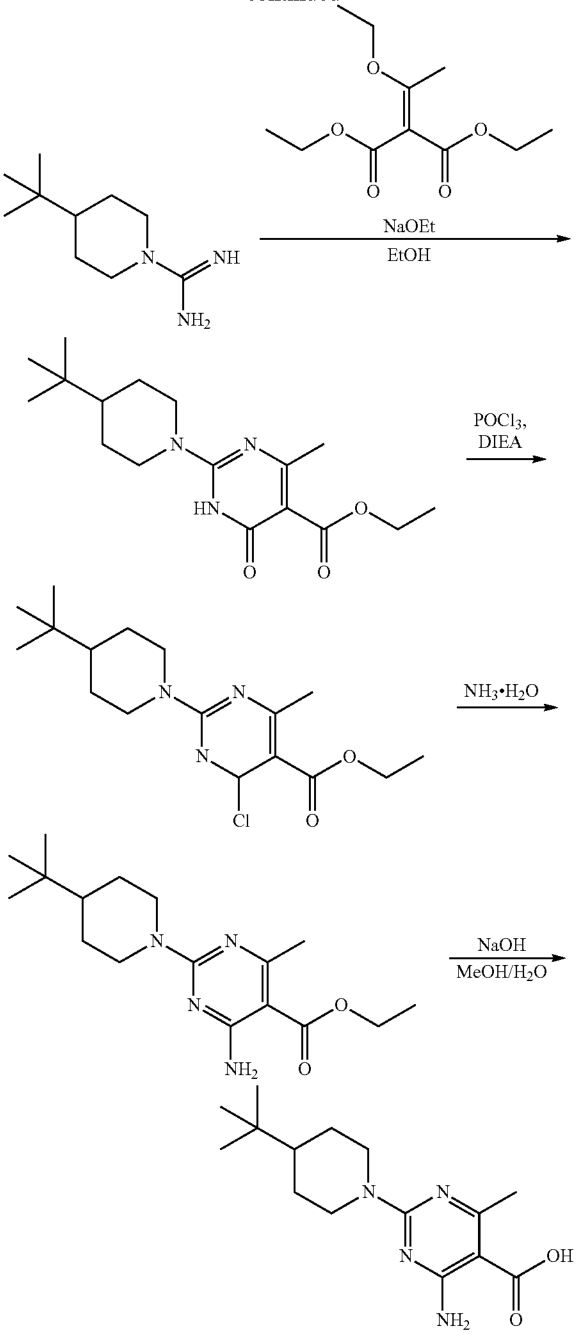

Step 1: A mixture of 4-(tert-butyl)piperidine hydrochloride (1.00 g, 5.60 mmol), 1H-pyrazole-1-carboximidamide hydrochloride (0.82 g, 5.63 mmol) and DIEA (1.45 g, 11.3 mmol) in DMF (5.00 mL) was stirred at 60° C. for 16 h and diluted with MTBE (60 mL). The resulting suspension was stirred for 10 min and filtered. The solid was collected to give the crude 4-(tert-butyl)piperidine-1-carboximidamide (1.00 g, 97.0% yield) as a white solid.

Step 2: A mixture of 4-(tert-butyl)piperidine-1-carboximidamide (1.00 g, 5.46 mmol), NaOEt (742 mg, 10.9 mmol), and diethyl 2-(1-ethoxyethylidene)malonate (1.88 g, 8.18 mmol) in ethanol (20.0 mL) was heated at 50° C. for 20 h and concentrated to dryness. The residue was diluted with ethyl acetate (50 mL), washed with brine (2×30 mL), dried and concentrated. The residue was purified by column chromatography (silica gel, 100-200 mesh, 0-10% ethyl acetate in petroleum ether) to give ethyl 2-(4-(tert-butyl)piperidin-1-yl)-4-methyl-6-oxo-1,6-dihydropyrimidine-5-carboxylate (350 mg, 20.0% yield) as a light yellow solid.

Step 3: A mixture of ethyl 2-(4-(tert-butyl)piperidin-1-yl)-4-methyl-6-oxo-1,6-dihydropyrimidine-5-carboxylate (350 mg, 1.09 mmol) and $POCl_3$ (10 mL, 108 mmol) was heated at 90° C. for 20 h and concentrated to dryness. The residue was purified by preparative TLC (20% ethyl acetate in petroleum ether, $R_f$=0.8) to give ethyl 2-(4-(tert-butyl)piperidin-1-yl)-4-chloro-6-methylpyrimidine-5-carboxylate (270 mg, 73.0% yield) as a pale oil.

Step 4: A mixture of ethyl 2-(4-(tert-butyl)piperidin-1-yl)-4-chloro-6-methylpyrimidine-5-carboxylate (170 mg, 0.50 mmol) and $NH_3.H_2O$ (2.00 mL, 55.1 mmol) in MeOH (5 mL) was heated at 60° C. for 60 h. After cooling to room temperature, the reaction mixture was diluted with ethyl acetate (40 mL), washed with brine (20 mL), dried and concentrated. The residue was purified by preparative TLC (10% ethyl acetate in petroleum ether, $R_f$=0.4) to give ethyl 4-amino-2-(4-(tert-butyl)piperidin-1-yl)-6-methylpyrimidine-5-carboxylate (130 mg, 81.1% yield) as a pale yellow solid.

Step 5: A mixture of ethyl 4-amino-2-(4-(tert-butyl)piperidin-1-yl)-6-methylpyrimidine-5-carboxylate (130 mg, 0.41 mmol) and NaOH (40.6 mg, 1.01 mmol) in MeOH (5 mL) and water (1 mL) was heated at 80° C. for 16 h and concentrated. The aqueous residue was adjusted to pH=2 with 1 M HCl and extracted with ethyl acetate (3×10 mL). The combined organic layers were concentrated to give crude 4-amino-2-(4-(tert-butyl)piperidin-1-yl)-6-methylpyrimidine-5-carboxylic acid (100 mg, 84.3% yield) as a white solid.

The title compound was prepared as a white solid using the procedure of Example 1, replacing 1-(4-(tert-butyl)phenyl)-6-oxo-1,6-dihydropyridazine-4-carboxylic acid with 4-amino-2-(4-(tert-butyl)piperidin-1-yl)-6-methylpyrimidine-5-carboxylic acid. $^1$H NMR (400 MHz, MeOH-$d_4$) δ (ppm)=8.30 (s, 1H), 7.17-7.14 (m, 1H), 6.95 (s, 1H), 6.89-6.76 (m, 2H), 6.64-6.54 (m, 1H), 6.50 (s, 1H), 5.12-5.22 (m, 1H), 4.75-4.71 (m, 2H), 4.55 (s, 1H), 4.28-4.04 (m, 5H), 3.62-3.57 (m, 1H), 3.41-3.33 (m, 2H), 3.32-3.35 (m, 2H), 3.21-3.10 (m, 2H), 3.10-3.04 (m, 3H), 3.01 (s, 1H), 2.94-2.82 (m, 1H), 2.81-2.74 (m, 2H), 2.74-2.64 (m, 1H), 2.42-2.33 (m, 3H), 1.85-1.73 (m, 2H), 1.40-1.28 (m, 4H), 1.26-1.13 (m, 2H), 0.91 (s, 9H). LCMS (Method 5-95 AB, ESI): $R_T$=0.747 min, $[M/2+H]^+$=508.5.

Example 13

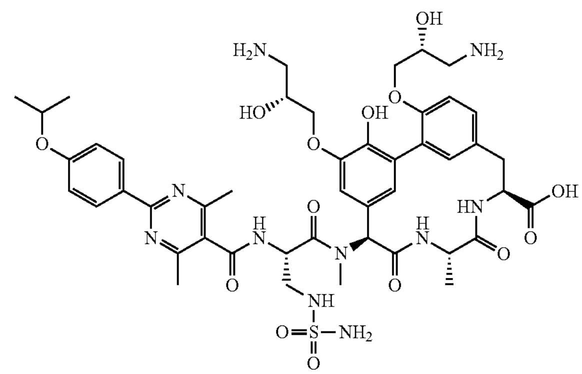 [SMILES: Cc1nc(-c2ccc(OC(C)C)cc2)nc(C)c1C(=O)N[C@@H](CNS(N)(=O)=O)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O]

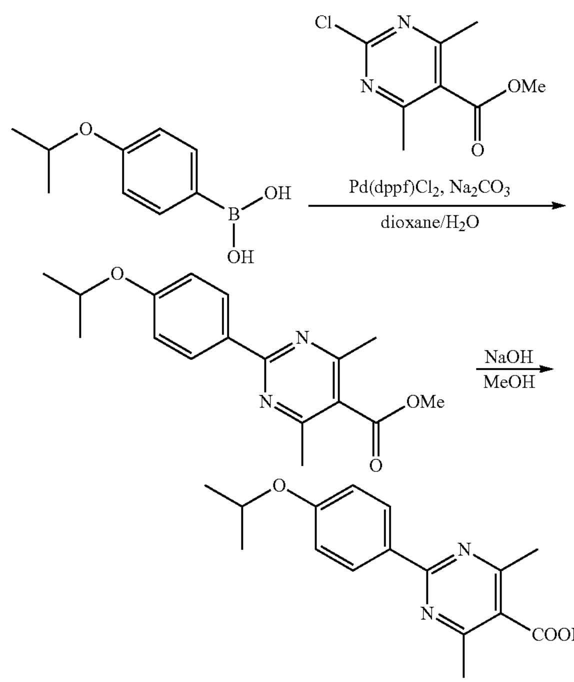

Step 1: A mixture of 4-isopropoxy phenylboronic acid (29.6 g, 164 mmol), methyl 2-chloro-4,6-dimethylpyrimidine-5-carboxylate (30.0 g, 150 mmol), $Na_2CO_3$ (31.7 g, 299 mmol) and $Pd(dppf)Cl_2$ (10.9 g, 15.0 mmol) in water (15 mL) and 1,4-dioxane (150 mL) was heated at 100° C. for 16 h under an atmosphere of nitrogen and then filtered. The filtrate was concentrated to dryness. The residue was partitioned between ethyl acetate (500 mL) and water (500 mL). The aqueous layer was extracted with ethyl acetate (500 mL). The combined organic layers were washed with brine (3×500 mL), dried and concentrated to dryness. The residue was purified by column chromatography (silica gel, 100-200 mesh, 0-5% ethyl acetate in petroleum ether) to give methyl 2-(4-isopropoxyphenyl)-4,6-dimethylpyrimidine-5-carboxylate (42.0 g, 93.5% yield) as a white solid.

Step 2: A mixture of methyl 2-(4-isopropoxyphenyl)-4,6-dimethylpyrimidine-5-carboxylate (21.0 g, 69.9 mmol) and NaOH (8.39 g, 210 mmol) in MeOH (100 mL) and water (10 mL) was heated at 80° C. for 22 h and concentrated. The aqueous residue was adjusted to pH=5 by addition of 1M HCl and filtered. The collected solid was dried to give crude 2-(4-isopropoxyphenyl)-4,6-dimethylpyrimidine-5-carboxylic acid (19.0 g, 95.0% yield) as a white solid.

The title compound was prepared as a white solid using the procedure of Example 1, replacing 1-(4-(tert-butyl)phenyl)-6-oxo-1,6-dihydropyridazine-4-carboxylic acid with 2-(4-isopropoxyphenyl)-4,6-dimethylpyrimidine-5-carboxylic acid. $^1H$ NMR (400 MHz, MeOH-$d_4$): δ (ppm) 8.47 (s, 1H), 8.30-8.28 (m, 2H), 7.02-6.94 (m, 2H), 6.82-6.70 (m, 4H), 6.57 (s, 1H), 6.43 (s, 1H), 5.33-5.32 (m, 1H), 4.69-4.66 (m, 2H), 4.35-4.09 (m, 6H), 3.57-3.56 (m, 1H), 3.39-3.37 (m, 1H), 3.25-3.00 (m, 9H), 2.54 (s, 6H), 1.35-1.33 (m, 9H). LCMS (Method 5-95 AB, ESI): $R_T$=0.608 min, $[M+H]^+$=1009.5.

Example 14

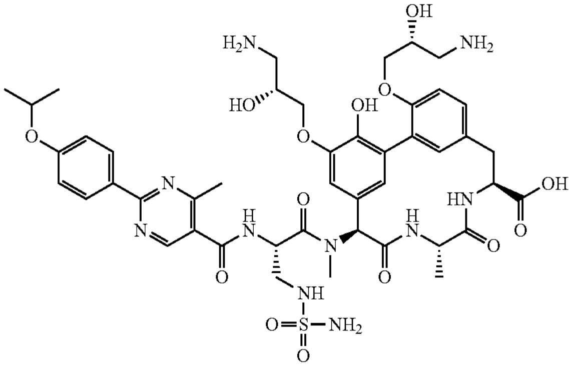 [SMILES: Cc1nc(-c2ccc(OC(C)C)cc2)ncc1C(=O)N[C@@H](CNS(N)(=O)=O)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O]

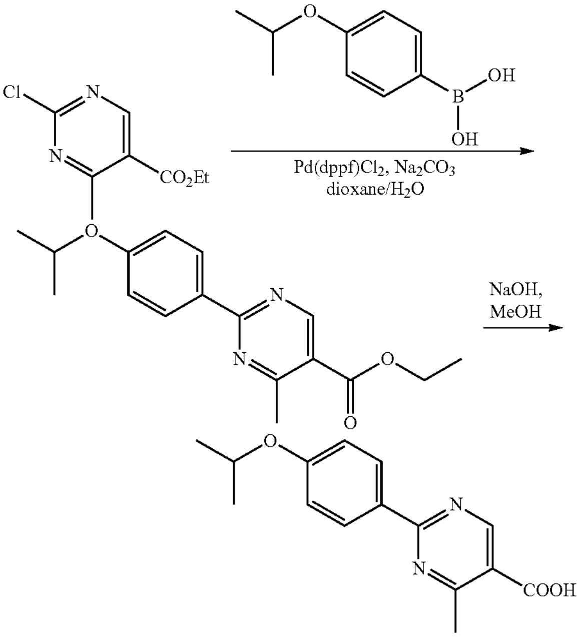

Step 1: A mixture of ethyl 2-chloro-4-methylpyrimidine-5-carboxylate (30.0 g, 150 mmol), (4-isopropoxyphenyl)boronic acid (28.3 g, 157 mmol), sodium carbonate (31.7 g, 299 mmol) and $Pd(dppf)Cl_2$ (10.9 g, 15.0 mmol) in water (30 mL) and 1,4-dioxane (300 mL) was heated at 100° C. for 16 h under an atmosphere of nitrogen. The reaction was cooled to room temperature and the mixture was diluted with ethyl acetate (300 mL) and filtered. The filtrate was washed with brine (100 mL), dried and concentrated to dryness. The residue was purified by column chromatography (silica gel, 100-200 mesh, 2% ethyl acetate in petroleum ether) to obtain ethyl 2-(4-isopropoxyphenyl)-4-methylpyrimidine-5-carboxylate (32.5 g, 72.4% yield) as a white solid.

Step 2: A mixture of ethyl 2-(4-isopropoxyphenyl)-4-methylpyrimidine-5-carboxylate (32.5 g, 108 mmol) and sodium hydroxide (21.6 g, 541 mmol) in MeOH (150 mL) and water (15 mL) was stirred at 80° C. for 3 h and concentrated. The aqueous residue was adjusted to pH=5 with 2M HCl and filtered. The filter cake was washed with water (3×50 mL) and dried to give crude 2-(4-isopropoxyphenyl)-4-methylpyrimidine-5-carboxylic acid (28.0 g, 95.0% yield) as a white solid.

The title compound was prepared using the procedure of Example 1, replacing 1-(4-(tert-butyl)phenyl)-6-oxo-1,6-dihydropyridazine-4-carboxylic acid with 2-(4-isopropoxyphenyl)-4-methylpyrimidine-5-carboxylic acid. $^1$H NMR (400 MHz, MeOH-$d_4$): δ (ppm) 8.82 (br s, 1H), 8.35 (d, J=8.8 Hz, 2H), 7.11 (d, J=8.4 Hz, 1H), 6.99 (d, J=8.8 Hz, 2H), 6.90 (d, J=8.0 Hz, 1H), 6.86-6.76 (m, 2H), 6.59 (br s, 1H), 6.45 (s, 1H), 5.27-5.16 (m, 1H), 4.75-4.66 (m, 2H), 4.65-4.45 (m, 2H), 4.37-4.19 (m, 1H), 4.17-4.00 (m, 5H), 3.71-3.54 (m, 1H), 3.50-3.44 (m, 1H), 3.42-3.35 (m, 1H), 3.29-3.09 (m, 5H), 3.06 (s, 3H), 2.69 (s, 3H), 1.33-1.38 (m, 9H). LCMS (Method 5-95 AB, ESI): $R_T$=0.609 min, [M+H]$^+$=996.7.

Example 15

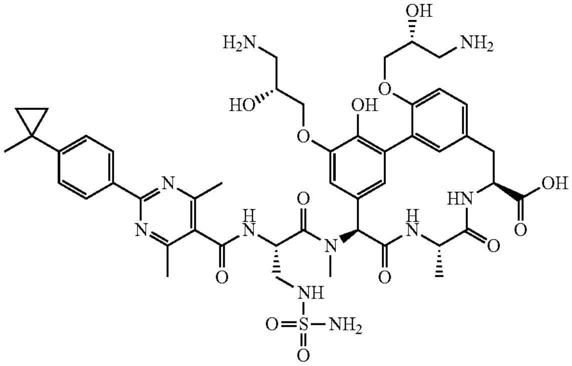 [SMILES: Cc1nc(-c2ccc(C3(C)CC3)cc2)nc(C)c1C(=O)N[C@@H](CNS(N)(=O)=O)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O]

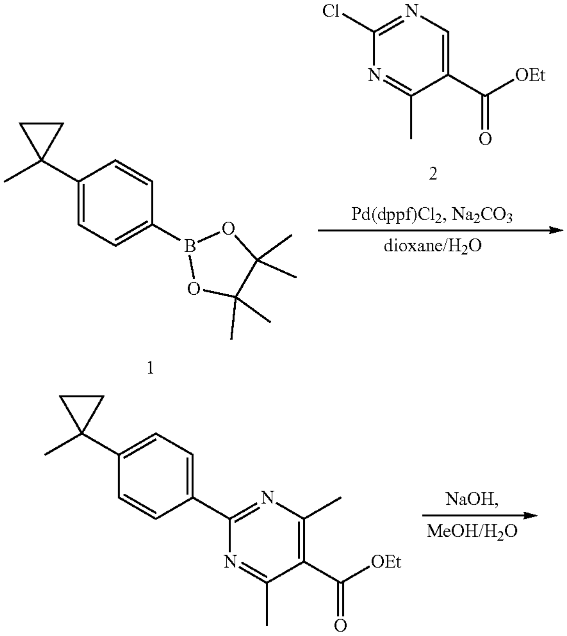

1 2 3

-continued

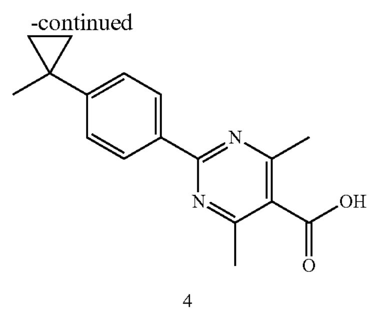

4

Step 1: A mixture of 4,4,5,5-tetramethyl-2-(4-(1-methylcyclopropyl)phenyl)-1,3,2-dioxaborolane (4.67 g, 18.1 mmol), ethyl 2-chloro-4-methyl pyrimidine-5-carboxylate (3.30 g, 16.5 mmol), sodium carbonate (3.49 g, 32.9 mmol) and Pd(dppf)$Cl_2$ (1.20 g, 1.64 mmol) in water (3 mL) and 1,4-dioxane (30 mL) was heated at 100° C. for 16 h under an atmosphere of nitrogen. The reaction was cooled to room temperature and the reaction mixture was diluted with ethyl acetate (300 mL) and filtered. The filtrate was washed with water (100 mL), brine (50 mL), dried concentrated to dryness. The residue was purified by column chromatography (silica gel, 100-200 mesh, 0-10% ethyl acetate in petroleum ether) to get ethyl 4,6-dimethyl-2-(4-(1-methylcyclopropyl)phenyl)pyrimidine-5-carboxylate (2.10 g, 43.1% yield) as a white solid.

Step 2: A mixture of ethyl 4,6-dimethyl-2-(4-(1-methylcyclopropyl)phenyl)pyrimidine-5-carboxylate (2.10 g, 7.09 mmol) and sodium hydroxide (567 mg, 14.2 mmol) in MeOH (30 mL) and water (3 mL) was stirred at 80° C. for 4 h and concentrated. The aqueous residue was adjusted to pH=5 with 1M HCl and extracted with ethyl acetate (2×50 mL). The combined organic layers were washed with brine (50 mL), dried and concentrated. The crude was recrystallized with 10% ethyl acetate in petroleum ether (10 mL) to give 4,6-dimethyl-2-(4-(1-methylcyclopropyl)phenyl)pyrimidine-5-carboxylic acid (1.10 g, 55% yield) as a white solid.

The title compound was prepared using the procedure of Example 1, replacing 1-(4-(tert-butyl)phenyl)-6-oxo-1,6-dihydropyridazine-4-carboxylic acid with 4,6-dimethyl-2-(4-(1-methylcyclopropyl) phenyl)pyrimidine-5-carboxylic acid. $^1$H NMR (400 MHz, DMSO-$d_6$): δ (ppm) 8.27 (d, J=8.4H, 2H), 7.34 (d, J=8.0 Hz, 2H), 7.17-7.06 (m, 1H), 7.04-6.90 (m, 1H), 6.87-6.70 (m, 2H), 6.44 (s, 1H), 6.30 (m, 1H), 5.39-5.05 (m, 1H), 4.75-4.58 (m, 1H), 4.48-4.35 (m, 1H), 4.18-3.90 (m, 6H), 3.31-3.13 (m, 3H), 3.06-2.95 (m, 5H), 2.93-2.64 (m, 3H), 2.44 (s, 6H), 1.42 (s, 3H), 1.21 (d, J=6.4 Hz, 3H), 0.93-0.86 (m, 2H), 0.85-0.77 (m, 2H). LCMS (Method 5-95 AB, ESI): $R_T$=0.631 min, [M+H]$^+$=1006.3.

Example 16

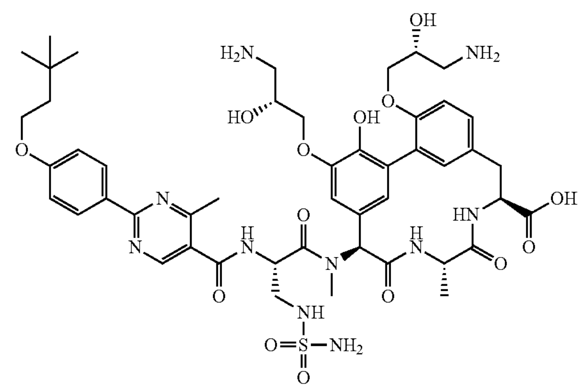 [SMILES: Cc1nc(-c2ccc(OCCC(C)(C)C)cc2)ncc1C(=O)N[C@@H](CNS(N)(=O)=O)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O]

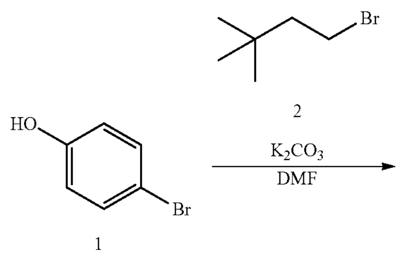

2

1

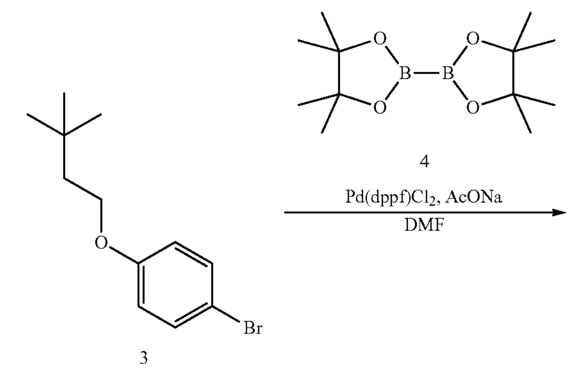

4

3

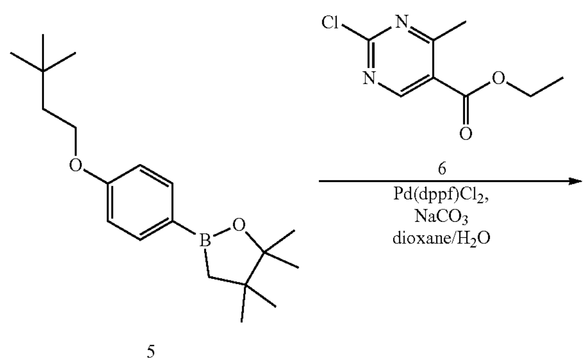

6

5

-continued

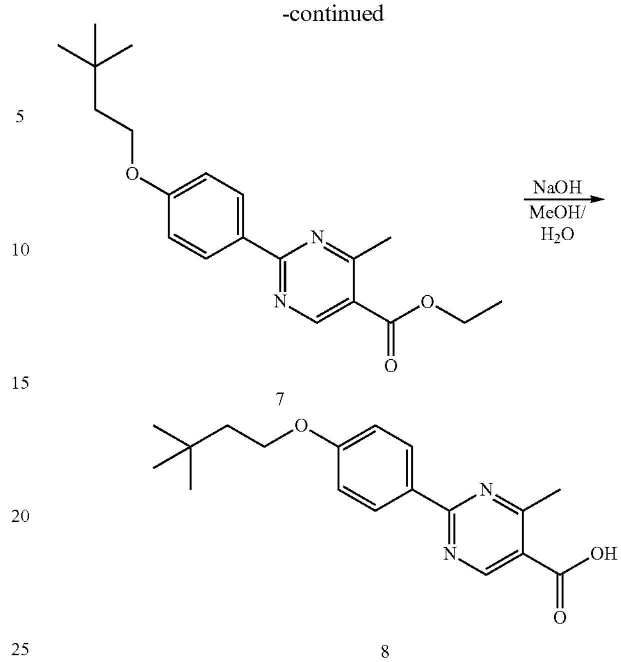

7

8

Step 1: To a solution of 4-bromophenol (14.3 g, 86.7 mmol) in DMF (100 mL) were added 1-bromo-3,3-dimethylbutane (10.0 g, 57.8 mmol) and potassium carbonate (20.0 g, 145 mmol). The reaction mixture was stirred at 50° C. for 16 h. The reaction was cooled to room temperature and the mixture was diluted with ethyl acetate (500 mL) and filtered. The filtrate was washed with brine (400 mL) and concentrated to dryness. The residue was purified by column chromatography (silica gel, 100-200 mesh, 0%-2% ethyl acetate in petroleum ether) to obtain 1-bromo-4-(3,3-dimethylbutoxy)benzene (14.5 g, 97.5% yield) as a white solid.

Step 2: A mixture of 1-bromo-4-(3,3-dimethylbutoxy) benzene (10.0 g, 38.9 mmol), bis(pinacolato)diboron (10.4 g, 40.8 mmol), potassium acetate (11.5 g, 116.7 mmol) and Pd(dppf)$_2$Cl$_2$ (2.85 g, 3.89 mmol) in DMF (100 mL) was heated at 80° C. for 16 h under an atmosphere of nitrogen and filtered. The filtered was diluted with water (500 mL) and extracted with ethyl acetate (3×500 mL). The combined organic layers were washed with brine (500 mL), dried and concentrated to dryness. The residue was purified by column chromatography (silica gel, 100-200 mesh, 2% ethyl acetate in petroleum ether) to obtain 2-(4-(3,3-dimethylbutoxy) phenyl)-4,4,5,5-tetramethyl-1,3,2-dioxaborolane (16.0 g, 52.6 mmol) as a colorless oil.

Step 3: A mixture of 2-(4-(3,3-dimethylbutoxy)phenyl)-4,4,5,5-tetramethyl-1,3,2-dioxaborolane (1.00 g, 3.29 mmol), ethyl 2-chloro-4-methylpyrimidine-5-carboxylate (692 mg, 3.45 mmol), sodium carbonate (697 mg, 6.57 mmol) and Pd(dppf) $C_{12}$ (240 mg, 0.33 mmol) in water (1 mL) and 1,4-dioxane (10 mL) was heated at 100° C. for 16 h under an atmosphere of nitrogen and diluted with ethyl acetate (100 mL). The resulting mixture was filtered and the filtrate was washed with water (2×40 mL), brine (50 mL), dried and concentrated to dryness. The residue was purified by column chromatography (silica gel, 100-200 mesh, 0-2% ethyl acetate in petroleum ether) to obtain ethyl 2-(4-(3,3-dimethylbutoxy)phenyl)-4-methylpyrimidine-5-carboxylate (460 mg, 40.9% yield) as a colorless oil.

Step 4: A mixture of ethyl 2-(4-(3,3-dimethylbutoxy) phenyl)-4-methylpyrimidine-5-carboxylate (460 mg, 1.34 mmol) and sodium hydroxide (269 mg, 6.72 mmol) in MeOH (10 mL) and water (10 mL) was stirred at 80° C. for 16 h and concentrated. The aqueous residue was adjusted to pH=5 with 1M HCl and filtered. The filter cake was dried to give crude 2-(4-(3,3-dimethylbutoxy)phenyl)-4-methylpyrimidine-5-carboxylic acid (400 mg, 94.7% yield) as a white solid.

The title compound was prepared using the procedure of Example 1, replacing 1-(4-(tert-butyl)phenyl)-6-oxo-1,6-dihydropyridazine-4-carboxylic acid with 2-(4-(3,3-dimethylbutoxy)phenyl)-4-methylpyrimidine-5-carboxylic acid. $^1H$ NMR (400 MHz, MeOH-$d_4$): δ (ppm) 8.80 (s, 1H), 8.27 (d, J=8.8 Hz, 2H), 7.06-7.05 (m, 1H), 6.93 (d, J=8.8 Hz, 2H), 6.85-6.86 (m, 1H), 6.69-6.66 (m, 2H), 6.49 (s, 1H), 6.37 (s, 1H), 5.23-5.21 (m, 1H), 4.55-4.50 (m, 2H), 4.23-4.05 (m, 1H), 3.60-3.58 (m, 1H), 3.50-3.38 (m, 1H), 3.26-3.24 (m, 2H), 3.17-3.11 (m, 2H), 3.18-2.99 (m, 4H), 2.64 (s, 3H), 1.76-1.70 (m, 2H), 1.35 (d, J=6.4 Hz, 3H), 0.99 (s, 9H). LCMS (Method 5-95 AB, ESI): $R_T$=0.844 min, $[M+H]^+$=1037.4.

Example 17

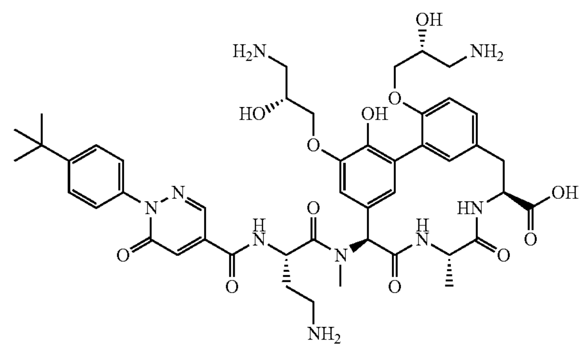 [SMILES: C[C@@H]1NC(=O)[C@@H](N(C)C(=O)[C@H](CCN)NC(=O)c2cnn(-c3ccc(C(C)(C)C)cc3)c(=O)c2)c2cc(OC[C@H](O)CN)c(O)c(c2)-c2cc(ccc2OC[C@H](O)CN)C[C@@H](C(=O)O)NC1=O]

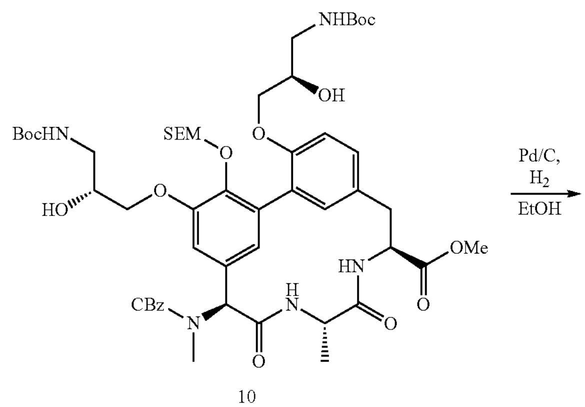

10

-continued

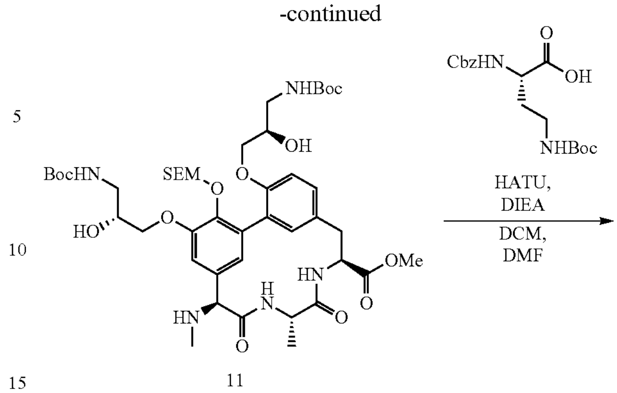

11

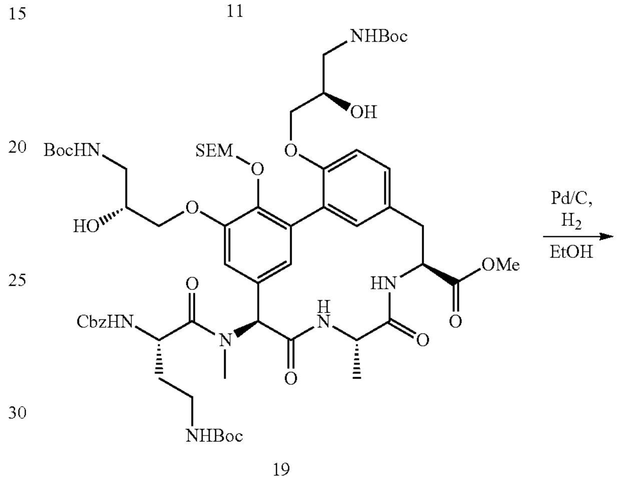

19

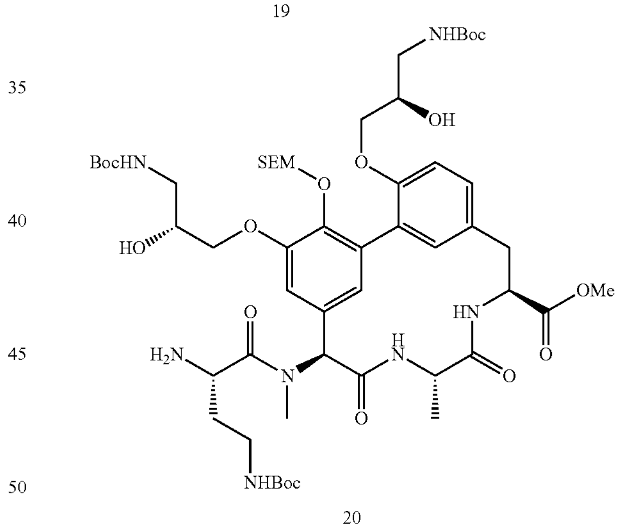

20

Step 1: To a solution of compound 10 (200 mg, 0.19 mmol) and a drop of $NH_3$—$H_2O$ in ethanol (15 mL) was added 10% Pd/C (60.6 mg, 0.06 mmol). The reaction mixture was stirred at 30° C. under $H_2$ atmosphere (15 psi) for 2 h and filtrated. The filtrate was concentrated to give crude compound 11 (174 mg, 100% yield) as a white solid.

Step 2: To a solution of compound 11 (174 mg, 0.19 mmol) in dichloromethane (10 mL) was added DIEA (0.13 mL, 0.76 mmol) and (S)-2-(((benzyloxy)carbonyl)amino)-4-((tert-butoxycarbonyl)amino)butanoic acid (134 mg, 0.38 mmol) at 0° C., followed by a solution of HATU (86.8 mg, 0.23 mmol) in DMF (1 mL). The mixture was stirred at 20° C. for 2 h and quenched with MeOH (0.5 mL). The mixture was diluted with water (10 mL) and extracted with ethyl acetate (3×30 mL). The combined organic layers were washed with brine (3×30 mL), dried and concentrated. The residue was purified by column chromatography (silica gel, 100-200 mesh, 5% MeOH in dichloromethane) to yield compound 19 (200 mg, 83.8% yield) as a white solid.

Step 3: To a solution of compound 19 (200 mg, 0.16 mmol) and a drop of ammonium hydroxide in ethanol (15 mL) was added 10% Pd/C (76.4 mg, 0.07 mmol). The reaction mixture was stirred at 40° C. under $H_2$ atmosphere (15 psi) for 6 h and filtered. The filtrate was concentrated to get crude compound 20 (178 mg, 100% yield) as a white solid.

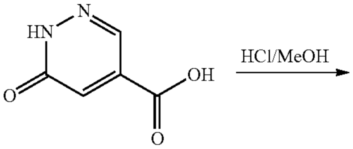

6

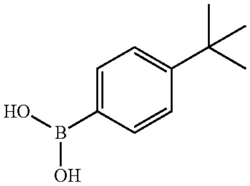

8

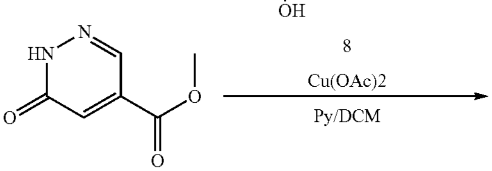

7

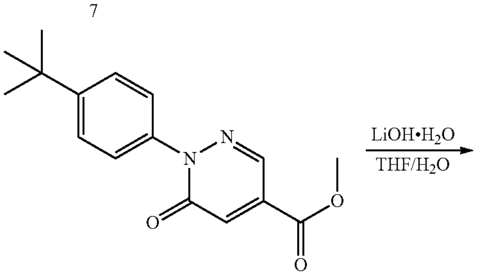

9

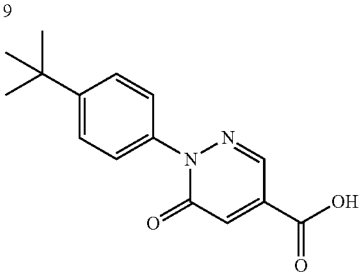

10

Step 1: A mixture of 6-oxo-1,6-dihydropyridazine-4-carboxylic acid (2.00 g, 14.3 mmol) and HCl (4 M in MeOH, 15.0 mL, 60.0 mmol) was stirred at 25° C. for 24 h and concentrated. The residue was purified by column chromatography (silica gel, 100-200 mesh, 30%-60% ethyl acetate in petroleum ether) to give methyl 6-oxo-1,6-dihydropyridazine-4-carboxylate (1.00 g, 45.5% yield) as a white solid.

Step 2: A mixture of (4-(tert-butyl)phenyl)boronic acid (118 mg, 0.65 mmol), methyl 6-oxo-1,6-dihydropyridazine-4-carboxylate (500 mg, 3.24 mmol), copper (II) acetate (24 mg, 0.13 mmol)) and pyridine (2 mL) in dichloromethane (10 mL) was stirred at 25° C. for 24 h and concentrated. The residue was diluted with ethyl acetate (80 mL) and washed with brine (2×30 mL), dried and concentrated. The crude was purified by column chromatography (silica gel, 100-200 mesh, 33% ethyl acetate in petroleum ether) to give methyl 1-(4-(tert-butyl)phenyl)-6-oxo-1,6-dihydropyridazine-4-carboxylate (770 mg, 82.9% yield) as a white solid.

Step 3: A mixture of methyl 1-(4-(tert-butyl)phenyl)-6-oxo-1,6-dihydropyridazine-4-carboxylate (770 mg, 2.69 mmol) and lithium hydroxide hydrate (247 mg, 10.8 mmol) in THF (10 mL) and water (2 mL) was stirred for 2 h at 25° C. and concentrated. The residue was adjusted to pH=3 with 1M HCl and extracted with ethyl acetate (2×50 mL). The combined organic layers were dried and concentrated to give crude 1-(4-(tert-butyl)phenyl)-6-oxo-1,6-dihydropyridazine-4-carboxylic acid (730 mg, 99.7% yield) as a white solid.

The title compound was prepared using the procedure of Example 1, replacing compound 14 with compound 20. $^1H$ NMR (400 MHz, DMSO-$d_6$): δ (ppm) 8.43 (s, 1H), 8.38-8.28 (m, 2H), 8.14-8.07 (m, 1H), 7.60-7.44 (m, 5H), 7.10-7.04 (m, 1H), 6.93-6.91 (m, 1H), 6.78 (s, 2H), 6.35 (s, 1H), 6.24 (s, 1H), 5.05-4.94 (m, 1H), 4.67-4.65 (m, 3H), 4.35 (s, 1H), 4.12-3.93 (m, 11H), 3.3-3.27 (m, 2H), 3.17-3.10 (m, 3H), 2.99-2.97 (m, 4H), 2.80 (s, 4H), 2.67-2.64 (m, 1H), 2.12-2.03 (m, 2H), 1.33-1.28 (m, 9H), 1.17-1.00 (m, 3H). LCMS (Method 5-95 AB, ESI): $R_T$=0.797 min, $[M+H]^+$=929.4.

Example 18

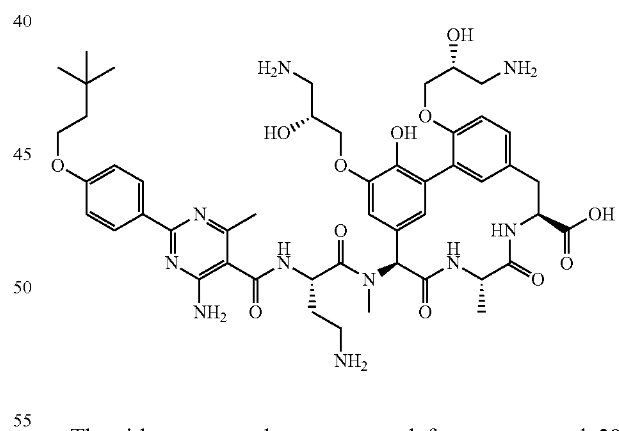

The title compound was prepared from compound 20 using the procedure of Example 1, replacing 1-(4-(tert-butyl)phenyl)-6-oxo-1,6-dihydropyridazine-4-carboxylic acid with 4-amino-2-(4-(isopentyloxy)phenyl)-6-methylpyrimidine-5-carboxylic acid. $^1H$ NMR (400 MHz, MeOH-$d_4$) δ (ppm) 8.41 (s, 1H), 8.23 (d, J=8.8 Hz, 2H), 7.18-7.04 (m, 1H), 6.97 (d, J=8.8 Hz, 2H), 6.93-6.87 (m, 1H), 6.84 (s, 1H), 6.81 (s, 1H), 6.60 (s, 1H), 6.46 (s, 1H), 4.87-4.73 (m, 2H), 4.52-4.41 (m, 1H), 4.24-4.01 (m, 8H), 3.27-2.97 (m, 11H), 2.45 (s, 3H), 2.31-2.11 (m, 2H), 1.75 (t, J=6.8 Hz, 2H), 1.34 (d, J=6.8 Hz, 3H), 1.02 (s, 9H). LCMS (Method 5-95 AB, ESI): $R_T$=0.767 min, $[M+H]^+$=987.8.

Example 19

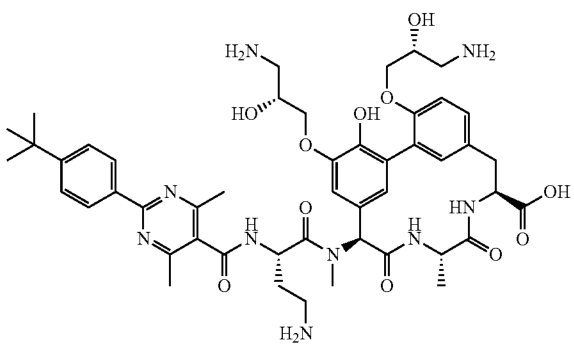 [SMILES: Cc1nc(-c2ccc(C(C)(C)C)cc2)nc(C)c1C(=O)N[C@@H](CCN)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O]

The title compound was prepared from compound 20 using the procedure of Example 1, replacing 1-(4-(tert-butyl)phenyl)-6-oxo-1,6-dihydropyridazine-4-carboxylic acid with 2-(4-(tert-butyl)phenyl)-4,6-dimethylpyrimidine-5-carboxylic acid. $^1$H NMR (400 MHz, MeOH-$d_4$) δ (ppm) 8.34 (s, 1H), 8.28 (d, J=8.4 Hz, 2H), 7.48 (d, J=8.8 Hz, 2H), 7.02 (d, J=8.0 Hz, 1H), 6.89 (d, J=8.8 Hz, 1H), 6.81-6.80 (m, 1H), 6.66 (s, 1H), 6.55 (s, 1H), 6.56 (s, 1H), 5.21-5.18 (m, 1H), 4.81-4.76 (m, 1H), 4.41-4.39 (m, 1H), 4.24-4.06 (m, 6H), 3.27-3.22 (m, 2H), 3.19-3.12 (m, 4H), 3.10-3.07 (m, 1H), 3.03 (s, 3H), 2.99-2.95 (m, 1H), 2.51 (s, 6H), 2.30-2.17 (m, 2H), 1.37 (s, 9H), 1.34 (d, J=6.8 Hz, 3H). LCMS (Method 5-95 AB, ESI): $R_T$=0.622 min, $[M+H]^+$=942.4.

Example 20

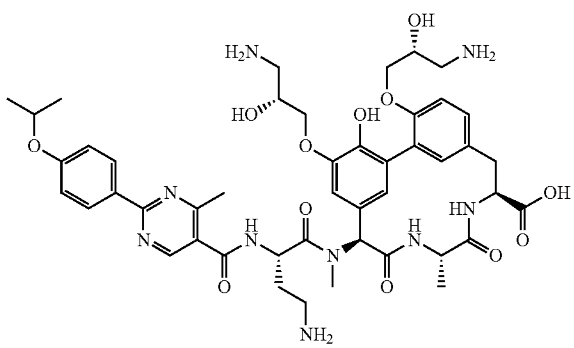 [SMILES: Cc1nc(-c2ccc(OC(C)C)cc2)ncc1C(=O)N[C@@H](CCN)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O]

The title compound was prepared from compound 20 using the procedure of Example 1 replacing 1-(4-(tert-butyl) phenyl)-6-oxo-1,6-dihydropyridazine-4-carboxylic acid with 2-(4-isopropoxyphenyl)-4-methylpyrimidine-5-carboxylic acid. $^1$H NMR (400 MHz, MeOH-$d_4$): δ (ppm) 8.89 (s, 1H), 8.23 (d, J=8.8 Hz, 2H), 7.05-6.92 (m, 4H), 6.87-6.82 (m, 1H), 6.66 (s, 1H), 6.51 (s, 1H), 6.42 (s, 1H), 5.20-5.11 (m, 1H), 4.83-4.72 (m, 2H), 4.69-4.59 (m, 1H), 4.40-4.03 (m, 6H), 3.40-3.32 (m, 1H), 3.29-3.07 (m, 6H), 2.99 (s, 3H), 2.97-2.80 (m, 1H), 2.70 (s, 12H), 2.68 (s, 3H), 2.39-2.15 (m, 2H), 1.47-1.30 (m, 9H). LCMS (Method 5-95 AB, ESI): $R_T$=0.732 min, $[M+H]^+$=930.7.

Example 21

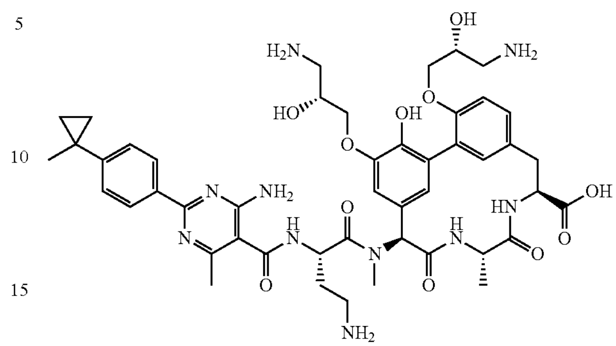

The title compound was prepared from compound 20 using the procedure of Example 1, replacing 1-(4-(tert-butyl)phenyl)-6-oxo-1,6-dihydropyridazine-4-carboxylic acid with 4-amino-6-methyl-2-(4-(1-methylcyclopropyl) phenyl)pyrimidine-5-carboxylic acid. $^1$H NMR (400 MHz, MeOH-$d_4$): δ (ppm) 8.36 (s, 1H), 8.18-8.15 (m, 2H), 7.33-7.31 (m, 2H), 7.11 (s, 1H), 6.93-6.91 (m, 1H), 6.86-6.81 (m, 2H), 6.58-6.46 (m, 3H), 5.04-5.03 (m, 1H), 4.82 (s, 2H), 4.54 (s, 1H), 4.22-4.05 (m, 6H), 3.18-2.98 (m, 10H), 2.46 (s, 3H), 2.25-2.18 (m, 2H), 1.44 (s, 3H), 1.34 (d, J=6.4 HZ, 2H), 0.93-0.91 (m, 2H), 0.82-0.80 (m, 2H). LCMS (Method 5-95 AB, ESI): $R_T$=0.58 min, $[M+H]^+$=941.5.

Example 22

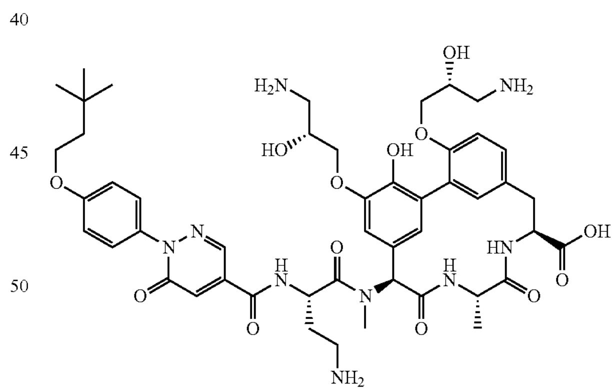

The title compound was prepared from compound 20 using the procedure of Example 1, replacing 1-(4-(tert-butyl)phenyl)-6-oxo-1,6-dihydropyridazine-4-carboxylic acid with 1-(4-(3,3-dimethylbutoxy)phenyl)-6-oxo-1,6-dihydropyridazine-4-carboxylic acid. $^1$H NMR (400 MHz, MeOH-$d_4$): δ (ppm) 8.08 (s, 1H), 7.45-6.85 (m, 9H), 6.60 (s, 1H), 6.31 (s, 1H), 5.03-5.01 (m, 1H), 4.74-4.71 (m, 1H), 4.37 (s, 1H), 4.25 (s, 1H), 4.11-4.06 (m, 4H), 3.91-3.90 (m, 1H), 3.38-3.31 (m, 3H), 3.30-3.12 (m, 3H), 2.99-2.90 (m, 7H), 2.18 (s, 2H), 1.76-1.73 (m, 2H), 1.37-1.35 (m, 3H), 1.02 (s, 2H). LCMS (Method 5-95 AB, ESI): $R_T$=0.660 min, $[M+H]^+$=974.6.

Example 23

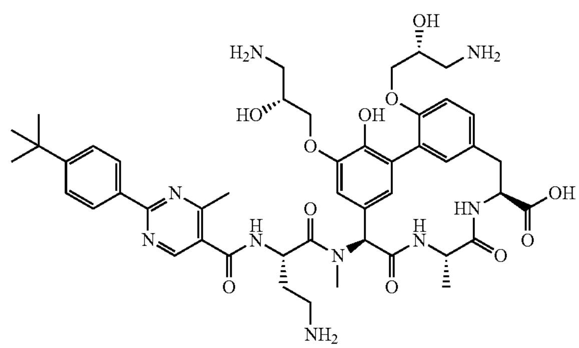 [SMILES: Cc1nc(-c2ccc(C(C)(C)C)cc2)ncc1C(=O)N[C@@H](CCN)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O]

The title compound was prepared from compound 20 using the procedure of Example 1, replacing 1-(4-(tert-butyl)phenyl)-6-oxo-1,6-dihydropyridazine-4-carboxylic acid with 2-(4-(tert-butyl)phenyl)-4-methylpyrimidine-5-carboxylic acid. $^1$H NMR (400 MHz, MeOH-$d_4$): δ (ppm) 8.72 (s, 1H), 8.34 (m, 1H), 8.26-8.24 (d, J=8.0 Hz, 1H), 7.47-7.45 (d, J=8.0 Hz, 2H), 6.92-6.91 (d, J=4.0 Hz, 1H), 6.81-6.79 (d, J=8.0 Hz, 2H), 6.61 (s, 1H), 6.47 (s, 2H), 5.10-5.09 (m, 1H), 4.80-4.76 (m, 2H), 4.48-4.46 (m, 1H), 4.29-4.27 (d, J=8.0 Hz, 1H), 4.18-4.12 (m, 4H), 4.03-4.02 (d, J=4.0 Hz, 1H), 3.26 (s, 1H), 3.20-3.15 (m, 4H), 3.10-3.14 (m, 1H), 2.97 (s, 3H), 2.92-2.89 (d, J=12.0 Hz, 1H), 2.76-2.67 (m, 1H), 2.62-2.60 (m, 3H), 2.29-2.23 (m, 3H), 1.35-1.32 (m, 12H). LCMS (Method 5-95 AB, ESI): $R_T$=0.769 min, $[M+H]^+$=928.8.

Example 24

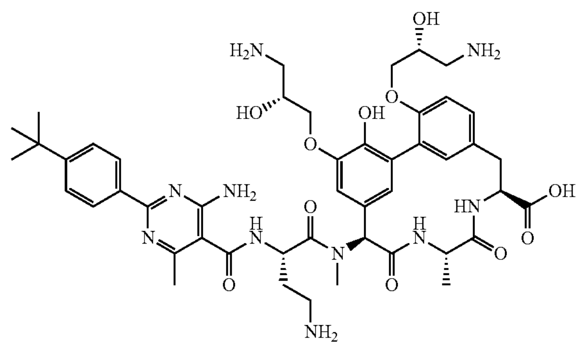 [SMILES: Cc1nc(-c2ccc(C(C)(C)C)cc2)nc(N)c1C(=O)N[C@@H](CCN)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O]

The title compound was prepared from compound 20 using the procedure of Example 1, replacing 1-(4-(tert-butyl)phenyl)-6-oxo-1,6-dihydropyridazine-4-carboxylic acid with 4-amino-2-(4-(tert-butyl)phenyl)-6-methylpyrimidine-5-carboxylic acid. $^1$H NMR (400 MHz, MeOH-$d_4$): δ (ppm) 8.24 (s, 1H), 8.23-8.17 (m, 2H), 7.54-7.48 (m, 1H), 7.21-7.14 (m, 1H), 7.02-6.92 (m, 1H), 6.88 (s, 1H), 6.85 (s, 1H), 6.59 (s, 1H), 6.45 (s, 1H), 5.30-5.01 (m, 1H), 4.83-4.79 (m, 2H), 4.66-4.52 (m, 1H), 4.25-4.04 (m, 6H), 3.25-2.99 (m, 10H), 2.52-2.43 (m, 3H), 2.33-2.08 (m, 2H), 1.40-1.33 (s, 12H). LCMS (Method 5-95 AB, ESI): $R_T$=0.592 min, $[M+H]^+$=943.4.

Example 25

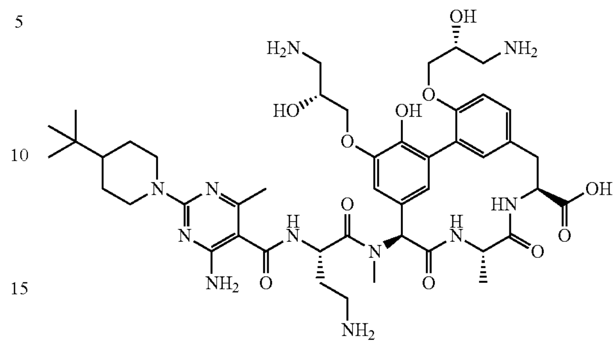

The title compound was prepared from compound 20 using the procedure of Example 1, replacing 1-(4-(tert-butyl)phenyl)-6-oxo-1,6-dihydropyridazine-4-carboxylic acid with 4-amino-2-(4-(tert-butyl)piperidin-1-yl)-6-methylpyrimidine-5-carboxylic acid. $^1$H NMR (400 MHz, MeOH-$d_4$): δ (ppm) 7.27-7.21 (m, 1H), 7.04 (d, J=8 Hz, 1H), 6.92-6.87 (m, 2H), 6.55 (m, 1H), 6.38 (s, 1H), 5.04-5.01 (m, 1H), 4.72 (m, 2H), 4.28-4.07 (m, 6H), 3.52-3.34 (m, 2H), 3.31-3.04 (m, 8H), 2.99 (s, 3H), 2.95-2.86 (m, 2H), 2.40 (s, 3H), 2.28-2.12 (m, 2H), 1.85 (m, 2H), 1.44-1.33 (m, 4H), 1.30-1.19 (m, 2H), 0.92 (s, 9H). LCMS (Method 5-95 AB, ESI): $R_T$=0.731 min, $[M/2+H]^+$=479.5.

Example 26

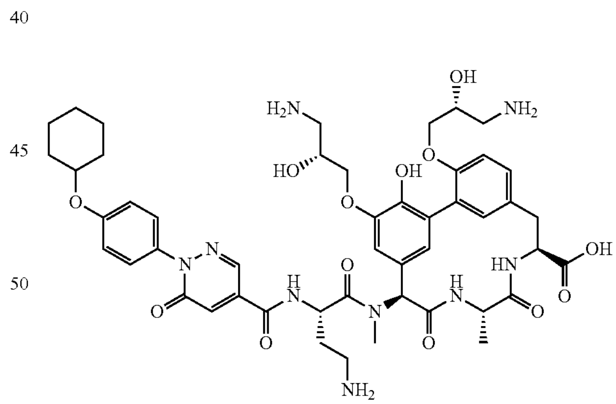

The title compound was prepared from compound 20 using the procedure of Example 1, replacing 1-(4-(tert-butyl)phenyl)-6-oxo-1,6-dihydropyridazine-4-carboxylic acid with 1-(4-(cyclohexyloxy)phenyl)-6-oxo-1,6-dihydropyridazine-4-carboxylic acid. $^1$H NMR (400 MHz, MeOH-$d_4$): δ (ppm) 8.34-8.14 (m, 1H), 7.48-7.33 (m, 1H), 7.19-6.62 (m, 9H), 6.35-6.30 (m, 1H), 5.01-4.90 (m, 1H), 4.73-4.71 (m, 1H), 4.37-3.92 (m, 7H), 3.36-3.30 (m, 4H), 3.18-2.91 (m, 9H), 2.28-2.18 (m, 2H), 2.18-1.98 (m, 2H), 1.82-1.80 (m, 2H), 1.55-1.43 (m, 6H), 1.36-1.35 (m, 3H). LCMS (Method 5-95 AB, ESI): $R_T$=0.696 min, $[M/2+H]^+$=485.9.

Example 27

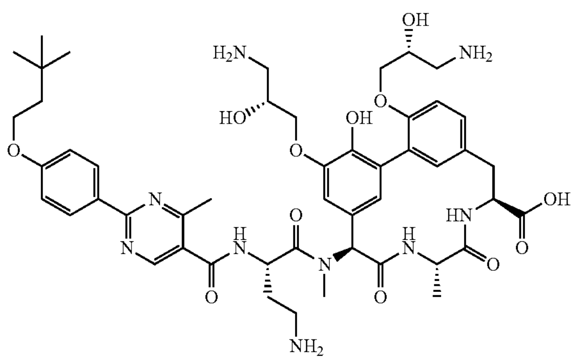 [SMILES: Cc1nc(-c2ccc(OCCC(C)(C)C)cc2)ncc1C(=O)N[C@@H](CCN)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O]

The title compound was prepared from compound 20 using the procedure of Example 1, replacing 1-(4-(tert-butyl)phenyl)-6-oxo-1,6-dihydropyridazine-4-carboxylic acid with 2-(4-(3,3-dimethylbutoxy)phenyl)-4-methylpyrimidine-5-carboxylic acid. $^1H$ NMR (400 MHz, MeOH-$d_4$): δ (ppm) 8.79 (s, 1H), 8.37 (d, J=8.4 Hz, 2H), 7.07-7.00 (m, 3H), 6.87-6.83 (m, 2H), 6.72 (s, 1H), 6.58 (s, 1H), 6.47 (s, 1H), 4.84-4.83 (m, 2H), 4.41 (s, 1H), 4.27-4.03 (m, 8H), 3.32-2.99 (m, 11H), 2.74-2.68 (m, 3H), 2.32-2.19 (m, 2H), 1.78-1.75 (m, 2H), 1.39-1.34 (m, 3H), 1.04 (s, 9H). LCMS (Method 5-95 AB, ESI): $R_T$=0.825 min, $[M+H]^+$=973.0.

Example 28

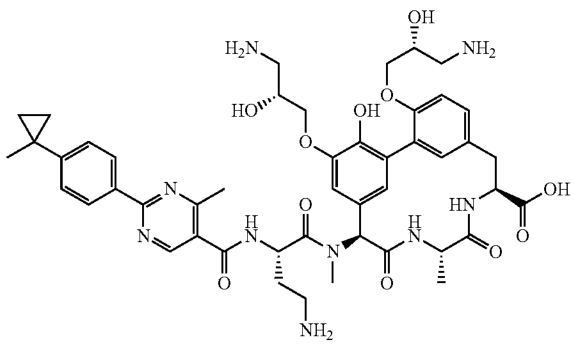 [SMILES: Cc1nc(-c2ccc(C3(C)CC3)cc2)ncc1C(=O)N[C@@H](CCN)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O]

The title compound was prepared from compound 20 using the procedure of Example 1, replacing 1-(4-(tert-butyl)phenyl)-6-oxo-1,6-dihydropyridazine-4-carboxylic acid with 4-methyl-2-(4-(1-methylcyclopropyl)phenyl) pyrimidine-5-carboxylic acid. $^1H$ NMR (400 MHz, MeOH-$d_4$): δ (ppm) 8.79 (s, 1H), 8.20 (d, J=8.4 Hz, 2H), 7.31 (d, J=8.4 Hz, 2H), 7.00-6.80 (m, 3H), 6.88 (s, 1H), 6.44 (s, 1H), 6.40 (s, 1H), 5.18-5.10 (m, 1H), 4.84-4.71 (m, 1H), 4.65-4.53 (m, 1H), 4.37-4.30 (m, 1H), 4.28-4.17 (m, 2H), 4.16-3.97 (m, 3H), 3.27-3.08 (m, 6H), 3.06-2.73 (m, 5H), 2.70 (s, 12H), 2.62 (s, 3H), 2.37-2.15 (m, 2H), 1.47 (s, 3H), 1.37 (d, J=6.8 Hz, 3H), 1.02-0.92 (m, 2H), 0.91-0.82 (m, 2H). LCMS (Method 5-95 AB, ESI): $R_T$=0.763 min, $[M+H]^+$=926.3.

Example 29

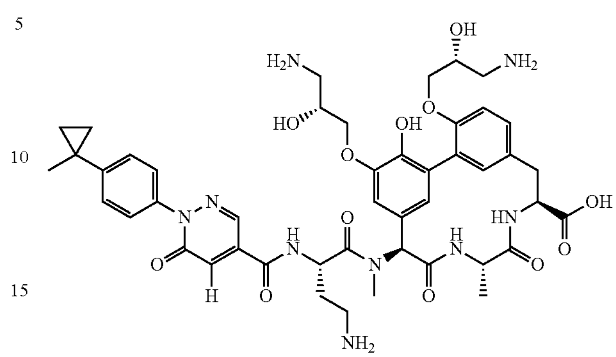

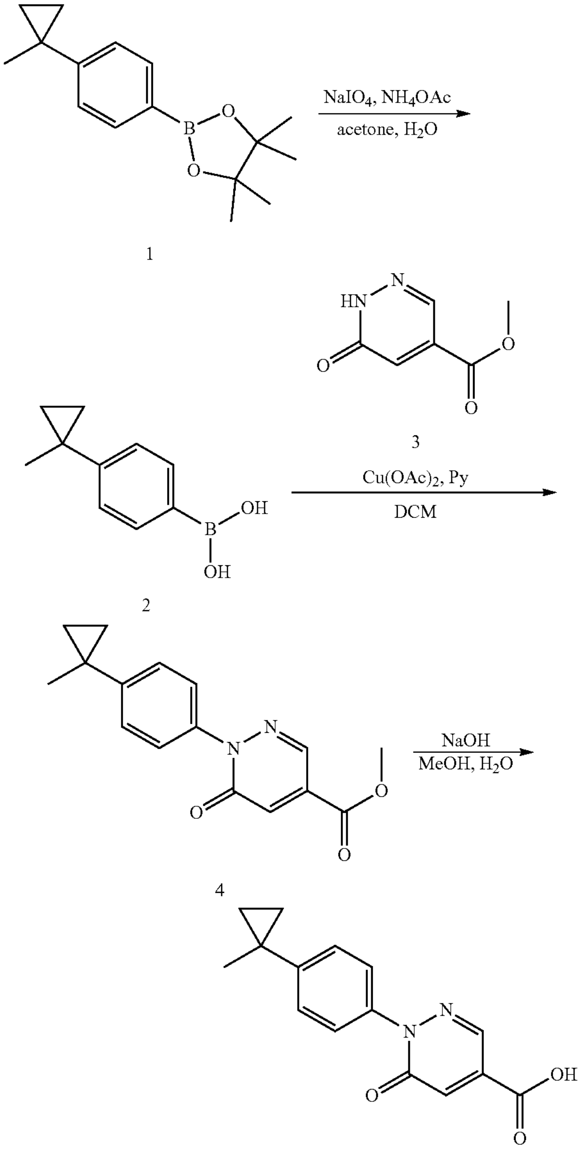

1 2 3 4 5

Step 1: A mixture of 4,4,5,5-tetramethyl-2-(4-(1-methylcyclopropyl)phenyl)-1,3,2-dioxaborolane (8.0 g, 31.0 mmol), sodium periodate (33.1 g, 155 mmol) and ammonium acetate (11.9 g, 155 mmol) in acetone (80 mL) and water (80 mL) was stirred at 25° C. for 16 h and filtered. The filtrate was concentrated and the aqueous residue was extracted with ethyl acetate (2×150 mL). The combined organic layers were concentrated. The residue was purified by column chromatography (silica gel, 100-200 mesh, 0-25% ethyl acetate in petroleum ether) to give (4-(1-methylcyclopropyl)phenyl)boronic acid (5.4 g, 99.0% yield) as a white solid.

Step 2: A mixture of (4-(1-methylcyclopropyl)phenyl) boronic acid (1.00 g, 5.68 mmol), copper (II) acetate (0.21 g, 1.14 mmol), methyl 6-oxo-1,6-dihydropyridazine-4-carboxylate (0.92 g, 5.97 mmol) in dichloromethane (10 mL) and pyridine (1 mL) was stirred at 25° C. for 16 h. The mixture was diluted with 1M HCl (50 mL) and then extracted with dichloromethane (2×100 mL). The combined organic layers were washed with brine (100 mL), dried and concentrated. The residue was purified by column chromatography (silica gel, 100-200 mesh, 0-25% ethyl acetate in petroleum ether) to give methyl 1-(4-(1-methylcyclopropyl) phenyl)-6-oxo-1,6-dihydropyridazine-4-carboxylate (1.00 g, 61.7%) as a yellow solid.

Step 3: A mixture of methyl 1-(4-(1-methylcyclopropyl) phenyl)-6-oxo-1,6-dihydropyridazine-4-carboxylate (6.0 g, 21.1 mmol) and sodium hydroxide (2.1 g, 52.76 mmol) in MeOH (50 mL) and water (20 mL) was heated at 80° C. for 2 h and concentrated. The aqueous residue was adjusted to pH=5 with 1N HCl and extracted with ethyl acetate (3×100 mL). The combined organic layers were washed with brine (200 mL), dried and concentrated to give crude 1-(4-(1-methylcyclopropyl)phenyl)-6-oxo-1,6-dihydropyridazine-4-carboxylic acid (5.30 g, 92.9% yield) as a light yellow solid.

The title compound was prepared from compound 20 using the procedure of Example 1, replacing 1-(4-(tert-butyl)phenyl)-6-oxo-1,6-dihydropyridazine-4-carboxylic acid with 1-(4-(1-methylcyclopropyl)phenyl)-6-oxo-1,6-dihydropyridazine-4-carboxylic acid. $^1$H NMR (400 MHz, MeOH-d$_4$): δ (ppm) 8.32 (d, J=2.0 Hz, 1H), 7.53 (d, J=2.0 Hz, 1H), 7.39-7.32 (m, 4H), 7.15-7.13 (m, 1H), 7.02-7.00 (m, 1H), 6.90 (s, 1H), 6.68 (s, 1H), 6.50 (s, 1H), 6.41 (s, 1H), 4.87-4.78 (m, 2H), 4.36-4.34 (m, 1H), 4.20-4.04 (m, 6H), 3.37-3.30 (m, 3H), 3.21-3.05 (m, 5H), 2.87 (s, 3H), 2.71 (s, 12H), 3.33-3.21 (m, 2H), 1.43 (s, 3H), 1.37 (d, J=6.8 Hz, 3H), 0.91-0.88 (m, 2H), 0.81-0.78 (m, 2H). LCMS (Method 5-95 AB, ESI): R$_T$=0.739 min, [M+H]$^+$=928.4.

Example 30

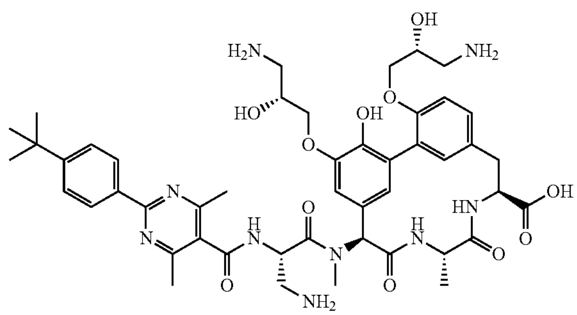 [SMILES: Cc1nc(-c2ccc(C(C)(C)C)cc2)nc(C)c1C(=O)N[C@@H](CN)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O]

The title compound was prepared using the procedure of Example 22, replacing (S)-2-(((benzyloxy)carbonyl) amino)-4-((tert-butoxycarbonyl)amino)butanoic acid with (S)-2-(((benzyloxy)carbonyl)amino)-3-((tert-butoxycarbonyl)amino)propanoic acid and then using General Procedure B, replacing 1-(4-(tert-butyl)phenyl)-6-oxo-1,6-dihydropyridazine-4-carboxylic acid with 2-(4-(tert-butyl)phenyl)-4,6-dimethyl pyrimidine-5-carboxylic acid. $^1$H NMR (400 MHz, MeOH-d$_4$): δ (ppm) 8.43 (s, 1H), 8.33 (d, J=8.8 Hz, 2H), 7.53 (d, J=8.8 Hz, 2H), 7.07 (d, J=8.0 Hz, 1H), 6.88 (d, J=8.4 Hz, 1H), 6.83 (s, 1H), 6.76 (s, 1H), 6.61 (s, 1H), 6.39 (s, 1H), 5.33-5.30 (m, 1H), 4.38-4.36 (m, 2H), 4.21-4.03 (m, 2H), 3.49-3.44 (m, 6H), 3.26-2.96 (m, 10H), 2.57 (s, 6H), 1.38 (s, 9H), 1.34 (d, J=6.8 Hz, 3H). LCMS (Method 5-95 AB, ESI), R$_T$=0.611 min, [M+H]$^+$=928.5.

Example 31

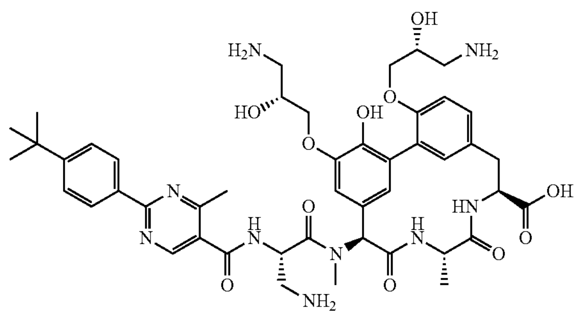 [SMILES: Cc1nc(-c2ccc(C(C)(C)C)cc2)ncc1C(=O)N[C@@H](CN)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O]

The title compound was prepared using the procedure of Example 22, replacing (S)-2-(((benzyloxy)carbonyl) amino)-4-((tert-butoxycarbonyl)amino)butanoic acid with (S)-2-(((benzyloxy)carbonyl)amino)-3-((tert-butoxycarbonyl)amino)propanoic acid and then using General Procedure B, replacing 1-(4-(tert-butyl)phenyl)-6-oxo-1,6-dihydropyridazine-4-carboxylic acid with 2-(4-(tert-butyl) phenyl)-4-methylpyrimidine-5-carboxylic acid. $^1$H NMR (400 MHz, MeOH-d$_4$): δ (ppm) 8.91 (s, 1H), 8.35 (d, J=8.4 Hz, 2H), 7.54 (d, J=8.8 Hz, 2H), 7.08-7.00 (m, 1H), 6.96-6.80 (m, 2H), 6.71-6.60 (m, 1H), 6.54 (s, 1H), 6.41-6.27 (m, 1H), 5.50-5.25 (m, 1H), 4.76-4.58 (m, 1H), 4.54-4.41 (m, 1H), 4.26-3.95 (m, 6H), 3.57-3.48 (m, 1H), 3.41-3.35 (m, 1H), 3.28-2.84 (m, 9H), 2.71-2.66 (m, 3H), 1.42-1.30 (m, 12H). LCMS (Method 5-95 AB, ESI): R$_T$=0.770 min, [M+H]$^+$=914.8.

Example 32

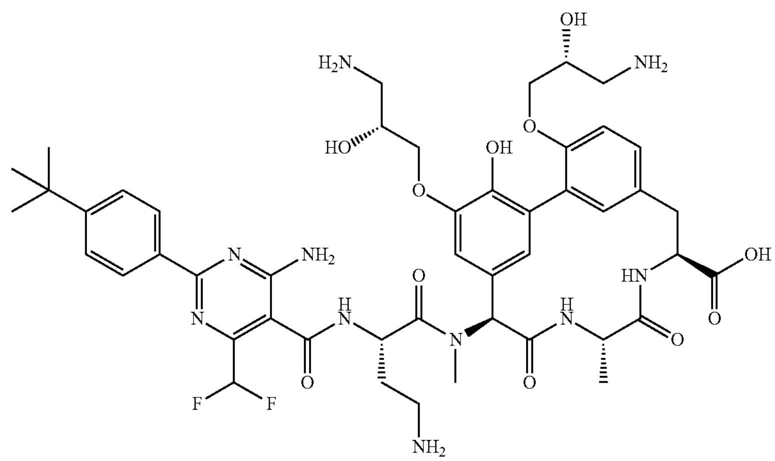 [SMILES: C[C@@H]1NC(=O)[C@@H](N(C)C(=O)[C@H](CCN)NC(=O)c2c(N)nc(-c3ccc(C(C)(C)C)cc3)nc2C(F)F)c2cc(OC[C@H](O)CN)c(O)c(c2)-c2cc(ccc2OC[C@H](O)CN)C[C@@H](C(=O)O)NC1=O]

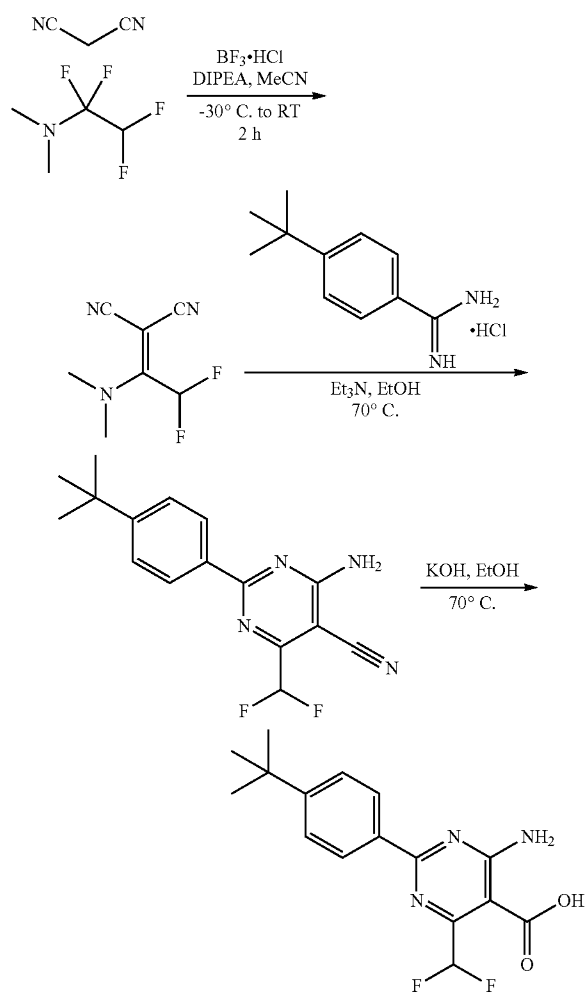

The general procedure for the synthesis of the 4-amino-2-(4-tert-butylphenyl)-6-(difluoromethyl)pyrimidine-5-carbonitrile was performed using procedures from *Chem. Eur. J.* 2018, 24, 1311-1316.

Step 1: A solution of boron trifluoride diethyl etherate (2.68 mL, 21.71 mmol, 1.05 equiv) in acetonitrile (19.2 mL) was stirred for 15 min under $N_2$ at −30° C. 1,1,2,2-tetrafluoro-N,N-dimethyl-ethanamine (3.0 g, 20.68 mmol, 1.0 equiv) in acetonitrile (27 mL) was added and the mixture was stirred for 5 min. The reaction was brought back to room temperature. A solution of malononitrile (1.37 g, 20.68 mmol, 1.0 equiv) in dry acetonitrile (19.2 mL) was added to the solution under inert atmosphere at 25° C., rapidly followed by N,N-diisopropylethylamine (5.4 mL, 31.01 mmol, 1.5 equiv). The mixture was stirred for 2 hrs. The reaction was quenched by addition of silica gel. The solution was concentrated under reduced pressure to give a yellow solid residue, which purified by column chromatography (silica gel, 100-200 mesh, 10-50% EtOAc in heptanes) to yield 2-[1-(dimethylamino)-2,2-difluoro-ethylidene]propanedinitrile (1.68 g, 9.816 mmol, 48% yield) as a yellow solid.

Step 2: 2-[1-(dimethylamino)-2,2-difluoro-ethylidene]propanedinitrile (150 mg, 0.8800 mmol, 1.0 equiv) and (4-tert-butylbenzenecarboximidoyl)ammonium chloride (372.87 mg, 1.75 mmol, 2.0 equiv) were dissolved in absolute ethanol (2.9214 mL, 0.3 M) and capped in a microwave vial. The reaction was heated to 70° C. under microwave irradiation and stirred for 30 minutes. After cooling to room temperature, the reaction mixture was concentrated under reduced pressure. The crude reaction mixture was then purified by flash chromatography (silica gel, 100-200 mesh, 0-50% EtOAc in heptanes) to yield 4-amino-2-(4-tert-butylphenyl)-6-(difluoromethyl)pyrimidine-5-carbonitrile (175 mg, 0.5789 mmol, 66% yield) as a white solid.

Step 3: 4-amino-2-(4-tert-butylphenyl)-6-(difluoromethyl)pyrimidine-5-carbonitrile (160 mg, 0.5300 mmol, 1.0 equiv) was dissolved in absolute EtOH (2.6 mL). An aqueous solution of 4 M potassium hydroxide (0.66 mL, 2.65 mmol, 5.0 equiv) was added and reaction mixture was heated to 70° C. for 18 h. The reaction mixture was cooled to room temperature, a 1 N solution of $KHSO_4$ was added and the reaction mixture was diluted with EtOAc (20 mL). The phases were separated and the aqueous layer was extracted with EtOAc (2×20 mL). The organic layers were combined, washed with brine (2×20 mL), dried over $Na_2SO_4$, filtered and concentrated under reduced pressure to yield 4-amino-2-(4-(tert-butyl)phenyl)-6-(difluoromethyl)pyrimidine-5-carboxylic acid as a yellow solid (170 mg, 0.53 mmol, 99% crude yield) which was used without further purification.

The title compound was prepared from compound 20 using the procedure of Example 1, replacing 1-(4-(tert-butyl)phenyl)-6-oxo-1,6-dihydropyridazine-4-carboxylic acid with 4-amino-2-(4-(tert-butyl)phenyl)-6-(difluoromethyl)pyrimidine-5-carboxylic acid. $^1$H NMR (400 MHz, DMSO-$d_6$) δ (ppm) 9.25 (d, 5.6 Hz, 1H), 8.85 (d, J=8.1 Hz, 1H), 8.32 (d, J=7.6 Hz, 1H), 8.21 (d, J=8.6 Hz, 2H), 7.52 (d, J=8.7 Hz, 2H), 7.19 (dd, J=8.6, 2.2 Hz, 1H), 7.01 (d, J=8.6 Hz, 1H), 6.83 (s, 1H), 6.73 (s, 1H), 6.66-6.75 (m, 2H), 6.26-6.33 (m, 2H), 4.80 (m, 1H), 4.73-4.60 (m, 2H), 4.08-3.88 (m, 6H), 3.28 (d, J=15.1 Hz, 1H), 3.03-2.78 (m, 11H), 2.35 (s, 3H), 2.09-1.99 (m, 1H), 1.97-1.86 (m, 1H), 1.29 (s, 9H), 1.17 (d, J=6.7 Hz, 3H). LCMS (Method 5-100 AB, 6 min): $R_T$=1.66 min, $[M+H]^+$=979.3.

Example 33

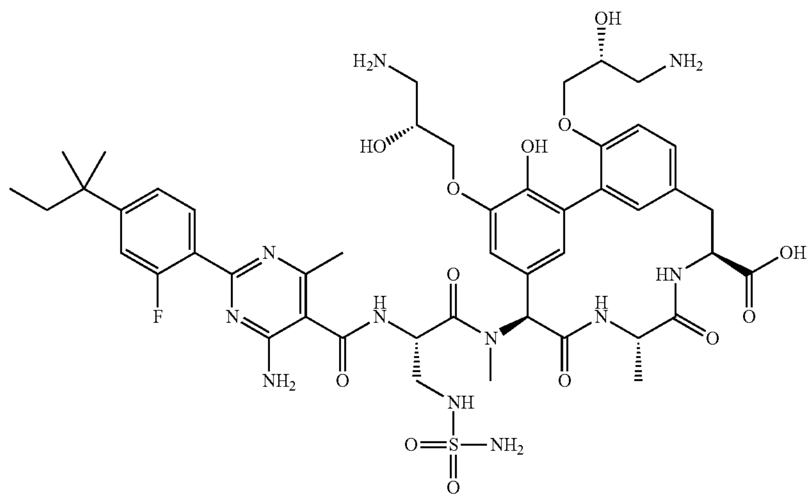 [SMILES: CCC(C)(C)c1ccc(-c2nc(C)c(C(=O)N[C@@H](CNS(N)(=O)=O)C(=O)N(C)[C@@H]3C(=O)N[C@@H](C)C(=O)N[C@H](C(=O)O)Cc4ccc(OC[C@H](O)CN)c(c4)-c4cc3cc(OC[C@H](O)CN)c4O)c(N)n2)c(F)c1]

The title compound was prepared as described in Example 1, replacing 1-(4-(tert-butyl)phenyl)-6-oxo-1,6-dihydropyridazine-4-carboxylic acid with 4-amino-2-(2-fluoro-4-(tert-pentyl)phenyl)-6-methylpyrimidine-5-carboxylic acid. $^1$H NMR (400 MHz, MeOH-$d_4$) δ (ppm) 8.49 (s, 1H), 7.77-7.73 (m, 1H), 7.29-7.27 (m, 1H), 7.20-7.05 (m, 3H), 6.86-6.77 (m, 2H), 6.61-6.48 (m, 2H), 5.30-5.20 (m, 1H), 4.36-4.14 (m, 8H), 3.63-3.60 (m, 1H), 3.40-3.36 (m, 1H), 3.21-3.01 (m, 9H), 2.48 (s, 3H), 1.74-1.71 (m, 2H), 1.33 (s, 9H), 0.74-0.70 (m, 3H). LCMS (Method 5-95 AB, ESI): $R_T$=0.752 min, $[M+H]^+$=1040.5.

Example 34

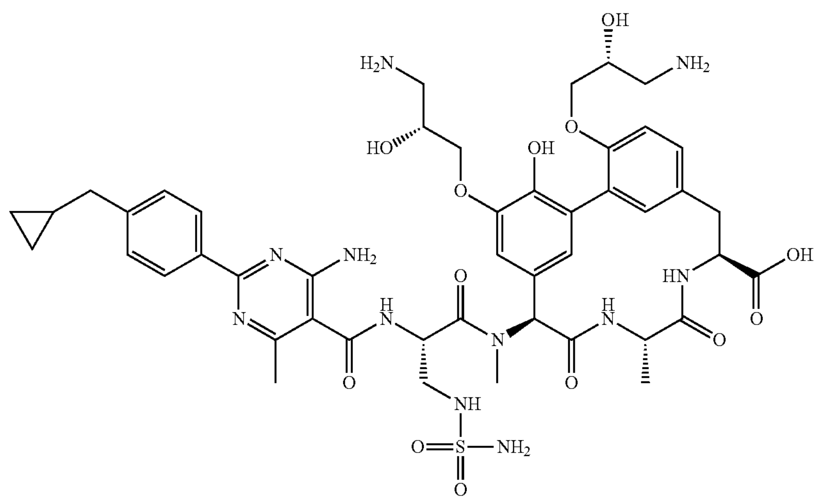 [SMILES: Cc1nc(-c2ccc(CC3CC3)cc2)nc(N)c1C(=O)N[C@@H](CNS(N)(=O)=O)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O]

4-amino-2-(4-(cyclopropylmethyl)phenyl)-6-methylpyrimidine-5-carboxylic acid was prepared as described in Example 54, replacing 2-(3,3-dimethylbutoxy)-5-(4,4,5,5-tetramethyl-1,3,2-dioxaborolan-2-yl)pyridine with 2-(4-(cyclopropylmethyl)phenyl)-4,4,5,5-tetramethyl-1,3,2-dioxaborolane. The title compound was prepared as described in Example 1, replacing 1-(4-(tert-butyl)phenyl)-6-oxo-1,6-dihydropyridazine-4-carboxylic acid with 4-amino-2-(4-(cyclopropylmethyl)phenyl)-6-methylpyrimidine-5-carboxylic acid. $^{1}$H NMR (400 MHz, MeOH-$d_4$) δ (ppm) 8.18 (d, J=7.6 Hz, 2H), 7.34 (d, J=8.0 Hz, 2H), 7.12-7.04 (m, 1H), 6.90-6.74 (m, 3H), 6.59 (s, 1H), 6.52-6.42 (m, 1H), 5.22-5.13 (m, 1H), 4.82-4.80 (m, 2H), 4.27-3.91 (m, 6H), 3.63-3.54 (m, 1H), 3.25-3.14 (m, 3H), 3.06 (s, 3H), 3.03-2.95 (m, 2H), 2.59 (d, J=6.8 Hz, 2H), 2.47 (s, 3H), 1.40-1.29 (m, 3H), 1.07-0.95 (s, 1H), 0.57-0.50 (m, 2H), 0.26-0.19 (m, 2H) ppm. LCMS (Method 5-95 AB, ESI): $R_T$=0.750 min, $[M+H]^+$=1006.3.

Example 35

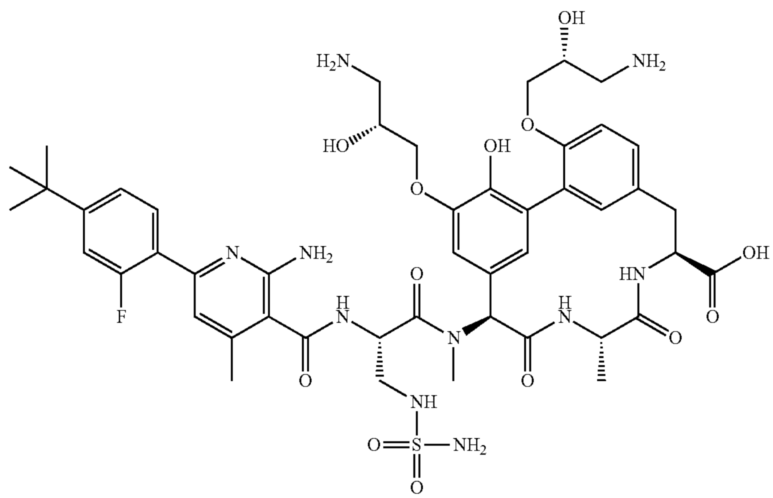 [SMILES: Cc1cc(-c2ccc(C(C)(C)C)cc2F)nc(N)c1C(=O)N[C@@H](CNS(N)(=O)=O)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O]

2-amino-6-(4-(tert-butyl)-2-fluorophenyl)-4-methylnicotinic acid was produced using an approach similar to the procedure used to prepare 2-amino-6-(4-(tert-butyl)phenyl)-4-methylnicotinic acid described in WO2017084630, the content of which is incorporated herein by reference in its entirety. The title compound was prepared as a formic acid salt as described in Example 1, replacing 1-(4-(tert-butyl)phenyl)-6-oxo-1,6-dihydropyridazine-4-carboxylic acid with 2-amino-6-(4-(tert-butyl)-2-fluorophenyl)-4-methylnicotinic acid. $^1$H NMR (400 MHz, MeOH-$d_4$) δ (ppm) 8.38 (s, 2H), 7.70-7.68 (m, 1H), 7.30-7.18 (m, 2H), 7.03-6.55 (m, 6H), 5.21 (m, 1H), 4.39-3.99 (m, 8H), 3.62-3.38 (m, 3H), 3.18-2.86 (m, 9H), 2.32-2.28 (m, 3H), 1.35 (s, 12H). LCMS (Method 5-95 AB, ESI): $R_T$=0.783 min, $[M+H]^+$=1025.5.

Example 36

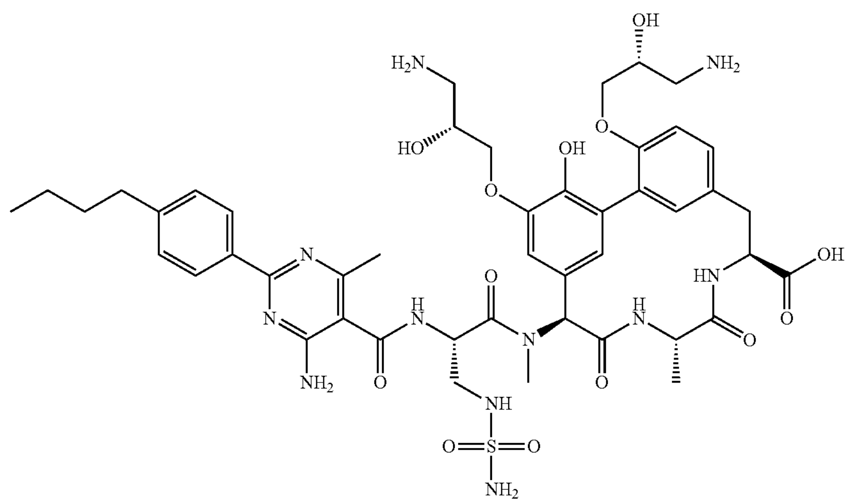 [SMILES: CCCCc1ccc(-c2nc(C)c(C(=O)N[C@@H](CNS(N)(=O)=O)C(=O)N(C)[C@@H]3C(=O)N[C@@H](C)C(=O)N[C@H](C(=O)O)Cc4ccc(OC[C@H](O)CN)c(c4)-c4cc3cc(OC[C@H](O)CN)c4O)c(N)n2)cc1]

The title compound was prepared as described in Example 1, replacing 1-(4-(tert-butyl)phenyl)-6-oxo-1,6-dihydropyridazine-4-carboxylic acid with 4-amino-2-(4-butylphenyl)-6-methylpyrimidine-5-carboxylic acid. $^1$H NMR (400 MHz, MeOH-$d_4$) 8.45 (s, 1H), 8.14 (d, J=8.4 Hz 1H), 7.28 (d, J=8.4 Hz 1H), 7.12-7.10 (m, 1H), 6.91-6.86 (m, 2H), 6.79 (s, 1H), 6.59 (s, 1H), 6.44 (s, 1H), 5.19-5.16 (m, 1H), 4.32-4.04 (m, 7H), 3.64-3.59 (m, 1H), 3.23-3.07 (m, 10H), 2.69-2.65 (m, 3H), 2.47 (s, 3H), 1.38-1.35 (m, 5H), 0.97-0.93 (m, 3H). LCMS (Method 5-95 AB, ESI): $R_T$=0.781 min, $[M+H]^+$=1008.5.

Example 37

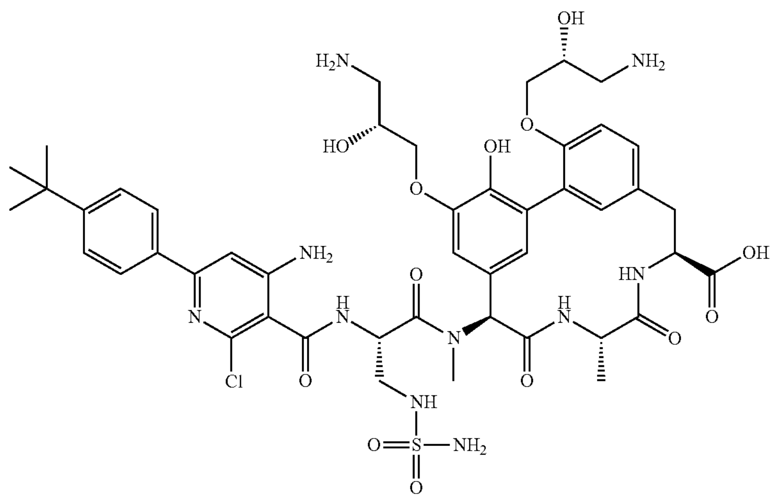 [SMILES: C[C@@H]1NC(=O)[C@@H](N(C)C(=O)[C@H](CNS(N)(=O)=O)NC(=O)c2c(N)cc(-c3ccc(C(C)(C)C)cc3)nc2Cl)c2cc(OC[C@H](O)CN)c(O)c(c2)-c2cc(ccc2OC[C@H](O)CN)C[C@@H](C(=O)O)NC1=O]

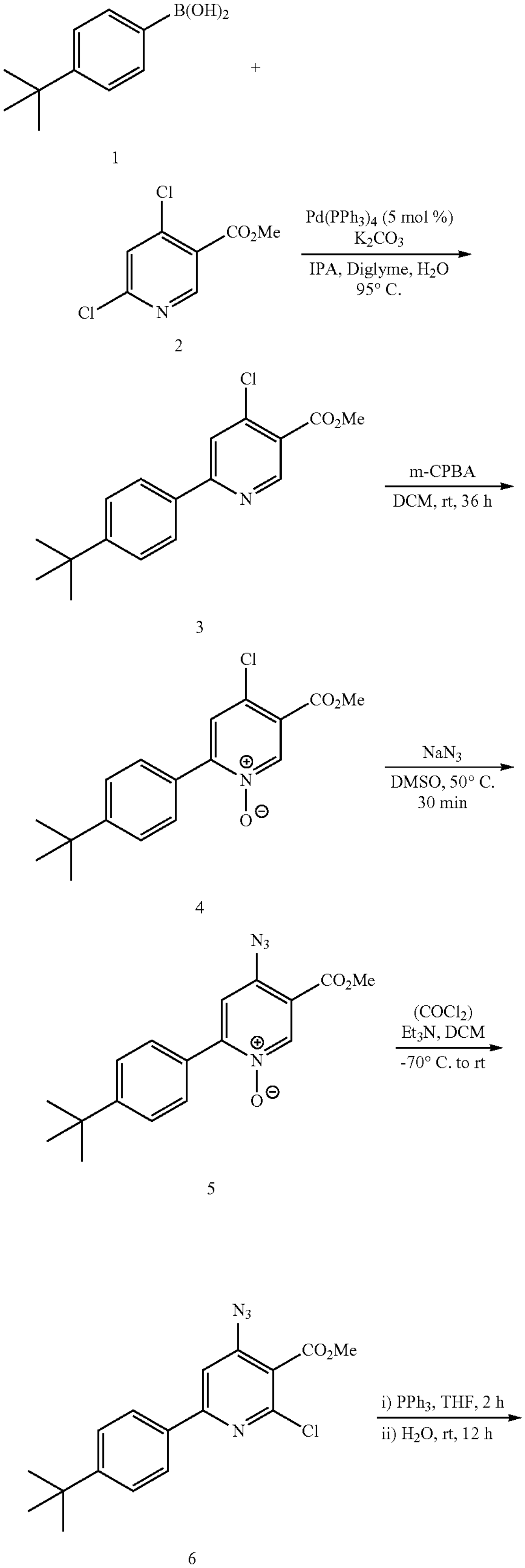

-continued

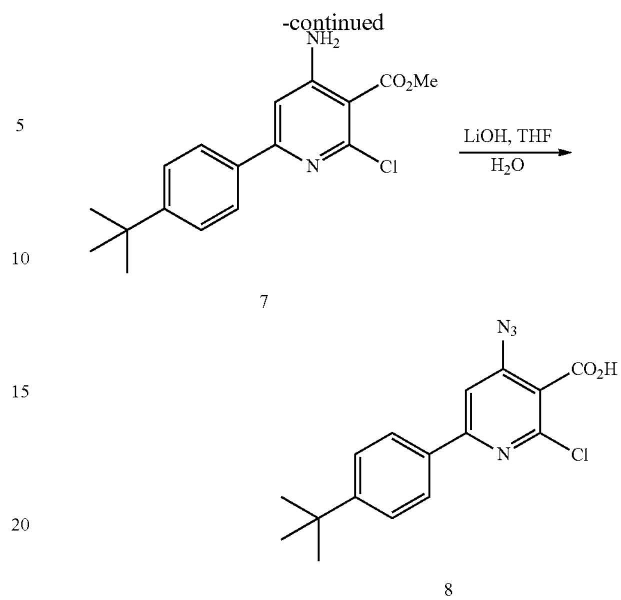

7

8

The general procedure for the synthesis of the methyl 6-(4-(tert-butyl)phenyl)-4-chloronicotinate was performed using procedures from *J. Med. Chem.* 2013, 56, 1023-1040.

Step 1: Methyl 4,6-dichloropyridine-3-carboxylate (3072 mg, 14.91 mmol, 1.05 equiv) and $Pd(PPh_3)_4$ (820 mg, 0.71 mmol, 0.05 mmol) were stirred in diglyme (13 mL) at room temperature for 15 min. To this suspension was then added 4-tert-butylbenzeneboronic acid (2528 mg, 14.2 mmol, 1.0 equiv) in IPA (15 mL) and a 2.0 M aqueous solution of $K_2CO_3$ (13.14 mL, 26.27 mmol, 1.85 equiv). The mixture was stirred at 95° C. for 2 h. The reaction was cooled to room temperature and concentrated under reduced pressure. $NaHCO_3$ sat. aq. and DCM were added to the crude reaction mixture. The phases were separated, the aqueous layer was extracted with additional DCM (2×40 mL) and organic layers were combined. The organic layer was then washed with brine (2×30 mL), dried over $Na_2SO_4$, filtered, and concentrated under reduced pressure. The solid was then redissolved in DCM and silica gel was added (20 g) and the obtained mixture was concentrated under reduced pressure to give a dry pack of yellow solid. The crude reaction mixture was then purified by flash chromatography (silica gel, 100-200 mesh, 0-30% EtOAc in heptanes) to yield methyl 6-(4-tert-butylphenyl)-4-chloro-pyridine-3-carboxylate (2950 mg, 9.711 mmol, 68.4% yield) as a clear oil.

Step 2: Methyl 6-(4-tert-butylphenyl)-4-chloro-pyridine-3-carboxylate (5000 mg, 16.46 mmol, 1.0 equiv) was dissolved in DCM (54.8 mL) and 70% wt. 3-chloroperbenzoic acid (m-CPBA) (8521 mg, 24.69 mmol, 1.5 equiv) was added. The reaction mixture was stirred at rt for 36 h. The reaction mixture was diluted with sat. solution of $NaHCO_3$ and extracted with DCM (3×40 mL). Organics were combined, washed with water (1×40 mL), brine (1×40 mL), dried with $Na_2SO_4$, filtered, and concentrated under reduced pressure. The crude reaction mixture was then purified by flash chromatography (silica gel, 100-200 mesh, 10-80% EtOAc in heptanes) to yield methyl 6-(4-tert-butylphenyl)-4-chloro-1-oxo-pyridine-3-carboxylate (3100 mg, 9.6942 mmol, 59% yield) as a beige solid.

Step 3: Methyl 6-(4-tert-butylphenyl)-4-chloro-1-oxido-pyridin-1-ium-3-carboxylate (3100 mg, 9.69 mmol, 1.0 equiv) was dissolved in DMSO (19.4 mL) and sodium azide (1891 mg, 29.08 mmol, 3.0 equiv) was added. The reaction mixture was stirred at 50° C. for 30 min. The reaction mixture was cooled to rt and poured into water and extracted with EtOAc (3×40 mL). Organics were combined, washed with water (1×40 mL), brine (1×40 mL), dried with anhydrous $Na_2SO_4$, filtered over a sintered funnel, and concentrated under reduced pressure to yield methyl 4-azido-6-(4-tert-butylphenyl)-1-oxido-pyridin-1-ium-3-carboxylate (2052 mg, 6.29 mmol, 64.9% yield) as a pale orange solid which carried over the next step without purification.

The general procedure for the synthesis of the methyl 6-(4-(tert-butyl)phenyl)-4-chloronicotinate was performed using procedures from *Org. Lett.* 2015, 17, 2948-2951.

Step 4: To a flame-dried, nitrogen flushed flask was added methyl 4-azido-6-(4-tert-butylphenyl)-1-oxido-pyridin-1-ium-3-carboxylate (500 mg, 1.53 mmol, 1.0 equiv) and DCM (4.7 mL). The reaction mixture was cooled to −70° C. and $Et_3N$ (0.43 mL, 3.06 mmol, 2.0 equiv) was added followed by oxalyl chloride (0.26 mL, 3.06 mmol, 2.0 equiv). The reaction was then stirred from −70° C. to rt over 3 hours. $NaHCO_3$ sat. aq. was added and the reaction was diluted with EtOAc (30 mL). The phases were separated and aqueous layer was extracted with more EtOAc (2×10 mL). The organic layers were combined, washed with brine (2×20 mL), dried over $Na_2SO_4$, filtered over a sintered funnel, and concentrated under reduced pressure. The crude reaction mixture was then purified by flash chromatography (silica gel, 100-200 mesh, 0-50% EtOAc in heptanes) to yield methyl 4-azido-6-(4-tert-butylphenyl)-2-chloro-pyridine-3-carboxylate (280 mg, 0.812 mmol, 53% yield) as a yellow solid.

Step 5: Triphenylphosphine (197.8 mg, 0.750 mmol, 1.0 equiv) was added to a stirring solution of methyl 4-azido-6-(4-tert-butylphenyl)-2-chloro-pyridine-3-carboxylate (260 mg, 0.750 mmol) in THF (7.54 mL). The reaction was stirred at rt for 2 hours whereupon $H_2O$ (2 mL) was added. The reaction was stirred at rt for 12 hours. $NaHCO_3$ sat. aq. and EtOAc (20 mL) were added and the phases were separated. The aqueous layer was extracted with more EtOAc (2×10 mL). The organic layers were combined, layer washed with brine (2×20 mL), dried over $Na_2SO_4$, filtered, and filtrate was concentrated under reduced pressure. The crude reaction mixture was then purified by flash chromatography (silica gel, 100-200 mesh, 0-100% EtOAc in heptanes) to yield methyl 4-amino-6-(4-tert-butylphenyl)-2-chloro-pyridine-3-carboxylate (180 mg, 0.565 mmol, 74.9% yield) as a white powder.

Step 6: Methyl 4-amino-6-(4-tert-butylphenyl)-2-chloro-pyridine-3-carboxylate (180 mg, 0.5600 mmol) was dissolved in THF (5.65 mL) and an 1.0 M aqueous solution of lithium hydroxide (0.62 mL, 0.620 mmol, 1.1 equiv) was added and the reaction was stirred for 24 hours at rt. $KHSO_4$ 1N (40 mL) and EtOAc (40 mL) were added and the phases were separated. The aqueous layer was extracted with EtOAc (2×40 mL). The organic layers were combined, washed with brine (3×40 mL), dried over $Na_2SO_4$, filtered over a sintered funnel, and filtrate was concentrated under reduced pressure to yield 4-amino-6-(4-tert-butylphenyl)-2-chloro-pyridine-3-carboxylic acid (180 mg, 0.5906 mmol, 104% yield) isolated as a white solid which was carried over the next step without purification.

The title compound was prepared as described in Example 1, replacing 1-(4-(tert-butyl)phenyl)-6-oxo-1,6-dihydropyridazine-4-carboxylic acid with 4-amino-6-(4-tert-butylphenyl)-2-chloro-pyridine-3-carboxylic acid. 1H NMR (400 MHz, DMSO-$d_6$+$D_2O$) δ 8.31 (s, 1H), 7.79 (d, J=8.6 Hz, 2H), 7.47 (d, J=8.6 Hz, 2H), 7.08 (s, 1H), 7.09-7.04 (m, 1H), 6.89 (d, J=7.8 Hz, 1H), 6.74-6.64 (m, 2H), 6.34 (s, 1H), 6.24 (s, 1H), 4.94-4.85 (m, 1H), 4.60-4.58 (m, 1H), 4.18-3.87 (m, 7H), 3.34-3.31 (m, 1H), 3.27-3.19 (m, 1H), 3.17-3.09 (m, 1H), 3.05-2.76 (m, 8H), 1.27 (s, 9H), 1.16 (d, J=7.0 Hz, 3H). LCMS (Method 5-100 AB, 7 min): $R_T$=1.85 min, $[M+H]^+$=1027.5.

Example 38

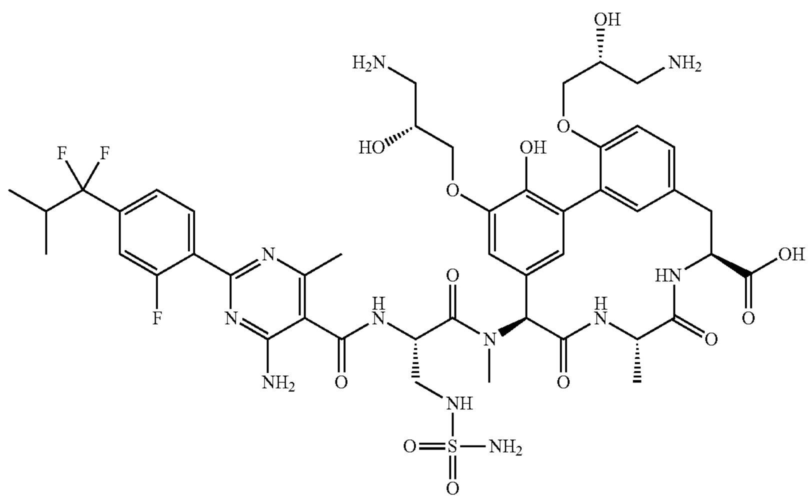 [SMILES: Cc1nc(-c2ccc(C(F)(F)C(C)C)cc2F)nc(N)c1C(=O)N[C@@H](CNS(N)(=O)=O)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O]

The title compound was prepared as described in Example 1, replacing 1-(4-(tert-butyl)phenyl)-6-oxo-1,6-dihydropyridazine-4-carboxylic acid with 4-amino-2-(4-(1,1-difluoro-2-methylpropyl)phenyl)-6-methylpyrimidine-5-carboxylic acid. $^1H$ NMR (400 MHz, MeOH-$d_4$) δ (ppm) 8.42-8.34 (m, 3H), 7.61-7.49 (m, 2H), 7.21-7.03 (m, 1H), 6.97-6.72 (m, 3H), 6.68-6.56 (m, 1H), 6.47 (s, 1H), 5.20-5.10 (m, 1H), 4.84-4.73 (m, 2H), 4.41-4.00 (m, 6H), 3.75-3.32 (m, 3H), 3.27-2.91 (m, 8H), 2.64-2.30 (m, 4H), 1.45-1.25 (m, 3H), 1.00 (d, J=6.8 Hz, 6H). LCMS (Method 5-95 AB, ESI): $R_T$=0.645 min, $[M+H]^+$=1045.0.

Example 39

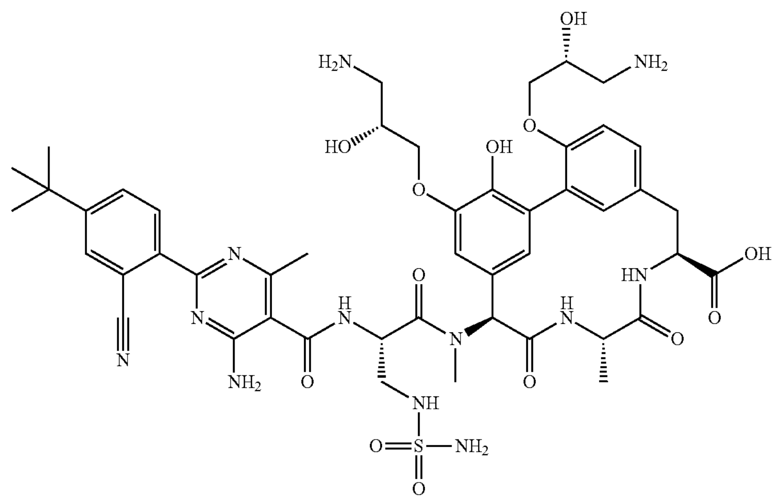 [SMILES: Cc1nc(-c2ccc(C(C)(C)C)cc2C#N)nc(N)c1C(=O)N[C@@H](CNS(N)(=O)=O)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O]

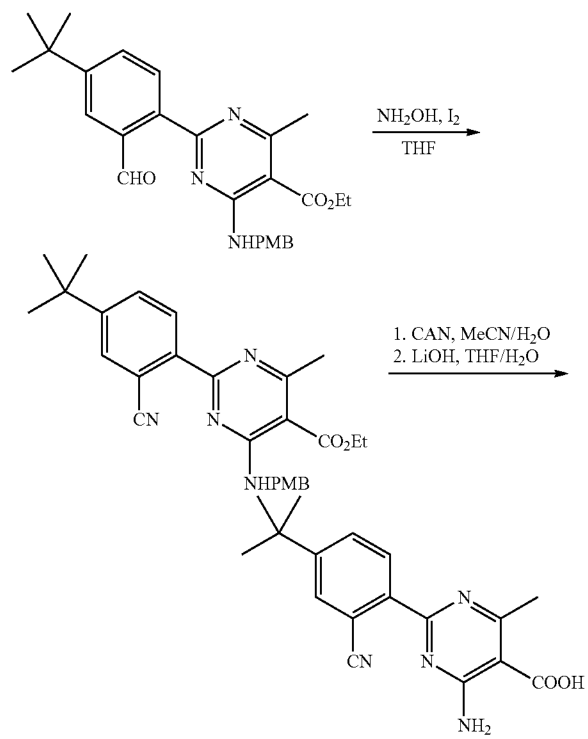

To a solution of ethyl 2-(4-(tert-butyl)-2-formylphenyl)-4-((4-methoxybenzyl)amino)-6-methylpyrimidine-5-carboxylate (140 mg, 0.30 mmol) in THF (2.00 mL) and $NH_3$—$H_2O$ (4.00 mL, 0.30 mmol) was added $I_2$ (84.7 mg, 0.33 mmol). The reaction was stirred at 20° C. for 2 h. The solution was concentrated to dryness. The residue was partitioned between ethyl acetate (40 mL) and water (40 mL). The organic phase was washed with $Na_2S_2O_3$ saturated solution (2×30 mL) and brine (30 mL). The organic phase was dried over $Na_2SO_4$ and concentrated to dryness. The residue was purified by preparative TLC (ethyl acetate: petroleum ether=1:10) to give ethyl 2-(4-(tert-butyl)-2-cyanophenyl)-4-((4-methoxybenzyl)amino)-6-methylpyrimidine-5-carboxylate (135 mg, 97.1% yield) as a yellow solid.

To a solution of ethyl 2-(4-(tert-butyl)-2-cyanophenyl)-4-((4-methoxybenzyl)amino)-6-methylpyrimidine-5-carboxylate (135 mg, 0.29 mmol) in acetonitrile (6.0 mL) and water (3.0 mL) was added CAN (646 mg, 1.18 mmol). The reaction mixture was stirred at 20° C. for 30 min. The reaction mixture was partitioned between ethyl acetate (40.0 mL) and water (40.0 mL). The organic phase was washed with brine (2×40 mL), dried with $Na_2SO_4$ and concentrated to dryness. The residue was purified by preparative TLC (Ethyl acetate: Petroleum ether=2:10) to give ethyl 4-amino-2-(4-(tert-butyl)-2-cyanophenyl)-6-methylpyrimidine-5-carboxylate (80.0 mg, 80.3% yield) as a yellow solid.

Step 3: To a solution of ethyl 4-amino-2-(4-(tert-butyl)-2-cyanophenyl)-6-methylpyrimidine-5-carboxylate (80.0 mg, 0.23 mmol) in THF (6.0 mL) and water (2.0 mL) was added $LiOH.H_2O$ (24.4 mg, 0.58 mmol). The reaction was stirred at 80° C. for 1 h. The mixture was concentrated to remove methanol, and then water (20 mL) was added to the reaction mixture. The mixture was adjusted to pH=2 with 1M HCl. The aqueous layer was extracted with ethyl acetate (2×20 mL). The combined organic layers were concentrated to dryness to give 4-amino-2-(4-(tert-butyl)-2-cyanophenyl)-6-methylpyrimidine-5-carboxylic acid (50 mg, 69.2% yield) as a white solid.

The title compound was prepared as described in Example 1, replacing 1-(4-(tert-butyl)phenyl)-6-oxo-1,6-dihydropyridazine-4-carboxylic acid with 4-amino-2-(4-(tert-butyl)-2-cyanophenyl)-6-methylpyrimidine-5-carboxylic acid. $^1H$ NMR (400 MHz, MeOH-$d_4$) 8.53 (s, 1H), 8.15-8.13 (m, 1H), 7.85-7.75 (m, 2H), 7.07 (br, 1H), 7.00-6.84 (m, 2H), 8.60 (s, 1H), 8.48 (s, 1H), 5.20 (s, 1H), 4.38-4.01 (m, 5H), 3.63-3.60 (m, 1H), 3.38-2.94 (m, 5H), 2.50-2.45 (m, 3H), 1.38 (s, 12H). LCMS (Method 5-100 AB, 1.5 min): $R_T$=0.633 min, $[M+H]^+$=1033.7.

Example 40

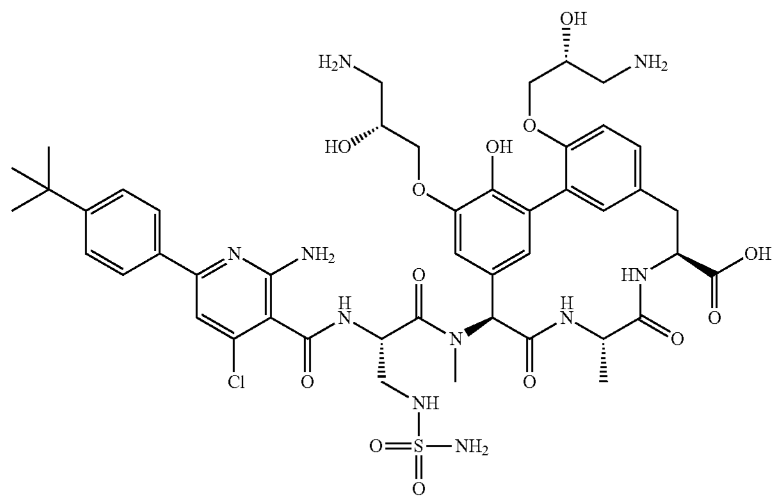 [SMILES: C[C@@H]1NC(=O)[C@@H](N(C)C(=O)[C@H](CNS(N)(=O)=O)NC(=O)c2c(Cl)cc(-c3ccc(C(C)(C)C)cc3)nc2N)c2cc(OC[C@H](O)CN)c(O)c(c2)-c2cc(ccc2OC[C@H](O)CN)C[C@@H](C(=O)O)NC1=O]

Step 1: To a mixture of 4-tert-butylbenzeneboronic acid (500 mg, 2.81 mmol) in 1,4-dioxane (25 mL) was added methyl 2-amino-4,6-dichloro-pyridine-3-carboxylate (745 mg, 3.37 mmol), $Pd(PPh_3)_4$ (162 mg, 0.140 mmol), $K_3PO_4$ (894 mg, 4.21 mmol), and $H_2O$ (3 mL). The reaction mixture was degassed with N2 gas then stirred at 60° C. for 18 h. The reaction was quenched with saturated aqueous $NaHCO_3$ (25 mL) then extracted with EtOAc (3×75 mL). The organic layers were combined, washed with brine, dried over $Na_2SO_4$, filtrated over Celite and concentrated under reduced pressure. The residue was purified by column chromatography (silica gel, 100-200 mesh, 0-100% EtOAc in heptanes) to yield methyl 2-amino-6-(4-tert-butylphenyl)-4-chloro-pyridine-3-carboxylate (565 mg, 1.77 mmol) as a yellow solid.

Step 2: To a mixture of methyl 2-amino-6-(4-tert-butylphenyl)-4-chloro-pyridine-3-carboxylate (679 mg, 2.13 mmol) in 1,4-dioxane (5.6 mL) was added 1M aqueous LiOH (4.26 mL, 4.26 mmol). The reaction mixture was stirred at 60° C. for 15 h then cooled to room temperature. Diethyl ether was added and the precipitate was collected by filtration to afford 2-amino-6-(4-tert-butylphenyl)-4-chloro-pyridine-3-carboxylic acid (502 mg, 77.3% yield) as a pale yellow solid.

The title compound was prepared as described in Example 1, replacing 1-(4-(tert-butyl)phenyl)-6-oxo-1,6-dihydro-pyridazine-4-carboxylic acid with 2-amino-6-(4-tert-butylphenyl)-4-chloro-pyridine-3-carboxylic acid. $^1H$ NMR (400 MHz, DMSO+D2O) δ 8.35 (s, 2H), 7.93 (d, J=8.5 Hz, 2H), 7.48 (d, J=8.6 Hz, 2H), 7.19 (s, 1H), 7.07 (d, J=9.7 Hz, 1H), 6.89 (d, J=8.6 Hz, 1H), 6.75 (s, 1H), 6.71 (s, 1H), 6.37 (s, 1H), 6.27 (s, 1H), 4.94-4.87 (m, 1H), 4.67-4.58 (m, 1H), 4.17-4.10 (m, 1H), 4.08-3.90 (m, 6H), 3.41-3.09 (m, 4H), 3.07-2.76 (m, 7H), 1.29 (s, 9H), 1.17 (d, J=6.7 Hz, 3H). LCMS (Method 5-100 AB, 7 min): $R_T$=1.97 min, $[M+H]^+$=1027.5.

Example 41

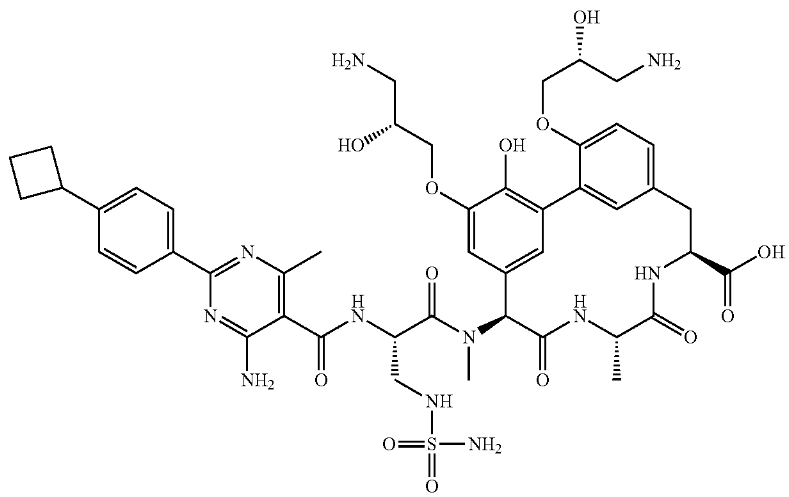 [SMILES: Cc1nc(-c2ccc(C3CCC3)cc2)nc(N)c1C(=O)N[C@@H](CNS(N)(=O)=O)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O]

The title compound was prepared as described in Example 1, replacing 1-(4-(tert-butyl)phenyl)-6-oxo-1,6-dihydropyridazine-4-carboxylic acid with 4-amino-2-(4-cyclobutylphenyl)-6-methylpyrimidine-5-carboxylic acid. $^1$H NMR (400 MHz, MeOH-$d_4$) 8.48 (s, 1H), 8.15 (d, J=8.0 Hz 2H), 7.35 (d, J=8.0 Hz 2H), 7.18-7.16 (m, 1H), 6.97-6.95 (m, 2H), 6.89 (s, 1H), 6.82 (s, 1H), 6.61 (s, 1H), 6.43 (s, 1H), 5.23-5.19 (m, 1H), 4.47-4.44 (m, 2H), 4.33-4.08 (m, 6H), 3.67-3.59 (m, 2H), 3.42-3.36 (m, 1H), 3.29-3.16 (m, 4H), 3.09-3.04 (m, 5H), 2.50 (s, 3H), 2.40-2.38 (m, 2H), 2.21-2.08 (m, 3H), 1.94-1.89 (m, 1H), 1.39 (d, J=7.2 Hz, 3H). LCMS (Method 5-95 AB, ESI): $R_T$=0.737 min, $[M+H]^+$=1006.6.

Example 42

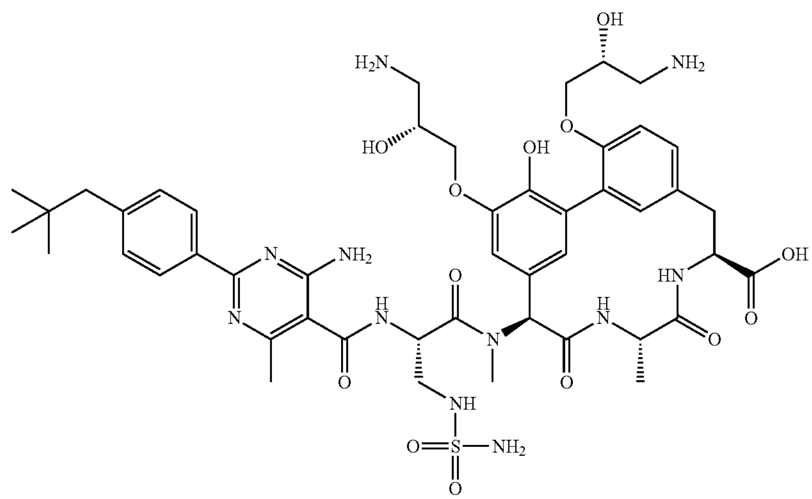 [SMILES: Cc1nc(-c2ccc(CC(C)(C)C)cc2)nc(N)c1C(=O)N[C@@H](CNS(N)(=O)=O)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O]

The title compound was prepared as described in Example 1, replacing 1-(4-(tert-butyl)phenyl)-6-oxo-1,6-dihydropyridazine-4-carboxylic acid with 4-amino-6-methyl-2-(4-neopentylphenyl)pyrimidine-5-carboxylic acid. $^1$H NMR (400 MHz, MeOH-$d_4$) δ (ppm) 8.40 (br s, 1H), 8.15 (d, J=8.0 Hz, 2H), 7.24 (d, J=8.0 Hz, 2H), 7.15-7.06 (m, 1H), 6.85-6.78 (m, 3H), 6.60 (br, s, 1H), 6.48 (s, 1H), 5.18 (s, 1H), 4.50-4.22 (m, 6H), 4.22-4.01 (m, 6H), 3.62-3.34 (m, 2H), 3.24-2.99 (m, 8H), 2.58-2.34 (m, 5H), 1.38-1.35 (m, 3H), 0.94 (s, 9H). LCMS (Method 5-95 AB, ESI): $R_T$=0.798 min, $[M+H]^+$=1022.3.

Example 43

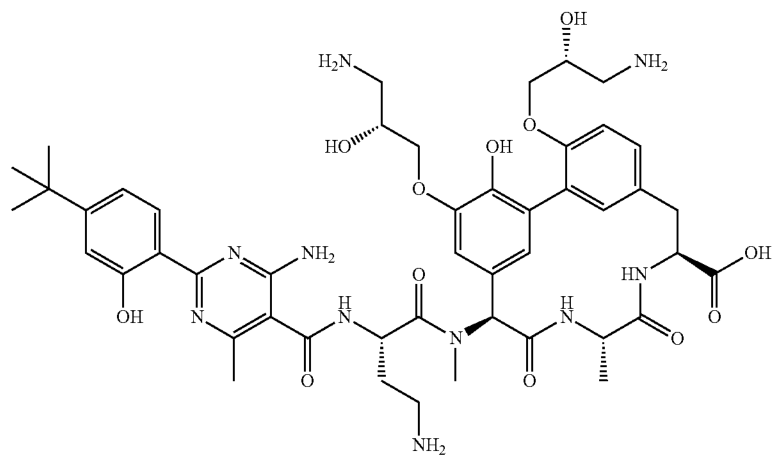 [SMILES: Cc1nc(-c2ccc(C(C)(C)C)cc2O)nc(N)c1C(=O)N[C@@H](CCN)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O]

The title compound was prepared from compound 20 using the procedure of Example 1, replacing 1-(4-(tert-butyl)phenyl)-6-oxo-1,6-dihydropyridazine-4-carboxylic acid with 4-amino-2-(4-(tert-butyl)-2-hydroxyphenyl)-6-methylpyrimidine-5-carboxylic acid. $^1$H NMR (400 MHz, DMSO) δ 8.87 (d, J=8.1 Hz, 1H), 8.33 (d, J=7.8 Hz, 1H), 8.17 (d, J=8.4 Hz, 1H), 7.21 (d, J=8.7 Hz, 1H), 7.02 (d, J=8.6 Hz, 1H), 6.97 (dd, J=8.5, 1.9 Hz, 1H), 6.87 (d, J=1.9 Hz, 1H), 6.75 (s, 1H), 6.69 (d, J=1.5 Hz, 1H), 6.33 (s, 1H), 6.30 (s, 1H), 4.84 (dd, J=9.6, 4.1 Hz, 1H), 4.74-4.63 (m, 2H), 4.11-3.90 (m, 6H), 3.34-3.25 (m, 1H), 3.12-2.79 (m, 10H), 2.37 (s, 3H), 2.36 (s, 15H), 2.10-1.89 (m, 2H), 1.27 (s, 9H), 1.18 (d, J=6.7 Hz, 3H). LCMS (Method 5-100 AB, 7 min): $R_T$=1.64 min, $[M+H]^+$=959.7.

Example 44

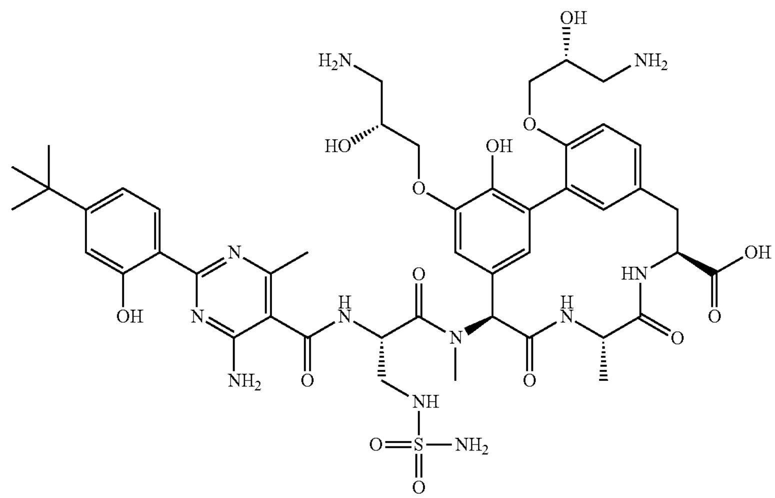

4-amino-2-(4-(tert-butyl)-2-hydroxyphenyl)-6-methylpyrimidine-5-carboxylic acid was prepared as described in Example 54, replacing 2-(3,3-dimethylbutoxy)-5-(4,4,5,5-tetramethyl-1,3,2-dioxaborolan-2-yl)pyridine with 2-(2-(benzyloxy)-4-(tert-butyl)phenyl)-4,4,5,5-tetramethyl-1,3,2-dioxaborolane. The title compound was prepared as described in Example 1, replacing 1-(4-(tert-butyl)phenyl)-6-oxo-1,6-dihydropyridazine-4-carboxylic acid with 4-amino-2-(4-(tert-butyl)-2-hydroxyphenyl)-6-methylpyrimidine-5-carboxylic acid. $^1$H NMR (400 MHz, MeOH-$d_4$) δ (ppm) 8.45 (s, 1H), 8.29-8.19 (m, 1H), 7.11-7.00 (m, 1H), 6.99-6.71 (m, 5H), 6.66-6.56 (m, 1H), 6.50 (s, 1H), 5.23-5.09 (m, 1H), 4.83-4.52 (m, 1H), 4.41 (s, 1H), 4.31-3.94 (m, 6H), 3.66-3.54 (m, 1H), 3.42-3.34 (m, 1H), 3.29-2.93 (m, 9H), 2.51-2.36 (m, 3H), 1.40-1.27 (m, 12H). LCMS (Method 5-95 AB, ESI): $R_T$=0.791 min, $[M+H]^+$=1024.9.

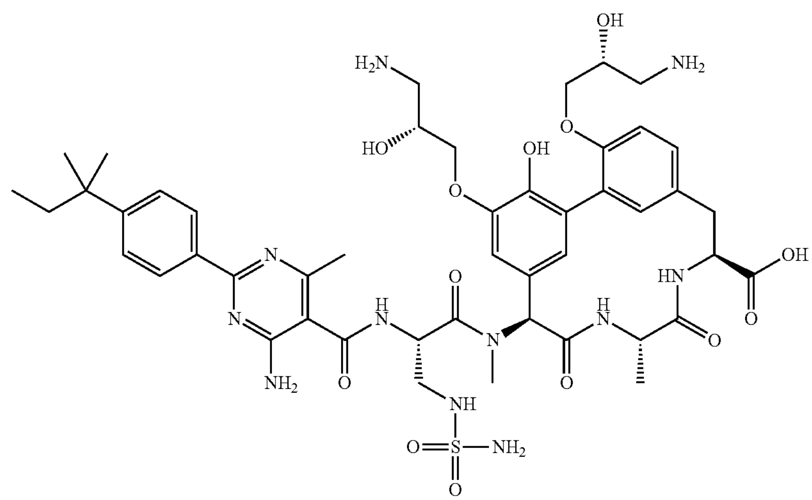 [SMILES: CCC(C)(C)c1ccc(-c2nc(C)c(C(=O)N[C@@H](CNS(N)(=O)=O)C(=O)N(C)[C@@H]3C(=O)N[C@@H](C)C(=O)N[C@H](C(=O)O)Cc4ccc(OC[C@H](O)CN)c(c4)-c4cc3cc(OC[C@H](O)CN)c4O)c(N)n2)cc1]

Step 1: To a stirred, ice cold DCM (50 mL) solution of 4-(1,1-dimethylpropyl)phenol (1.00 g, 6.09 mmol, 1.0 equiv) under nitrogen was added pyridine (981 uL, 12.18 mmol, 2.0 equiv) followed by dropwise addition of trifluoromethanesulfonic anhydride (1.23 mL, 7.31 mmol, 1.2 equiv). The mixture was stirred 30 minutes at 0° C. then was allowed to warm to room temperature. The reaction was washed with aqueous 1.0 M $KHSO_4$ (30 mL), then sat. aqueous $NaHCO_3$ (2×30 mL), sat. aqueous brine (30 mL). The solution was dried over anhydrous $MgSO_4$, filtered, and the filtrate was concentrated under reduced pressure. The crude reaction mixture was then purified by flash chromatography (silica gel, 100-200 mesh, 0-100% EtOAc in heptanes) to yield [4-(1,1-dimethylpropyl)phenyl]trifluoromethanesulfonate (1800 mg, 6.075 mmol, 99.7% yield) as a clear oil.

Step 2: To a stirred solution of [4-(1,1-dimethylpropyl) phenyl]trifluoromethanesulfonate (400 mg, 1.35 mmol, 1.0 equiv) in anhydrous DMSO (6 mL) was added bis(pinacolato)diboron (377 mg, 1.48 mmol, 1.1 equiv) followed by KOAc (132 mg, 1.35 mmol, 1.0 equiv). The mixture was stirred and sparged with a flow of argon for 1 hour. Then, $PdCl_2$(dppf) $CH_2Cl_2$ (49 mg, 0.067 mmol, 0.05 equiv) was added and sparging of argon continued for 15 min. Mixture was kept under argon and heated to 80° C. for 3 hrs. The reaction mixture was allowed to cool to room temperature, was diluted with EtOAc (75 mL), washed with water (50 mL) and sat. aqueous brine (4×25 mL). The organic layer was dried over $MgSO_4$, filtered, and the filtrate was concentrated under reduced pressure. The crude reaction mixture was then purified by flash chromatography (silica gel, 100-200 mesh, 0-100% EtOAc in heptanes) to yield 2-[4-(1,1-dimethylpropyl)phenyl]-4,4,5,5-tetramethyl-1,3,2-dioxaborolane (310 mg, 1.13 mmol, 83.7% yield) as a white solid.

Step 3: To a flame-dried, nitrogen-flushed vial was added 2-[4-(1,1-dimethylpropyl)phenyl]-4,4,5,5-tetramethyl-1,3,2-dioxaborolane (336 mg, 1.23 mmol, 1.3 equiv), $K_2CO_3$ (261 mg, 1.88 mmol, 2.0 equiv), methyl 4-amino-2-chloro-6-methyl-pyrimidine-5-carboxylate (190 mg, 0.9400 mmol, 1.0 equiv), and $PdCl_2$ (dppf)$CH_2C_{12}$ (77 mg, 0.0900 mmol, 0.1 equiv). The solids were suspended in a mixture of 1,4-dioxane (2.36 mL) and Water (0.24 mL) and degassed with nitrogen for 5 minutes. The vial was sealed and heated to 100° C. for 2 hours. The reaction was cooled to rt and $NaHCO_3$ sat. aq. and EtOAc were added. The layers were separated and aqueous layer was extracted with EtOAc (2×10 mL). The organic layers were combined, washed with brine (2×20 mL), dried over $Na_2SO_4$, filtered, and concentrated under reduced pressure. The crude reaction mixture was then purified by flash chromatography (silica gel, 100-200 mesh, 0-60% EtOAc in heptanes) to yield methyl 4-amino-2-[4-(1,1-dimethylpropyl)phenyl]-6-methyl-pyrimidine-5-carboxylate (80 mg, 0.255 mmol, 27% yield) as a white solid.

Step 4: To a scintillation vial equipped with a magnetic stirbar was added methyl 4-amino-6-chloro-2-[4-(1,1-dimethylpropyl)phenyl]pyrimidine-5-carboxylate (70 mg, 0.21 mmol, 1.0 equiv), THF (2.1 mL) and an 1.0 M aqueous solution of lithium hydroxide (0.23 mL, 0.2300 mmol, 1.1 equiv). The reaction mixture was stirred at rt for 12 hours. The reaction was concentrated under reduced pressure to yield Lithium 4-amino-6-chloro-2-[4-(1,1-dimethylpropyl) phenyl]pyrimidine-5-carboxylate (67 mg, 0.2095 mmol, 99.9% yield) as a bright yellow solid which was used directly without purification.

The title compound was prepared as described in Example 1, replacing 1-(4-(tert-butyl)phenyl)-6-oxo-1,6-dihydropyridazine-4-carboxylic acid with lithium 4-amino-6-chloro-2-[4-(1,1-dimethylpropyl) phenyl]pyrimidine-5-carboxylate. $^1$H NMR (400 MHz, DMSO-$d_4$+$D_2O$) δ 8.11 (d, J=7.9 Hz, 2H), 7.51 (d, J=8.0 Hz, 2H), 7.19 (d, J=10.0 Hz, 1H), 6.99 (d, J=8.8 Hz, 1H), 6.70 (s, 2H), 6.28 (s, 1H), 6.20 (s, 1H), 5.00-4.88 (m, 1H), 4.73-4.55 (m, 2H), 4.11-3.90 (m, 6H), 3.37-3.23 (m, 2H), 3.16-2.90 (m, 4H), 2.91-2.75 (m, 4H), 2.67-2.62 (m, 1H), 2.42 (s, 3H), 2.36 (s, 12H), 1.63 (q, J=7.9 Hz, 2H), 1.25 (s, 6H), 1.16 (d, J=6.7 Hz, 3H), 0.60 (t, J=7.4 Hz, 3H). LCMS (Method 5-100 AB, 7 min): $R_T$=1.83 min, $[M+H]^+$=1022.7.

Example 46

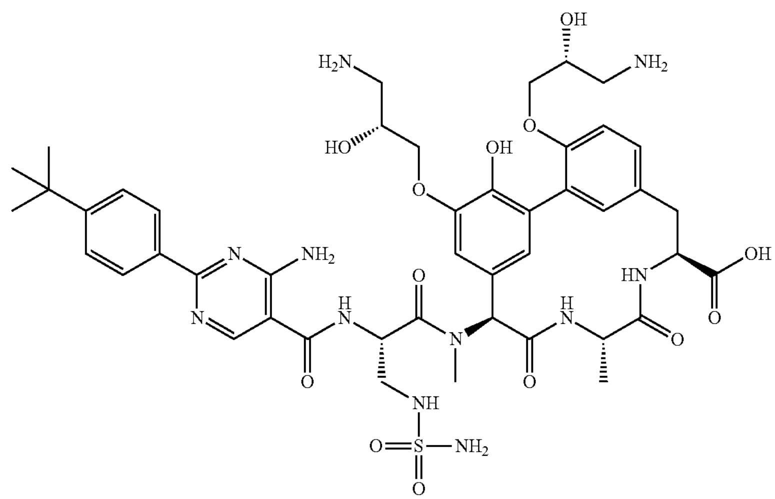 [SMILES: C[C@@H]1NC(=O)[C@@H](N(C)C(=O)[C@H](CNS(N)(=O)=O)NC(=O)c2cnc(-c3ccc(C(C)(C)C)cc3)nc2N)c2cc(OC[C@H](O)CN)c(O)c(c2)-c2cc(ccc2OC[C@H](O)CN)C[C@@H](C(=O)O)NC1=O]

The title compound was prepared as described in Example 1, replacing 1-(4-(tert-butyl)phenyl)-6-oxo-1,6-dihydropyridazine-4-carboxylic acid with 4-amino-2-(4-(tert-butyl)phenyl)pyrimidine-5-carboxylic acid. H NMR (400 MHz, MeOH-$d_4$) 8.81-8.72 (m, 1H), 8.47 (s, 1H), 8.17 (d, J=6.8 Hz, 2H), 7.47 (d, J=6.8 Hz, 2H), 7.06 (s, 1H), 6.78-6.67 (m, 2H), 6.48-6.40 (m, 2H), 4.77-3.48 (m, 12H), 3.13-2.69 (m, 6H), 1.49-1.22 (m, 12H). LCMS (Method 5-95 AB, ESI): $R_T$=0.778 min, $[M+H]^+$=994.4.

Example 47

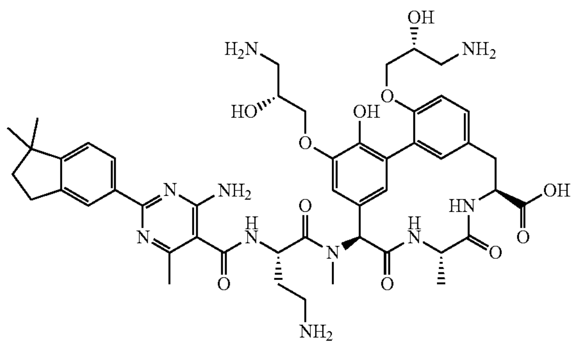 [SMILES: Cc1nc(-c2ccc3c(c2)CCC3(C)C)nc(N)c1C(=O)N[C@@H](CCN)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O]

The title compound was prepared from compound 20 using the procedure of Example 1, replacing 1-(4-(tert-butyl)phenyl)-6-oxo-1,6-dihydropyridazine-4-carboxylic acid with 4-amino-2-(1,1-dimethylindan-5-yl)-6-methyl-pyrimidine-5-carboxylic acid. H NMR (400 MHz, DMSO+D2O) δ 8.32 (s, 3H), 8.07-8.05 (m, 2H), 7.22 (d, J=8.8 Hz, 1H), 7.08 (d, J=9.6 Hz, 1H), 6.89 (d, J=8.5 Hz, 1H), 6.72 (s, 1H), 6.69 (s, 1H), 6.37 (s, 1H), 6.24 (s, 1H), 4.85-4.79 (m, 1H), 4.62-4.55 (m, 1H), 4.11-4.06 (m, 1H), 4.06-3.96 (m, 4H), 3.95-3.91 (m, 2H), 3.26-3.19 (m, 1H), 3.02-2.80 (m, 12H), 2.32 (s, 3H), 2.09-1.83 (m, 4H), 1.20 (s, 6H), 1.16 (d, J=7.0 Hz, 3H). LCMS (Method 5-100 AB, 7 min): $R_T$=1.59 min, $[M+H]^+$=962.5.

Example 48

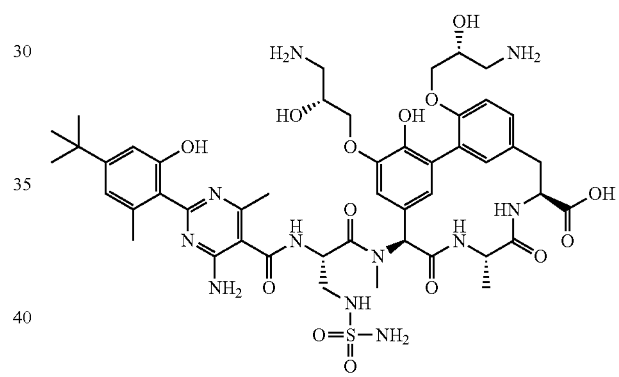

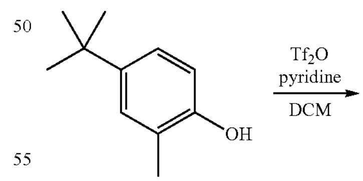

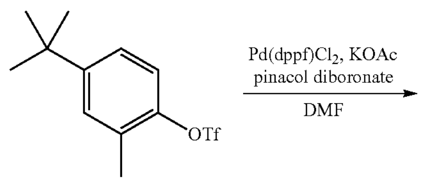

-continued

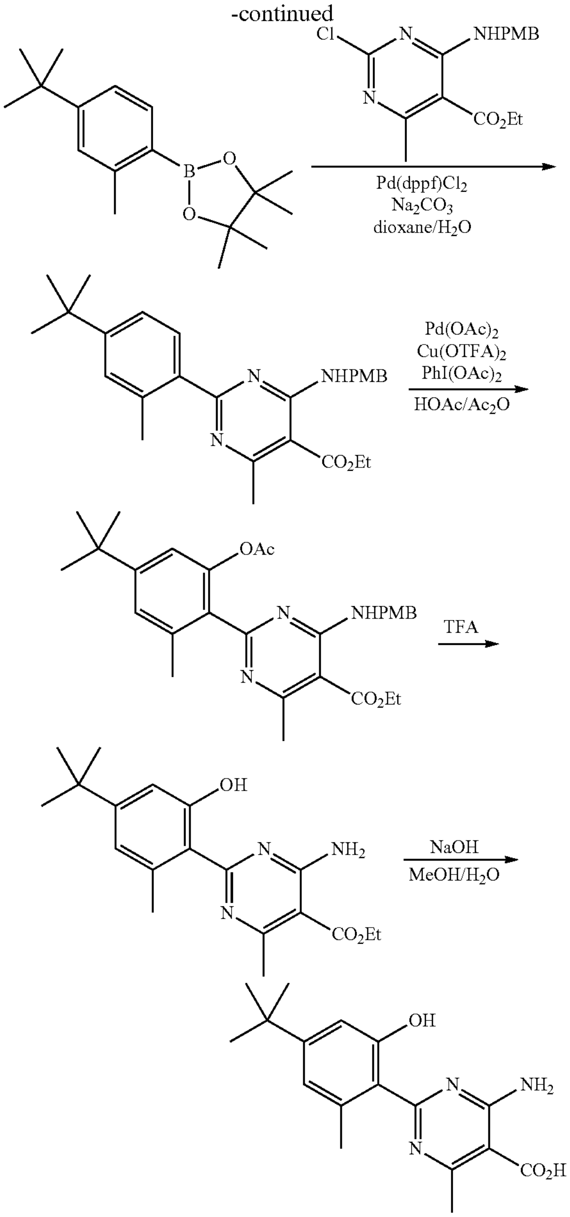

To a mixture of 4-(tert-butyl)-2-methylphenol (400 mg, 2.44 mmol) in dichloromethane (5.0 mL) was added pyridine (0.39 mL, 4.87 mmol) and $Tf_2O$ (0.61 mL, 3.65 mmol) at 0° C. The reaction mixture was stirred at 0° C. for 2 h. The reaction mixture was diluted with dichloromethane (30 mL). The organic layer was washed with 1M HCl (10 mL), saturated $NaHCO_3$ (20 mL), brine (2×50 mL). The organic layer was dried over $Na_2SO_4$ and concentrated to dryness. The residue was purified by column (silica gel, 100-200 mesh, 0-5% ethyl acetate in petroleum) to obtain 4-(tert-butyl)-2-methylphenyl trifluoromethanesulfonate (710 mg, 98.4% yield) as colorless oil.

A mixture of 4-(tert-butyl)-2-methylphenyl trifluoromethanesulfonate (710.0 mg, 2.4 mmol), potassium acetate (705 mg, 7.19 mmol), $Pd(dppf)Cl_2$ (178 mg, 0.24 mmol), and bis(pinacolato)diboron (791 mg, 3.11 mmol) in DMF (10.0 mL) was stirred under nitrogen at 80° C. for 16 h. The mixture was diluted with ethyl acetate (80 mL), which was filtered and the filtrate was washed with brine (3×80 mL). The organic layer was concentrated in vacuo. The residue was purified by column (silica gel, 100-200 mesh, 0-5% ethyl acetate in petroleum) to give 2-(4-(tert-butyl)-2-methylphenyl)-4,4,5,5-tetramethyl-1,3,2-dioxaborolane (530 mg, 80.7% yield) as a white solid.

A mixture of 2-(4-(tert-butyl)-2-methylphenyl)-4,4,5,5-tetramethyl-1,3,2-dioxaborolane (530 mg, 1.93 mmol), ethyl 2-chloro-4-((4-methoxybenzyl)amino)-6-methylpyrimidine-5-carboxylate (681 mg, 2.03 mmol), $Pd(dppf)Cl_2$ (70.7 mg, 0.10 mmol) and $Na_2CO_3$ (615 mg, 5.80 mmol) were suspended in 1,4-dioxane (6.0 mL) and water (0.60 mL), purged with $N_2$ (15 psi) and heated at 100° C. for 16 h. The reaction mixture was diluted with ethyl acetate (20 mL). The reaction mixture was washed with brine (2×20 mL), dried with $Na_2SO_4$ and concentrated. The residue was purified by column (silica gel, 100-200 mesh, 0-5% ethyl acetate in petroleum) to give ethyl 2-(4-(tert-butyl)-2-methylphenyl)-4-((4-methoxybenzyl)amino)-6-methylpyrimidine-5-carboxylate (500 mg, 57.8% yield) as a colorless oil.

Step 4: A solution of ethyl 2-(4-(tert-butyl)-2-methylphenyl)-4-((4-methoxybenzyl)amino)-6-methylpyrimidine-5-carboxylate (200 mg, 0.45 mmol), (diacetoxyiodo)benzene (216 mg, 0.67 mmol), $Cu(OTFA)_2$ (12.9 mg, 0.04 mmol) and $Pd(OAc)_2$ (5.02 mg, 0.02 mmol) in acetic acid (0.30 mL) and acetic anhydride (4.50 mL) was stirred at 80° C. under air for 24 h. The solvent was removed under vacuum. The residue was diluted with saturated $NaHCO_3$ solution (15.0 mL), extracted with ethyl acetate (3×30 mL). All the organic layers were combined and washed with brine, dried over $Na_2SO_4$ and concentrated in vacuo. The residue was purified using column chromatography (silica gel, 100-200 mesh, 0-20% ethyl acetate in petroleum) to give ethyl 2-(2-acetoxy-4-(tert-butyl)-6-methylphenyl)-4-((4-methoxybenzyl)amino)-6-methylpyrimidine-5-carboxylate (110 mg, 48.7% yield) as a light yellow oil.

Step 5: A solution of ethyl 2-(2-acetoxy-4-(tert-butyl)-6-methylphenyl)-4-((4-methoxybenzyl)amino)-6-methylpyrimidine-5-carboxylate (110 mg, 0.22 mmol) in trifluoroacetic acid (3.0 mL, 0.22 mmol) was a stirred at 75° C. for 16 h. The mixture was concentrated to dryness and purified by column (silica gel, 100-200 mesh, 0-20% ethyl acetate in petroleum ether) to give ethyl 4-amino-2-(4-(tert-butyl)-2-hydroxy-6-methylphenyl)-6-methylpyrimidine-5-carboxylate (74.0 mg, 99% yield) as a white solid.

Step 6: To a solution of ethyl 4-amino-2-(4-(tert-butyl)-2-hydroxy-6-methylphenyl)-6-methylpyrimidine-5-carboxylate (74.0 mg, 0.22 mmol) in methanol (5.00 mL) was added NaOH (34.5 mg, 0.86 mmol) in water (1.00 mL). The reaction was stirred at 80° C. for 1 h. The mixture was concentrated to dryness and diluted with water (30 mL). The mixture was adjusted to pH=5 with 1M HCl, and the aqueous layer was extracted with ethyl acetate (2×60 mL). The combined organic layers were dried over $Na_2SO_4$, concentrated in vacuo to give 4-amino-2-(4-(tert-butyl)-2-hydroxy-6-methylphenyl)-6-methylpyrimidine-5-carboxylic acid (65.0 mg, 95.7% yield) as a white solid.

The title compound was prepared as described in Example 1, replacing 1-(4-(tert-butyl)phenyl)-6-oxo-1,6-dihydropyridazine-4-carboxylic acid with 4-amino-2-(4-(tert-butyl)-2-hydroxy-6-methylphenyl)-6-methylpyrimidine-5-carboxylic acid. $^1H$ NMR (400 MHz, MeOH-$d_4$) 8.46 (s, 1H), 7.10-7.00 (m, 1H), 6.87-6.76 (m, 5H), 6.61 (s, 1H), 6.47 (s, 1H), 5.19-5.16 (m, 1H), 4.37-3.90 (m, 8H), 3.63-3.58 (m, 3H), 3.19-2.99 (m, 10H), 2.51 (s, 3H), 2.46 (s, 3H), 1.35 (d, J=6.8 Hz, 3H), 1.30 (s, 9H). LCMS (Method 5-95 AB, ESI): $R_T$=0.670 min, $[M+H]^+$=1009.6.

Example 49
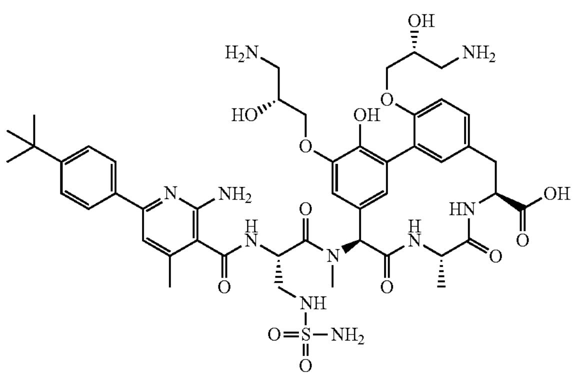 [SMILES: Cc1cc(-c2ccc(C(C)(C)C)cc2)nc(N)c1C(=O)N[C@@H](CNS(N)(=O)=O)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O]
The title compound was prepared as described in Example 1, replacing 1-(4-(tert-butyl)phenyl)-6-oxo-1,6-dihydropyridazine-4-carboxylic acid with 2-amino-6-(4-(tert-butyl)phenyl)-4-methylnicotinic acid. $^1$H NMR (400 MHz, DMSO+D2O) δ 8.93 (d, J=9.3 Hz, 1H), 8.37 (d, J=9.2 Hz, 1H), 7.81 (d, J=8.5 Hz, 2H), 7.60 (d, J=8.5 Hz, 2H), 7.24-7.15 (m, 2H), 7.02 (d, J=8.9 Hz, 1H), 6.76-6.65 (m, 2H), 6.31 (s, 1H), 6.23 (s, 1H), 5.02-4.92 (m, 1H), 4.77-4.60 (m, 2H), 4.14-3.86 (m, 6H), 3.42-3.23 (m, 2H), 3.18-2.76 (m, 9H), 2.37 (s, 12H), 1.31 (s, 9H), 1.17 (d, J=6.7 Hz, 3H). LCMS (Method 5-100 AB, 7 min): $R_T$=1.77 min, $[M+H]^+$=1007.5.
General Procedure C:
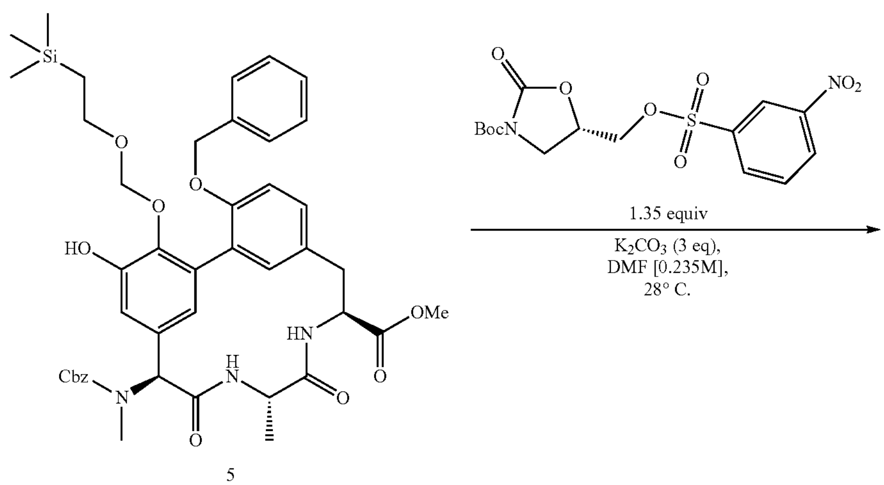
5
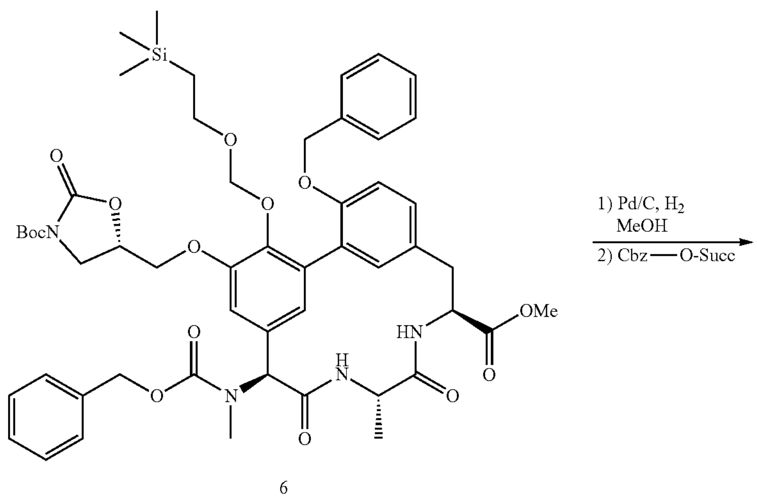
6

-continued
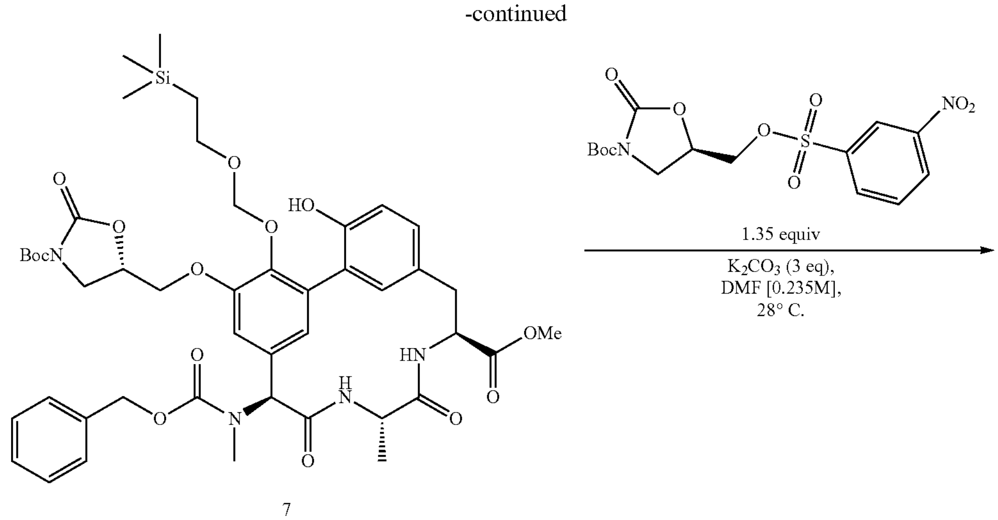
7
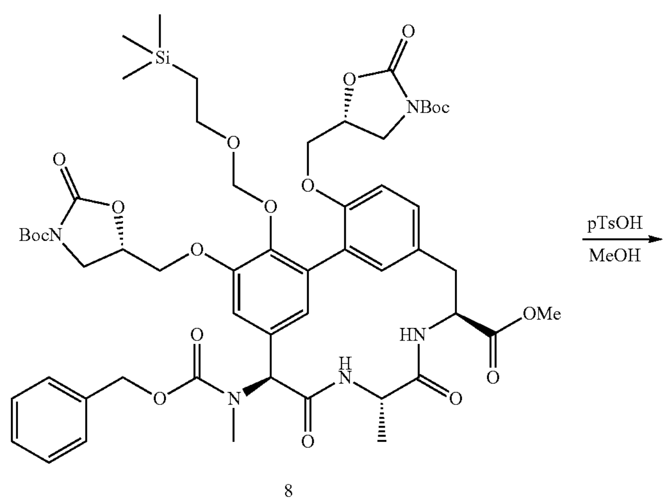
8
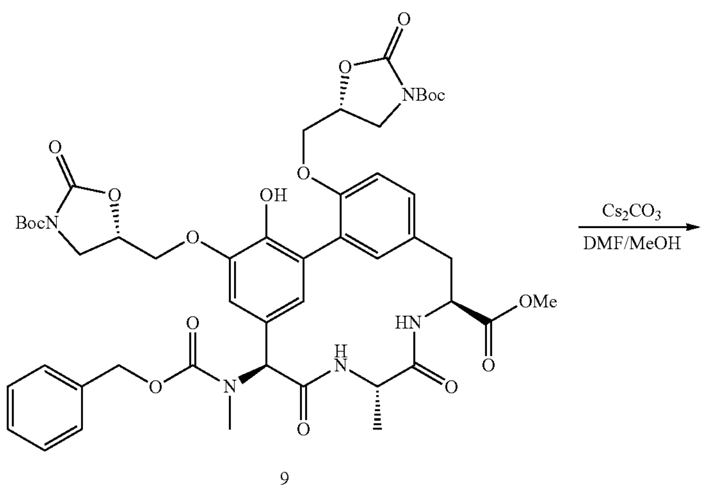
9

-continued

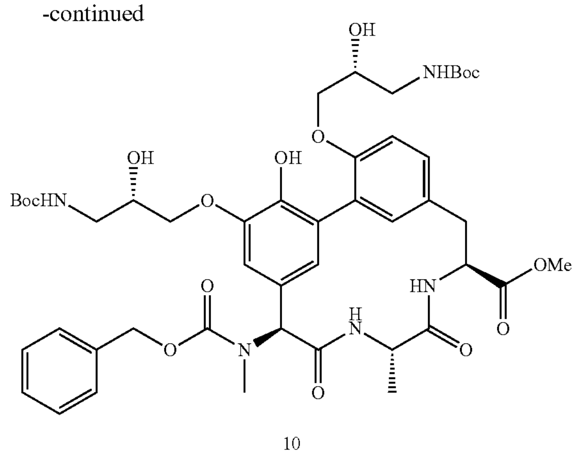

10

Step 1: To a solution of compound 5 (2.0 g, 2.5 mmol) (synthesized as in General Procedure A), in DMF (12 mL) was added tert-butyl (5S)-5-[(3-nitrophenyl)sulfonyloxymethyl]-2-oxo-oxazolidine-3-carboxylate (1.36 g, 3.38 mmol) (synthesized as in General Procedure D starting with (S)-3-amino-1,2-propanediol) and potassium carbonate (1.04 g, 7.52 mmol) at 25° C. under inert atmosphere. The reaction mixture was stirred for 16 h at 25° C. The reaction mixture was poured into water/sat. aqueous $NaHCO_3$ (1:1) dropwise under stirring. A beige solid precipitates and was recovered by filtration. The solid was purified by column chromatography (silica gel, 100-200 mesh, 25-100% EtOAc in (1:1) DCM/heptanes mixture) to yield compound 6 (1.99 g, 79.6% yield) as a white solid.

Step 2: Compound 6 (1.99 g, 2 mmol) was dissolved in methanol (12.7 mL) and the reaction flask was purged with nitrogen prior to the addition of the catalyst palladium on carbon 10% wt. (159 mg, 0.15 mmol). The reaction mixture was purged with hydrogen and was stirred under 1 atm hydrogen at 25° C. for 3 h. The reaction flask was purged with nitrogen bubbling into solution for 15 minutes prior to the addition of Cbz-O-succinimide (0.5 g, 2 mmol). The reaction was stirred at 25° C. for 16 h. The reaction mixture was filtered through Celite and concentrated under reduced pressure. The residue was diluted with ethyl acetate (100 mL), washed with water (2×100 mL) and brine (2×100 mL), dried over $Na_2SO_4$ and concentrated to dryness to give compound 7 (1.81 g, 99.8% yield) as an off white solid.

Step 4: To a solution of compound 8 (1.72 g, 1.55 mmol) in methanol (17 mL) was added p-toluenesulfonic acid (29 mg, 0.155 mmol). The reaction mixture was stirred at 25° C. for 16 h. The reaction mixture was poured into water/aqueous sat. $NaHCO_3$ (1:1) dropwise under stirring. A beige solid precipitates and was recovered by filtration. The solid was dissolved in DCM, dried with $Na_2SO_4$, filtered and concentrated under reduced pressure to yield crude compound 9 (1.52 g, 100% yield) as an off white solid.

Step 5: A solution of compound 9 (1.52 g, 1.55 mmol) in DMF (15 mL) and methanol (0.565 mL) under inert atmosphere ($N_2$) was cooled to −15° C. To the cold solution was added cesium carbonate (1.07 g, 3.28 mmol) and the reaction mixture was stirred at −20 to −15° C. over 6 h. The filtrate was concentrated to obtain crude compound 6 (35.0 g, 97.4% yield) as a white solid. The reaction mixture was diluted with EtOAc (20 mL) and water (20 mL) at −15° C. Phases were separated and the organic phase was washed with water (2×30 mL) and brine (2×30 mL) then dried over $Na_2SO_4$ and concentrated under reduced pressure. The solid was purified by column chromatography (silica gel, 100-200 mesh, 2-10% MeOH in DCM) to yield compound 10 (1.07 g, 75% yield) as a white solid.

General Procedure D:

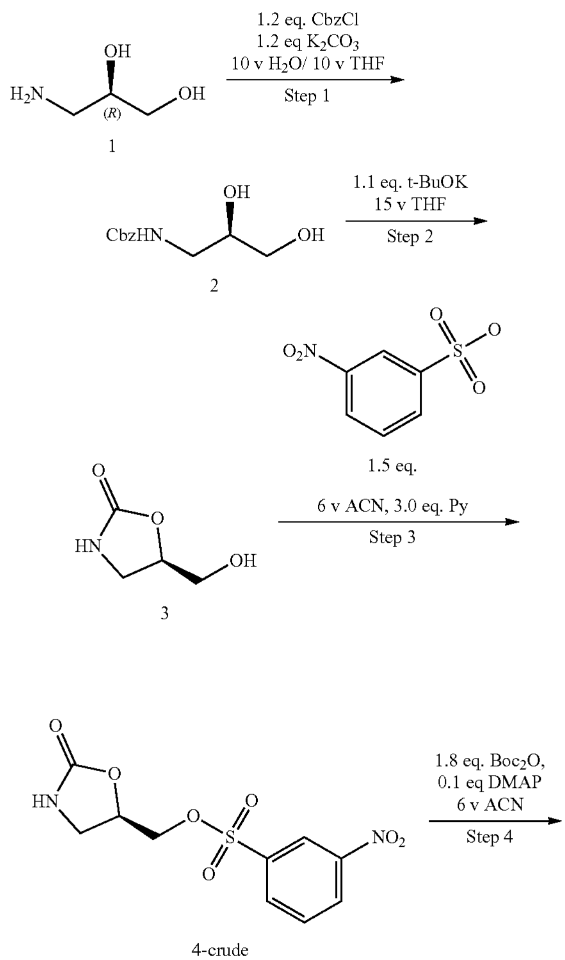

1

2

1.5 eq.

3

4-crude

-continued

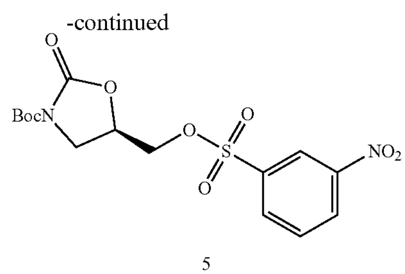

5

Step 1: A 5 L flask was charged with (R)-3-amino-1,2-propanediol (107 mL, 1.38 mol) and 10 volume of both THF (1260 mL) and water (1260 mL) were added. The reaction material was stirred at room temperature until complete dissolution (20 minutes). Then, the solution was cooled to 0° C. and potassium carbonate (229.4 g, 1.66 mol) was added. Finally, benzyl chloroformate (237 mL, 1.66 mol) was charged into an addition funnel and was added dropwise to the reaction mixture while keeping internal temperature under 8° C. (on a period of 60 minutes). After completion of the reaction (2 h), layers were separated. The organic layer was concentrated under reduced pressure (by half) while water phase was extracted 3 times with EtOAc (3×1260 mL). All organics were combined, washed with brine, dried with anhydrous sodium sulfate, filtered and concentrated to 2-3 volume. Heptanes (1260 mL) was added to the residue and it was stirred between 10-20° C. for 2-3 hours. The white solid formed was filtered and washed with heptanes. The solid was transferred to a flask and placed under high vacuum to dry and yielded compound 2 (325 g, 104% yield) as a white solid.

Compound 2 (175 g, 779 mmol) was charged in a 3 neck, 5 L round bottom flask equipped with a thermometer and was dissolved in THF (2631 mL). The solution was cooled to 0° C. and potassium tert-butoxide (96.13 g, 857 mmol) was added portion wise while keeping temperature between 0-10° C. Once addition of the reagent was completed, the reaction mixture was allowed to warm to 25° C. and was stirred for 3 h. Upon completion, the reaction mixture was cooled again using ice bath to maintain internal temperature around 10° C. while 4M HCl in dioxane was added to the reaction mixture until pH reach 5-6. The reaction mixture was then stirred at 25° C. for 30 minutes. The precipitate was filtered and washed with MeCN (700 mL) twice. The wet cake was charged in a 2 L erlenmeyer and stirred with 1.5 L of MeCN for 30 minutes. The solid was again filtered and washed with MeCN (700 mL) twice. All organics were combined and concentrated under reduced pressure into 2-3 V below 45° C. To the resulting suspension was added MTBE (1.5 L) and the suspension was concentrated again under reduced pressure until 2-3 V below 45° C. 1-1.5 L of MTBE was added to the suspension and it was stirred at room temperature for 30 minutes. The solid was then collected by filtration and washed with MTBE (1 L). The solid was dried under vacuum to yield compound 3 (85.5 g, 93.8% yield) as an off white solid.

Compound 3 (75 g, 640 mmol) was charged in a 2 L round bottom flask and 6V of MeCN (450 mL) was added followed by pyridine (155 mL, 1.92 mol). The resulting solution was cooled to 0° C. Then, 3-nitrobenzenesulfonyl chloride (149 g, 673 mmol) was added portion wise while maintaining the temperature under 10° C. The reaction mixture was stirred at 0° C. for 2 h. Upon completion, the reaction mixture was concentrated under reduced pressure to 2-3 V. MTBE (10 V, 750 mL) was then added to the flask and the resulting mixture was concentrated under reduced pressure to 2-3 V. 1.5 L of sat. $NaHCO_3$ solution (20 V) was added. The mixture was vigorously stirred at 10-20° C. for 30 minutes. The resulting mixture was filtered and washed with water twice (1000 mL×2). The wet cake was collected and charge back into a round bottom flask. 1.5 L of sat. $NaHCO_3$ solution (20 V) was added. The mixture was vigorously stirred at 10-20° C. for 30 minutes. The resulting mixture was filtered and washed with water twice (1000 mL×2). The wet cake was collected and charge back into a round bottom flask. Water (10 V, 750 mL) and MTBE (5 V, 375 mL) were added and the resulting biphasic suspension was vigorously stirred for 30 minutes. The solids were filtered, washed twice with MTBE (400 mL×2). The cake was dried under high vacuum to yield compound 4 (178 g, 92% yield) as an off white solid.

Compound 4 (182.7 g, 604 mmol) was added in 5 L round bottom flask with 4-dimethylaminopyridine (7.38 g, 60.4 mmol) and MeCN (1.1 L) was added. The reaction mixture was cooled to 0° C. and di-tert-butyl dicarbonate (237.5 g, 1.1 mol) was added keeping reaction temperature under 0° C. The reaction mixture was stirred at 0° C. for 1 h. Upon completion, the reaction mixture was concentrated under reduced pressure. MeOH (500 mL) was added to the mixture and it was concentrated under reduced pressure to a thick orange gum. 700 mL of MeOH was added to the mixture. The reaction flask was placed under sonication for 3 minutes. A white precipitate formed and it was stirred at room temperature for 30 minutes. The solid was recovered by filtration and washed with cold MeOH to afford compound 5 (191.4 g, 78.7% yield) as a white solid. 98.95% ee. 1H NMR (400 MHz, $CDCl_3$) δ 8.77 (t, J=1.9 Hz, 1H), 8.56 (ddd, J=8.3, 2.2, 1.0 Hz, 1H), 8.25 (ddd, J=7.9, 1.7, 1.1 Hz, 1H), 7.85 (t, J=8.0 Hz, 1H), 4.75-4.67 (m, 1H), 4.36 (dd, J=11.5, 3.5 Hz, 1H), 4.30 (dd, J=11.5, 4.2 Hz, 1H), 4.05 (dd, J=10.6, 9.2 Hz, 1H), 3.82 (dd, J=10.6, 6.2 Hz, 1H), 1.53 (s, 9H).

Example 50

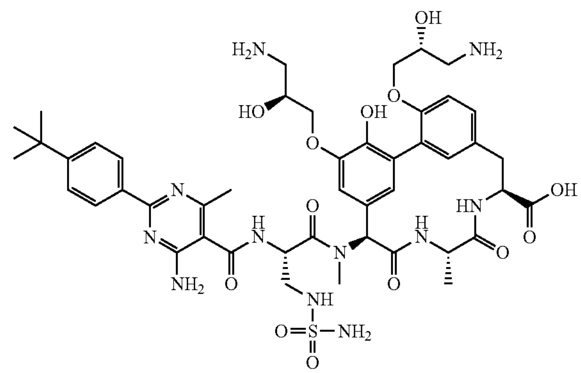 [SMILES: Cc1nc(-c2ccc(C(C)(C)C)cc2)nc(N)c1C(=O)N[C@@H](CNS(N)(=O)=O)C(=O)N(C)[C@@H]1C(=O)N[C@@H](C)C(=O)N[C@H](C(=O)O)Cc2ccc(OC[C@H](O)CN)c(c2)-c2cc1cc(OC[C@@H](O)CN)c2O]

The title compound was prepared as described in Example 1, replacing 1-(4-(tert-butyl)phenyl)-6-oxo-1,6-dihydropyridazine-4-carboxylic acid with 4-amino-2-(4-(tert-butyl)phenyl)-6-methylpyrimidine-5-carboxylic acid and compound 14 by compound 10 described in procedure C. $^1H$ NMR (400 MHz, DMSO-$d_6$+$D_2O$) δ (ppm) δ 9.28 (d, J=3.9 Hz, 1H), 8.91 (d, J=6.7 Hz, 1H), 8.31 (d, J=5.0 Hz, 1H), 8.06 (d, J=7.9 Hz, 2H), 7.63 (d, J=8.2 Hz, 2H), 7.19 (d, J=7.8 Hz, 1H), 7.00 (d, J=8.7 Hz, 1H), 6.69 (d, J=6.2 Hz, 2H), 6.28 (s, 1H), 6.17 (s, 1H), 5.06-4.93 (m, 1H), 4.73-4.59 (m, 2H), 4.17-3.94 (m, 8H), 3.41-3.33 (m, 1H), 3.32-3.22 (m, 1H), 3.17-3.06 (m, 1H), 3.05-2.95 (m, 2H), 2.92-2.76 (m, 1H), 2.85 (s, 3H), 2.42 (s, 3H), 2.39 (s, 9H), 1.29 (s, 9H), 1.16 (d, J=6.4 Hz, 3H). LCMS (Method 5-100 AB, 7 min): $R_T$=1.62 min, $[M+H]^+$=1008.5.

Example 51

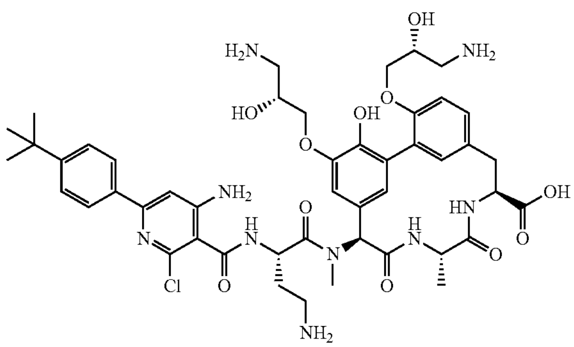

The title compound was prepared from compound 20 using the procedure of Example 1, replacing 1-(4-(tert-butyl)phenyl)-6-oxo-1,6-dihydropyridazine-4-carboxylic acid with 4-amino-6-(4-tert-butylphenyl)-2-chloro-pyridine-3-carboxylic acid, prepared as described in Example 37. $^1$H NMR (400 MHz, DMSO-$d_6$+$D_2O$) δ 8.34 (s, 3H), 7.80 (d, J=8.5 Hz, 2H), 7.48 (d, J=8.6 Hz, 2H), 7.09 (s, 1H), 7.06 (d, J=8.8 Hz, 1H), 6.87 (d, J=8.6 Hz, 1H), 6.74 (s, 1H), 6.67 (s, 1H), 6.37 (s, 1H), 6.24 (s, 1H), 4.86-4.80 (m, 1H), 4.65-4.55 (m, 1H), 4.13-3.94 (m, 7H), 3.26-3.21 (m, 1H), 3.09-2.76 (m, 10H), 2.03-1.92 (m, 2H), 1.28 (s, 9H), 1.15 (d, J=6.7 Hz, 3H). LCMS (Method 5-100 AB, 7 min): $R_T$=1.59 min, $[M+H]^+$=962.5.

Example 52

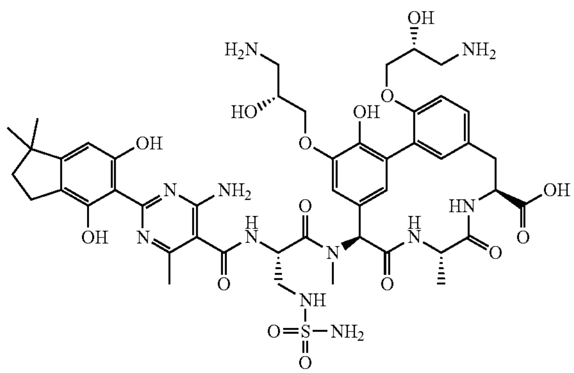 [SMILES: Cc1nc(-c2c(O)cc3c(c2O)CCC3(C)C)nc(N)c1C(=O)N[C@@H](CNS(N)(=O)=O)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O]

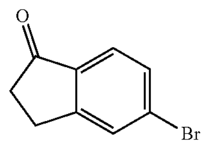

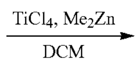

-continued

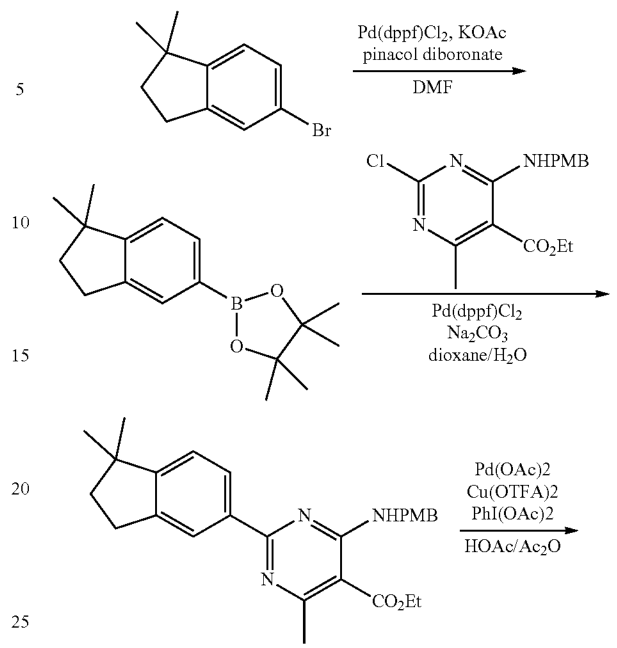

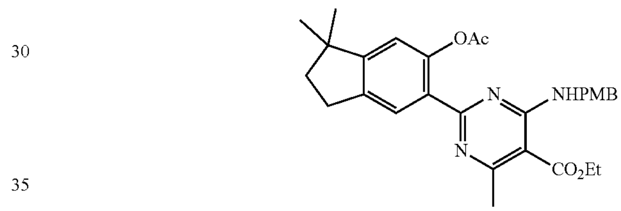

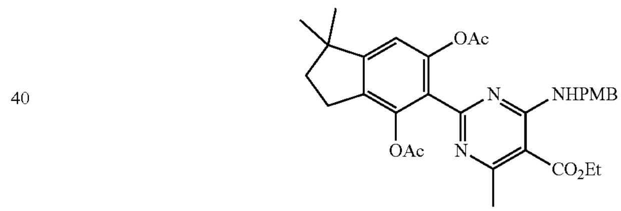

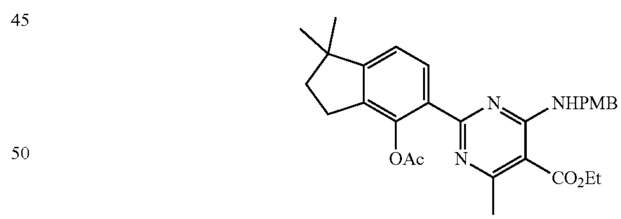

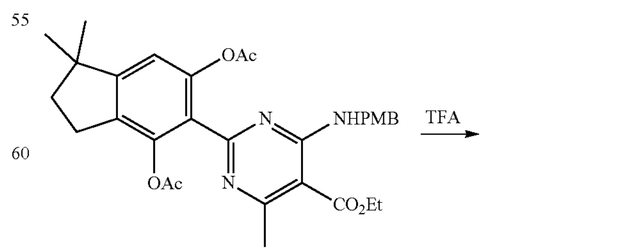

-continued

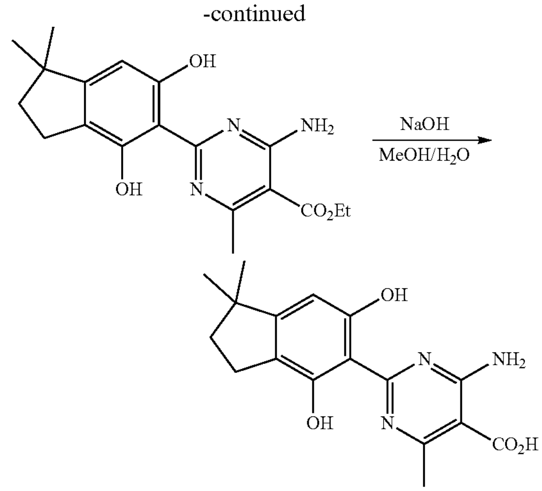

Step 1: $TiCl_4$ (14.3 mL, 127 mmol) was added to DCM (45.0 mL) in a three-necked RB flask, and maintained the temperature at −78° C. under an atmosphere of nitrogen. Then followed by addition of 1M $Zn(CH_3)_2$ in toluene (127 mL, 127 mmol) while maintaining the temperature. The orange-brown solution obtained was stirred vigorously at −78° C. for one hour. A solution of 5-bromo-2,3-dihydro-1H-inden-1-one (4.50 g, 21.3 mmol) in DCM (45.0 mL) was added dropwise to the above mixture. The reaction solution was allowed to stir for 2 h at −78° C. then warmed to −10° C. and stirred for 16 h. The reaction mixture was quenched by addition of ice-cold saturated $NH_4Cl$ solution dropwise. The organics were separated and the aqueous layer was extracted with ethyl acetate (3×100 mL) and the organic layers were washed with brine (3×100 mL). The organics were combined and dried over $Na_2SO_4$ before concentration to dryness. The crude was then purified by flash column chromatography (silica gel, 100-200 mesh, 0-5% ethyl acetate in petroleum) to give 5-bromo-1,1-dimethyl-2,3-dihydro-1H-indene (4.80 g, 99.8% yield) as yellow oil.

Step 2: A mixture of 5-bromo-1,1-dimethyl-2,3-dihydro-1H-indene (5.7 g, 25.3 mmol), $Pd(dppf)Cl_2$ (926 mg, 1.27 mmol), KOAc (7.45 g, 75.9 mmol) and pinacol diboronate (9.64 g, 37.9 mmol) in DMF (57.0 mL) was stirred under N2 at 80° C. for 3 h. The solvent was removed and the residue was purified by flash column chromatography (silica gel, 100-200 mesh, 0-5% ethyl acetate in petroleum) to give 2-(1,1-dimethyl-2,3-dihydro-1H-inden-5-yl)-4,4,5,5-tetramethyl-1,3,2-dioxaborolane (6.5 g, 94.3% yield) as a white solid.

Step 3: A mixture of 2-(1,1-dimethyl-2,3-dihydro-1H-inden-5-yl)-4,4,5,5-tetramethyl-1,3,2-dioxaborolane (1.95 g, 7.15 mmol), ethyl 2-chloro-4-((4-methoxybenzyl)amino)-6-methylpyrimidine-5-carboxylate ethyl 2-chloro-4-((4-methoxybenzyl)amino)-6-methylpyrimidine-5-carboxylate (2.00 g, 5.96 mmol), $Pd(dppf)Cl_2$ (0.22 g, 0.30 mmol) and $Na_2CO_3$ (1.89 g, 17.8 mmol) in a mixture solvent of water (2.00 mL) and 1,4-dioxane (40.0 mL) was purged with $N_2$ (15 psi) and heated at 100° C. for 16 h. After filtration, 50.0 mL ethyl acetate was added to the mixture. The mixture was washed with brine (2×50.0 mL). The organic was combined and dried with $Na_2SO_4$ and concentrated to dryness. The crude was purified by column (silica gel, 100-200 mesh, 0-5% ethyl acetate in petroleum) to give ethyl 2-(6-acetoxy-1,1-dimethyl-2,3-dihydro-1H-inden-5-yl)-4-((4-methoxybenzyl)amino)-6-methylpyrimidine-5-carboxylate (2.50 g, 94.2% yield) as a colorless oil.

Step 4: A solution of ethyl 2-(6-acetoxy-1,1-dimethyl-2,3-dihydro-1H-inden-5-yl)-4-((4-methoxybenzyl)amino)-6-methylpyrimidine-5-carboxylate (1.00 g, 2.24 mmol), PhI $(OAc)_2$ (1.08 g, 3.37 mmol), $Cu(OTFA)_2$ (64.9 mg, 0.22 mmol) and $Pd(OAc)_2$ (25.1 mg, 0.11 mmol) in HOAc (1.00 mL) and $Ac_2O$ (15 mL) was stirred at 80° C. under air for 16 h. The solvent was removed under vacuum. The residue was diluted with saturated $NaHCO_3$ solution (30.0 mL), extracted with ethyl acetate (3×100 mL), washed with brine (100 mL), dried over $Na_2SO_4$, and concentrated in vacuum. The given crude product was purified using column chromatography (silica gel, 100-200 mesh, 0-5% ethyl acetate in petroleum) to give 5-(5-(ethoxycarbonyl)-4-((4-methoxybenzyl)amino)-6-methylpyrimidin-2-yl)-1,1-dimethyl-2,3-dihydro-1H-indene-4,6-diyl diacetate (300 mg, 0.5957 mmol, 26.5% yield), ethyl 2-(6-acetoxy-1,1-dimethyl-2,3-dihydro-1H-inden-5-yl)-4-((4-methoxybenzyl)amino)-6-methylpyrimidine-5-carboxylate (300 mg, 0.5957 mmol, 26.5% yield), ethyl 2-(4-acetoxy-1,1-dimethyl-2,3-dihydro-1H-inden-5-yl)-4-((4-methoxybenzyl)amino)-6-methylpyrimidine-5-carboxylate (330 mg) as a light yellow oil.

Step 5: A solution of 5-(5-(ethoxycarbonyl)-4-((4-methoxybenzyl)amino)-6-methylpyrimidin-2-yl)-1,1-dimethyl-2,3-dihydro-1H-indene-4,6-diyl diacetate (330 mg, 0.590 mmol) in TFA (5.00 mL) was stirred at 75° C. for 16 h. The mixture was concentrated. Ethyl acetate (40 mL) was added. The organic layer was washed with $NaHCO_3$ (aq., 30.0 mL), brine (30.0 mL), dried over $Na_2SO_4$ and concentrated. The crude material was purified by column on silica gel (16% ethyl acetate in petroleum ether) to obtain ethyl 4-amino-2-(4,6-dihydroxy-1,1-dimethyl-2,3-dihydro-1H-inden-5-yl)-6-methylpyrimidine-5-carboxylate (160 mg, 76.2% yield) as a yellow solid.

Step 6: To a solution of ethyl 4-amino-2-(4,6-dihydroxy-1,1-dimethyl-2,3-dihydro-1H-inden-5-yl)-6-methylpyrimidine-5-carboxylate (160 mg, 0.450 mmol) in MeOH (5.00 mL) and water (1.00 mL) was added NaOH (71.6 mg, 1.79 mmol). The reaction was stirred at 80° C. for 3 h. The mixture was adjust to pH=2 with 1 M HCl (aq.). The mixture was partitioned between ethyl acetate (50.0 mL) and water (30.0 mL). The organic layer was washed with brine (40.0 mL), dried over $Na_2SO_4$ and filtered. The filtrate was concentrated to obtain 4-amino-2-(4,6-dihydroxy-1,1-dimethyl-2,3-dihydro-1H-inden-5-yl)-6-methylpyrimidine-5-carboxylic acid (100 mg, 67.8% yield) as a yellow solid.

The title compound was prepared as described in Example 1, replacing 1-(4-(tert-butyl)phenyl)-6-oxo-1,6-dihydropyridazine-4-carboxylic acid with 4-amino-2-(4,6-dihydroxy-1,1-dimethyl-2,3-dihydro-1H-inden-5-yl)-6-methylpyrimidine-5-carboxylic acid. $^1H$ NMR (400 MHz, MeOH-$d_4$) δ (ppm) 8.42 (br s, 1H), 7.25-6.95 (m, 1H), 6.91-6.45 (m, 5H), 6.21 (s, 1H), 5.26-5.08 (m, 1H), 4.64-3.88 (m, 8H), 3.68-3.34 (m, 2H), 3.26-2.93 (m, 9H), 2.79-2.70 (m, 2H), 2.43 (s, 3H), 1.95-1.83 (m, 2H), 1.36 (d, J=6.4 Hz, 3H), 1.23 (s, 6H). LCMS (Method 5-95AB, ESI): $R_T$=0.799 min, $[M+H]^+$=1052.5.

Example 53

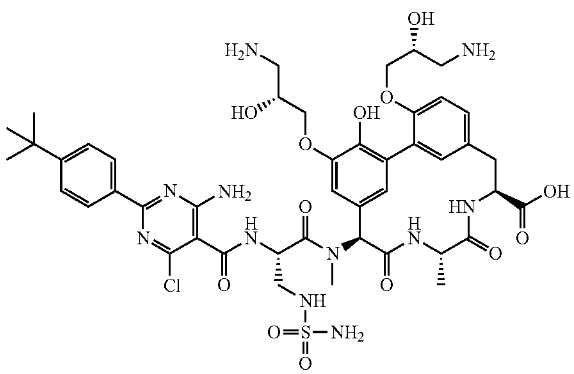 [SMILES: C[C@@H]1NC(=O)[C@@H](N(C)C(=O)[C@H](CNS(N)(=O)=O)NC(=O)c2c(N)nc(-c3ccc(C(C)(C)C)cc3)nc2Cl)c2cc(OC[C@H](O)CN)c(O)c(c2)-c2cc(ccc2OC[C@H](O)CN)C[C@@H](C(=O)O)NC1=O]

Step 1: Sodium methoxide (25 wt. % in methanol, 16.4 mL, 71.5 mmol) was added to a solution of 4-tert-butylbenzamide (4.20 g, 23.8 mmol) in methanol (11.9 mL). The reaction mixture was stirred at room temperature for 10 min then diethyl malonate (3.62 mL, 23.8 mmol) was added. The reaction mixture was stirred at room temperature for 16 h then concentrated under reduced pressure. $H_2O$ was added followed by concentrated HCl to get acidic pH. The resulting mixture was extracted with EtOAc (3×). The organic layers were combined, washed with water, brine, dried over $Na_2SO_4$, filtered and concentrated under reduced pressure to yield 2-(4-tert-butylphenyl)pyrimidine-4,6-diol (4.08 g, 70.1% yield) as an off-white solid. Crude material was used in the next step without any further purification.

Step 2: DMF (1.33 mL, 17.2 mmol) was added to $POCl_3$ (21.5 mL, 230 mmol) at 0° C. The reaction mixture was stirred at 0° C. for 1 h. This solution was then added to 2-(4-tert-butylphenyl)pyrimidine-4,6-diol (4.01 g, 16.4 mmol) and the reaction mixture was stirred at room temperature for 30 min then at 100° C. for 16 h. The mixture was then cooled to room temperature and poured onto ice/water. The resulting mixture was extracted with EtOAc (3×). The organic layers were combined, washed with brine, dried over $Na_2SO_4$, filtered and concentrated under reduced pressure. The residue was purified by column chromatography (silica gel, 100-200 mesh, 0-10% EtOAc in heptanes) to yield 2-(4-tert-butylphenyl)-4,6-dichloro-pyrimidine-5-carbaldehyde (2.94 g, 57.9% yield) as an off-white solid.

Step 3: A solution of sodium chlorite (1.20 g, 13.3 mmol) in water (4.2 mL) was added to a solution of 2-(4-tert-butylphenyl)-4,6-dichloro-pyrimidine-5-carbaldehyde (2.94 g, 9.51 mmol) and sulfamic acid (1.29 g, 13.3 mmol) in tert-butanol (21 mL) and water (8.4 mL). The reaction mixture was stirred at room temperature for 5 h then additional portions of sulfamic acid (260 mg, 2.68 mmol) and sodium chlorite (240 mg, 2.65 mmol) were added. The reaction mixture was stirred at room temperature for an additional 2 h. Water was added and the mixture was extracted with EtOAc (3×). The organic layers were combined, washed with brine, dried over $Na_2SO_4$, filtered and concentrated under reduced pressure to yield 2-(4-tert-butylphenyl)-4,6-dichloro-pyrimidine-5-carboxylic acid (3.09 g, 99.9% yield) as an off-white solid. The crude material was used in the next step without any further purification.

Step 4: Potassium carbonate (3.28 g, 23.8 mmol) was added to a solution of 2-(4-tert-butylphenyl)-4,6-dichloro-pyrimidine-5-carboxylic acid (3.09 g, 9.50 mmol) in DMF (47.5 mL). The reaction mixture was stirred at room temperature for 15 min then iodoethane (1.91 mL, 23.8 mmol) was added. The reaction mixture was stirred at room temperature for 16 h then diluted with EtOAc. The resulting mixture was washed with water (2×), and with brine, dried over $Na_2SO_4$, filtered and concentrated under reduced pressure. The crude material was purified by column chromatography (silica gel, 100-200 mesh, 0-10% EtOAc in heptanes) to yield ethyl 2-(4-tert-butylphenyl)-4,6-dichloro-pyrimidine-5-carboxylate (2.95 g, 87.9% yield) as an off-white solid.

Step 5: A solution of ethyl 2-(4-tert-butylphenyl)-4,6-dichloro-pyrimidine-5-carboxylate (800 mg, 2.26 mmol) and 2M ammonia in iPrOH (24.0 mL, 48.0 mmol) was stirred at room temperature for 16 h. $H_2O$ was then added and the mixture was extracted with EtOAc (3×). The organic layers were combined, washed with brine, dried over $Na_2SO_4$, filtered and concentrated under reduced pressure to yield ethyl 4-amino-2-(4-tert-butylphenyl)-6-chloro-pyrimidine-5-carboxylate (765 mg, quantitative) as colorless oil. The crude material was used in the next step without any further purification.

Step 6: 1N aqueous lithium hydroxide (2.40 mL, 2.40 mmol) was added to a solution of ethyl 4-amino-2-(4-tert-butylphenyl)-6-chloro-pyrimidine-5-carboxylate (200 mg, 0.599 mmol) in THF (6.0 mL). The reaction mixture was stirred at 50° C. for 16 h then cooled to room temperature. 1N aqueous HCl was added and the resulting mixture was extracted with a 4:1 solution of $CHCl_3$/iPrOH (3×). The organic layers were combined, dried over $Na_2SO_4$, filtered and concentrated under reduced pressure to yield 4-amino-2-(4-tert-butylphenyl)-6-chloro-pyrimidine-5-carboxylic acid (190 mg, quantitative) as an off-white solid.

The title compound was prepared as described in Example 1, replacing 1-(4-(tert-butyl)phenyl)-6-oxo-1,6-dihydropyridazine-4-carboxylic acid with 4-amino-2-(4-tert-butylphenyl)-6-chloro-pyrimidine-5-carboxylic acid. $^1H$ NMR (400 MHz, DMSO+D2O) δ 8.34 (s, 1H), 8.16 (d, J=8.5 Hz, 2H), 7.52 (d, J=8.6 Hz, 2H), 7.07 (d, J=8.9 Hz, 1H), 6.89 (d, J=8.4 Hz, 1H), 6.72 (s, 1H), 6.70 (s, 1H), 6.35 (s, 1H), 6.25 (s, 1H), 4.94-4.88 (m, 1H), 4.66-4.56 (m, 1H), 4.19-4.11 (m, 1H), 4.08-3.99 (m, 3H), 3.99-3.93 (m, 3H), 3.40-3.29 (m, 1H), 3.25-3.10 (m, 2H), 3.07-2.98 (m, 2H), 2.97-2.79 (m, 6H), 1.28 (s, 9H), 1.17 (d, J=6.8 Hz, 3H). LCMS (Method 5-100 AB, 7 min): $R_T$=1.88 min, $[M+H]^+$=1028.2.

Example 54

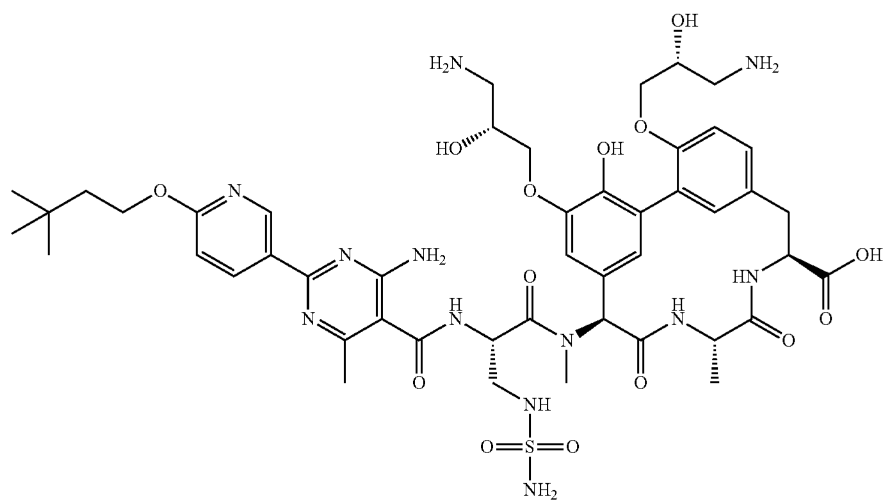 [SMILES: Cc1nc(-c2ccc(OCCC(C)(C)C)nc2)nc(N)c1C(=O)N[C@@H](CNS(N)(=O)=O)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O]

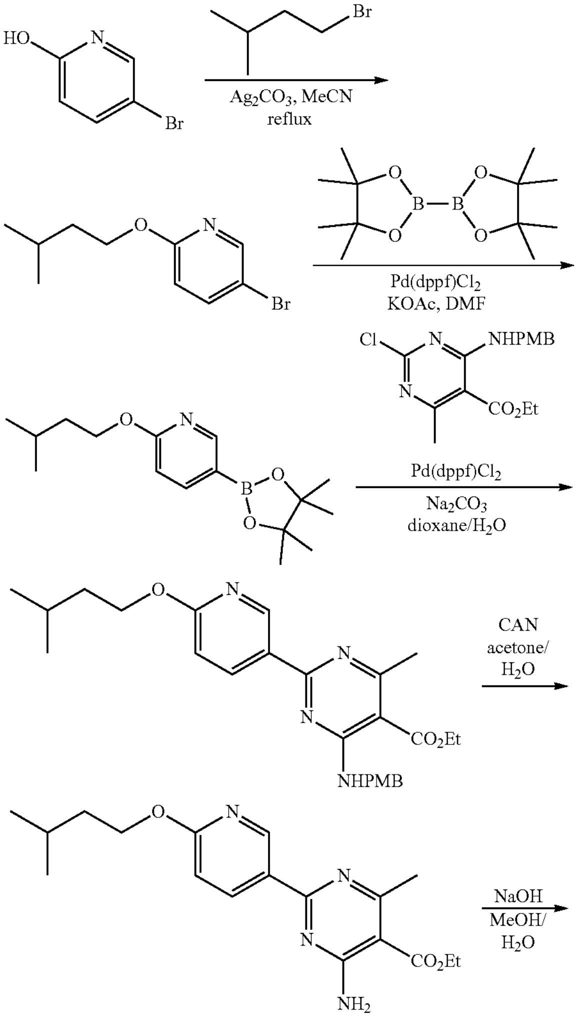

-continued

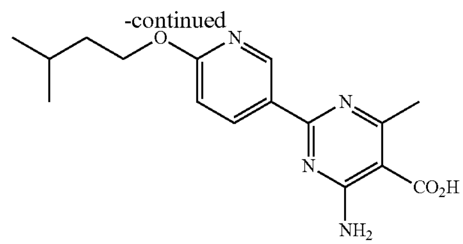

Step 1: To a solution of 5-bromopyridin-2-ol (2.00 g, 11.49 mmol) in DMF (10.0 mL) was added 1-bromo-3,3-dimethylbutane (2.85 g, 17.2 mmol) and $Ag_2CO_3$ (9.51 g, 34.5 mmol). The reaction mixture was stirred at 110° C. for 2 h. The reaction mixture was diluted with ethyl acetate (40 mL). After filtration, the filtrate was washed with brine (3×40 mL), and dried over $Na_2SO_4$. After filtration, the filtrate was concentrated to dryness. The residue was purified by column (silica gel, 100-200 mesh, 0-10% ethyl acetate in petroleum) to obtain 5-bromo-2-(3,3-dimethylbutoxy)pyridine (1.00 g, 33.7% yield) as yellow oil.

Step 2: A mixture of 5-bromo-2-(3,3-dimethylbutoxy) pyridine (1.20 g, 4.65 mmol), KOAc (1.37 g, 14.0 mmol), $Pd(dppf)Cl_2$ (345 mg, 0.46 mmol), bis(pinacolato)diboron (1.77 g, 6.97 mmol) in DMF (10.0 mL) was stirred under nitrogen at 80° C. for 16 h. The reaction mixture was diluted with ethyl acetate (20 mL), then filtered and the filtrate was washed with brine (3×20 mL). The organic layer was concentrated in vacuo to dryness. The residue was purified by column chromatography (silica gel, 100-200 mesh, 50-100% ethyl acetate in petroleum) to give 2-(3,3-dimethylbutoxy)-5-(4,4,5,5-tetramethyl-1,3,2-dioxaborolan-2-yl) pyridine (480 mg, 33.8% yield) as a yellow oil.

Step 3: A mixture of 2-(3,3-dimethylbutoxy)-5-(4,4,5,5-tetramethyl-1,3,2-dioxaborolan-2-yl)pyridine (300 mg, 0.98 mmol), ethyl 2-chloro-4-((4-methoxybenzyl)amino)-6-methylpyrimidine-5-carboxylate (347 mg, 1.03 mmol), $Pd(dppf)Cl_2$ (36.0 mg, 0.05 mmol) and $Na_2CO_3$ (312 mg, 2.95 mmol) in a mixture of 1,4-dioxane (6.0 mL) and water (0.60 mL) was purged with $N_2$ (15 psi) and heated at 100° C. for 16 h. After filtration, 20 mL ethyl acetate was added to the mixture. The mixture was washed with brine (2×20 mL). The organic layer was dried with $Na_2SO_4$ and concentrated to dryness. The crude material was purified by column (silica gel, 100-200 mesh, 0-5% ethyl acetate in petroleum) to give ethyl 2-(6-(3,3-dimethylbutoxy)pyridin-3-yl)-4-((4-methoxybenzyl)amino)-6-methylpyrimidine-5-carboxylate (370 mg, 78.7% yield) as a yellow solid.

Step 4: To a solution of ethyl 2-(6-(3,3-dimethylbutoxy)pyridin-3-yl)-4-((4-methoxybenzyl)amino)-6-methylpyrimidine-5-carboxylate (175.0 mg, 0.37 mmol) in acetonitrile (4.00 mL) and water (2.00 mL) was added ceric ammonium nitrate (802 mg, 1.46 mmol). The reaction was stirred at 20° C. for 30 min. The reaction mixture was partitioned between ethyl acetate (20 mL) and water (20 mL). The organic layer was washed with brine (2×20 mL), dried with $Na_2SO_4$ and concentrated to dryness. The crude was purified by preparative TLC (ethyl acetate:petroleum ether=1:10, Rf=0.3) to give ethyl 4-amino-2-(6-(3,3-dimethylbutoxy)pyridin-3-yl)-6-methylpyrimidine-5-carboxylate (100 mg, 76.3% yield) as a yellow solid.

Step 5: To a solution of ethyl 4-amino-2-(6-(3,3-dimethylbutoxy)pyridin-3-yl)-6-methylpyrimidine-5-carboxylate (100 mg, 0.28 mmol) in methanol (5.00 mL) and water (1.00 mL) was added NaOH (44.6 mg, 1.12 mmol). The reaction mixture was stirred at 80° C. for 1 h. The mixture was concentrated to dryness. The mixture was adjust to pH 2 with HCl (1 M). The aqueous layer was extracted with ethyl acetate (2×60 mL) and the combined organic layers were concentrated to obtain 4-amino-2-(6-(3,3-dimethylbutoxy)pyridin-3-yl)-6-methylpyrimidine-5-carboxylic acid (80 mg, 86.8% yield) as a white solid.

The title compound was prepared as described in Example 1, replacing 1-(4-(tert-butyl)phenyl)-6-oxo-1,6-dihydropyridazine-4-carboxylic acid with 4-amino-2-(6-(3,3-dimethylbutoxy)pyridin-3-yl)-6-methylpyrimidine-5-carboxylic acid. $^1H$ NMR (400 MHz, MeOH-$d_4$) 9.04 (s, 1H), 8.51-8.42 (m, 2H), 7.12-6.99 (m, 1H), 6.89-6.69 (m, 3H), 6.55 (s, 1H), 5.27-5.10 (m, 1H), 4.83-4.73 (m, 2H), 4.53-4.29 (m, 3H), 4.18-4.07 (m, 3H), 4.05-3.92 (m, 1H), 3.67-3.52 (m, 1H), 3.44-3.37 (m, 1H), 3.36-3.33 (m, 1H), 3.29-3.19 (m, 2H), 3.18-3.09 (m, 2H), 3.07 (s, 3H), 3.00-2.91 (m, 1H), 2.45 (s, 3H), 1.79-1.67 (m, 2H), 1.41-1.28 (m, 2H), 1.00 (s, 9H). LCMS (Method 10-80 AB, ESI): $R_T$=1.868 min, $[M+H]^+$=1054.6.

Example 55

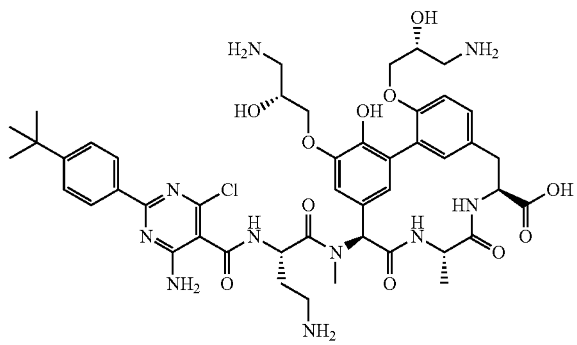 [SMILES: C[C@@H]1NC(=O)[C@@H](N(C)C(=O)[C@H](CCN)NC(=O)c2c(N)nc(-c3ccc(C(C)(C)C)cc3)nc2Cl)c2cc(OC[C@H](O)CN)c(O)c(c2)-c2cc(ccc2OC[C@H](O)CN)C[C@@H](C(=O)O)NC1=O]

The title compound was prepared using the procedure of Example 1, replacing compound 14 with compound 20 and replacing 1-(4-(tert-butyl)phenyl)-6-oxo-1,6-dihydropyridazine-4-carboxylic acid with 4-amino-2-(4-tert-butylphenyl)-6-chloro-pyrimidine-5-carboxylic acid described in Example 53. $^1H$ NMR (400 MHz, DMSO+D2O) δ 8.87 (d, J=8.0 Hz, 1H), 8.30 (d, J=7.7 Hz, 1H), 8.15 (d, J=8.1 Hz, 2H), 7.52 (d, J=8.2 Hz, 2H), 7.19 (d, J=8.5 Hz, 1H), 7.00 (d, J=8.6 Hz, 1H), 6.71 (s, 2H), 6.30 (s, 1H), 6.25 (s, 1H), 4.86-4.80 (m, 1H), 4.73-4.58 (m, 2H), 4.20-3.96 (m, 5H), 3.85-3.64 (m, 3H), 3.35-3.23 (m, 1H), 3.15-2.77 (m, 11H), 2.74-2.55 (m, 1H), 2.46-2.36 (m, 2H), 2.40 (s, 12H), 2.38-2.20 (m, 1H), 2.13-1.86 (m, 2H), 1.28 (s, 9H), 1.18 (d, J=7.1 Hz, 3H) LCMS (Method 5-100 AB, 7 min): $R_T$=1.63 min, $[M+H]^+$=963.6

Example 56

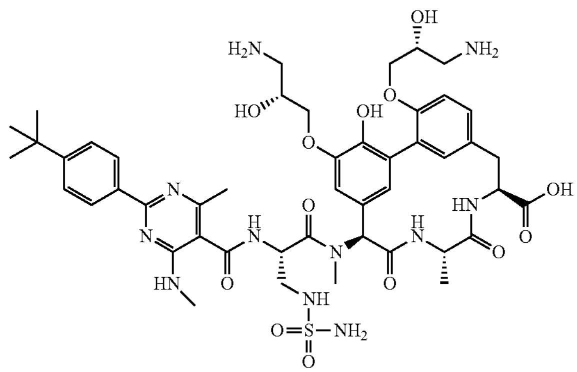 [SMILES: CNc1nc(-c2ccc(C(C)(C)C)cc2)nc(C)c1C(=O)N[C@@H](CNS(N)(=O)=O)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O]

Ethyl 2-(4-(tert-butyl)phenyl)-4-chloro-6-methylpyrimidine-5-carboxylate (150 mg, 0.45 mmol), TEA (188 uL, 1.35 mmol) and methylamine (33.4 mg, 0.50 mmol) in ethanol (5.00 mL) were stirred at 60° C. for 1 h. The reaction mixture was diluted with ethyl acetate (40 mL). The organic layer was washed with brine (2×30 mL), dried over $Na_2SO_4$ and concentrated to dryness. The residue was purified by prep-TLC (10% ethyl acetate in petroleum ether, $R_f$=0.4) to obtain ethyl 4-amino-2-(4-(tert-butyl)-2-methylphenyl)-6-methylpyrimidine-5-carboxylate (125 mg, 85.0% yield) as a white solid.

Step 5: Ethyl 4-amino-2-(4-(tert-butyl)-2-methylphenyl)-6-methylpyrimidine-5-carboxylate (120 mg, 0.37 mmol) was dissolved in MeOH (10.0 mL) and water (2.0 mL). NaOH (58.6 mg, 1.47 mmol) was added, and the mixture was stirred at 80° C. for 2 h. The reaction mixture was concentrated and the pH adjusted to pH=3 with 1M HCl. The reaction mixture was partitioned between ethyl acetate (50.0 mL) and water (50.0 mL). Then the aqueous layer was extracted with ethyl acetate (50.0 mL*2). The combined organic layers were dried over $Na_2SO_4$ and concentrated to give with 2-(4-(tert-butyl)phenyl)-4-methyl-6-(methylamino)pyrimidine-5-carboxylic acid (100 mg, 91% yield) as a white solid.

The title compound was prepared as described in Example 1, replacing 1-(4-(tert-butyl)phenyl)-6-oxo-1,6-dihydropyridazine-4-carboxylic acid with 2-(4-(tert-butyl)phenyl)-4-methyl-6-(methylamino)pyrimidine-5-carboxylic acid. $^1H$ NMR (400 MHz, MeOH-$d_4$) 8.38 (s, 1H), 8.24 (d, J=7.6 Hz, 2H), 7.50 (d, J=8.4 Hz, 2H), 7.10-7.04 (m, 1H), 6.50-6.77 (m, 2H), 6.59 (s, 1H), 6.48 (s, 1H), 5.20-5.16 (m, 1H), 4.37-3.97 (m, 8H), 3.61-3.58 (m, 1H), 3.38-3.35 (m, 1H), 3.19-2.98 (m, 12H), 2.44 (s, 3H), 1.36-1.34 (m, 12H). LCMS (Method 5-95 AB, ESI): $R_T$=0.794 min, $[M+H]^+$=1022.5.

Example 57

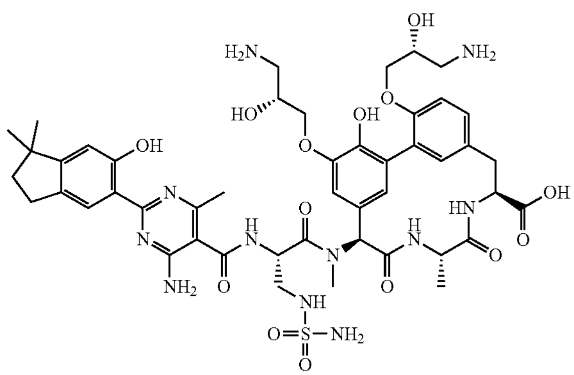 [SMILES: Cc1nc(-c2cc3c(cc2O)C(C)(C)CC3)nc(N)c1C(=O)N[C@@H](CNS(N)(=O)=O)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O]

The title compound was prepared as described in Example 1, replacing 1-(4-(tert-butyl)phenyl)-6-oxo-1,6-dihydropyridazine-4-carboxylic acid with 4-amino-2-(6-hydroxy-1,1-dimethyl-2,3-dihydro-1H-inden-5-yl)-6-methylpyrimidine-5-carboxylic acid, which was prepared using the procedures described in Example 52. $^{1}H$ NMR (400 MHz, MeOH-$d_4$) δ (ppm) 8.47 (br s, 1H), 8.11 (s, 1H), 7.02 (br s, 1H), 6.88-6.70 (m, 3H), 6.65 (s, 1H), 6.59 (br s, 1H), 6.52 (br s, 1H), 5.18 (br d, J=8 Hz 1H), 4.44-3.95 (m, 8H), 3.6 (br d, J=10.4 Hz, 1H), 3.43-3.32 (m, 1H), 3.26-2.96 (m, 9H), 2.86-2.79 (m, 2H), 2.44 (s, 3H), 1.96-1.88 (m, 2H), 1.35 (br d, J=6.4 Hz, 3H), 1.25 (br s, 6H). LCMS (Method 5-95 AB, ESI): $R_T$=0.783 min, $[M+H]^+$=1036.5.

Example 58

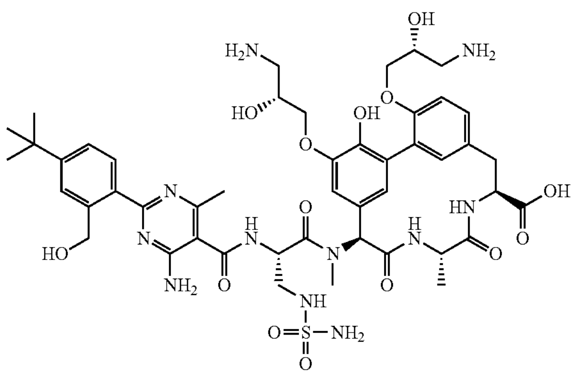 [SMILES: Cc1nc(-c2ccc(C(C)(C)C)cc2CO)nc(N)c1C(=O)N[C@@H](CNS(N)(=O)=O)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O]

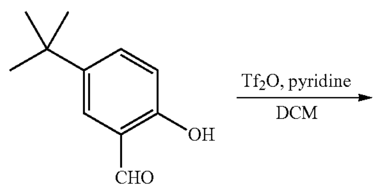

-continued

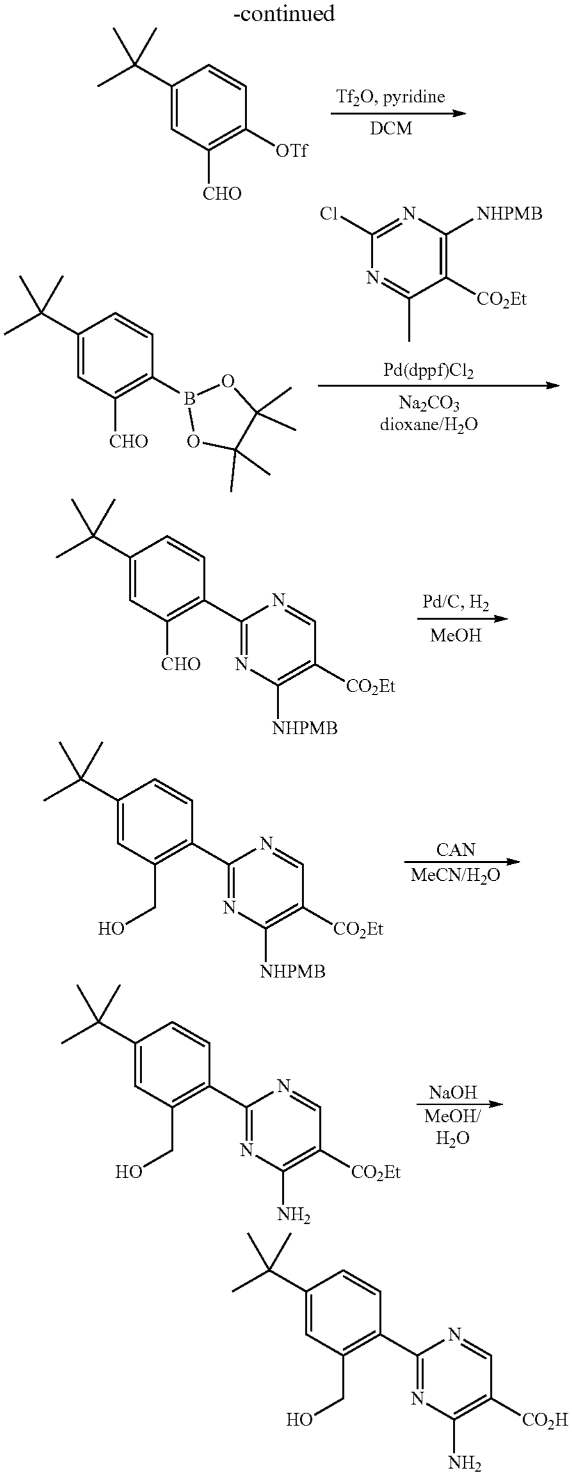

Step 1: To a mixture of 5-(tert-butyl)-2-hydroxybenzaldehyde (4.30 g, 24.1 mmol) in DCM (60 mL) at 0° C. was added pyridine (3.89 mL, 48.3 mmol) and triflic anhydride (6.09 mL, 36.2 mmol). The reaction mixture was stirred at 0° C. for 2 h. The reaction mixture was dilute with ethyl acetate (100 mL). The organic layer was washed successively with 1M HCl (50 mL), saturated $NaHCO_3$ (50 mL) and brine (50 mL). The organic layer was dried over $Na_2SO_4$ and concentrated to dryness. The residue was purified by column chromatography (silica gel, 100-200 mesh, 0-20% ethyl acetate in petroleum) to obtain 4-(tert-butyl)-2-formylphenyl trifluoromethanesulfonate (4.50 g, 60.1% yield) as yellow oil.

Step 2: A mixture of 4-(tert-butyl)-2-formylphenyl trifluoromethanesulfonate (3.90 g, 12.6 mmol), bis(pinacolato) diboron (4.78 g, 18.85 mmol), potassium acetate (3.75 g, 37.7 mmol), $Pd(PPh_3)Cl_2$ (882 mg, 1.26 mmol) in DMF (40.0 mL) was stirred for 16 h under $N_2$ (15 psi) at 80° C. The mixture was filtered and diluted with ethyl acetate (80 mL). The organic layers was washed with brine (2×100 mL), dried over $Na_2SO_4$ and concentrated to dryness. The residue was purified using column chromatography (silica gel, 100-200 mesh, 0-5% ethyl acetate in petroleum) to obtain the crude product. The crude product was purified by prep-HPLC (using a gradient of acetonitrile and water (containing 0.225% formic acid)) to give 5-(tert-butyl)-2-(4,4,5,5-tetramethyl-1,3,2-dioxaborolan-2-yl)benzaldehyde (1.30 g, 35.9% yield) as a yellow solid.

Step 3: A mixture of 5-(tert-butyl)-2-(4,4,5,5-tetramethyl-1,3,2-dioxaborolan-2-yl)benzaldehyde (300 mg, 1.04 mmol), ethyl 2-chloro-4-((4-methoxybenzyl)amino)-6-methylpyrimidine-5-carboxylate (402 mg, 1.2 mmol), $Pd(dppf)Cl_2$ (76.2 mg, 0.10 mmol) and $Na_2CO_3$ (331 mg, 3.12 mmol) in a mixed solvent of 1,4-dioxane (10.0 mL) and water (1.0 mL) was purged with $N_2$ (15.0 psi) and heated at 100° C. for 16 h. After filtration, 20 mL ethyl acetate was added to the reaction mixture. The mixture was washed with brine (2×30 mL), dried over $Na_2SO_4$ and concentrated to dryness. The crude was purified by column chromatography (silica gel, 100-200 mesh, 0-5% ethyl acetate in petroleum) to give ethyl 2-(4-(tert-butyl)-2-formylphenyl)-4-((4-methoxybenzyl)amino)-6-methylpyrimidine-5-carboxylate (220 mg, 45.8% yield) as a white solid.

Step 4: To a solution of ethyl 2-(4-(tert-butyl)-2-formylphenyl)-4-((4-methoxybenzyl)amino)-6-methylpyrimidine-5-carboxylate (220 mg, 0.48 mmol) in methanol (10.0 mL), 10% Pd/C (101 mg, 0.10 mmol) was added. The mixture was stirred under hydrogen (50 psi) at 40° C. for 6 h. The mixture was filtered and the filtrate was concentrated to give ethyl 2-(4-(tert-butyl)-2-(hydroxymethyl)phenyl)-4-((4-methoxybenzyl)amino)-6-methylpyrimidine-5-carboxylate (180 mg, 81.5% yield) as a white solid.

Step 5: To a solution of ethyl 2-(4-(tert-butyl)-2-(hydroxymethyl)phenyl)-4-((4-methoxybenzyl)amino)-6-methylpyrimidine-5-carboxylate (180 mg, 0.39 mmol) in acetonitrile (8.0 mL) and water (4.0 mL) was added ceric ammonium nitrate (851 mg, 1.55 mmol). The reaction was stirred at 20° C. for 30 min. The reaction mixture was partitioned between ethyl acetate (40 mL) and water (40 mL). The organic phase was washed with brine (2×40 mL), dried with $Na_2SO_4$ and concentrated to dryness. The crude was purified by preparative TLC (ethyl acetate:petroleum ether=1:10, TLC: 15% EtOAc in petroleum, $R_f$=0.3) to give ethyl 4-amino-2-(4-(tert-butyl)-2-(hydroxymethyl)phenyl)-6-methylpyrimidine-5-carboxylate (100 mg, 75% yield) as a yellow solid.

Step 6: To a solution of ethyl 4-amino-2-(4-(tert-butyl)-2-(hydroxymethyl)phenyl)-6-methylpyrimidine-5-carboxylate (100 mg, 0.29 mmol) in methanol (10.0 mL) and water (3.0 mL) was added NaOH (46.59 mg, 1.16 mmol). The reaction was stirred at 80° C. for 1 h. The mixture was concentrated to remove methanol. Water (20 mL) was added to the mixture, and the mixture was adjusted to pH=2 with 1M HCl. The aqueous layer was extracted with ethyl acetate (2×20 mL). The combined organic layers were concentrated to obtain 4-amino-2-(4-(tert-butyl)-2-(hydroxymethyl)phenyl)-6-methylpyrimidine-5-carboxylic acid (80.0 mg, 87.1% yield) as a white solid.

Step 7: The title compound was prepared as described in Example 1, replacing 1-(4-(tert-butyl)phenyl)-6-oxo-1,6-dihydropyridazine-4-carboxylic acid with 4-amino-2-(4-(tert-butyl)-2-(hydroxymethyl)phenyl)-6-methylpyrimidine-5-carboxylic acid. $^1H$ NMR (400 MHz, MeOH-$d_4$) 8.42 (s, 2H), 7.90 (d, J=8.4 Hz, 2H), 7.55-7.48 (m, 1H), 7.46 (br, 1H), 7.09-7.82 (m, 3H), 6.63 (s, 1H), 6.50 (s, 1H), 5.22-5.19 (m, 1H), 4.96-4.26 (m, 1H), 4.25 (br, 1H), 4.24-4.15 (m, 4H), 3.22-3.05 (m, 4H), 2.45-2.44 (m, 3H), 1.39 (s, 12H). LCMS (Method 5-95 AB, ESI): $R_T$=0.713 min, $[M+H]^+$=1038.5.

Example 59

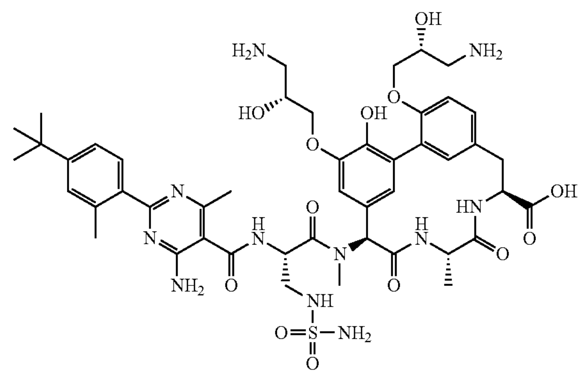 [SMILES: Cc1cc(C(C)(C)C)ccc1-c1nc(C)c(C(=O)N[C@@H](CNS(N)(=O)=O)C(=O)N(C)[C@@H]2C(=O)N[C@@H](C)C(=O)N[C@H](C(=O)O)Cc3ccc(OC[C@H](O)CN)c(c3)-c3cc2cc(OC[C@H](O)CN)c3O)c(N)n1]

The title compound was prepared as described in Example 1, replacing 1-(4-(tert-butyl)phenyl)-6-oxo-1,6-dihydropyridazine-4-carboxylic acid with 4-amino-2-(4-(tert-butyl)-2-methylphenyl)-6-methylpyrimidine-5-carboxylic acid. $^1H$ NMR (400 MHz, MeOH-$d_4$) 8.41 (s, 1H), 7.49-7.39 (m, 1H), 7.36-7.26 (m, 2H), 7.18-7.01 (m, 1H), 6.94-6.73 (m, 3H), 6.67-6.57 (m, 1H), 6.49-6.28 (m, 1H), 5.23-5.10 (m, 1H), 4.74-4.50 (m, 2H), 4.45-3.91 (m, 6H), 3.66-3.31 (m, 3H), 3.26-2.70 (m, 8H), 2.52-2.29 (m, 6H), 1.42-1.25 (m, 12H). LCMS (Method 5-95 AB, ESI): $R_T$=0.627 min, $[M+H]^+$=1022.8.

Example 60

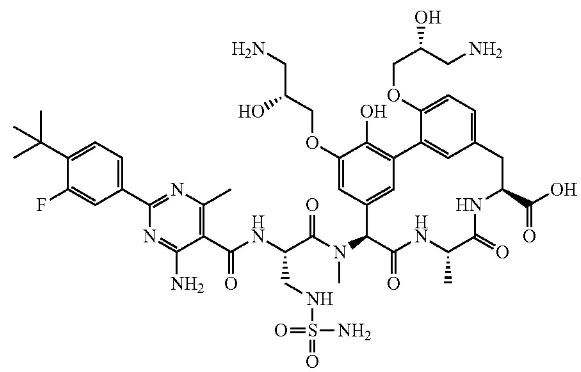 [SMILES: Cc1nc(-c2ccc(C(C)(C)C)c(F)c2)nc(N)c1C(=O)N[C@@H](CNS(N)(=O)=O)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O]

The title compound was prepared as described in Example 1, replacing 1-(4-(tert-butyl)phenyl)-6-oxo-1,6-dihydropyridazine-4-carboxylic acid with 4-amino-2-(4-(tert-butyl)-3-fluorophenyl)-6-methylpyrimidine-5-carboxylic acid. $^1$H NMR (400 MHz, MeOH-$d_4$) δ (ppm) 8.42 (br s, 1H), 7.46-7.36 (m, 1H), 7.18-7.00 (m, 1H), 6.95-6.72 (m, 3H), 6.59 (s, 1H), 6.46 (s, 1H), 5.23-5.08 (m, 1H), 4.80-4.77 (m, 2H), 4.50-3.94 (m, 6H), 3.68-3.33 (m, 3H), 3.29-2.95 (m, 8H), 2.47 (s, 3H), 1.45-1.31 (m, 12H). LCMS (Method 5-95 AB, ESI): $R_T$=0.774 min, $[M+H]^+$=1026.6.

Example 61

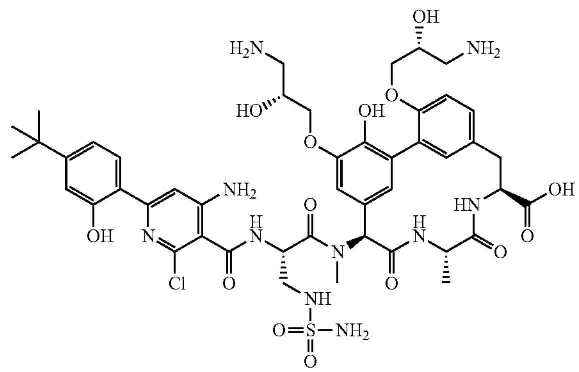 [SMILES: C[C@@H]1NC(=O)[C@@H](N(C)C(=O)[C@H](CNS(N)(=O)=O)NC(=O)c2c(N)cc(-c3ccc(C(C)(C)C)cc3O)nc2Cl)c2cc(OC[C@H](O)CN)c(O)c(c2)-c2cc(ccc2OC[C@H](O)CN)C[C@@H](C(=O)O)NC1=O]

Step 1: To a flame-dried, nitrogen-flushed flask was added DIPEA (16.4 mL, 94.17 mmol, 2.0 equiv) followed by chloromethyl methyl ether (MOMCl) (5.4 mL, 70.6 mmol, 1.5 equiv) to a solution of 5-tert-butyl-2-iodo-phenol (13.0 g, 47.08 mmol, 1.0 equiv) in DCM (157 mL) at room temperature. The reaction mixture was stirred at room temperature for 16 hours. A saturated aqueous $NaHCO_3$ solution was added to the reaction mixture (40 mL) at 0° C. The mixture was then extracted with DCM (3×40 mL). The organic layers were combined, dried over $Na_2SO_4$, filtered over a sintered funnel and filtrate was concentrated under reduced pressure. The crude material was purified by filtration of over a pad of silica gel (800 g) with elution of 20% EtOAc in heptanes to yield 4-tert-butyl-1-iodo-2-(methoxymethoxy)benzene (13.8 g, 43.1 mmol, 91.5% yield) as a yellow oil.

To a flame-dried, nitrogen-flushed flask was added 4-tert-butyl-1-iodo-2-(methoxymethoxy)benzene (13.0 g, 40.6 mmol, 1.0 equiv) and 2-isopropoxy-4,4,5,5-tetramethyl-1,3,2-dioxaborolane (28.9 mL, 142.11 mmol, 3.5 equiv) and anhydrous THF (203 mL). The solution was cooled to −78° C. and a 2.5 M solution of n-BuLi in heptanes (48.7 mL, 121.8 mmol, 3.0 equiv) was added dropwise and the reaction was stirred for 3 hours. $NaHCO_3$ sat. aq. was added at −78° C., warming flask to rt, and dilution with EtOAc (300 mL). The phases were separated and the aqueous layer was extracted with more EtOAc (2×100 mL). The organic layers were then washed with brine (2×200 mL), dried over $Na_2SO_4$, filtered and concentrated under reduced pressure. The crude material was purified by flash chromatography (silica gel, 100-200 mesh, 0-30% EtOAc in heptanes) to yield 2-[4-tert-butyl-2-(methoxymethoxy)phenyl]-4,4,5,5-tetramethyl-1,3,2-dioxaborolane (3542 mg, 11.061 mmol, 27% yield) as a white solid.

The title compound was prepared as described in Example 17, replacing 1-(4-(tert-butyl)phenyl)-6-oxo-1,6-dihydropyridazine-4-carboxylic acid with 4-amino-6-((4-tert-butyl)-2-hydroxyphenyl)-2-chloro-pyridine-3-carboxylic acid prepared as in Example 37 replacing 4-tert-butylbenzeneboronic acid with 2-[4-tert-butyl-2-(methoxymethoxy)phenyl]-4,4,5,5-tetramethyl-1,3,2-dioxaborolane. $^1$H NMR (400 MHz, DMSO-$d_4$+$D_2O$) δ 8 8.32 (s, 2H), 7.65 (d, J=8.7 Hz, 1H), 7.21 (s, 1H), 7.07 (d, J=8.0 Hz, 1H), 6.95 (dd, J=8.4, 1.9 Hz, 1H), 6.89 (d, J=8.3 Hz, 1H), 6.85 (d, J=1.9 Hz, 1H), 6.73 (s, 1H), 6.70 (s, 1H), 6.36 (s, 1H), 6.25 (s, 1H), 4.92-4.88 (m, 1H), 4.64-4.53 (m, 1H), 4.11 (dd, J=5.6, 4.7 Hz, 1H), 4.05-3.91 (m, 6H), 3.37-3.30 (m, 1H), 3.26-3.18 (m, 1H), 3.19-3.09 (m, 1H), 3.02-2.88 (m, 6H), 2.86-2.75 (m, 2H), 1.24 (s, 9H), 1.16 (d, J=6.8 Hz, 3H). LCMS (Method 5-100 AB, 7 min): $R_T$=2.03 min, $[M+H]^+$=1043.5.

Example 62

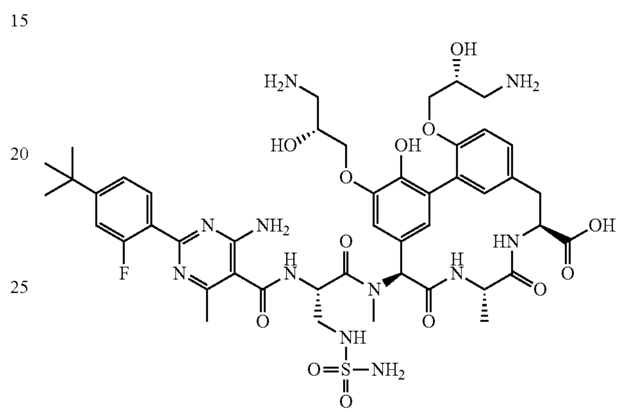

4-amino-2-(4-(tert-butyl)-2-fluorophenyl)-6-methylpyrimidine-5-carboxylic acid was prepared as described in Example 54, replacing 2-(3,3-dimethylbutoxy)-5-(4,4,5,5-tetramethyl-1,3,2-dioxaborolan-2-yl)pyridine with 2-(4-(tert-butyl)-2-fluorophenyl)-4,4,5,5-tetramethyl-1,3,2-dioxaborolane. The title compound was prepared as described in Example 1, replacing 1-(4-(tert-butyl)phenyl)-6-oxo-1,6-dihydropyridazine-4-carboxylic acid with 4-amino-2-(4-(tert-butyl)-2-fluorophenyl)-6-methylpyrimidine-5-carboxylic acid. $^1$H NMR (400 MHz, MeOH-$d_4$) δ (ppm) 7.75-7.69 (m, 1H), 7.34-7.26 (m, 1H), 7.25-7.17 (m, 1H), 7.12-7.01 (m, 1H), 6.96-6.73 (m, 3H), 6.63-6.54 (m, 1H), 6.44 (s, 1H), 5.21-5.10 (m, 1H), 4.82-4.65 (m, 4H), 4.44 (s, 1H), 4.32-3.87 (m, 6H), 3.66-3.48 (m, 1H), 3.42-3.32 (m, 1H), 3.25-2.87 (m, 8H), 2.49-2.32 (m, 3H), 1.39-1.29 (m, 12H). LCMS (Method 5-95 AB, ESI): $R_T$=0.769 min, $[M+H]^+$=1026.5.

Example 63

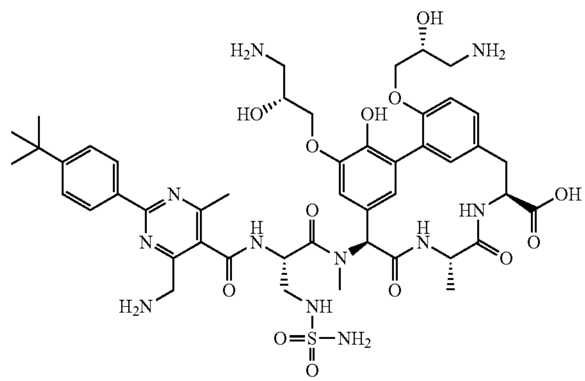 [SMILES: Cc1nc(-c2ccc(C(C)(C)C)cc2)nc(CN)c1C(=O)N[C@@H](CNS(N)(=O)=O)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O]

The general procedure for the synthesis of the ethyl 6-(4-(tert-butyl)phenyl)-4-chloro-2-methylnicotinate was performed using procedures from *J. Med. Chem.* 2013, 56, 1023-1040.

Step 1: Ethyl 4,6-dichloro-2-methyl-pyridine-3-carboxylate (966 mg, 4.13 mmol, 1.05 equiv) and $Pd(PPh_3)_4$ (227 mg, 0.2000 mmol, 0.05 equiv) were stirred in Diglyme (3.6 mL) at room temperature for 15 min. To this suspension was then added 4-tert-butylbenzeneboronic acid (700 mg, 3.93 mmol, 1.0 equiv) in IPA (4.2 mL) followed by a 2 M aqueous solution of $K_2CO_3$ (3.64 mL, 7.27 mmol, 1.85 equiv). The mixture was stirred at 95° C. for 2 hours. The reaction mixture was allowed to cool to room temperature and was concentrated under reduced pressure. $NaHCO_3$ sat. aq. and DCM were added to the reaction mixture and the layers were separated. The aqueous layer was extracted with DCM (2×40 mL) and organic layers were combined. The organic layer was then washed with brine (2×30 mL), dried over $Na_2SO_4$, filter and concentrated under reduced pressure to yield Ethyl 6-(4-tert-butylphenyl)-4-chloro-2-methyl-pyridine-3-carboxylate (1.02 g, 3.0738 mmol, 78.2% yield) as a yellow solid which was carried to the next step without purification.

Step 2: To a flame-dried nitrogen-flushed vial was added ethyl 6-(4-tert-butylphenyl)-4-chloro-2-methyl-pyridine-3-carboxylate (350 mg, 1.05 mmol, 1.0 equiv) and palladium acetate (35.5 mg, 0.1600 mmol, 0.15 equiv) with Catacxium A (113.5 mg, 0.3200 mmol, 0.3 equiv). The powders were dissolved in Ethylene glycol (2.64 mL) and 1,4-Dioxane (2.64 mL) (1;1) and the solution was sparged with a stream of nitrogen. Potassium (tert-butoxycarbonylamino)methyl-trifluoro-boranuide (1000 mg, 4.22 mmol, 4.0 equiv) and DIPEA (735 uL, 4.22 mmol, 4.0 equiv) were added which and the suspension was heated to 100° C. in an oil bath. After 4 hours, the reaction was cooled to room temperature and $NaHCO_3$ sat. aq. and EtOAc were added. The phases were separated and the aqueous layer was extracted with more EtOAc (2×10 mL) and organic layers were combined. The organic layer was then washed with brine (2×20 mL), dried over $Na_2SO_4$, filtered, and concentrated under reduced pressure to yield a black residue. The crude material was purified by flash chromatography (silica gel, 100-200 mesh, 0-40% EtOAc in heptanes) to yield ethyl 4-[(tert-butoxycarbonylamino)methyl]-6-(4-tert-butylphenyl)-2-methyl-pyridine-3-carboxylate (175 mg, 0.3399 mmol, 32% yield) as a thick red oil.

Step 3: To a scintillation vial equipped with a magnetic stirbar was added ethyl 4-[(tert-butoxycarbonylamino)methyl]-6-(4-tert-butylphenyl)-2-methyl-pyridine-3-carboxylate (145 mg, 0.3400 mmol, 1.0 equiv). It was dissolved in THF (1.7 mL). Then, a 1.0 M aqueous solution of lithium hydroxide (0.37 mL, 0.37 mmol, 1.1 equiv) was added. The reaction was then heated to 50° C. for 1 hour. The reaction mixture was cool to room temperature and concentrated under reduced pressure to yield lithium 4-[(tert-butoxycarbonylamino)methyl]-6-(4-tert-butylphenyl)-2-methyl-pyridine-3-carboxylate (135 mg, 0.3388 mmol, 99.7% yield) as a yellow foam/solid. This salt was used as is in the next step.

The title compound was prepared as described in Example 1, replacing 1-(4-(tert-butyl)phenyl)-6-oxo-1,6-dihydropyridazine-4-carboxylic acid with lithium 4-[(tert-butoxycarbonylamino)methyl]-6-(4-tert-butylphenyl)-2-methyl-pyridine-3-carboxylate. $^1H$ NMR (400 MHz, DMSO-$d_4$+$D_2O$) δ 7.94 (d, J=8.4 Hz, 2H), 7.84 (s, 1H), 7.52 (d, J=8.5 Hz, 2H), 7.18 (d, J=8.9 Hz, 1H), 6.99 (d, J=8.7 Hz, 1H), 6.72 (s, 1H), 6.67 (s, 1H), 6.28 (s, 1H), 6.14 (s, 1H), 5.09-5.03 (m, 1H), 4.71-4.58 (m, 2H), 4.18-3.91 (m, 9H), 3.90-3.75 (m, 2H), 3.41-3.22 (m, 1H), 3.12-2.95 (m, 3H), 2.85-2.77 (m, 4H), 2.54 (s, 3H), 2.39 (s, 12H), 1.27 (s, 9H), 1.21-1.11 (m, 3H). LCMS (Method 5-100 AB, 7 min): $R_T$=1.48 min, $[M+H]^+$=1021.6.

Example 64

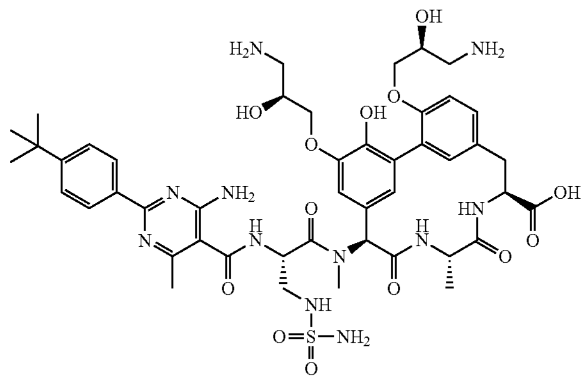 [SMILES: Cc1nc(-c2ccc(C(C)(C)C)cc2)nc(N)c1C(=O)N[C@@H](CNS(N)(=O)=O)C(=O)N(C)[C@@H]1C(=O)N[C@@H](C)C(=O)N[C@H](C(=O)O)Cc2ccc(OC[C@@H](O)CN)c(c2)-c2cc1cc(OC[C@@H](O)CN)c2O]

The title compound was prepared as described in Example 50, replacing tert-butyl (5R)-5-[(3-nitrophenyl)sulfonyloxymethyl]-2-oxo-oxazolidine-3-carboxylate in step 3 with tert-butyl (5S)-5-[(3-nitrophenyl)sulfonyloxymethyl]-2-oxo-oxazolidine-3-carboxylate. $^1H$ NMR (400 MHz, DMSO+D2O) δ 8.98-8.90 (m, 1H), 8.40-8.31 (m, 1H), 8.12 (d, J=8.5 Hz, 2H), 7.62 (d, J=8.4 Hz, 2H), 7.21 (d, J=7.3 Hz, 1H), 7.04 (d, J=8.6 Hz, 1H), 6.76-6.67 (m, 2H), 6.30 (s, 1H), 6.21 (s, 1H), 5.00-4.96 (m, 1H), 4.74-4.62 (m, 2H), 4.14-3.95 (m, 5H), 3.93-3.82 (m, 1H), 3.40-3.24 (m, 2H), 3.18-2.93 (m, 4H), 2.92-2.83 (m, 4H), 2.82-2.75 (m, 1H), 2.46 (s, 3H), 2.37 (s, 9H), 1.31 (s, 9H), 1.22-1.15 (m, 3H). LCMS (Method 5-100 AB, 7 min): $R_T$=1.67 min, $[M+H]^+$=1008.6.

Example 65

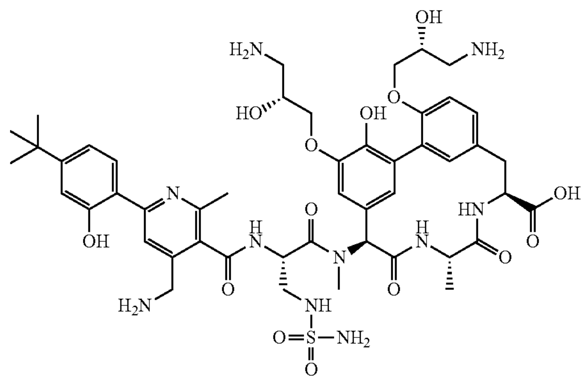 [SMILES: Cc1nc(-c2ccc(C(C)(C)C)cc2O)cc(CN)c1C(=O)N[C@@H](CNS(N)(=O)=O)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O]

The title compound was prepared as described in Example 1, replacing 1-(4-(tert-butyl)phenyl)-6-oxo-1,6-dihydropyridazine-4-carboxylic acid with 4-(aminomethyl)-6-(4-(tert-butyl)-2-hydroxyphenyl)-2-methylnicotinic acid. 4-(aminomethyl)-6-(4-(tert-butyl)-2-hydroxyphenyl)-2-methylnicotinic acid was prepared as described in Example 63 replacing 4-tert-butylbenzeneboronic acid with 2-[4-tert-butyl-2-(methoxymethoxy)phenyl]-4,4,5,5-tetramethyl-1,3,2-dioxaborolane. $^1H$ NMR (400 MHz, DMSO+D2O) δ 8.32

(s, 2H), 8.07 (s, 1H), 7.93 (d, J=8.5 Hz, 1H), 7.08 (d, J=8.8 Hz, 1H), 6.99 (d, J=8.4 Hz, 1H), 6.94-6.87 (m, 2H), 6.74 (s, 1H), 6.71 (s, 1H), 6.37 (s, 1H), 6.25 (s, 1H), 5.08 (dd, J=8.8, 4.6 Hz, 1H), 4.66-4.58 (m, 1H), 4.21-4.12 (m, 1H), 4.09-3.88 (m, 6H), 3.85 (s, 2H), 3.39-3.29 (m, 1H), 3.27-3.19 (m, 1H), 3.17-3.08 (m, 1H), 3.06-2.76 (m, 8H), 2.54 (s, 3H), 1.27 (s, 9H), 1.22-1.15 (m, 3H). LCMS (Method 5-100 AB, 7 min): $R_T$=1.68 min, $[M+H]^+$=1037.6.

Example 66

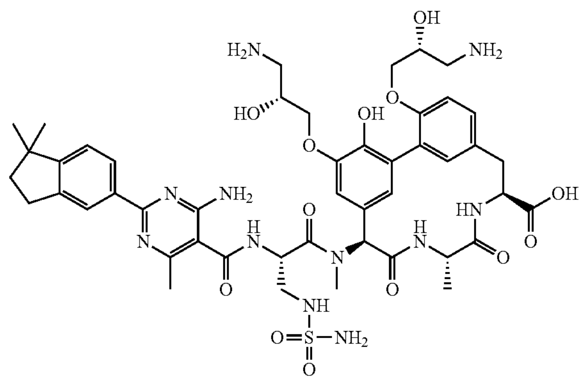 [SMILES: Cc1nc(-c2ccc3c(c2)CCC3(C)C)nc(N)c1C(=O)N[C@@H](CNS(N)(=O)=O)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O]

The general procedure for the synthesis of the 5-bromo-1,1-dimethyl-2,3-dihydro-1H-indene was performed using procedures from *Chem. Ber.* 1985, 118, 1050.

Step 1: To a flame-dried, nitrogen flushed flask was added titanium (IV) chloride (1.71 mL, 15.64 mmol, 2.2 equiv) and DCM (14.2 mL). The solution was cooled to −30° C. and stirred for 5 minutes. Then, dimethylzinc, 1 M in toluene (15.64 mL, 15.64 mmol, 2.2 equiv) was added dropwise and the reaction was stirred for 30 minutes. Then, 5-bromo-1-indanone (1500 mg, 7.11 mmol, 1.0 equiv) was added in one portion to the slurry which was stirred from −30° C. to rt overnight. The reaction was then cooled 0° C. and ice cubes were added portionwise followed by $NaHCO_3$. The reaction was diluted with EtOAc and solid was decanted and the layers were separated. The aqueous layer was extracted with EtOAc (3×40 mL). The organic layers were combined, dried over $Na_2SO_4$, filtered and concentrated under reduced pressure. The crude product was diluted in DCM and filtered over a pad of silica gel (200 g). Flush silica gel with 50% EtOAc in hexanes. Evaporate the solution to dryness to provide crude 5-Bromo-1,1-dimethyl-indane (1495 mg, 6.6409 mmol, 93.4% yield) as a translucent oil which was carried to the next step without further purification.

Step 2: To a flame-dried, nitrogen-flushed vial was added 5-bromo-1,1-dimethyl-indane (1500 mg, 6.66 mmol, 1.0 equiv) and bis(pinacolato)diboron (3384 mg, 13.33 mmol, 2.0 equiv). The solids were dissolved in anhydrous toluene (22 mL) and the solution was sparged with nitrogen for 15 minutes. KOAc (2.59 g, 19.99 mmol, 3.0 equiv) was added followed by $PdCl_2$(dppf) $CH_2Cl_2$ (272 mg, 0.330 mmol, 0.05 equiv). The vial was sealed with a microwave cap and then solution was heated to 100° C. and stirred overnight. The reaction was cooled to rt and diluted with EtOAc (100 mL). The organic layer was washed with $NaHCO_3$ sat. aq., then brine, dried over $Na_2SO_4$, and filtered over a sintered funnel. Silica gel was added and the suspension was evaporated under reduced pressure to a black solid which as purified by flash chromatography (silica gel, 100-200 mesh, 0-20% EtOAc in heptanes) to yield 2-(1,1-dimethylindan-5-yl)-4,4,5,5-tetramethyl-1,3,2-dioxaborolane (1324 mg, 4.8642 mmol, 73% yield) as a gummy orange solid.

Step 3: To a flame-dried sealed tube was added methyl 4-amino-2-chloro-6-methyl-pyrimidine-5-carboxylate (150 mg, 0.7400 mmol, 1.0 equiv), 1,4-dioxane (3.7201 mL) and water (0.3618 mL). The solution was sparged with flow of nitrogen for 10 minutes. Then, 2-(1,1-dimethylindan-5-yl)-4,4,5,5-tetramethyl-1,3,2-dioxaborolane (243 mg, 0.8900 mmol, 1.2 equiv), $PdCl_2$(dppf) $CH_2Cl_2$ (60.8 mg, 0.0700 mmol, 0.1 equiv), and $K_2CO_3$ (206 mg, 1.49 mmol, 2.0 equiv) were added to the reaction. The tube was sealed with a microwave cap and heated to 95° C. in an oil bath for 12 hours. After that period, the solution was cooled to rt, $NaHCO_3$ sat. aq. and EtOAc were added. The phases were separated, the aqueous layer was extracted with EtOAc (2×10 mL) and organic layers were combined. The organic layer was then washed with brine (2×20 mL), dried over $Na_2SO_4$, filtered and concentrated under reduced pressure. The crude reaction mixture was then purified by flash chromatography (silica gel, 100-200 mesh, 0-50% EtOAc in heptanes) to yield methyl 4-amino-2-(1,1-dimethylindan-5-yl)-6-methyl-pyrimidine-5-carboxylate (81 mg, 0.2601 mmol, 35% yield) isolated as a yellow solid.

Step 4: Methyl 4-amino-2-(1,1-dimethylindan-5-yl)-6-methyl-pyrimidine-5-carboxylate (180 mg, 0.5800 mmol) was dissolved in THF (1.93 mL) and an 1.0 M aqueous solution of lithium hydroxide (2.31 mL, 2.31 mmol, 4.0 equiv) was added. The reaction was then heated at 50° C. and stirred overnight. The reaction was cooled and $KHSO_4$ 1.0 M (40 mL) and EtOAc (40 mL) were added. The phases were separated and the aqueous layer was extracted with EtOAc (2×40 mL). The organic layers were combined, washed with brine (3×40 mL), dried over $Na_2SO_4$, filtered, and concentrated under reduced pressure to yield 4-Amino-2-(1,1-dimethylindan-5-yl)-6-methyl-pyrimidine-5-carboxylic acid (165 mg, 0.5549 mmol, 96% yield) as a white solid which was carried directly to the next step without purification.

The title compound was prepared as described in Example 1, replacing 1-(4-(tert-butyl)phenyl)-6-oxo-1,6-dihydropyridazine-4-carboxylic acid with 4-amino-2-(1,1-dimethylindan-5-yl)-6-methyl-pyrimidine-5-carboxylic acid. $^1H$ NMR (400 MHz, DMSO-$d_6$+$D_2O$) δ 8.36 (s, 1H), 8.10-8.08 (m, 2H), 7.26-7.14 (m, 1H), 7.03 (d, J=8.8 Hz, 1H), 6.85 (d, J=8.2 Hz, 1H), 6.73 (s, 1H), 6.69 (s, 1H), 6.35 (s, 1H), 6.24 (s, 1H), 4.98-4.85 (m, 1H), 4.69-4.50 (m, 1H), 4.21-4.11 (m, 1H), 4.07-3.87 (m, 6H), 3.38-3.29 (m, 1H), 3.24-3.08 (m, 2H), 3.04-2.79 (m, 8H), 2.34 (s, 3H), 1.88 (t, J=7.1 Hz, 2H), 1.27-1.11 (m, 9H). LCMS (Method 5-100 AB, 7 min): $R_T$=1.66 min, $[M+H]^+$=1020.5.

Example 67

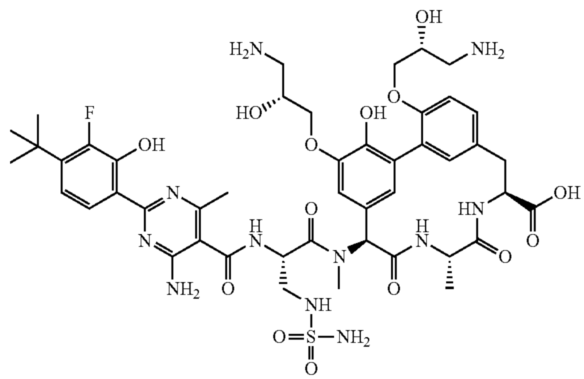 [SMILES: Cc1nc(-c2ccc(C(C)(C)C)c(F)c2O)nc(N)c1C(=O)N[C@@H](CNS(N)(=O)=O)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O]

The title compound was prepared as described in Example 1, replacing 1-(4-(tert-butyl)phenyl)-6-oxo-1,6-dihydropyridazine-4-carboxylic acid with 4-amino-2-(4-(tert-butyl)-3-fluoro-2-hydroxyphenyl)-6-methylpyrimidine-5-carboxylic acid. $^1$H NMR (400 MHz, MeOH-$d_4$) δ (ppm) 8.42 (br s, 2H), 8.00 (d, J=7.6 Hz, 1H), 7.12-6.51 (m, 7H), 5.26-5.16 (m, 1H), 4.83-4.80 (m, 1H), 4.49-3.94 (m, 7H), 3.69-3.32 (m, 3H), 3.25-2.92 (m, 8H), 2.42 (s, 3H), 1.43-1.33 (m, 12H). LCMS (Method 5-95 AB, ESI): $R_T$=0.792 min, $[M+H]^+$=1042.6.

Example 68

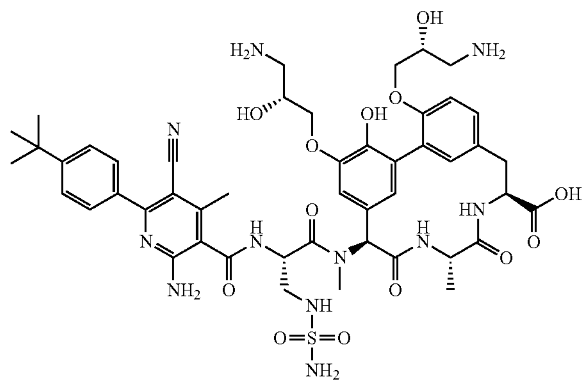 [SMILES: Cc1c(C#N)c(-c2ccc(C(C)(C)C)cc2)nc(N)c1C(=O)N[C@@H](CNS(N)(=O)=O)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O]

Step 1: To a mixture of 4-t-Butylbenzeneboronic acid (1150 mg, 6.46 mmol, 1 equiv) in 1,4-Dioxane (58 mL) was added methyl 2-amino-4,6-dichloro-pyridine-3-carboxylate (1571 mg, 7.11 mmol, 1.1 equiv), $Pd(PPh_3)_4$ (373 mg, 0.32 mmol, 0.05 equiv), $K_3PO_4$ (2057 mg, 9.69 mmol, 1.5 equiv), $H_2O$ (5 mL) and degassed with $N_2$ gas. After stirring for 18 hrs at 60° C., the reaction was quenched with $NaHCO_3$ aq. sat. (25 mL) and diluted then extracted with EtOAc (3×75 mL). The organic layer was washed with brine, dried over $Na_2SO_4$, filtrated over celite and concentrated under reduced pressure. The crude material was purified by column chromatography (silica gel, 100-200 mesh, 10-50% EtOAc in heptanes) to yield methyl 2-amino-4,6-dichloro-pyridine-3-carboxylate (1510 mg, 4.74 mmol, 73% yield) as yellow solid.

Step 2: A mixture of methyl 2-amino-6-(4-tert-butylphenyl)-4-chloro-pyridine-3-carboxylate (500 mg, 1.57 mmol, 1 equiv), Methylboronic acid (282 mg, 4.71 mmol, 3 equiv), 1,1'-Bis(diphenylphosphino)ferrocene dichloropalladium (II) (115 mg, 0.16 mmol, 0.1 equiv), and $K_3PO_4$ (999 mg, 4.71 mmol, 3 equiv) in $N_2$ degassed 1,4-Dioxane (7.8419 mL) was stirred at 110° C. for 1 h. The reaction was quenched with $NaHCO_3$ aq. sat. (10 mL) and diluted then extracted with EtOAc (3×50 mL). The organic layer was washed with brine, dried over $Na_2SO_4$, and concentrated under reduced pressure. The crude material was purified by column chromatography (silica gel, 100-200 mesh, 10-50% EtOAc in heptanes) to yield methyl 2-amino-6-(4-tert-butylphenyl)-4-methyl-pyridine-3-carboxylate (342 mg, 1.15 mmol, 73% yield) as yellow solid.

Step 3: N-Iodosuccinimide (396 mg, 1.76 mmol, 1.5 equiv) was added to a solution of methyl 2-amino-6-(4-tert-butylphenyl)-4-methyl-pyridine-3-carboxylate (350 mg, 1.17 mmol, 1 equiv) in DMF (12 mL). The reaction mixture was stirred at 65° C. for 30 h. The reaction was quenched with $NaHCO_3$ aq. sat. (20 mL) and diluted then extracted with EtOAc (3×50 mL). The organic layer was washed with brine, dried over $Na_2SO_4$, and concentrated under reduced pressure. The crude material was purified by column chromatography (silica gel, 100-200 mesh, 0-80% EtOAc in heptanes) to yield methyl 2-amino-6-(4-tert-butylphenyl)-5-iodo-4-methyl-pyridine-3-carboxylate (279 mg, 0.66 mmol, 56% yield) as orange solid.

Step 4: To a mixture of methyl 2-amino-6-(4-tert-butylphenyl)-5-iodo-4-methyl-pyridine-3-carboxylate (200 mg, 0.47 mmol, 1 equiv) in $N_2$ degassed DMA (4.7 mL) was added $ZnCN_2$ (166 mg, 1.41 mmol, 3 equiv) and $N_2$ degassed again before adding XPhos Pd G3 (74 mg, 0.09 mmol, 0.2 equiv). After stirring for 2 hrs at 120° C., the reaction was quenched with $NaHCO_3$ (10 mL) and diluted then extracted with EtOAc (3×50 mL). The organic layer was washed with brine, dried over $MgSO_4$, filtrated over celite and concentrated under reduced pressure to yield methyl 2-amino-6-(4-tert-butylphenyl)-5-cyano-4-methyl-pyridine-3-carboxylate (104 mg, 0.32 mmol, 68% yield) as orange solid. The solid was used as is for the next step without purification.

Step 5: LiOH 1M, aq. (3.22 mL, 3.22 mmol, 10 equiv) was added to a solution of methyl 2-amino-6-(4-tert-butylphenyl)-5-cyano-4-methyl-pyridine-3-carboxylate (104 mg, 0.32 mmol, 1 equiv) in THF (3.2 mL) and the reaction mixture was stirred at 22° C. for 5 h. The reaction was quenched with NaCl aq. sat. (10 mL) then extracted with EtOAc (3×50 mL). The organic layer was washed with brine, dried over $Na_2SO_4$, and concentrated under reduced pressure to yield [2-amino-6-(4-tert-butylphenyl)-5-cyano-4-methyl-pyridine-3-carbonyl]oxylithium (101 mg, 0.32 mmol, 99% yield) as yellow solid. The solid was used as is for the next step without purification.

The title compound was prepared as described in Example 1, replacing 1-(4-(tert-butyl)phenyl)-6-oxo-1,6-dihydropyridazine-4-carboxylic acid with [2-amino-6-(4-tert-butylphenyl)-5-cyano-4-methyl-pyridine-3-carbonyl]oxylithium. $^1$H NMR (400 MHz, DMSO-$d_4$+$D_2O$) δ 8.35 (s, 1H), 7.68 (d, J=8.4 Hz, 2H), 7.52 (d, J=8.4 Hz, 2H), 7.09 (d, J=7.8 Hz, 1H), 6.90 (d, J=8.1 Hz, 1H), 6.73 (d, J=10.3 Hz, 11H), 6.37 (s, 1H), 6.26 (s, 1H), 4.95-4.91 (m, 1H), 4.63-4.58 (m, 1H), 4.14-4.07 (m, 1H), 4.06-3.91 (m, 5H), 3.38-3.34 (m, 1H), 3.26-3.22 (m, 1H), 3.15-3.11 (m, 1H), 3.01-2.90 (m, 4H), 2.87-2.76 (m, 2H), 2.70-2.66 (m, 1H), 2.36 (s, 3H), 2.34-2.32 (m, 2H), 1.30 (s, 9H), 1.22-1.14 (m, 3H). LCMS (Method 5-100 AB, 7 min): $R_T$=2.33 min, $[M+H]^+$=1032.6.

Example 69

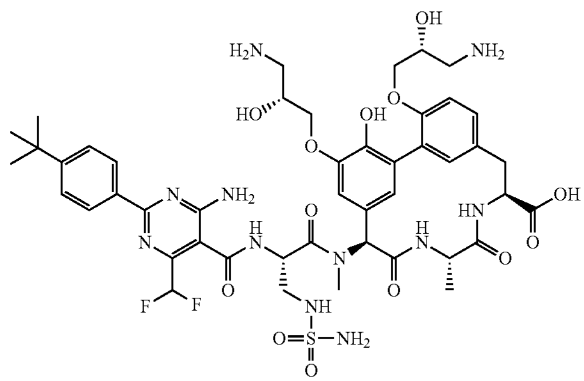 [SMILES: C[C@@H]1NC(=O)[C@@H](N(C)C(=O)[C@H](CNS(N)(=O)=O)NC(=O)c2c(N)nc(-c3ccc(C(C)(C)C)cc3)nc2C(F)F)c2cc(OC[C@H](O)CN)c(O)c(c2)-c2cc(ccc2OC[C@H](O)CN)C[C@@H](C(=O)O)NC1=O]

The title compound was prepared as described in Example 1, replacing 1-(4-(tert-butyl)phenyl)-6-oxo-1,6-dihydropyridazine-4-carboxylic acid with 4-amino-2-(4-(tert-butyl)phenyl)-6-(difluoromethyl)pyrimidine-5-carboxylic acid. $^1$H NMR (400 MHz, MeOH-$d_4$) δ (ppm) 8.29 (d, J=7.6 Hz, 2H), 7.48 (d, J=8.0 Hz, 2H), 7.11-6.96 (m, 1H), 6.90-6.80 (m, 2H), 6.79-6.69 (m, 2H), 6.66-6.56 (m, 1H), 6.53-6.41 (m, 1H), 5.22-5.12 (m, 1H), 4.82-4.80 (m, 2H), 4.43-4.29 (m, 5H), 3.63-3.53 (m, 1H), 3.49-3.40 (m, 1H), 3.38-3.34 (m, 2H), 3.28-3.24 (m, 2H), 3.24-3.12 (m, 3H), 3.06 (s, 3H), 3.01-2.90 (m, 2H), 1.43-1.28 (m, 12H). LCMS (Method 5-95 AB, ESI): $R_T$=0.825 min, $[M+H]^+$=1044.4.

Example 70

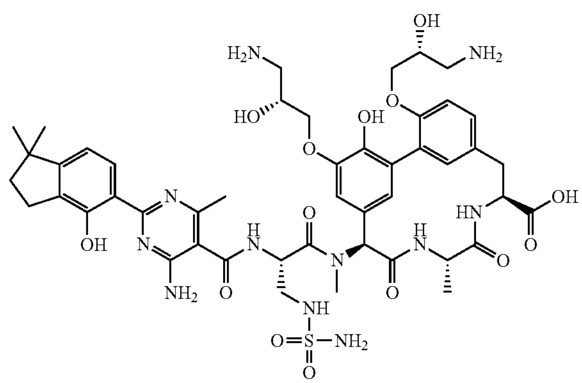 [SMILES: Cc1nc(-c2ccc3c(c2O)CCC3(C)C)nc(N)c1C(=O)N[C@@H](CNS(N)(=O)=O)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O]

The title compound was prepared as described in Example 1, replacing 1-(4-(tert-butyl)phenyl)-6-oxo-1,6-dihydropyridazine-4-carboxylic acid with 4-amino-2-(4-hydroxy-1,1-dimethyl-2,3-dihydro-1H-inden-5-yl)-6-methylpyrimidine-5-carboxylic acid, which was prepared using the procedures described in Example 52. $^1$H NMR (400 MHz, MeOH-$d_4$) δ (ppm) 8.41 (br s, 1H), 8.2 (d, J=8.4 Hz, 1H), 7.05 (br s, 1H), 6.93-6.73 (m, 3H), 6.7 (d, J=8 Hz, 1H), 6.59 (s, 1H), 6.5 (br s, 1H), 5.23-5.13 (m, 1H), 4.8 (br s, 1H), 4.43 (br s, 1H), 4.27-3.97 (m, 6H), 3.66-3.54 (m, 1H), 3.41-3.32 (m, 1H), 3.28-2.98 (m, 9H), 2.89-2.81 (m, 2H), 2.45 (s, 3H), 2.00-1.91 (m, 2H), 1.36 (br d, J=6.8 Hz, 3H), 1.26 (s, 6H). LCMS (Method 5-95 AB, ESI): $R_T$=0.795 min, $[M+H]^+$=1036.5.

Example 71

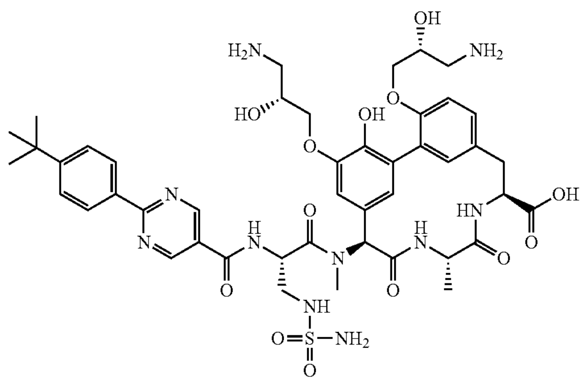 [SMILES: C[C@@H]1NC(=O)[C@@H](N(C)C(=O)[C@H](CNS(N)(=O)=O)NC(=O)c2cnc(-c3ccc(C(C)(C)C)cc3)nc2)c2cc(OC[C@H](O)CN)c(O)c(c2)-c2cc(ccc2OC[C@H](O)CN)C[C@@H](C(=O)O)NC1=O]

The title compound was prepared as described in Example 1, replacing 1-(4-(tert-butyl)phenyl)-6-oxo-1,6-dihydropyridazine-4-carboxylic acid with 2-(4-(tert-butyl)phenyl)pyrimidine-5-carboxylic acid. 1H NMR (400 MHz, MeOH-$d_4$) δ (ppm) 9.21-9.13 (m, 2H), 8.47-8.25 (m, 3H), 7.55-7.49 (m, 2H), 7.10-6.35 (m, 5H), 4.30-3.37 (m, 10H), 3.25-2.74 (m, 8H), 1.39-1.36 (m, 12H). LCMS (Method 5-95 AB, ESI): $R_T$=0.814 min, $[M+H]^+$=979.6.

Example 72

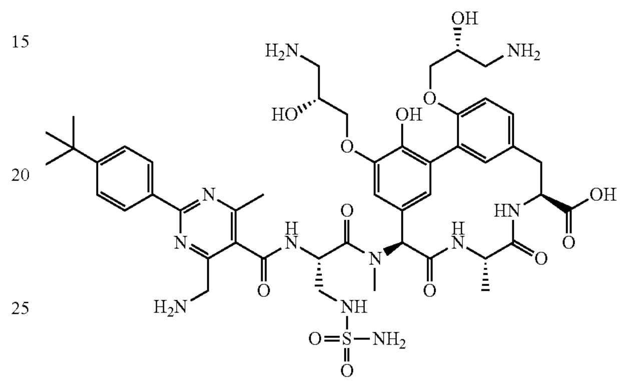

Step 1: Copper (II) acetylacetonate (237 mg, 0.905 mmol) was added to a solution of tert-butyl acetoacetate (3.0 mL, 18.1 mmol) and ethyl cyanoformate (1.8 mL, 18.2 mmol) in DCM (12.1 mL). The reaction mixture was stirred at room temperature for 48 h then concentrated under reduced pressure. The residue was purified by column chromatography (silica gel, 100-200 mesh, 0-60% EtOAc in heptanes) to yield O1-tert-butyl O4-ethyl(E)-2-acetyl-3-amino-but-2-enedioate (1.73 g, 37.2% yield) as a dark grey oil (mix of two geometric isomers).

Step 2: 1,1,3,3-Tetramethylguanidine (1.69 mL, 13.5 mmol) was added to a solution of O1-tert-butyl O4-ethyl (E)-2-acetyl-3-amino-but-2-enedioate (1.73 g, 6.72 mmol) and 4-tert-butylbenzamidine (1.30 g, 7.40 mmol) in DCM (13.4 mL). The reaction mixture was stirred at room temperature for 16 h then quenched with 1M aqueous $KHSO_4$. The mixture was extracted with EtOAc (3×). The organic layers were combined, dried over $Na_2SO_4$, filtered and concentrated under reduced pressure. The residue was purified by column chromatography (silica gel, 100-200 mesh, 0-10% MeOH in DCM) to yield the title compound 5-tert-butoxycarbonyl-2-(4-tert-butylphenyl)-6-methyl-pyrimidine-4-carboxylic acid (1.21 g, 48.6% yield) as off-white solid.

Step 3: Isobutyl chloroformate (501 uL, 3.86 mmol) was added to a solution of 5-tert-butoxycarbonyl-2-(4-tert-butylphenyl)-6-methyl-pyrimidine-4-carboxylic acid (1.30 g, 3.51 mmol) and triethylamine (538 uL, 3.86 mmol) in THF (35 mL) at 0° C. The reaction mixture was stirred at room temperature for 15 min then cooled to 0° C. Lithium borohydride (255 mg, 12.3 mmol) was added and the reaction mixture was stirred at room temperature for 1 h30. MeOH (10 mL) was added at 0° C. followed by saturated aqueous $NH_4Cl$. The mixture was then warmed to room temperature and extracted with EtOAc (3×). The organic layers were combined, washed with brine, dried over $Na_2SO_4$, filtered and concentrated under reduced pressure. The residue was purified by column chromatography (silica gel, 100-200 mesh, 0-10% MeOH in DCM) to yield tert-butyl 2-(4-tert-butylphenyl)-4-(hydroxymethyl)-6-methyl-pyrimidine-5-carboxylate (679 mg, 54.3% yield) as yellow oil.

Step 4: Carbon tetrabromide (444 mg, 1.34 mmol), triphenylphosphine (367 mg, 1.40 mmol) and sodium azide (396 mg, 6.09 mmol) were added to a solution of tert-butyl 2-(4-tert-butylphenyl)-4-(hydroxymethyl)-6-methyl-pyrimidine-5-carboxylate (434 mg, 1.22 mmol) in DMF (8.1 mL). Triethylamine (373 uL, 2.68 mmol) was then added and the reaction mixture was stirred at room temperature for 1 h. Additional portions of carbon tetrabromide (444 mg, 1.34 mmol), triphenylphosphine (367 mg, 1.40 mmol), and triethylamine (373 uL, 2.68 mmol) were added and the reaction mixture was stirred at room temperature for 16 h. The reaction mixture was diluted with EtOAc then washed with saturated aqueous $NaHCO_3$, water, and brine. The organic layers were combined, dried over $Na_2SO_4$, filtered and concentrated under reduced pressure. The crude material was purified by column chromatography (silica gel, 100-200 mesh, 0-20% EtOAc in heptanes) to yield tert-butyl 4-(azidomethyl)-2-(4-tert-butylphenyl)-6-methyl-pyrimidine-5-carboxylate (315 mg, 67.8% yield) as yellow oil.

Step 5: Fmoc chloride (384 mg, 1.49 mmol) and sodium carbonate (182 mg, 1.71 mmol) were added to a solution of tert-butyl 4-(azidomethyl)-2-(4-tert-butylphenyl)-6-methyl-pyrimidine-5-carboxylate (436 mg, 1.14 mmol) in ethanol (8.7 mL). The reaction mixture was purged with $N_2$ for 5 min then palladium on carbon (10% loading) 55% wet (122 mg, 0.114 mmol) was added. The reaction was purged with $H_2$ for 5 min then stirred under $H_2$ (1 atm) for 16 h. The reaction mixture was purged with $N_2$. Additional portions of sodium carbonate (121 mg, 1.14 mmol) and Fmoc chloride (147 mg, 0.568 mmol) were added. The reaction mixture was stirred at room temperature for 5 h then filtered through Celite. The filter cake was washed with MeOH then filtrate was concentrated under reduced pressure. The crude was purified by column chromatography (silica gel, 100-200 mesh, 0-30% EtOAc in heptanes) to yield tert-butyl 2-(4-tert-butylphenyl)-4-[(9H-fluoren-9-ylmethoxycarbonylamino)methyl]-6-methyl-pyrimidine-5-carboxylate (487 mg, 73.8% yield) as colorless oil.

Step 6: Trifluoroacetic acid (6.5 mL) was added to a solution of tert-butyl 2-(4-tert-butylphenyl)-4-[(9H-fluoren-9-ylmethoxycarbonylamino)methyl]-6-methyl-pyrimidine-5-carboxylate (487 mg, 0.843 mmol) in DCM (13 mL). The reaction mixture was stirred at room temperature for 12 h then concentrated under reduced pressure. The crude material was purified by column chromatography (C-18, 5-70% acetonitrile in 10 mM aqueous $NH_4HCO_2$) to yield 2-(4-tert-butylphenyl)-4-[(9H-fluoren-9-ylmethoxycarbonylamino)-methyl]-6-methyl-pyrimidine-5-carboxylic acid (303 mg, 68.9% yield) as an off-white solid.

The title compound was prepared as described in Example 1, replacing 1-(4-(tert-butyl)phenyl)-6-oxo-1,6-dihydropyridazine-4-carboxylic acid with 2-(4-tert-butylphenyl)-4-[(9H-fluoren-9-ylmethoxycarbonylamino)-methyl]-6-methyl-pyrimidine-5-carboxylic acid. $^1H$ NMR (400 MHz, DMSO+H2O) δ 8.40 (d, J=8.4 Hz, 2H), 8.34 (s, 2H), 7.55 (d, J=7.8 Hz, 2H), 7.09-7.00 (m, 1H), 6.93-6.85 (m, 1H), 6.77-6.71 (m, 1H), 6.68 (s, 1H), 6.38 (s, 1H), 6.26 (s, 1H), 5.13-5.05 (m, 1H), 4.62 (q, J=5.6 Hz, 1H), 4.18-3.85 (m, 9H), 3.39-3.30 (m, 2H), 3.28-3.18 (m, 1H), 3.18-3.09 (m, 1H), 3.08-2.75 (m, 7H), 2.55 (s, 3H), 1.32 (s, 9H), 1.17 (d, J=6.7 Hz, 3H). LCMS (Method 5-100 AB, 7 min): $R_T$=1.46 min, $[M+H]^+$=1022.5.

Example 73

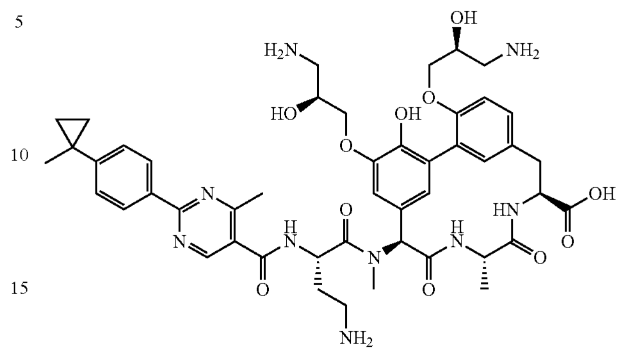

The title compound was prepared using the procedure of Example 1, replacing compound 10 in Example 17 by compound 10 described in procedure C replacing tert-butyl (5R)-5-[(3-nitrophenyl)sulfonyloxymethyl]-2-oxo-oxazolidine-3-carboxylate in step 3 with tert-butyl (5S)-5-[(3-nitrophenyl)sulfonyloxymethyl]-2-oxo-oxazolidine-3-carboxylate and replacing 1-(4-(tert-butyl)phenyl)-6-oxo-1,6-dihydropyridazine-4-carboxylic acid with 4-methyl-2-(4-(1-methylcyclopropyl)phenyl)pyrimidine-5-carboxylic acid prepared as described in Example 5. $^1H$ NMR (400 MHz, DMSO+D2O) δ 8.91 (d, J=7.1 Hz, 1H), 8.79 (s, 1H), 8.30 (d, J=8.5 Hz, 2H), 7.36 (d, J=8.6 Hz, 2H), 7.20 (d, J=8.0 Hz, 1H), 7.04 (d, J=8.5 Hz, 1H), 6.74 (s, 1H), 6.72 (s, 1H), 6.31 (s, 1H), 6.25 (s, 1H), 4.95-4.88 (m, 1H), 4.74-4.61 (m, 2H), 4.14-4.05 (m, 1H), 4.05-3.95 (m, 4H), 3.92-3.85 (m, 1H), 3.33-3.25 (m, 1H), 3.13-2.75 (m, 10H), 2.62 (s, 3H), 2.38 (s, 15H), 2.12-1.92 (m, 2H), 1.42 (s, 3H), 1.18 (d, J=6.7 Hz, 3H), 0.96-0.89 (m, 2H), 0.88-0.82 (m, 2H). LCMS (Method 5-100 AB, 7 min): $R_T$=1.45 min, $[M+H]^+$=926.6.

Example 74

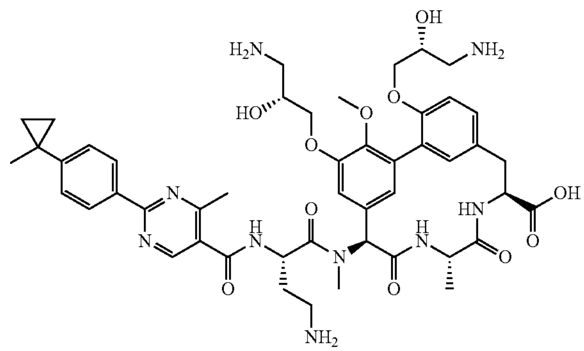 [SMILES: COc1c(OC[C@H](O)CN)cc2cc1-c1cc(ccc1OC[C@H](O)CN)C[C@@H](C(=O)O)NC(=O)[C@H](C)NC(=O)[C@H]2N(C)C(=O)[C@H](CCN)NC(=O)c1cnc(-c2ccc(C3(C)CC3)cc2)nc1C]

The title compound was prepared using General Procedure B. $^1H$ NMR (400 MHz, MeOH-$d_4$) δ (ppm) 8.83 (s, 1H), 8.35 (d, J=8.4 Hz, 2H), 7.38 (d, J=8.4 Hz, 2H), 7.20-7.14 (m, 1H), 7.03-6.91 (m, 2H), 6.82 (s, 1H), 6.61 (s, 1H), 6.47 (s, 1H), 5.18-5.06 (m, 1H), 4.84-4.76 (m, 2H), 4.61-4.50 (m, 1H), 4.35-3.92 (m, 6H), 3.60 (s, 3H), 3.26-3.00 (m, 10H), 2.77-2.67 (m, 3H), 2.38-2.12 (m, 2H), 1.47 (s, 3H), 1.37 (d, J=7.2 Hz, 3H), 0.97-0.91 (m, 2H), 0.89-0.81 (m, 2H). LCMS (Method 5-95 AB, ESI): $R_T$=0.764 min, $[M+H]^+$=940.4.

Example 75

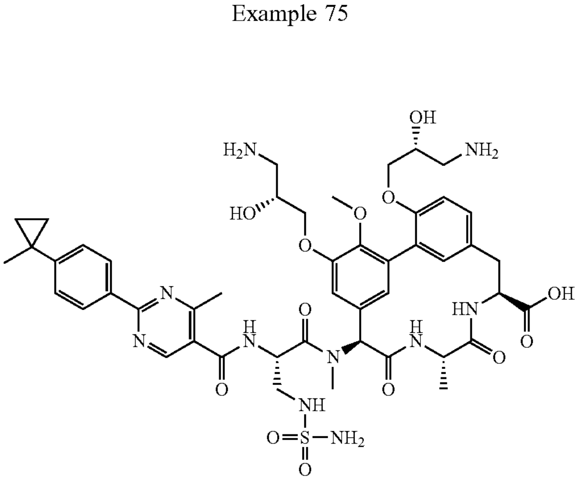

The title compound was prepared using General Procedure B. $^1$H NMR (400 MHz, MeOH-$d_4$) δ (ppm) 8.46 (br s, 1H), 8.21 (d, J=8.0 Hz, 2H), 7.50 (d, J=8.0 Hz, 2H), 7.40-7.20 (m, 1H), 7.11 (d, J=7.6 Hz, 1H), 6.91-6.83 (m, 1H), 6.80 (s, 1H), 6.63 (s, 1H), 6.57 (s, 1H), 5.24-5.17 (m, 1H), 4.85-4.78 (m, 2H), 4.46-4.39 (m, 1H), 4.38-4.28 (m, 1H), 4.27-4.20 (m, 2H), 4.19-4.10 (m, 2H), 4.09-3.94 (m, 3H), 3.70-3.56 (m, 2H), 3.55-3.45 (m, 3H), 3.43-3.34 (m, 1H), 3.25-3.12 (m, 2H), 3.10 (s, 3H), 3.08-2.94 (m, 3H), 2.49 (s, 3H), 1.41-1.31 (m, 12H). LCMS (Method 5-95 AB, ESI): $R_T$=0.636 min, $[M+H]^+$=1022.6.

Example 76

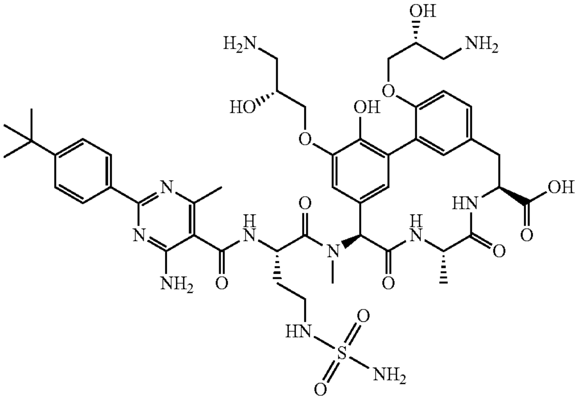 [SMILES: Cc1nc(-c2ccc(C(C)(C)C)cc2)nc(N)c1C(=O)N[C@@H](CCNS(N)(=O)=O)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O]

The title compound was prepared using General Procedure B $^1$H NMR (400 MHz, MeOH-$d_4$) δ (ppm) 8.34 (br s, 1H), 8.20 (d, J=8.8 Hz, 2H), 7.50 (d, J=8.4 Hz, 2H), 7.12 (d, J=9.2 Hz, 1H), 6.94-6.79 (m, 3H), 6.60 (s, 1H), 6.50 (s, 1H), 5.15-5.03 (m, 1H), 4.83-4.72 (m, 1H), 4.52-4.42 (m, 1H), 4.26-4.02 (m, 6H), 3.28-3.00 (m, 11H), 2.47 (s, 3H), 2.23-2.06 (m, 1H), 2.03-1.85 (m, 1H), 1.39-1.34 (m, 12H). LCMS (Method 5-95 AB, ESI): $R_T$=0.767 min, $[M+H]^+$=1022.6.

BIOLOGICAL ASSAYS

Example B1: LepB Assay

In vitro antimicrobial activity of each compound was determined by measuring minimal inhibitor concentrations (MICs) using the broth micro-dilution technique as approved by the Clinical and Laboratory Standards Institute (CLSI) (Methods for Dilution Antimicrobial Susceptibility Tests for Bacteria that Grow Aerobically; Approved Standard—Eighth Edition. CLSI document M07-A8. Wayne, PA: Clinical and Laboratory Standards; 2009). Antibacterial activity was measure against *Escherichia coli* strain ATCC 25922 (*E. coli*), *Klebsiella pneumoniae* ATCC 700603 (*K. pneumoniae*), *Acinetobacter baumannii* ATCC 17978 (*A. baumannii*), and *Pseudomonas aeruginosa* PA01 (*P. aeruginosa*), each of which is representative of a clinically relevant Gram-negative species. Cells were inoculated onto plates of Mueller Hinton Agar and grown at 37° C. for 16-18 hours. Inocula suspensions were prepared by scraping cells into 1 mL of testing media (Mueller Hinton II cation adjusted Broth) and diluting to a final OD 600 nm of 0.01.

Test compounds were prepared in DMSO at a concentration of 64 ug/ml. The compounds were tested under several different dilution formats. In protocol 1, the compound stocks were diluted into testing media at a concentration of 64 μg/ml and serial 2-fold dilutions were made in the same media, in 96-well U bottom microtiter dishes, for a total of 10 compound concentrations. In protocol 2, the compound stocks were diluted into testing media at a concentration of 4 μg/mL and serial 2-fold dilutions were made in the same media, in 96-well U bottom microtiter dishes, for a total of 10 compound concentrations. In protocol 3, compound stocks were diluted into testing media at a concentration of 0.5 μg/mL, with serial 2-fold dilutions conducted as described above. In protocol 4, compound stocks were diluted into testing media at a concentration of 0.13 μg/mL, with serial 2-fold dilutions conducted as described above. Inocula suspensions were added to the 2-fold serial dilutions of test compounds to a final density of OD 600 nm of 0.0005 and incubated at 35° C. for 22 hours. After incubation the plates were examined visually and the lowest concentration of test compound that completely prevented bacterial growth were recorded as the MICs. To assess antimicrobial activity in the presence of plasma proteins, MICs were also determined in growth media supplemented with 50% serum. Bacterial inocula and test compound dilution plates were prepared using the same protocol as described above for the standard MICs assay, with the exception that a mixture of 50% v/v Mueller Hinton II cation adjusted Broth and 50% v/v mouse sterile filtered serum (Equitech-Bio) was used in place of 100% Mueller Hinton II cation adjusted Broth. The results are listed in Table 3 (MIC, $IC_{50}$ values micromolar).

Example B2: Measurement of Oxygen Consumption

Isolation of Liver Mitochondria

Male Sprague-Dawley rats (8-10 weeks of age) were euthanized with an overdose of carbon dioxide. The liver was rapidly excised and placed in ice-cold phosphate-buffered saline (PBS) before isolation process. Mitochondria were isolated using the MitoCheck® Mitochondrial Isolation Kit (Cayman Chemical #701010, Ann Arbor, MI) according to manufacturer's instructions. In brief, approximately 10-14 grams of liver tissues were finely minced using a pair of scissors, and washed repeatedly with ice-cold PBS, followed by Mito Isolation Buffer. The minced tissues were homogenized with 30 ml Mito Homogenization Buffer in 40 ml dounce homogenizer and a smooth glass grinder. The homogenate was split into two clean 30 ml polycarbonate tubes and centrifuged at 1,000×g, 4° C., for 3 minutes. The supernatant was subjected to further centrifugation at 10,000×g, 4° C., for 10 minutes. The supernatant was discarded and mitochondrial pellet was suspended in Mito Isolation Buffer using a glass stirring rod and stored on ice until use. Protein concentration of mitochondria was determined using a bicinchoninic acid protein assay kit (Thermo Scientific, Waltham, MA).

Measurement of Oxygen Consumption

Oxygen consumption was monitored as essentially described by Will et al., "Analysis of mitochondrial function using phosphorescent oxygen-sensitive probes," Nature Protocols Vol. 1(6) (2006) 2563. Briefly, isolated mitochondria (50 μg mitochondrial proteins/state 3 (S3) of mitochondrial respiration for inhibitor identification, 100 μg/S2 for uncoupler identification) were incubated with compounds in 25 μl of Measurement Buffer (MB: 250 mM sucrose, 15 mM KCl, 1 mM EGTA, 5 mM $MgCl_2$, 30 mM $K_2HPO_4$, pH 7.4) including 1% DMSO on ice for 1 hour, then mixed with 25 μl of substrate mixture including an oxygen-sensitive phosphorescent dye (MitoXpress Xtra, Agilent, Santa Clara, CA), glutamate (25 mM, G1626, Sigma, St. Louis, MO), malate (25 mM, M6413, Sigma), ADP (3.3 mM, A2754, Sigma, only for S3 of mitochondrial respiration), Fatty acid free BSA (0.1%, A0281, Sigma), and a complex 11-specific inhibitor TTFA (2 μM, T27006, Sigma for the assessment of complex I-mitochondrial respiration with glutamate/malate) in a black wall/clear bottom 384-well plate. The mixtures were covered with HS mineral oil (Agilent) using the Viaflo 384-channel pipette (Integra, Hudson, NH). Oxygen consumption was measured for 30 min at 30° C. using a spectrofluorimeter (FLUOstar Omega, BMG Labtech, Cary, NC). In S3, DMSO vehicle control and antimycin A (10 μM) were used to define 0% and 100% inhibition. In S2, DMSO vehicle and FCCP (0.5-1 μM) was used to define 0% and 100% uncoupling, respectively. Area under curve typically in a range of 0-12 min (S3) or 0-24 min (S2) was used for calculations. $IC_{50}$ or $UC_{50}$ (uncoupling concentration), a concentration that causes 50% of inhibition or maximal (uncoupling) activation of oxygen consumption, was used to evaluate experimental quality. Data were presented as μM (per 50 μg (S3) or 100 μg (S2) mitochondrial proteins). Compounds with $IC_{50}$: <100 μM (S3) and/or $UC_{50}$: <200 μM (S2) were considered as high-risk on mitochondrial toxicity. Compounds with 25-50% changes in inhibition and/or uncoupling were categorized as medium-risk, since compounds with >25% changes are considered as responders.

Toxicity associated with mitochondrial dysfunction has presented a problem for promising potential antibiotics as we as other types of therapeutics. The mitochondrial oxygen consumption rate (OCR) assay is considered a reliable indicator of potential internal organ toxicity issues that may occur with powerful antibiotics. The carboxylate compounds of the invention show unexpected lower toxicity than prior art "glycine nitrile" arylomycin analogs (see, e.g., WO 2018/149419) in the mitochondrial oxygen consumption rate (OCR) assay. The subject compounds in general exhibit OCR IC50 values that are better by an order of magnitude compared to such compounds. Exemplary OCR values for the compounds of the invention are shown in Table 3.

TABLE 3

| Ex. # | Mitochondrial Oxygen Consumption Rate $IC_{50}$ (μM) |
|---|---|
| 2 | 261 |
| 7 | >250 |
| 8 | 28 |
| 14 | >250 |
| 16 | 33 |
| 18 | 119 |
| 19 | >250 |
| 20 | >250 |
| 23 | 22 |
| 24 | >200 |
| 27 | 20 |
| 28 | >250 |
| 30 | >250 |
| 32 | >100 |
| 38 | >100 |
| 43 | >100 |
| 44 | 44 |
| 47 | >100 |
| 50 | >100 |
| 62 | >100 |
| 64 | >100 |
| 66 | 69 |
| 69 | 44 |
| 70 | 48 |
| 72 | >200 |

The compounds of the invention are effective against gram-negative bacteria, and are surprisingly effective against non-fermenter bacteria. MIC values were determined for each of the compounds in both "broth" and serum-based assays, as the serum based assay more accurately represents the performance of the compounds as an antibiotic under physiological conditions. Serum MIC values for representative compounds against *E. coli, Klebsiella pneumoniae, Pseudomonas aeruginosa* and *Acinetobacter aaumanii* are shown in Table 4.

TABLE 4

| Ex. # | *E. coli* 25922 Serum MIC (μM) | *K. pneumoniae* 700603 Serum MIC (μM) | *P. aeruginosa* 01 Serum MIC (μM) | *A. baumanii* 17978 Serum MIC (μM) |
|---|---|---|---|---|
| 1 | 3 | 1.5 | 16 | 24 |
| 2 | 0.5 | 0.5 | 3.3 | 11 |
| 3 | 0.5 | 0.5 | 4 | 12 |
| 4 | 1 | 0.75 | 12 | 24 |
| 5 | 0.63 | 0.88 | 20 | 12 |
| 6 | 0.75 | 0.75 | 16 | 16 |
| 7 | 0.42 | 0.46 | 4.3 | 9.3 |
| 8 | 0.38 | 0.5 | 7 | 16 |
| 9 | 6 | 1.5 | 32 | 32 |
| 10 | 0.5 | 1 | 32 | 32 |
| 11 | 4 | 4 | 64 | 16 |
| 12 | 2 | 3 | 16 | 16 |
| 13 | 1.5 | 1.5 | 24 | 32 |
| 14 | 1.5 | 2 | 48 | 32 |
| 15 | 0.5 | 0.5 | 8 | 8 |
| 16 | 0.44 | 0.63 | 6 | 12 |
| 17 | 1 | 1 | 64 | 16 |
| 18 | 0.25 | 0.25 | 4 | 8 |
| 19 | 0.25 | 0.25 | 8 | 16 |
| 20 | 0.58 | 0.46 | 64 | 16 |
| 21 | 0.38 | 0.25 | 48 | 16 |
| 22 | 1 | 0.5 | 32 | 32 |
| 23 | 0.22 | 0.16 | 16 | 8 |
| 24 | 0.5 | 0.25 | 16 | 16 |
| 25 | 1 | 0.5 | 64 | 16 |
| 26 | 1 | 0.75 | 64 | 24 |
| 27 | 0.25 | 0.25 | 8 | 12 |
| 28 | 0.21 | 0.17 | 43 | 11 |

TABLE 4-continued

| Ex. # | E. coli 25922 Serum MIC (μM) | K. pneumoniae 700603 Serum MIC (μM) | P. aeruginosa 01 Serum MIC (μM) | A. baumanii 17978 Serum MIC (μM) |
|---|---|---|---|---|
| 29 | 2.7 | 1.8 | 64 | 32 |
| 30 | 1 | 0.75 | 16 | 32 |
| 31 | 1 | 0.75 | 48 | 32 |
| 32 | 0.25 | 0.25 | 16 | 4 |
| 33 | 1 | 1 | 8 | 48 |
| 34 | 0.5 | 0.75 | 12 | 16 |
| 35 | 0.5 | 0.5 | 8 | 16 |
| 36 | 0.75 | 1 | 16 | 16 |
| 37 | 0.5 | 0.5 | 4 | 8 |
| 38 | 0.5 | 0.5 | 12 | 16 |
| 39 | 1.5 | 2 | 8 | 24 |
| 40 | 0.75 | 0.5 | 8 | 16 |
| 41 | 1 | 1 | 16 | 16 |
| 42 | 0.5 | 0.75 | 4 | 8 |
| 43 | 0.25 | 0.25 | 8 | 8 |
| 44 | 0.5 | 0.5 | 4 | 8 |
| 45 | 0.5 | 0.5 | 3 | 8 |
| 46 | 0.5 | 0.5 | 16 | 8 |
| 47 | 0.25 | 0.25 | 16 | 16 |
| 48 | 0.75 | 1 | 3 | 16 |
| 49 | 0.5 | 1 | 8 | 16 |
| 50 | 0.75 | 0.75 | 4 | 8 |
| 51 | 0.19 | 0.13 | 8 | 8 |
| 52 | 0.5 | 1 | 8 | 16 |
| 53 | 0.38 | 0.5 | 3 | 6 |
| 54 | 0.38 | 0.5 | 4 | 8 |
| 55 | 0.19 | 0.19 | 6 | 6 |
| 56 | 0.25 | 0.5 | 3 | 6 |
| 57 | 0.75 | 1 | 8 | 16 |
| 58 | 4 | 4 | 16 | 48 |
| 59 | 1 | 1 | 4 | 16 |
| 60 | 0.5 | 0.75 | 4 | 12 |
| 61 | 0.38 | 0.5 | 3 | 16 |
| 62 | 1 | 1 | 6 | 16 |
| 63 | 1 | 0.5 | 16 | 16 |
| 64 | 0.5 | 0.5 | 4 | 8 |
| 65 | 1 | 1 | 16 | 32 |
| 66 | 0.75 | 0.75 | 6 | 12 |
| 67 | 0.5 | 1 | 4 | 16 |
| 68 | 1.5 | 1 | 6 | 16 |
| 69 | 0.25 | 0.38 | 6 | 4 |
| 70 | 0.5 | 1 | 4 | 16 |
| 71 | 0.25 | 0.5 | 8 | 8 |
| 72 | 0.5 | 0.31 | 8 | 14 |
| 73 | 0.38 | 0.25 | 64 | 16 |
| 74 | 0.5 | 0.5 | 64 | 32 |
| 75 | 0.75 | 0.5 | 8 | 16 |
| 76 | 2 | 1.5 | 16 | 24 |

For example, the compounds of the invention show unexpectedly good MIC values against *Acinetobacter baumnini* in the serum assay. Table 5 below shows the serum MIC values against *Acinetobacter baumnini* for each of the compounds.

TABLE 5

| Ex. # | Acinetobacter baumanii 17978 Serum MIC (μM) |
|---|---|
| 1 | 24 |
| 2 | 11 |
| 3 | 12 |
| 4 | 24 |
| 5 | 12 |
| 6 | 16 |
| 7 | 9.3 |
| 8 | 16 |
| 9 | 32 |
| 10 | 32 |
| 11 | 16 |
| 12 | 16 |
| 13 | 32 |
| 14 | 32 |
| 15 | 8 |
| 16 | 12 |
| 17 | 16 |
| 18 | 8 |
| 19 | 16 |
| 20 | 16 |
| 21 | 16 |
| 22 | 32 |
| 23 | 8 |
| 24 | 16 |
| 25 | 16 |
| 26 | 24 |
| 27 | 12 |
| 28 | 11 |
| 29 | 32 |
| 30 | 32 |
| 31 | 32 |
| 32 | 4 |
| 33 | 48 |
| 34 | 16 |
| 35 | 16 |
| 36 | 16 |
| 37 | 8 |
| 38 | 16 |
| 39 | 24 |
| 40 | 16 |
| 41 | 16 |
| 42 | 8 |
| 43 | 8 |
| 44 | 8 |
| 45 | 8 |
| 46 | 8 |
| 47 | 16 |
| 48 | 16 |
| 49 | 16 |
| 50 | 8 |
| 51 | 8 |
| 52 | 16 |
| 53 | 6 |
| 54 | 8 |
| 55 | 6 |
| 56 | 6 |
| 57 | 16 |
| 58 | 48 |
| 59 | 16 |
| 60 | 12 |
| 61 | 16 |
| 62 | 16 |
| 63 | 16 |
| 64 | 8 |
| 65 | 32 |
| 66 | 12 |
| 67 | 16 |
| 68 | 16 |
| 69 | 4 |
| 70 | 16 |
| 71 | 8 |
| 72 | 14 |
| 73 | 16 |
| 74 | 32 |
| 75 | 16 |
| 76 | 24 |

Mitochondrial oxygen consumption rate and serum MIC values against *E. coli, Klebsiella pneumioniae, Pseudomonas aeruginosa* and *Acinetobacter baumnini* for the compounds of Table 1 are shown in Tables 6 and 7, respectively.

TABLE 6

| Cp. # | Mitochondrial Oxygen Consumption Rate $IC_{50}$ (μM) |
| --- | --- |
| 254 | 20 |
| 582 | 10 |

TABLE 7

| Cp. # | *E. coli* 25922 Serum MIC (μM) | *K. pneumoniae* 700603 Serum MIC (μM) | *P. aeruginosa* 01 Serum MIC (μM) | *A. baumanii* 17978 Serum MIC (μM) |
| --- | --- | --- | --- | --- |
| 254 | 0.19 | 0.73 | 13 | 9.3 |
| 561-15 | 2 | 4 | 64 | 64 |
| 563 | 0.75 | 0.75 | 64 | 64 |
| 582 | 0.29 | 0.25 | 1.5 | 2 |
| 586 | 0.094 | 0.094 | 2 | 2 |
| 633 | 0.063 | 0.063 | 4 | 5 |
| 638 | 0.75 | 1 | 64 | 64 |
| 639 | 0.5 | 1 | 64 | 64 |
| 640 | 0.5 | 0.75 | 64 | 64 |
| 641 | 0.75 | 1 | 64 | 64 |
| 642 | 25 | 1.1 | 53 | 71 |
| 643 | 2.3 | 4.6 | 73 | 73 |
| 644 | 1.2 | 4.6 | 74 | 74 |
| 645 | 0.53 | 0.55 | 67 | 67 |
| 646 | 0.55 | 0.58 | 69 | 69 |
| 647 | 0.5 | 1 | 64 | 64 |
| 648 | 0.6 | 1.3 | >128 | >96 |
| 649 | 1 | 2 | 64 | 64 |

Example C1: Topical Gel Composition

To prepare a pharmaceutical topical gel composition, 100 mg of a compound disclosed herein is mixed with 1.75 g of hydroxypropyl cellulose, 10 mL of propylene glycol, 10 mL of isopropyl myristate and 100 mL of purified alcohol USP. The resulting gel mixture is then incorporated into containers, such as tubes, which are suitable for topical administration.

While preferred embodiments of the present disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments described herein may be employed in practicing the invention. It is intended that the following claims define the scope of the invention and that methods and structures within the scope of these claims and their equivalents be covered thereby.

What is claimed is:

1. A method of treatment of a bacterial infection in a patient in need thereof, comprising administering to the patient an effective amount of a compound selected from the group consisting of:

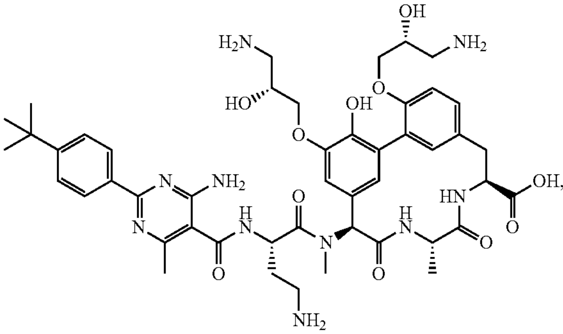

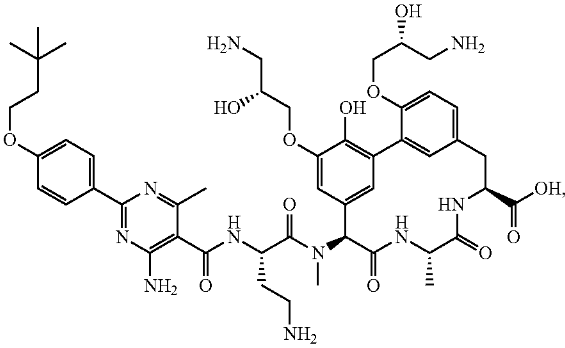

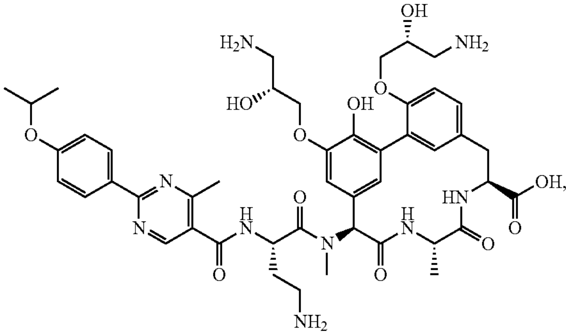

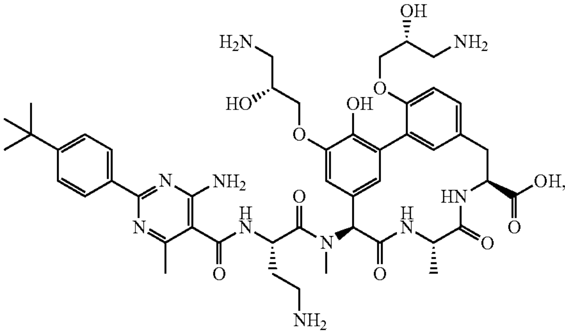

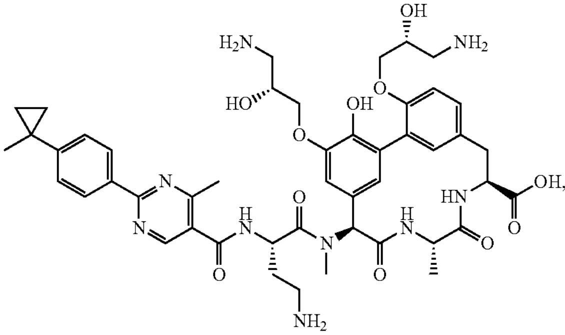

-continued

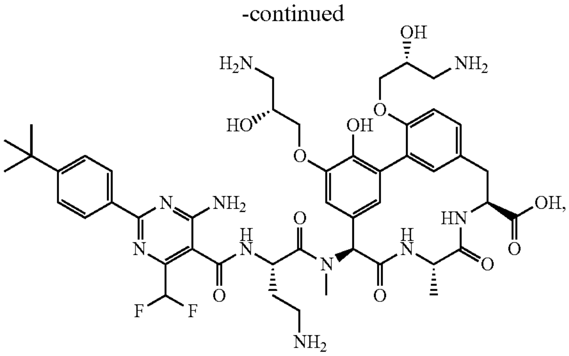

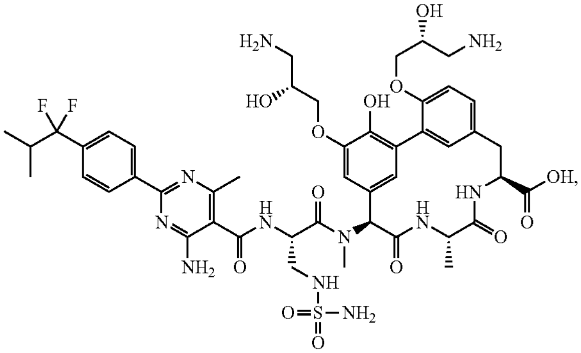

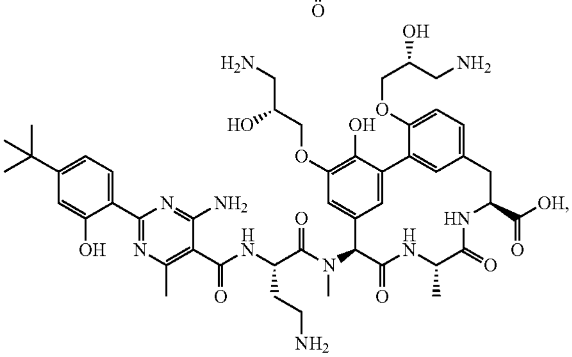

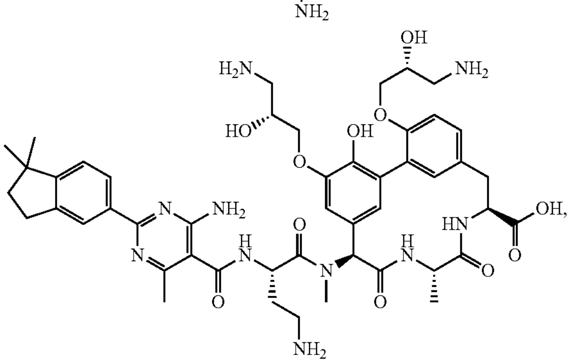

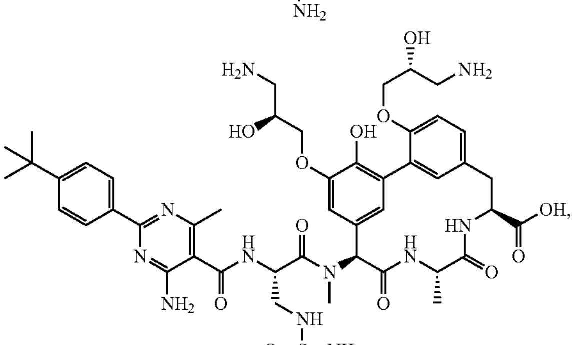

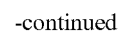

-continued

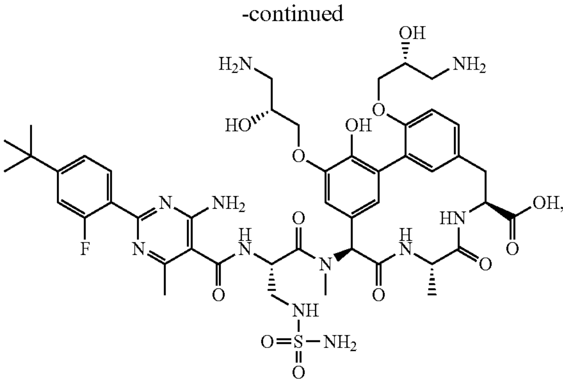

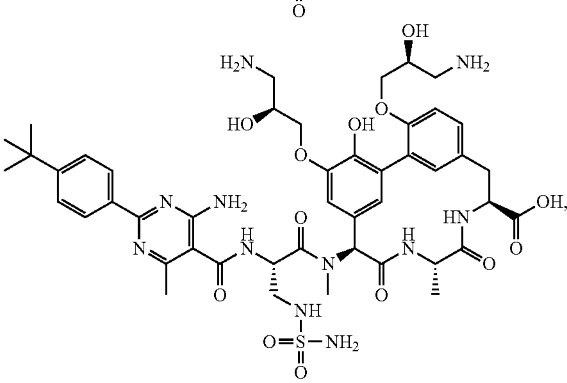

and

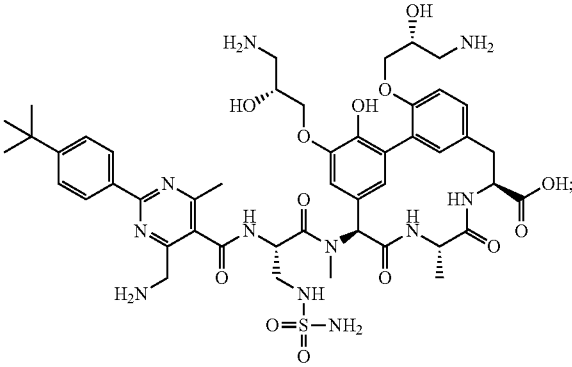 [SMILES: Cc1nc(-c2ccc(C(C)(C)C)cc2)nc(CN)c1C(=O)N[C@@H](CNS(N)(=O)=O)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O]

or a pharmaceutically acceptable salt thereof, wherein the bacterial infection is caused by *Pseudomonas aeruginosa, Escherichia coli, Klebsiella pneumoniae* or *Acinetobacter baumannii.*

2. The method of claim 1, wherein the bacterial infection is caused by *Acinetobacter baumannii.*

3. The method of claim 1, further comprising administering a second therapeutic agent.

4. The method of claim 3, wherein the second therapeutic agent is not a SpsB or LepB inhibitor.

5. The method of claim 4, wherein the second therapeutic agent is an aminoglycoside antibiotic, fluoroquinolone antibiotic, β-lactam antibiotic, macrolide antibiotic, glycopeptide antibiotic, rifampicin, chloramphenicol, fluoramphenicol, colistin, mupirocin, bacitracin, daptomycin, or linezolid.

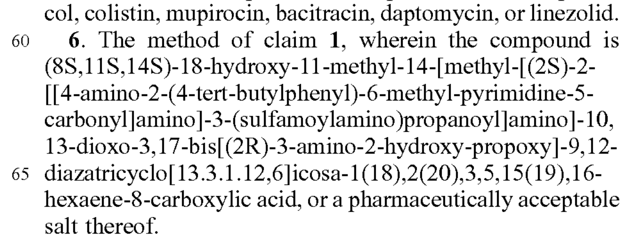

6. The method of claim 1, wherein the compound is (8S,11S,14S)-18-hydroxy-11-methyl-14-[methyl-[(2S)-2-[[4-amino-2-(4-tert-butylphenyl)-6-methyl-pyrimidine-5-carbonyl]amino]-3-(sulfamoylamino)propanoyl]amino]-10,13-dioxo-3,17-bis[(2R)-3-amino-2-hydroxy-propoxy]-9,12-diazatricyclo[13.3.1.12,6]icosa-1(18),2(20),3,5,15(19),16-hexaene-8-carboxylic acid, or a pharmaceutically acceptable salt thereof.

7. The method of claim 1, wherein the compound is (8S,11S,14S)-18-hydroxy-11-methyl-14-[methyl-[(2S)-4-amino-2-[[4-amino-2-(4-tert-butylphenyl)-6-methyl-pyrimidine-5-carbonyl]amino]butanoyl]amino]-10,13-dioxo-3,17-bis[(2R)-3-amino-2-hydroxy-propoxy]-9,12-diazatricyclo[13.3.1.12,6]icosa-1(18),2(20),3,5,15(19),16-hexaene-8-carboxylic acid, or a pharmaceutically acceptable salt thereof.

8. The method of claim 1, wherein the compound is (8S,11S,14S)-18-hydroxy-11-methyl-14-[methyl-[(2S)-4-amino-2-[[4-methyl-2-[4-(1-methylcyclopropyl)phenyl]pyrimidine-5-carbonyl]amino]butanoyl]amino]-10,13-dioxo-3,17-bis[(2R)-3-amino-2-hydroxy-propoxy]-9,12-diazatricyclo[13.3.1.12,6]icosa-1(18),2(20),3,5,15(19),16-hexaene-8-carboxylic acid, or a pharmaceutically acceptable salt thereof.

9. The method of claim 1, wherein the compound is (8S,11S,14S)-18-hydroxy-11-methyl-14-[methyl-[(2S)-4-amino-2-[[2-(4-tert-butylphenyl)-4-amino-6-difluoromethyl-pyrimidine-5-carbonyl]amino]butanoyl]amino]-10,13-dioxo-3,17-bis[(2R)-3-amino-2-hydroxy-propoxy]-9,12-diazatricyclo[13.3.1.12,6]icosa-1(18),2(20),3,5,15(19),16-hexaene-8-carboxylic acid, or a pharmaceutically acceptable salt thereof.

10. The method of claim 1, wherein the patient is a human.

11. The method of claim 1, wherein the bacterial infection is caused by *Acinetobacter baumannii, Klebsiella pneumoniae*, or *Pseudomonas aeruginosa.*

12. The method of claim 1, wherein the bacterial infection is caused by *Klebsiella pneumoniae.*

13. The method of claim 1, wherein the bacterial infection is caused by *Pseudomonas aeruginosa.*

14. The method of claim 4, wherein the bacterial infection is caused by *Escherichia coli.*

15. The method of claim 3, wherein the compound is:

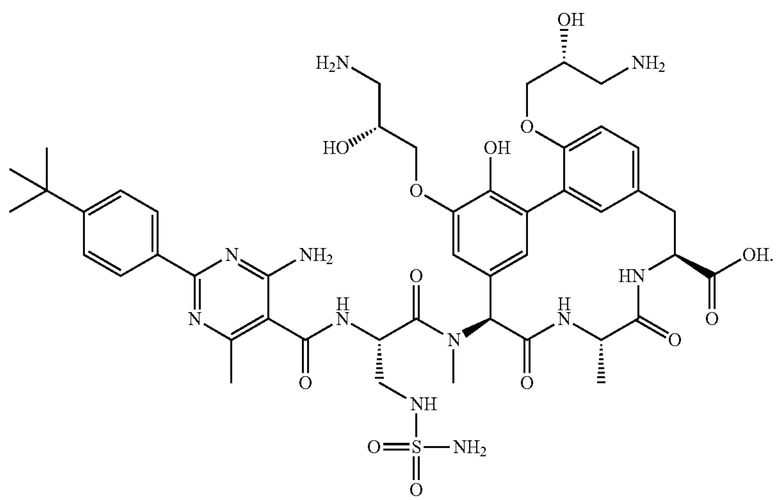 [SMILES: Cc1nc(-c2ccc(C(C)(C)C)cc2)nc(N)c1C(=O)N[C@@H](CNS(N)(=O)=O)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O]

16. The method of claim 1, wherein the compound is a pharmaceutically acceptable salt of:

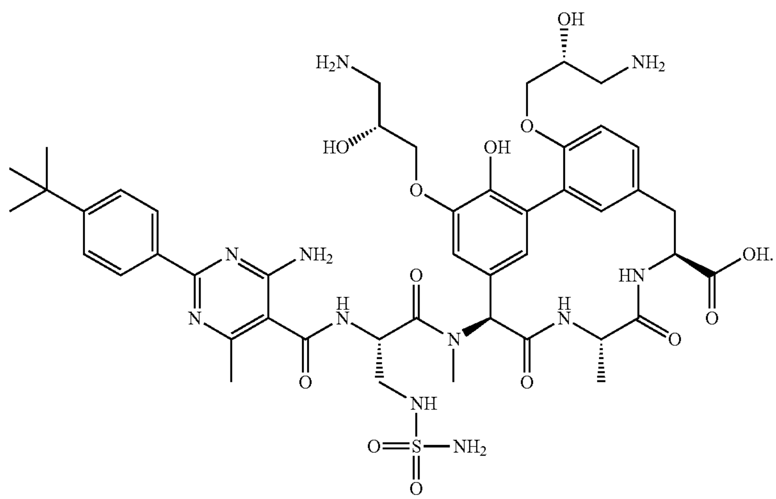 [SMILES: Cc1nc(-c2ccc(C(C)(C)C)cc2)nc(N)c1C(=O)N[C@@H](CNS(N)(=O)=O)C(=O)N(C)[C@@H]1C(=O)N[C@@H](C)C(=O)N[C@H](C(=O)O)Cc2ccc(OC[C@H](O)CN)c(c2)-c2cc1cc(OC[C@H](O)CN)c2O]

17. The method of claim 15, wherein the bacterial infection is caused by *Acinetobacter baumannii*.

18. The method of claim 15, further comprising administering a second therapeutic agent.

19. The method of claim 18, wherein the second therapeutic agent is not a SpsB or LepB inhibitor.

20. The method of claim 19, wherein the second therapeutic agent is an aminoglycoside antibiotic, fluoroquinolone antibiotic, β-lactam antibiotic, macrolide antibiotic, glycopeptide antibiotic, rifampicin, chloramphenicol, fluoramphenicol, colistin, mupirocin, bacitracin, daptomycin, or linezolid.

21. The method of claim 15, wherein the patient is a human.

22. The method of claim 15, wherein the bacterial infection is caused by *Acinetobacter baumannii, Klebsiella pneumoniae*, or *Pseudomonas aeruginosa*.

23. The method of claim 15, wherein the bacterial infection is caused by *Klebsiella pneumoniae*.

24. The method of claim 15, wherein the bacterial infection is caused by *Pseudomonas aeruginosa*.

25. The method of claim 6, wherein the bacterial infection is caused by *Escherichia coli*.

26. The method of claim 16, wherein the bacterial infection is caused by *Acinetobacter baumannii*.

27. The method of claim 16, further comprising administering a second therapeutic agent.

28. The method of claim 27, wherein the second therapeutic agent is not a SpsB or LepB inhibitor.

29. The method of claim 28, wherein the second therapeutic agent is an aminoglycoside antibiotic, fluoroquinolone antibiotic, β-lactam antibiotic, macrolide antibiotic, glycopeptide antibiotic, rifampicin, chloramphenicol, fluoramphenicol, colistin, mupirocin, bacitracin, daptomycin, or linezolid.

30. The method of claim 16, wherein the patient is a human.

31. The method of claim 16, wherein the bacterial infection is caused by *Acinetobacter baumannii, Klebsiella pneumoniae*, or *Pseudomonas aeruginosa*.

32. The method of claim 16, wherein the bacterial infection is caused by *Klebsiella pneumoniae*.

33. The method of claim 16, wherein the bacterial infection is caused by *Pseudomonas aeruginosa*.

34. The method of claim 16, wherein the bacterial infection is caused by *Escherichia* col.

* * * * *